United States Patent
Yanagisawa et al.

(10) Patent No.: US 8,486,980 B2
(45) Date of Patent: Jul. 16, 2013

(54) TRICYCLIC COMPOUND

(75) Inventors: Arata Yanagisawa, Shizuoka (JP); Keiji Uehara, Shizuoka (JP); Masahiro Matsubara, Shizuoka (JP); Kimihisa Ueno, Shizuoka (JP); Michihiko Suzuki, Shizuoka (JP); Takeshi Kuboyama, Shizuoka (JP); Keisuke Yamamoto, Shizuoka (JP); Tomohiro Tamura, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 11 days.

(21) Appl. No.: 13/057,599

(22) PCT Filed: Aug. 6, 2009

(86) PCT No.: PCT/JP2009/063957
§ 371 (c)(1),
(2), (4) Date: Apr. 28, 2011

(87) PCT Pub. No.: WO2010/016549
PCT Pub. Date: Feb. 11, 2010

(65) Prior Publication Data
US 2011/0201640 A1 Aug. 18, 2011

(30) Foreign Application Priority Data
Aug. 6, 2008 (JP) .................................. 2008-203216

(51) Int. Cl.
| | | |
|---|---|---|
| *A61K 31/4245* | (2006.01) | |
| *A61K 31/335* | (2006.01) | |
| *A61K 31/4184* | (2006.01) | |
| *A61K 31/4188* | (2006.01) | |
| *C07D 271/07* | (2006.01) | |
| *C07D 313/10* | (2006.01) | |
| *C07D 235/00* | (2006.01) | |
| *C07D 235/04* | (2006.01) | |

(52) U.S. Cl.
USPC ........... 514/364; 514/450; 514/394; 514/396; 548/132; 548/302.7; 548/305.1; 549/354

(58) Field of Classification Search
USPC . 514/364, 450, 394; 548/132, 302.7; 549/354
See application file for complete search history.

(56) References Cited

U.S. PATENT DOCUMENTS

| | | | |
|---|---|---|---|
| 4,687,777 A | | 8/1987 | Meguro et al. |
| 5,002,953 A | | 3/1991 | Hindley |
| 5,194,443 A | | 3/1993 | Hindley |
| 5,232,925 A | | 8/1993 | Hindley |
| 5,260,445 A | | 11/1993 | Hindley |
| 5,378,701 A | | 1/1995 | Ohshima et al. |
| 5,478,840 A | | 12/1995 | Ohshima et al. |
| 5,521,201 A | | 5/1996 | Hindley et al. |
| 5,607,955 A | * | 3/1997 | Ohshima et al. ............... 514/359 |
| 5,646,169 A | | 7/1997 | Hindley et al. |
| 5,756,525 A | | 5/1998 | Hindley et al. |
| 6,288,095 B1 | | 9/2001 | Hindley et al. |
| 6,686,475 B2 | | 2/2004 | Hindley |
| 7,232,828 B2 | | 6/2007 | Pershadsingh |
| 7,411,072 B2 | | 8/2008 | Coghlan et al. |
| 8,242,151 B2 | * | 8/2012 | Yanagisawa et al. ......... 514/364 |
| 2002/0049240 A1 | | 4/2002 | Hindley et al. |
| 2003/0149054 A1 | | 8/2003 | Hindley |
| 2004/0127443 A1 | | 7/2004 | Pershadsingh |
| 2005/0032854 A1 | | 2/2005 | Kawahara et al. |
| 2006/0025601 A1 | | 2/2006 | Bennani et al. |
| 2006/0063759 A1 | | 3/2006 | Coghlan et al. |
| 2006/0239999 A1 | | 10/2006 | Saki et al. |
| 2006/0252679 A1 | | 11/2006 | Saki et al. |
| 2007/0054949 A1 | | 3/2007 | Pershadsingh |
| 2007/0185070 A1 | | 8/2007 | Pershadsingh |

(Continued)

FOREIGN PATENT DOCUMENTS

| | | |
|---|---|---|
| GB | 1043158 | 9/1966 |
| JP | 61-267580 A | 11/1986 |

(Continued)

OTHER PUBLICATIONS

Benson et al., *Hypertension*, 43: 993-1002 (2004).
Berger et al., *Molecular Endocrinology*, 17(4): 662-676 (2003).
Copland et al., *Oncogene*, 25: 2304-2317 (2006).
Kiyama et al., *J. Med. Chem.*, 38: 2728-2741 (1995).
Krovat et al., *J. Med. Chem.*, 46: 716-726 (2003).
Lehmann et al., *The Journal of Biological Chemistry*, 270(22): 12953-12956 (1995).
Shimazaki et al., *European Journal of Cancer*, 44: 1734-1743 (2008).
Willson et al., *J. Med. Chem.*, 39: 665-668 (1996).
Japanese Patent Office, International Search Report for PCT/JP2008/052068 (Mar. 18, 2008), English translation.

(Continued)

*Primary Examiner* — Yong Chu
(74) *Attorney, Agent, or Firm* — Leydig, Voit & Mayer, Ltd.

(57) ABSTRACT

Provided is a tricyclic compound having a PPAR γ agonist activity, which is represented by the general formula (I) wherein Z represents a single bond or the like, Y represents a hydrogen atom, lower alkyl optionally having substituent(s) or the like, X represents a hydrogen atom or the like, A represents aryl or the like, B and C are the same or different and each represents an aromatic carbocycle or the like, $R^4$-$R^9$ are the same or different and each represents hydrogen or the like, V represents a single bond or the like, $R^{10}$ and $R^{11}$ are the same or different and each represents hydrogen or the like, or a pharmaceutically acceptable salt thereof or the like:

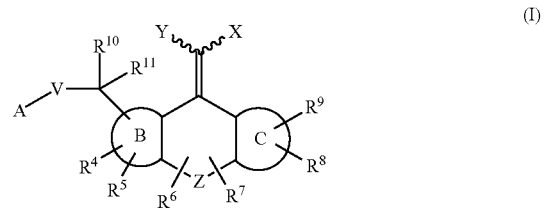

(I)

14 Claims, No Drawings

U.S. PATENT DOCUMENTS

| | | |
|---|---|---|
| 2007/0203213 A1 | 8/2007 | Pershadsingh |
| 2008/0009536 A1 | 1/2008 | Pershadsingh |
| 2009/0012171 A1 | 1/2009 | Polivka |
| 2009/0176760 A1 | 7/2009 | Yanagisawa et al. |

FOREIGN PATENT DOCUMENTS

| | | |
|---|---|---|
| JP | 01-131169 A | 5/1989 |
| JP | 06-228065 A | 8/1994 |
| JP | 07-061983 A | 3/1995 |
| JP | 2003-231636 A | 8/2003 |
| JP | 2006-515566 A | 6/2006 |
| WO | WO 2004/017994 A1 | 3/2004 |
| WO | WO 2004/017995 A1 | 3/2004 |
| WO | WO 2004/052847 A2 | 6/2004 |
| WO | WO 2005/105736 A1 | 11/2005 |
| WO | WO 2006/107062 A2 | 10/2006 |
| WO | WO 2007/081299 A2 | 7/2007 |
| WO | WO 2008/096829 A1 | 8/2008 |
| WO | WO 2008096829 A1 * | 8/2008 |

OTHER PUBLICATIONS

Japanese Patent Office, International Search Report for PCT/JP2009/063957 (Nov. 17, 2009), English translation.

Kawai et al., *Bioorganic & Medicinal Chemistry Letters*, 17: 5537-5542 (2007).

Patani et al., *Chem. Rev.*, 96: 3147-3176 (1996).

Silverman, *The Organic Chemistry of Drug Design and Drug Action*, $2^{nd}$ edition (2004), pp. 25-34.

U.S. Appl. No. 12/162,119, filed Jul. 24, 2008.

* cited by examiner

TRICYCLIC COMPOUND

TECHNICAL FIELD

The present invention relates to a tricyclic compound having a peroxisome proliferator-activated receptor (PPAR) γ agonist activity, which is useful as an agent for treating and/or preventing, for example, type 2 diabetes, impaired glucose tolerance, insulin resistance syndrome, hypertension, hyperlipidemia, metabolic syndrome, visceral obesity, obesity, hypertriglyceridemia, inflammatory skin diseases, inflammatory diseases, proliferative diseases, inflammatory neuropsychiatric diseases, angiogenesis and pathological angiogenesis relating to tumor growth and metastasis, neurodegenerative neuropsychiatric diseases or the like.

BACKGROUND ART

Peroxisome proliferator-activated receptor (PPAR) is a member of the nuclear receptor superfamily of ligand activated transcription factor. Three subtypes of PPAR, i.e., PPAR α, PPAR γ, and PPAR δ, have been cloned from mouse and human. PPAR is an important nuclear hormone receptor for the metabolism of carbohydrate and lipid, cell growth and differentiation, phenotype conversion, apoptosis, angiogenesis, immunoregulation, and inflammatory reaction. Compounds that activate PPAR are useful for the treatment or prophylaxis of various clinical diseases such as metabolic syndrome, obesity, prediabetes, type 2 diabetes and the other insulin resistance syndrome, hypertension, atherosclerosis, lipemia, inflammatory skin diseases such as psoriasis, inflammatory bowel disease, and inflammatory neurodegenerative diseases such as multiple sclerosis, Alzheimer's disease etc., proliferative diseases such as benign or malignant tumor, metastatic tumor or the like, or the like. PPAR γ specifically plays an important role in adipocyte differentiation. Hypertrophic adipocytes secrete large amounts of a cytokine such as TNF-α, and free fatty acid which induce insulin resistance. On the other hand, thiazolidinedione derivatives such as pioglitazone, rosiglitazone or the like improve insulin resistance by activating PPAR γ to decrease hypertrophic adipocytes by apoptosis, and promoting differentiation of preadipocytes into small adipocytes having normal function (non-patent documents 1 and 2). Pioglitazone and rosiglitazone, which are PPAR γ agonists, have already been clinically used as therapeutic drugs for diabetes (patent documents 1 and 2).

PPAR γ agonists are also useful as agents for treating and/or preventing diseases besides diabetes, such as metabolic syndrome, obesity, impaired glucose tolerance and other insulin resistance syndrome, which are prediabetic conditions, hypertension, atherosclerosis, hyperlipidemia, inflammatory diseases such as psoriasis or the like, inflammatory bowel disease, or the like. It has also been reported that it is useful as a therapeutic and/or prophylactic agent for proliferative diseases such as benign or malignant tumor, metastatic tumor, or the like (non-patent documents 3, 4).

It has been reported that selective partial agonists against PPAR γ do not accompany side effects such as body weight increase, adipocyte accumulation or the like, as compared to the existing full agonists (thiazolidinedione derivative or the like) (non-patent document 5).

A tricyclic compound represented by the following formula (A) and a derivative thereof are known as PPAR agonists/antagonists/regulators (patent document 3).

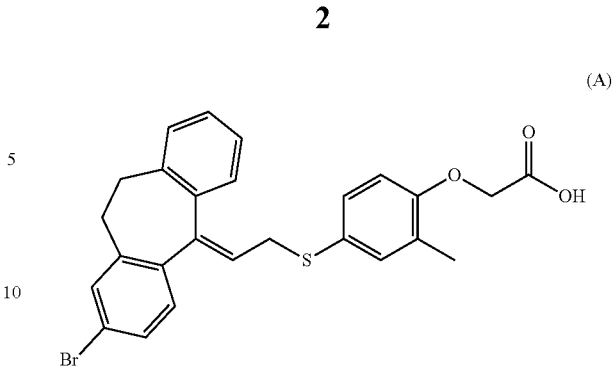

(A)

It is known that a compound represented by the following formula (B), which is a tricyclic compound, and a derivative thereof have a superior hypotensive action based on an angiotensin II receptor antagonistic action (see patent document 4).

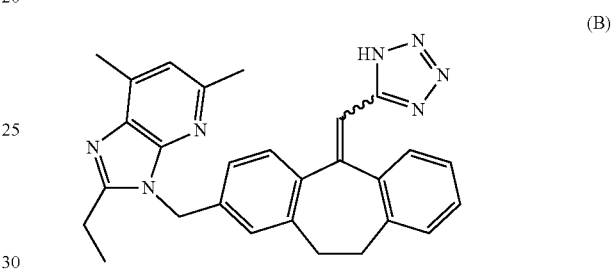

(B)

DOCUMENT LIST

Patent Documents patent document 1: JP-A-61-267580
patent document 2: JP-A-1-131169
patent document 3: WO2005/105736
patent document 4: JP-A-6-228065

Non-Patent Documents non-patent document 1: J. Biol. Chem., 1995, vol. 270, p. 12953
non-patent document 2: J. Med. Chem., 1996, vol. 39, p. 665
non-patent document 3: Oncogen, 2006, vol. 25, p. 2304
non-patent document 4: Eur. J. Cancer, 2008, vol. 44, No. 12, p. 1734
non-patent document 5: Molecular Endocrinology, 2003, vol. 17, No. 4, p. 662

SUMMARY OF THE INVENTION

Problems to be Solved by the Invention

An object of the present invention is to provide a novel tricyclic compound having a PPAR γ agonist activity or a pharmaceutically acceptable salt thereof and the like. The tricyclic compound provided by the present invention or a pharmaceutically acceptable salt thereof is useful as a therapeutic and/or prophylactic agent for type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis, growth of benign, malignant tumors or metastatic tumor etc.), inflammatory neuropsychiatric diseases (e.g., multiple sclerosis etc.), angiogenesis and pathological angiogenesis relating to tumor growth and tumor metastasis, neurodegenerative neuropsychiatric diseases (e.g., Alzheimer's disease, Parkinson's disease etc.), cardiovascular diseases (e.g., arteriosclerosis, cardiac disease, cerebral apoplexy, renal diseases etc.), or the like.

Another object of the present invention is to provide a PPAR γ agonist containing a tricyclic compound as an active ingredient.

Means of Solving the Problems

The present invention relates to the following (1)-(45).
(1) A tricyclic compound represented by the general formula (I)

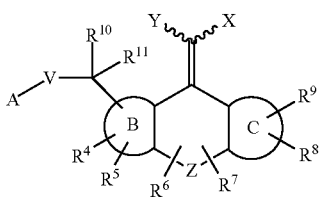

(I)

wherein Z represents a single bond, CH$_2$, CH$_2$CH$_2$, CH=CH, O, S, CH$_2$O, OCH$_2$, CH$_2$S(O)$_n$ or S(O)$_n$CH$_2$ wherein n is an integer of 0 to 2, Y represents a hydrogen atom, lower alkyl optionally having substituent(s), lower alkoxy optionally having substituent(s), cycloalkyl optionally having substituent(s) or halogen, X represents a hydrogen atom, lower alkyl, cyano, halogen, hydroxymethyl, aminomethyl, carboxy, lower alkoxycarbonyl optionally having substituent(s), carbamoyl, lower alkylcarbamoyl optionally having substituent(s), di-lower alkylcarbamoyl optionally having substituent(s), arylcarbamoyl optionally having substituent(s), lower alkylsulfonylcarbamoyl optionally having substituent(s), cycloalkylsulfonylcarbamoyl optionally having substituent(s), lower alkylaminosulfonylcarbamoyl optionally having substituent(s), arylsulfonylcarbamoyl optionally having substituent(s), aliphatic heterocyclyl carbonyl optionally having substituent(s), lower alkanoylaminomethyl optionally having substituent(s), lower alkylsulfonylaminomethyl optionally having substituent(s), an aliphatic heterocyclic group optionally having substituent(s) or an aromatic heterocyclic group optionally having substituent(s), A represents aryl optionally having substituent(s) or an aromatic heterocyclic group optionally having substituent(s), B and C are the same or different and each represents an aromatic carbocycle or aromatic heterocycle, R$^4$, R$^5$, R$^6$, R$^7$, R$^8$ and R$^9$ are the same or different and each represents a hydrogen atom, halogen, hydroxy, lower alkoxy or lower alkyl, V represents a single bond, O, NR$^A$ wherein R$^A$ represents a hydrogen atom, lower alkyl optionally having substituent(s), lower alkanoyl optionally having substituent(s), lower alkoxycarbonyl optionally having substituent(s), lower alkylcarbamoyl optionally having substituent(s) or lower alkylsulfonyl optionally having substituent(s), or S, and R$^{10}$ and R$^{11}$ are the same or different and each represents a hydrogen atom or lower alkyl,
or a pharmaceutically acceptable salt thereof.
(2) The tricyclic compound or the pharmaceutically acceptable salt thereof according to (1) wherein

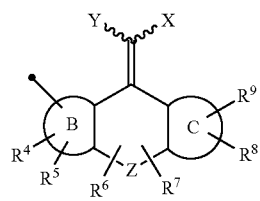

represents the following formula c20-c22

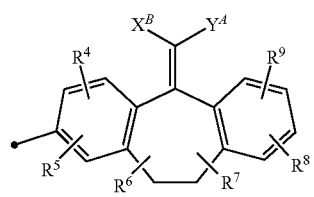

c20

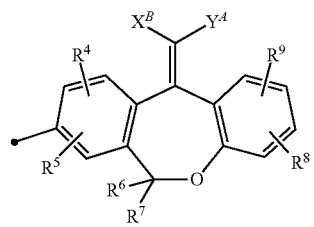

c21

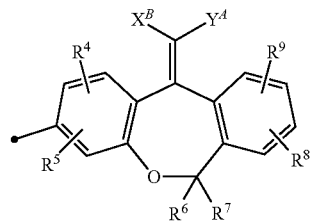

c22 wherein R$^4$, R$^5$, R$^6$, R$^7$, R$^8$, and R$^9$ are each as defined above, Y$^A$ represents lower alkyl or cycloalkyl optionally having substituent(s),
X$^B$ represents the following group (b19)-(b24)

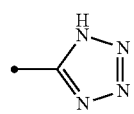

(b19)

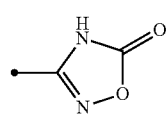

(b20)

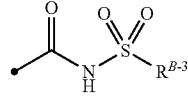

(b21)

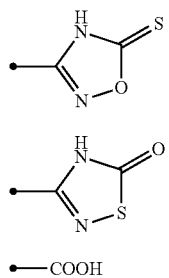

(b22)

(b23)

●—COOH (b24)

wherein $R^{B-3}$ represents lower alkyl optionally having substituent(s) or aryl optionally having substituent(s),
A represents the following group (a38) or (a39)

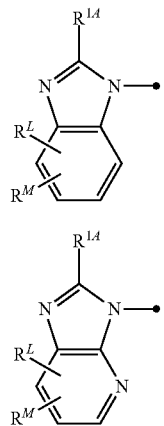

(a38)

(a39)

wherein $R^{1A}$ represents lower alkyl optionally having substituent(s), aryl optionally having substituent(s) or cycloalkyl optionally having substituent(s), $R^L$ and $R^M$ are the same or different and each represents a hydrogen atom, halogen, carbamoyl, lower alkylcarbamoyl optionally having substituent(s), lower alkyl optionally having substituent(s) or lower alkylsulfonylamino optionally having substituent(s),
V represents a single bond, and
$R^{10}$ and $R^{11}$ are the same or different and each is a hydrogen atom or lower alkyl.

(3) The tricyclic compound or the pharmaceutically acceptable salt thereof according to (2) wherein

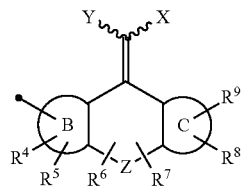

represents the following formula c20

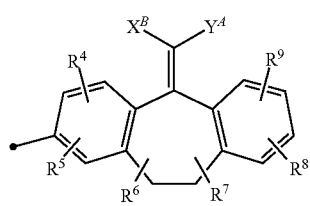

c20 wherein $R^4$, $R^5$, $R^6$, $R^7$, $R^6$, $R^9$, $X^B$, and $Y^A$ are each as defined above, A is represented by the following group (a38-1)

(a38-1)

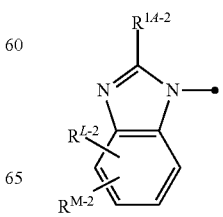

wherein $R^{1A-1}$ represents lower alkyl optionally having substituent(s) or cycloalkyl optionally having substituent(s), $R^{L-1}$ and $R^{M-1}$ are the same or different and each represents a hydrogen atom, halogen or lower alkyl optionally having substituent(s).

(4) The tricyclic compound or the pharmaceutically acceptable salt thereof according to (2) wherein

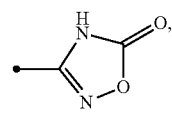

represents the following formula c24 c24

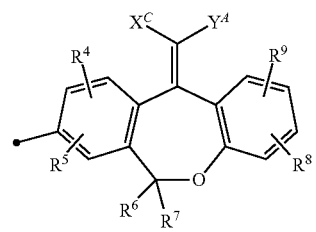

wherein $R^4$, $R^5$, $R^6$, $R^7$, $R^6$, $R^9$, and $Y^A$ are each as defined above, $X^C$ is represented by the following group (b20)

(b20)

$R^{1A}$ represents lower alkyl optionally having substituent(s) other than hydroxy, aryl optionally having substituent(s) or cycloalkyl optionally having substituent(s), and
$R^L$ and $R^M$ are the same or different and each represents a hydrogen atom, lower alkyl, halogen, carbamoyl or lower alkylcarbamoyl optionally having substituent(s).

(5) The tricyclic compound or the pharmaceutically acceptable salt thereof according to (4) wherein A is represented by the following group (a38-2)

(a38-2)

wherein $R^{14-2}$ represents lower alkyl optionally having substituent(s) other than hydroxy, aryl optionally having substituent(s), or cycloalkyl optionally having substituent(s), $R^{L-2}$ and $R^{M-2}$ are the same or different and each represents a hydrogen atom, lower alkyl, halogen, carbamoyl or lower alkylcarbamoyl optionally having substituent(s).

(6) The tricyclic compound or the pharmaceutically acceptable salt thereof according to (3) wherein $X^B$ is a group selected from the group consisting of the following formulas (b19), (b20) and (b22)

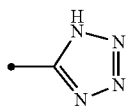
(b19)

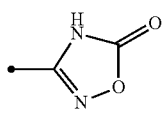
(b20)

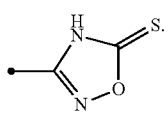
(b22)

(7) The tricyclic compound or the pharmaceutically acceptable salt thereof according to (3) wherein $X^B$ is represented by the following group (b20)

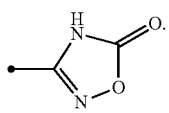
(b20)

(8) The tricyclic compound or the pharmaceutically acceptable salt thereof according to (1) wherein

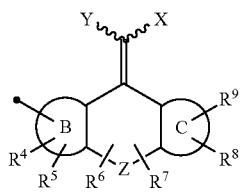

represents the following formula c7-c9

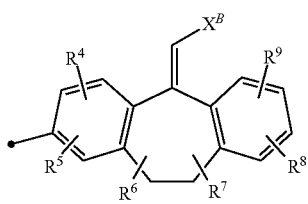
c7

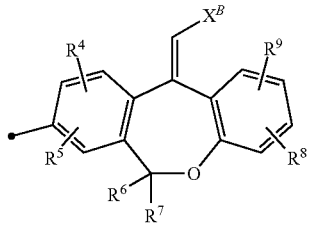
c8

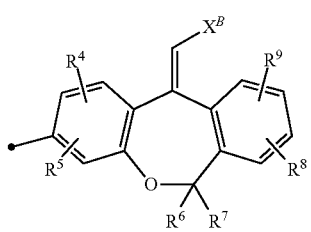
c9 wherein $R^4$, $R^5$, $R^6$, $R^7$, $R^8$, $R^9$, and $X^B$ are each as defined above, and A represents the following formula

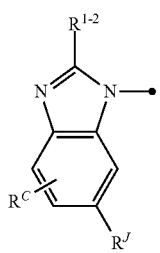

wherein $R^C$ represents a hydrogen atom, halogen, nitro, cyano, formyl, oxo, hydroxy, lower alkoxy optionally having substituent(s), lower alkanoyloxy optionally having substituent(s), lower alkyl optionally having substituent(s), lower alkenyl optionally having substituent(s), lower alkanoyl optionally having substituent(s), lower alkoxycarbonyl optionally having substituent(s), lower alkylsulfonylamino optionally having substituent(s), —$NR^FR^G$ wherein $R^F$ and $R^G$ are the same or different and each represents a hydrogen atom, lower alkyl optionally having substituent(s), lower alkanoyl optionally having substituent(s) or lower alkoxycarbonyl optionally having substituent(s), or $R^F$ and $R^G$ form, each together with the adjacent nitrogen atom, a nitrogen-containing heterocyclic group optionally having substituent(s), —$CONR^HR^I$ wherein $R^H$ and $R^I$ are the same or different and each represents a hydrogen atom, lower alkyl optionally having substituent(s), lower alkanoyl optionally having substituent(s) or lower alkoxycarbonyl optionally having substituent(s), or $R^H$ and $R^I$, form, together with the adjacent nitrogen atom, a nitrogen-containing heterocyclic group optionally having substituent(s), aryl optionally having substituent(s), cycloalkyl optionally having substituent(s), an aromatic heterocyclic group optionally having substituent(s) or an aliphatic heterocyclic group optionally having substituent(s), $R^{1-2}$ represents lower alkyl optionally having substituent(s), cycloalkyl optionally having substituent(s) or lower alkoxy optionally having substituent(s), $R^J$ represents aryl optionally having substituent(s), an aromatic heterocyclic group optionally having substituent(s) (except benzimidazolyl group) or an aliphatic heterocyclic group optionally having substituent(s), and V is a single bond.

(9) The tricyclic compound or the pharmaceutically acceptable salt thereof according to (8) wherein

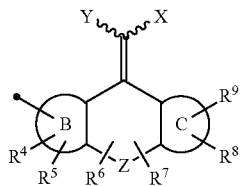

represents the following formula c17

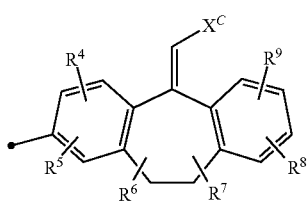

c17 wherein $X^C$, $R^4$, $R^5$, $R^6$, $R^7$, $R^8$ and $R^9$ are each as defined above, and $R^{1-2}$ is lower alkyl optionally having substituent(s) other than hydroxy.

(10) The tricyclic compound or the pharmaceutically acceptable salt thereof according to (8) wherein

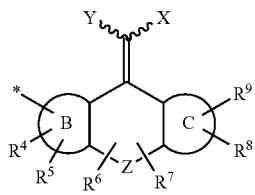

is the following formula c18

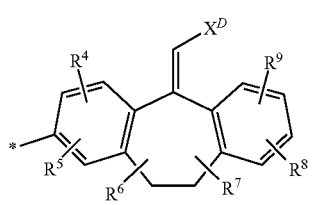

c18 wherein $X^D$ is the following group (b24)

·-COOH    (b24), and $R^4$, $R^5$, $R^6$, $R^7$, $R^8$ and $R^9$ are each as defined above.

(11) The tricyclic compound or the pharmaceutically acceptable salt thereof according to (8) wherein

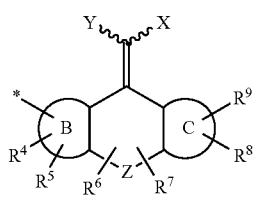

is the following formula c19

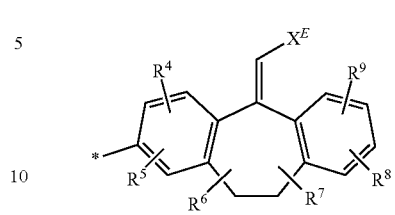

c19 is wherein $X^E$ is the following group (b19)

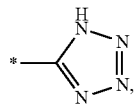

(b19)

$R^4$, $R^5$, $R^6$, $R^7$, $R^8$ and $R^9$ are each as defined above, $R^{1-2}$ is lower alkyl, and $R^J$ is phenyl optionally having a fluorine atom as a substituent, thienyl, oxazolyl, oxadiazolyl or 5-methyloxazol-2-yl.

(12) The tricyclic compound or the pharmaceutically acceptable salt thereof according to (8) wherein $X^B$ is the following formula (b20)

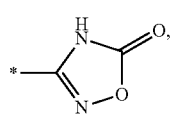

(b20)

and $R^{1-2}$ is lower alkyl.

(13) The tricyclic compound or the pharmaceutically acceptable salt thereof according to (1) wherein X represents a hydrogen atom, lower alkyl, cyano, halogen, hydroxymethyl, aminomethyl, lower alkoxycarbonyl optionally having substituent(s), carbamoyl, lower alkylcarbamoyl optionally having substituent(s), di-lower alkylcarbamoyl optionally having substituent(s), arylcarbamoyl optionally having substituent(s), lower alkylaminosulfonylcarbamoyl optionally having substituent(s), aliphatic heterocyclyl carbonyl optionally having substituent(s), lower alkanoylaminomethyl optionally having substituent(s), lower alkylsulfonylaminomethyl optionally having substituent(s) or any of the following formulas (b1)-(b16)

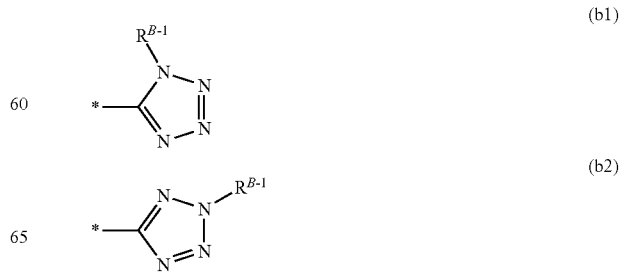

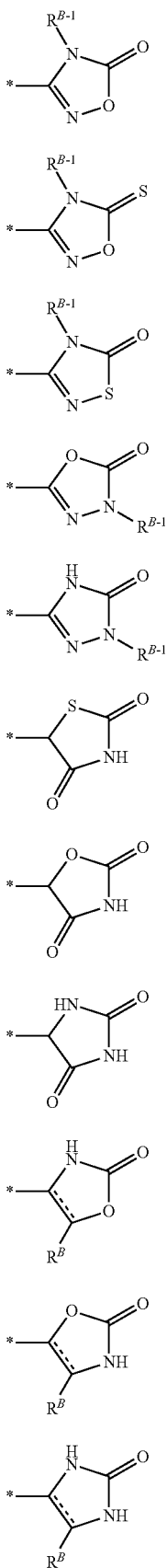
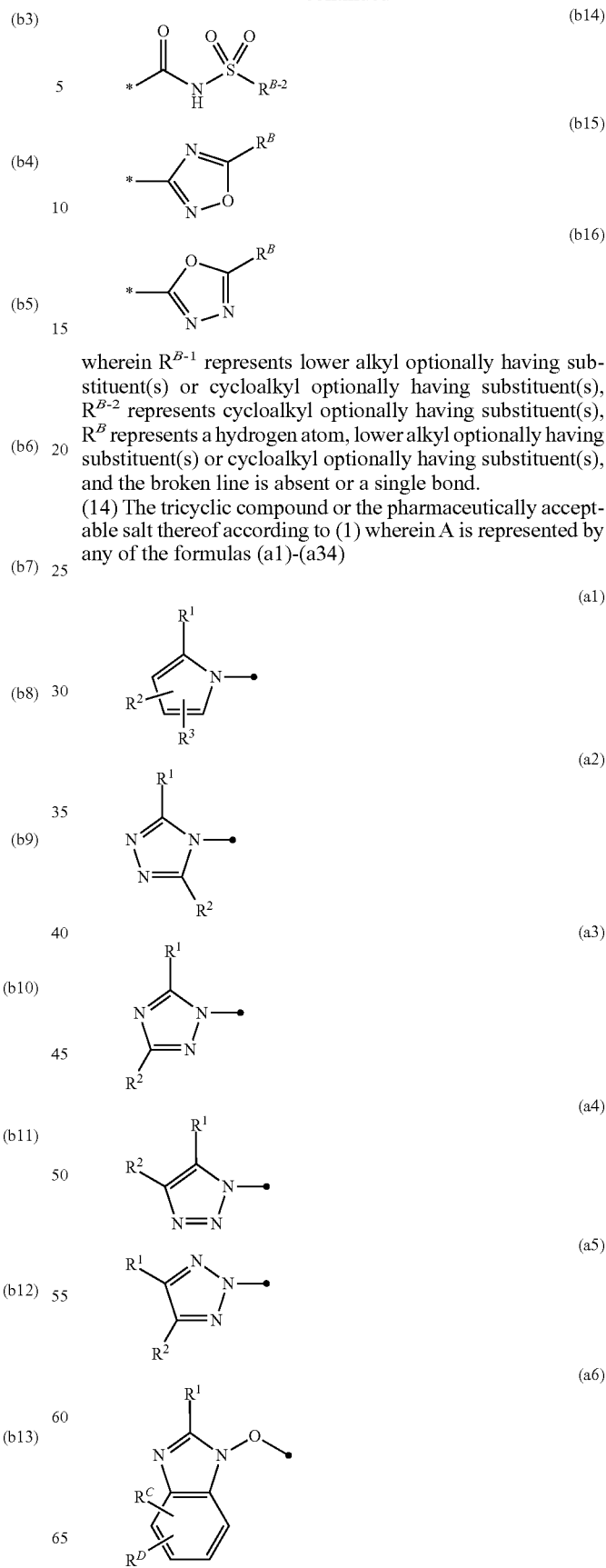

wherein $R^{B-1}$ represents lower alkyl optionally having substituent(s) or cycloalkyl optionally having substituent(s), $R^{B-2}$ represents cycloalkyl optionally having substituent(s), $R^B$ represents a hydrogen atom, lower alkyl optionally having substituent(s) or cycloalkyl optionally having substituent(s), and the broken line is absent or a single bond.

(14) The tricyclic compound or the pharmaceutically acceptable salt thereof according to (1) wherein A is represented by any of the formulas (a1)-(a34)

-continued
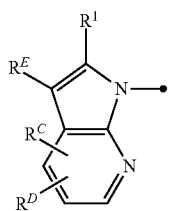 (a7)
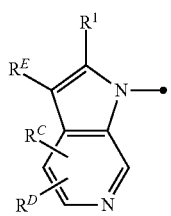 (a8)
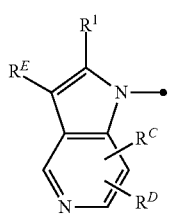 (a9)
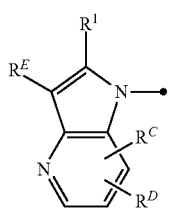 (a10)
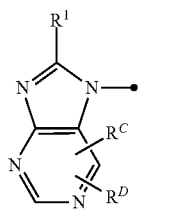 (a11)
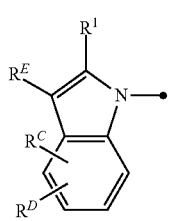 (a12)
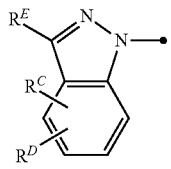 (a13)
-continued
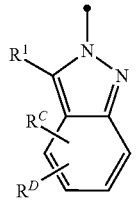 (a14)
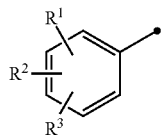 (a15)
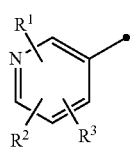 (a16)
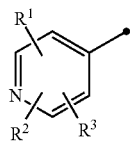 (a17)
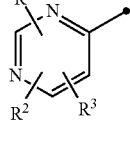 (a18)
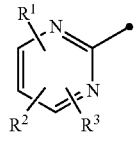 (a19)
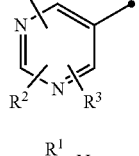 (a20)
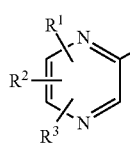 (a21)
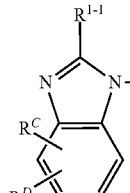 (a22)
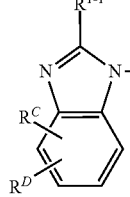 (a23)

(a24) 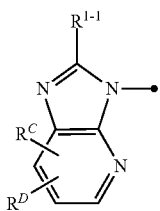

(a25) 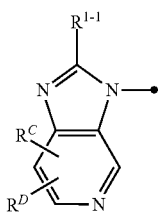

(a26) 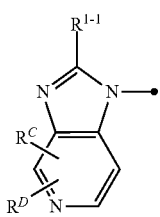

(a27) 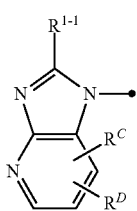

(a28) 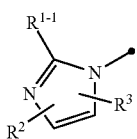

(a29) 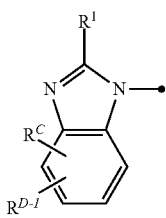

(a30) 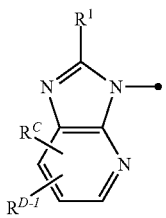

(a31) 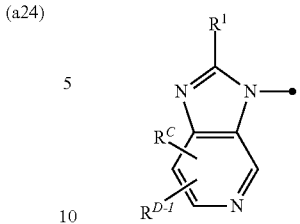

(a32) 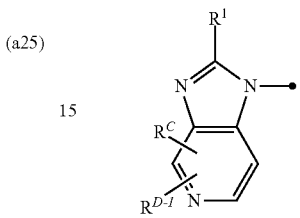

(a33) 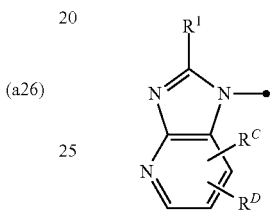

(a34) 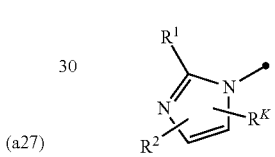

wherein $R^1$, $R^2$ and $R^3$ are the same or different and each represents a hydrogen atom, lower alkyl optionally having substituent(s), cycloalkyl optionally having substituent(s), halogen, lower alkoxy optionally having substituent(s), lower alkylsulfanyl optionally having substituent(s), lower alkenyl optionally having substituent(s), lower alkanoyl optionally having substituent(s), lower alkoxycarbonyl optionally having substituent(s), carbamoyl, lower alkylcarbamoyl optionally having substituent(s), di-lower alkylcarbamoyl optionally having substituent(s), aliphatic heterocyclyl carbonyl optionally having substituent(s), aryloxy optionally having substituent(s), aryl optionally having substituent(s), an aromatic heterocyclic group optionally having substituent(s), or an aliphatic heterocyclic group optionally having substituent(s), $R^{1-1}$ represents a hydrogen atom, lower alkenyl optionally having substituent(s), lower alkanoyl optionally having substituent(s), lower alkoxycarbonyl optionally having substituent(s), carbamoyl, lower alkylcarbamoyl optionally having substituent(s), di-lower alkylcarbamoyl optionally having substituent(s), aliphatic heterocyclyl carbonyl optionally having substituent(s), aryloxy optionally having substituent(s), aryl optionally having substituent(s), an aromatic heterocyclic group optionally having substituent(s), an aliphatic heterocyclic group optionally having substituent(s) or aralkyloxy optionally having substituent(s), $R^C$, $R^D$ and $R^E$ are the same or different and each is as defined for the aforementioned $R^C$, $R^K$ represents cycloalkyl optionally having substituent(s), halogen, lower alkoxy optionally having substituent(s), lower alkylsulfanyl optionally having substituent(s), carbamoyl, aryloxy optionally having substituent(s), aryl optionally having substituent(s), an aromatic heterocyclic group optionally having substituent(s), aralkyl optionally having substituent(s), or an aliphatic heterocyclic group optionally having substituent(s), $R^{D-1}$ represent cycloalkyl optionally having substituent(s).

(15) The tricyclic compound or the pharmaceutically acceptable salt thereof according to (1) or (14), wherein V is O, $NR^A$ wherein $R^A$ is as defined above, or S.

(16) The tricyclic compound or the pharmaceutically acceptable salt thereof according to (1) wherein at least one of $R^{10}$ and $R^{11}$ is lower alkyl.

(17) The tricyclic compound or the pharmaceutically acceptable salt thereof according to (1) wherein

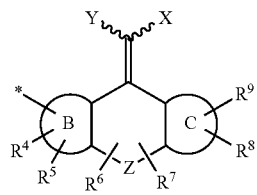

is represented by any of the following formulas c10-c13

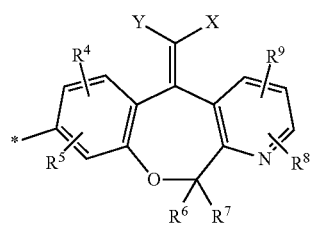
c10

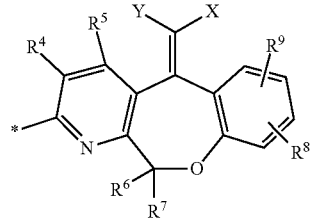
c11

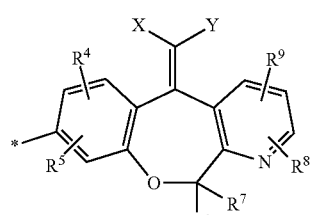
c12

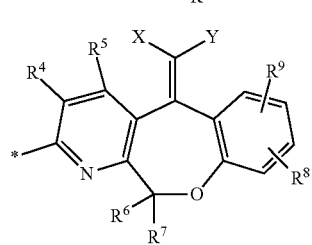
c13 wherein $R^4$, $R^5$, $R^6$, $R^7$, $R^8$, $R^9$, X and Y are each as defined above.

(18) The tricyclic compound or the pharmaceutically acceptable salt thereof according to any of (1), (14), (15) and (16), wherein X is the following formula (b17) or (b18)

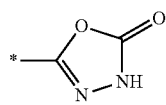
(b17)

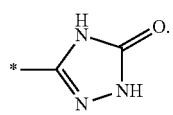
(b18)

(19) The tricyclic compound or the pharmaceutically acceptable salt thereof according to any of (1), (13) and (16), wherein A is a group selected from the group consisting of the following formulas (a1)-(a14) and (a23)-(a34)

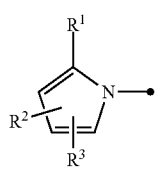
(a1)

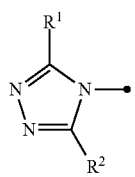
(a2)

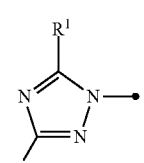
(a3)

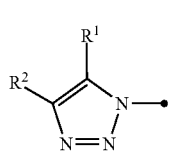
(a4)

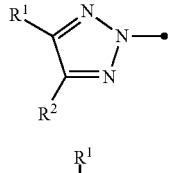
(a5)

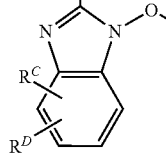
(a6)

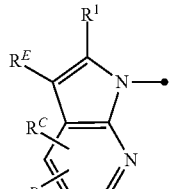
(a7)

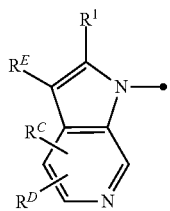 (a8)
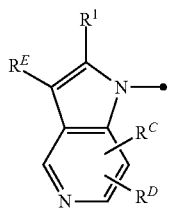 (a9)
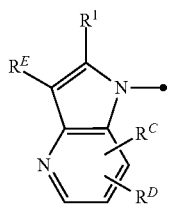 (a10)
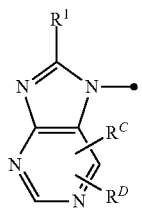 (a11)
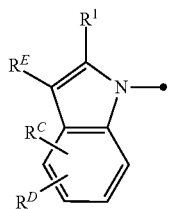 (a12)
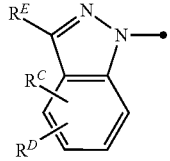 (a13)
 (a14)

-continued

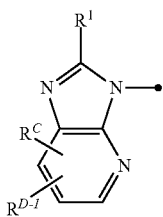
(a30)

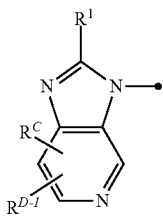
(a31)

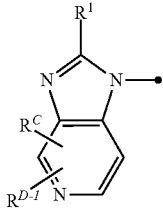
(a32)

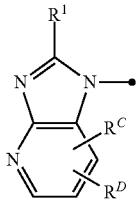
(a33)

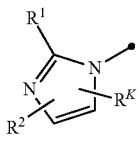
(a34)

wherein $R^1$, $R^2$, $R^3$, $R^{1-1}$, $R^{D-1}$, $R^C$, $R^D$, $R^E$ and $R^K$ are each as defined above, and V is a single bond.

(20) The tricyclic compound or the pharmaceutically acceptable salt thereof according to (13), (14) or (16), wherein V is O, $NR^A$ wherein $R^A$ is as defined above, or S.

(21) The tricyclic compound or the pharmaceutically acceptable salt thereof according to any of (1), (13) and (16), wherein A represents a group selected from the group consisting of the following formulas (a15)-(a22),

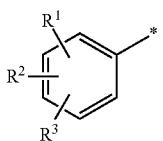
(a15)

-continued

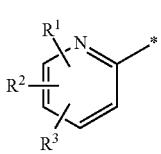
(a16)

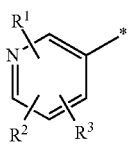
(a17)

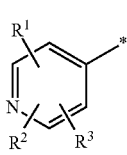
(a18)

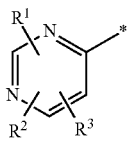
(a19)

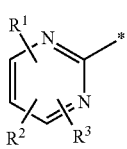
(a20)

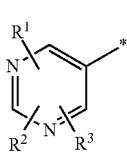
(a21)

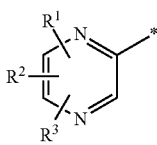
(a22)

wherein $R^1$, $R^2$ and $R^3$ are each as defined above, and

V is O or $NR^A$ wherein $R^A$ is as defined above.

(22) The tricyclic compound or the pharmaceutically acceptable salt thereof according to (1), (13), (15) or (16), wherein A is the following formula

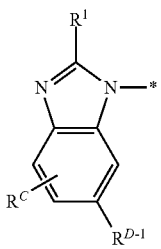

wherein $R^1$, $R^C$ and $R^{D-1}$ are each as defined above.

(23) The tricyclic compound or the pharmaceutically acceptable salt thereof according to any of (1), (14), (15) and (16), wherein
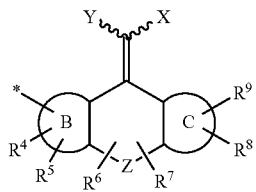
is a group selected from the group consisting of the following formulas c1-c3
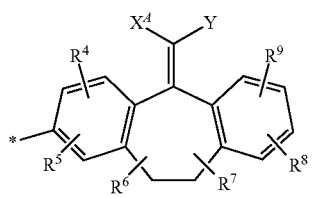
c1
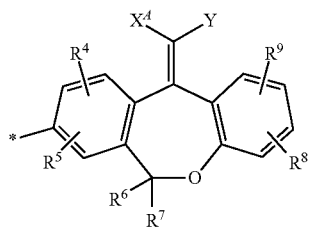
c2
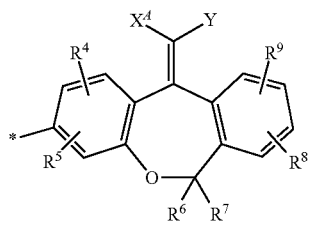
c3
wherein Y, $R^4$, $R^5$, $R^6$, $R^7$, $R^8$ and $R^9$ are each as defined above and $X^A$ represents any of the following formulas (b1)-(b16)
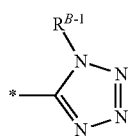
(b1)
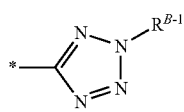
(b2)
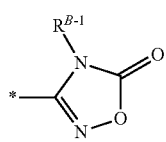
(b3)
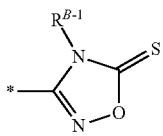
(b4)
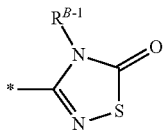
(b5)
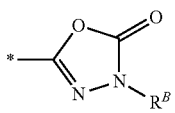
(b6)
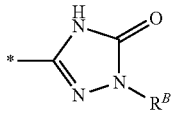
(b7)
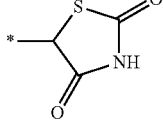
(b8)
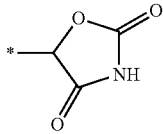
(b9)
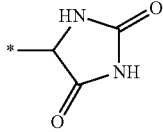
(b10)
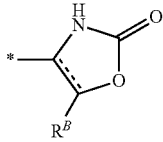
(b11)
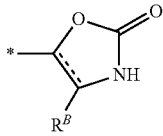
(b12)
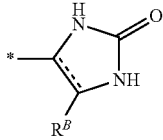
(b13)
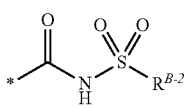
(b14)

-continued

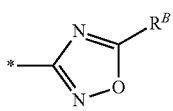
(b15)

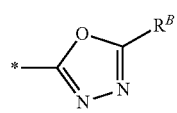
(b16)

wherein $R^{B-1}$, $R^{B-2}$ and $R^B$ are each as defined above, and the broken line is absent or a single bond.

(24) The tricyclic compound or the pharmaceutically acceptable salt thereof according to any of (1), (14), (15) and (16), wherein

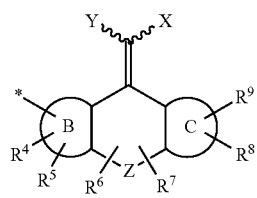

is a group selected from the group consisting of the following formulas c4-c6

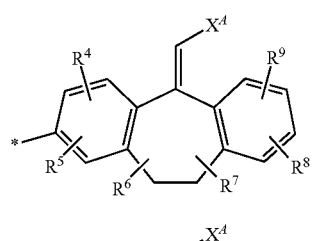
c4

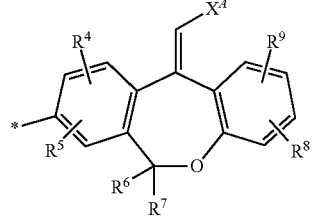
c5

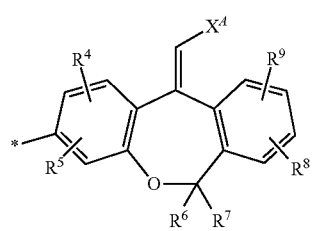
c6 wherein $X^A$, $R^4$, $R^5$, $R^6$, $R^7$, $R^8$ and $R^9$ are each as defined above.

(25) The tricyclic compound or the pharmaceutically acceptable salt thereof according to any of (13), (14) and (15), wherein at least one of $R^{10}$ and $R^{11}$ is lower alkyl.

(26) The tricyclic compound or the pharmaceutically acceptable salt thereof according to any of (14), (15), (16), (17), (19), (20), (21), (22) and (25), wherein X is the following formula (b19), (b20) or (b22)

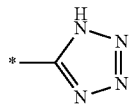
(b19)

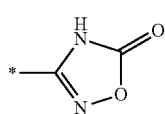
(b20)

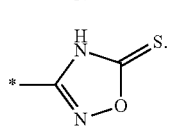
(b22)

(27) The tricyclic compound or the pharmaceutically acceptable salt thereof according to any of (14), (15), (16), (17), (19), (20), (21), (22) and (25), wherein X is the following formula (b19)

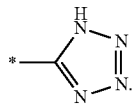
(b19)

(28) The tricyclic compound or the pharmaceutically acceptable salt thereof according to any of (14), (15), (16), (17), (19), (20), (21), (22) and (25), wherein X is the following formula (b20)

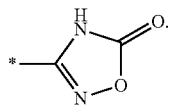
(b20)

(29) The tricyclic compound or the pharmaceutically acceptable salt thereof according to any of (13), (15), (16), (17), (18), (20), (23), (24), (25), (26), (27) and (28), wherein A is a group selected from the following formulas (a35)-(a37):

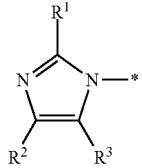
(a35)

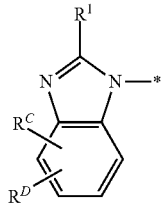
(a36)

-continued

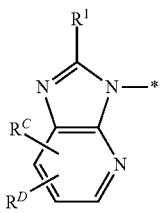
(a37)

wherein $R^1$, $R^2$, $R^3$, $R^C$ and $R^D$ are each as defined above.

(30) The tricyclic compound or the pharmaceutically acceptable salt thereof according to any of (13), (15), (16), (17), (18), (20), (23), (24), (25), (26), (27) and (28), wherein A is the following formula (a36):

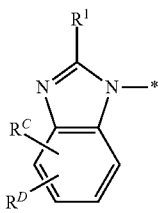
(a36)

wherein $R^1$, $R^C$ and $R^D$ are each as defined above.

(31) The tricyclic compound or the pharmaceutically acceptable salt thereof according to any of (13), (14), (16), (17), (18), (22), (23), (24), (25), (26), (27), (28), (29) and (30), wherein V is a single bond.

(32) The tricyclic compound or the pharmaceutically acceptable salt thereof according to any of (13), (14), (15), (17), (18), (19), (20), (21), (22), (23), (24), (26), (27), (28), (29), (30) and (31), wherein $R^{10}$ and $R^{11}$ are both hydrogen.

(33) The tricyclic compound or the pharmaceutically acceptable salt thereof according to any of (13), (14), (15), (16), (18), (19), (20), (21), (22), (25), (26), (27), (28), (30), (31) and (32), wherein

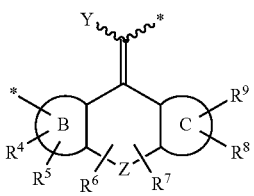

is represented by the following formula c14

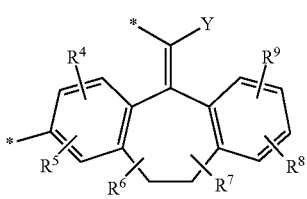
c14 wherein $R^4$, $R^5$, $R^6$, $R^7$, $R^8$, $R^9$, and Y are each as defined above.

(34) The tricyclic compound or the pharmaceutically acceptable salt thereof according to (13), (14), (15), (16), (18), (19), (20), (21), (22), (25), (26), (27), (28), (29), (30), (31) or (32), wherein

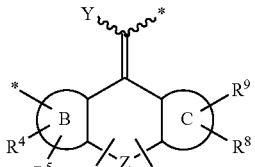

is represented by the following formula c15

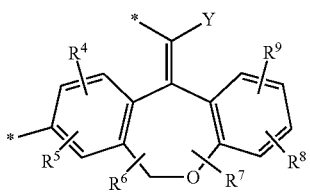
c15 wherein $R^4$, $R^5$, $R^6$, $R^7$, $R^8$, $R^9$, and Y are each as defined above.

(35) The tricyclic compound or the pharmaceutically acceptable salt thereof according to (13), (14), (15), (16), (18), (19), (20), (21), (22), (25), (26), (27), (29), (30), (31) or (32), wherein

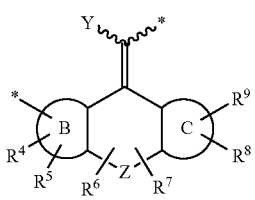

is represented by the following formula c16

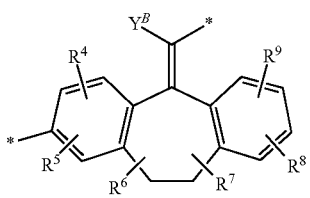
c16 wherein $Y^B$ is hydrogen, $R^4$, $R^5$, $R^6$, $R^7$, $R^8$, and $R^9$ are each as defined above.

(36) A pharmaceutical composition comprising the tricyclic compound or the pharmaceutically acceptable salt thereof according to any of (1) to (35), as an active ingredient.

(37) A PPAR γ agonist comprising the tricyclic compound or the pharmaceutically acceptable salt thereof according to any of (1) to (35) as an active ingredient.

(38) A therapeutic and/or prophylactic agent for a disease associated with PPAR γ, which comprises the tricyclic compound or the pharmaceutically acceptable salt thereof according to any of (1) to (35), as an active ingredient.

(39) The agent according to (38), wherein the disease associated with PPAR γ is a disease selected from the group consisting of type 2 diabetes, impaired glucose tolerance, insulin resistance syndrome, hypertension, hyperlipidemia, metabolic syndrome, visceral obesity, obesity, hypertriglyceridemia and tumor.

(40) A method of activating PPAR γ, comprising administering the tricyclic compound or the pharmaceutically acceptable salt thereof according to any of (1) to (35).

(41) A therapeutic and/or prophylactic method of a disease associated with PPAR γ, comprising administering the tricyclic compound or the pharmaceutically acceptable salt thereof according to any of (1) to (35).

(42) The method according to (41), wherein the disease associated with PPAR γ is a disease selected from the group consisting of type 2 diabetes, impaired glucose tolerance, insulin resistance syndrome, hypertension, hyperlipidemia, metabolic syndrome, visceral obesity, obesity, hypertriglyceridemia and tumor.

(43) Use of the tricyclic compound or the pharmaceutically acceptable salt thereof according to any of (1) to (35), for the manufacture of a PPAR γ agonist.

(44) Use of the tricyclic compound or the pharmaceutically acceptable salt thereof according to any of (1) to (35), for the manufacture of a therapeutic and/or prophylactic agent for a disease associated with PPAR γ.

(45) The use according to (44), wherein the disease associated with PPAR γ is a disease selected from the group consisting of type 2 diabetes, impaired glucose tolerance, insulin resistance syndrome, hypertension, hyperlipidemia, metabolic syndrome, visceral obesity, obesity, hypertriglyceridemia and tumor.

Effect of the Invention

According to the present invention, a novel tricyclic compound having a PPAR γ agonist activity, which is useful as a therapeutic and/or prophylactic agent for, for example, type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis, growth of benign tumor, malignant tumor or metastatic tumor etc.), inflammatory neuropsychiatric diseases (e.g., multiple sclerosis etc.), angiogenesis and pathological angiogenesis relating to tumor growth and metastasis, neurodegenerative neuropsychiatric diseases (e.g., Alzheimer's disease, Parkinson's disease etc.), cardiovascular diseases (e.g., arteriosclerosis, cardiac disease, cerebral apoplexy, renal diseases etc.), or the like, a pharmaceutically acceptable salt thereof and the like are provided.

In addition, a PPAR γ agonist containing a tricyclic compound as an active ingredient is provided.

DESCRIPTION OF EMBODIMENTS

Hereinafter a compound represented by the general formula (I) is referred to as compound (I). The same applies to the compounds of other formula numbers.

In the definition of each group of the formula (I),

Examples of lower alkyl, and the lower alkyl moiety of lower alkoxy, lower alkylsulfanyl, lower alkylsulfonyl, lower alkanoyloxy, lower alkanoyl, lower alkoxycarbonyl, lower alkylcarbamoyl, di-lower alkylcarbamoyl, lower alkylsulfonylcarbamoyl, lower alkylaminosulfonylcarbamoyl, lower alkanoylaminomethyl, lower alkylsulfonylamino, and lower alkylsulfonylaminomethyl include straight chain or branched alkyl having a carbon number of 1-10. More specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like. Two lower alkyl moieties of di-lower alkylcarbamoyl may be the same or different.

Examples of the lower alkenyl include straight chain or branched alkenyl having 2 to 10 carbon atoms, and more specific examples thereof include vinyl, allyl, 1-propenyl, butenyl, pentenyl, hexenyl, heptenyl, octenyl, nonenyl, decenyl and the like.

Examples of cycloalkyl and the cycloalkyl moiety of cycloalkylsulfonylcarbamoyl include cycloalkyl having 3 to 8 carbon atoms, and more specific examples thereof include cyclopropyl, cyclobutyl, cyclopentyl, cyclohexyl, cycloheptyl, cyclooctyl and the like.

Examples of aralkyl and the aralkyl moiety of aralkyloxy include aralkyl having 7 to 16 carbon atoms, and more specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of aryl and the aryl moiety of arylcarbamoyl, arylsulfonylcarbamoyl, and aryloxy include aryl having a carbon number of 6-14, and more specific examples thereof include phenyl, naphthyl, azulenyl, anthryl and the like.

Examples of the aromatic carbocycle include a benzene ring, a naphthalene ring and the like.

Examples of the aliphatic heterocyclic group and the aliphatic heterocyclic group moiety of aliphatic heterocyclylcarbonyl include a 5-membered or 6-membered monocyclic aliphatic heterocyclic group comprising at least one atom selected from a nitrogen atom, an oxygen atom and a sulfur atom, a bicyclic or tricyclic condensed aliphatic heterocyclic group containing at least one atom selected from a nitrogen atom, an oxygen atom and a sulfur atom, wherein 3- to 8-membered rings are condensed, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, 4,5-dihydrooxadiazolyl, thiomorpholinyl, 2H-oxazolyl, 2H-thioxazolyl, dihydroindolyl, dihydroisoindolyl, dihydrobenzofuranyl, benzimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic condensed aromatic heterocyclic group containing at least one atom selected from a nitrogen atom, an oxygen atom and a sulfur atom, wherein 3- to 8-membered rings are condensed, and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl and the like.

Examples of the aromatic heterocycle include thiophene ring, pyridine ring, pyridazine ring, pyrimidine ring, pyrazine ring, furan ring, pyrrole ring, pyrazole ring, imidazole ring, oxazole ring, thiazole ring, isoxazole ring, isothiazole ring and the like.

Examples of the nitrogen-containing heterocyclic group formed together with the adjacent nitrogen atom thereto include a 5-membered or 6-membered monocyclic heterocyclic group containing at least one nitrogen atom (said monocyclic heterocyclic group may contain other nitrogen atom, oxygen atom or sulfur atom), a bicyclic or tricyclic condensed heterocyclic group containing at least one nitrogen atom (said condensed heterocyclic group may contain other nitrogen atom, oxygen atom or sulfur atom), wherein 3- to 8-membered rings are condensed, and the like, and more specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl and the like.

Halogen means each atom of fluorine, chlorine, bromine or iodine.

The substituents of lower alkyl optionally having substituent(s), lower alkylsulfonyl optionally having substituent(s), lower alkenyl optionally having substituent(s), lower alkoxy optionally having substituent(s), lower alkylsulfanyl optionally having substituent(s), lower alkanoyloxy optionally having substituent(s), lower alkanoyl optionally having substituent(s), lower alkoxycarbonyl optionally having substituent(s), lower alkylcarbamoyl optionally having substituent(s), di-lower alkylcarbamoyl optionally having substituent(s), lower alkylsulfonylcarbamoyl optionally having substituent(s), lower alkylaminosulfonylcarbamoyl optionally having substituent(s), lower alkylsulfonylamino optionally having substituent(s), lower alkanoylaminomethyl optionally having substituent(s) and lower alkylsulfonylaminomethyl optionally having substituent(s) are the same or different and examples thereof include 1 to 3 substituents selected from the group consisting of halogen, hydroxy, sulfanyl, nitro, cyano, carboxy, carbamoyl, $C_{3-8}$ cycloalkyl, an aliphatic heterocyclic group, an aromatic heterocyclic group, $C_{1-10}$ alkoxy, $C_{3-8}$ cycloalkoxy, $C_{6-14}$ aryl, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —NR$^X$R$^Y$ wherein R$^X$ and R$^Y$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl, $C_{2-11}$ alkanoyl, $C_{7-15}$ aroyl, $C_{1-10}$ alkoxycarbonyl, $C_{6-14}$ aryloxycarbonyl, $C_{1-10}$ alkylsulfonylcarbamoyl, $C_{1-10}$ alkylcarbamoyl, di-$C_{1-10}$ alkylcarbamoyl and the like.

The substituents of aryl optionally having substituent(s), aryloxy optionally having substituent(s), aralkyl optionally having substituent(s), aralkyloxy optionally having substituent(s), arylcarbamoyl optionally having substituent(s), arylsulfonylcarbamoyl optionally having substituent(s), and an aromatic heterocyclic group optionally having substituent(s) are the same or different and examples thereof include 1 to 3 substituents selected from the group consisting of halogen, hydroxy, sulfanyl, nitro, cyano, carbamoyl, $C_{1-10}$ alkyl, $C_{7-16}$ aralkyl, trifluoromethyl, $C_{3-8}$ cycloalkyl, $C_{6-14}$ aryl, halogenated $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —NR$^X$R$^Y$ wherein R$^X$ and R$^Y$ are as defined above, $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl, $C_{1-10}$ alkoxy $C_{1-10}$ alkyl, hydroxy $C_{1-10}$ alkyl, $C_{1-10}$ alkoxycarbonyl $C_{1-10}$ alkyl, $C_{1-10}$ alkylsulfonylcarbamoyl $C_{1-10}$ alkyl, $C_{1-10}$ alkylcarbamoyl $C_{1-10}$ alkyl, a $C_{1-10}$ alkyl aromatic heterocyclic group, hydroxy aromatic heterocyclylcarbonyl, hydroxy $C_{1-10}$ alkylcarbamoyl, $C_{1-10}$ alkylsulfonylamino, halogenated $C_{1-10}$ alkyl and the like.

The substituents of cycloalkyl optionally having substituent (s), cycloalkylsulfonylcarbamoyl optionally having substituent (s), an aliphatic heterocyclic group optionally having substituent (s), aliphatic heterocyclyl carbonyl optionally having substituent (s) and a nitrogen-containing heterocyclic group optionally having substituent (s) which is formed together with the adjacent nitrogen atom are the same or different and examples thereof include 1 to 3 substituents selected from the group consisting of oxo, halogen, hydroxy, sulfanyl, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —NR$^X$R$^Y$ (wherein R$^X$ and R$^Y$ are as defined above), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

Examples of $C_{1-10}$ alkyl and the $C_{1-10}$ alkyl moiety of $C_{1-10}$ alkoxy, $C_{2-11}$ alkanoyloxy, $C_{1-10}$ alkylsulfanyl, $C_{2-11}$ alkanoyl, $C_{1-10}$ alkoxycarbonyl, $C_{1-10}$ alkylsulfonylcarbamoyl, $C_{1-10}$ alkylcarbamoyl and di-$C_{1-10}$ alkylcarbamoyl include the groups recited as examples of the aforementioned lower alkyl. Two $C_{1-10}$ alkyl of di-$C_{1-10}$ alkylcarbamoyl may be the same or different.

The $CO_{1-10}$ alkyl moiety of $C_{1-10}$ alkoxy of $C_{1-10}$ alkoxy $C_{1-10}$ alkyl is, for example, the groups recited as examples of the aforementioned $C_{1-10}$ alkyl, and the $C_{1-10}$ alkyl moiety of $C_{1-10}$ alkoxy $C_{1-10}$ alkyl is, for example, a group obtained by removing one hydrogen atom from the groups recited as examples of the aforementioned $C_{1-10}$ alkyl.

The $C_{1-10}$ alkyl moiety of hydroxy $C_{1-10}$ alkyl is, for example, a group obtained by removing one hydrogen atom from the groups recited as examples of the aforementioned $C_{1-10}$ alkyl.

The $C_{1-10}$ alkyl moiety of $C_{1-10}$ alkoxycarbonyl of $C_{1-10}$ alkoxycarbonyl $C_{1-10}$ alkyl is, for example, the groups recited as examples of the aforementioned $C_{1-10}$ alkyl, and the $C_{1-10}$ alkyl moiety of $C_{1-10}$ alkoxycarbonyl $C_{1-10}$ alkyl is, for example, a group obtained by removing one hydrogen atom from the groups recited as examples of the aforementioned $C_{1-10}$ alkyl.

The $CO_{1-10}$ alkyl moiety of $C_{1-10}$ alkylsulfonylcarbamoyl of $C_{1-10}$ alkylsulfonylcarbamoyl $C_{1-10}$ alkyl is, for example, the groups recited as examples of the aforementioned $C_{1-10}$ alkyl, and the $C_{1-10}$ alkyl moiety of $C_{1-10}$ alkylsulfonylcarbamoyl $C_{1-10}$ alkyl is, for example, a group obtained by removing one hydrogen atom from the groups recited as examples of the aforementioned $C_{1-10}$ alkyl.

The $C_{1-10}$ alkyl moiety of $C_{1-10}$ alkylcarbamoyl of $C_{1-10}$ alkylcarbamoyl $C_{1-10}$ alkyl is, for example, the groups recited as examples of the aforementioned $C_{1-10}$ alkyl, and the $C_{1-10}$ alkyl moiety of $C_{1-10}$ alkylcarbamoyl $C_{1-10}$ alkyl is, for example, a group obtained by removing one hydrogen atom from the groups recited as examples of the aforementioned $C_{1-10}$ alkyl.

The halogen moiety of halogenated $C_{6-14}$ aryl is, for example, the groups recited as examples of the aforementioned halogen, and the $C_{6-14}$ aryl moiety of halogenated $C_{6-14}$ aryl is, for example, a group obtained by removing one hydrogen atom from the groups recited as examples of the aforementioned $C_{6-14}$ aryl.

The $C_{1-10}$ alkyl moiety of $C_{1-10}$ alkyl aromatic heterocyclic group is, for example, the groups recited as examples of the aforementioned $C_{1-10}$ alkyl, and the aromatic heterocyclic group moiety of the $C_{1-10}$ alkyl aromatic heterocyclic group is, for example, a group obtained by removing one hydrogen atom from the groups recited as examples of the aforementioned aromatic heterocyclic group.

The aromatic heterocycle moiety of hydroxy aromatic heterocyclyl carbonyl is, for example, a group obtained by removing one hydrogen atom from the groups recited as examples of the aforementioned aromatic heterocyclic group.

The $C_{1-10}$ alkyl moiety of hydroxy $C_{1-10}$ alkylcarbamoyl is, for example, a group obtained by removing one hydrogen atom from the groups recited as examples of the aforementioned $C_{1-10}$ alkyl.

The $C_{1-10}$ alkyl moiety of $C_{1-10}$ alkylsulfonylamino is, for example, the groups recited as examples of the aforementioned $C_{1-10}$ alkyl.

The $CO_{1-10}$ alkyl moiety of halogenated $C_{1-10}$ alkyl is, for example, a group obtained by removing one hydrogen atom from the groups recited as examples of the aforementioned $C_{1-10}$ alkyl.

Examples of $C_{3-8}$ cycloalkyl and the cycloalkyl moiety of $C_{3-8}$ cycloalkoxy include the groups recited as examples of the aforementioned cycloalkyl.

Examples of $C_{6-14}$ aryl and the aryl moiety of $C_{6-14}$ aryloxy, $C_{7-15}$ aroyl, $C_{7-15}$ aroyloxy and $C_{6-14}$ aryloxycarbonyl include the groups recited as examples of the aforementioned aryl.

Examples of $C_{7-16}$ aralkyl and the $C_{7-16}$ aralkyl moiety of $C_{7-16}$ aralkyloxy and $C_{7-16}$ aralkyloxycarbonyl include the groups recited as examples of the aforementioned aralkyl.

Examples of the aliphatic heterocyclic group, the aromatic heterocyclic group and halogen include the groups recited as examples of the aforementioned aliphatic heterocyclic group, the aforementioned aromatic heterocyclic group and the aforementioned halogen, respectively.

The pharmaceutically acceptable salt of compound (I) comprises, for example, pharmaceutically acceptable acid addition salts, metal salts, ammonium salts, organic amine addition salts, amino acid addition salts and the like. Examples of the pharmaceutically acceptable acid addition salt of compound (I) include inorganic acid salts such as hydrochloride, hydrobromide, nitrate, sulfate, phosphate or the like, organic acid salts such as acetate, oxalate, maleate, fumarate, citrate, benzoate, methanesulfonate etc., or the like. Examples of the pharmaceutically acceptable metal salts include alkali metal salts such as sodium salt, potassium salt or the like, alkaline earth metal salts such as magnesium salt, calcium salt or the like, aluminum salt, zinc salt or the like. Examples of the pharmaceutically acceptable ammonium salt include salts of ammonium, tetramethylammonium or the like. Examples of the pharmaceutically acceptable organic amine addition salt include addition salts such as morpholine, piperidine or the like. Examples of the pharmaceutically acceptable amino acid addition salt include addition salts such as lysine, glycine, phenylalanine, aspartic acid, glutamic acid or the like.

As compound (I), the compounds described in (1)-(35) are preferable. More preferable specific embodiment is the general formula (IA-A) or (IA-B) including the substituents represented by D, $Y^X$, $Z^X$, $R^{1X}$, $R^{2X}$, $R^{3X}$, $R^{4X}$, $R^{5X}$, $R^{6X}$, $R^{7X}$, $R^{8X}$, $R^{9X}$, $R^{10X}$, $R^{11X}$, and $A^X$ or any combination of such substituents.

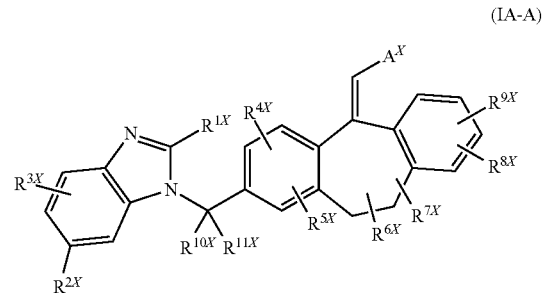

(IA-A)

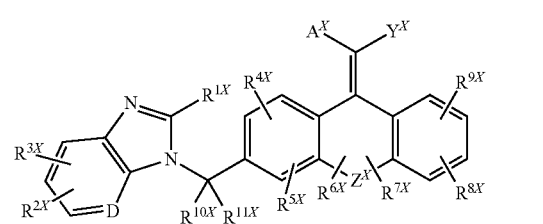

(IA-B)

1) In compound (IA-A),
$R^{4X}$, $R^{5X}$, $R^{6X}$, $R^{7X}$, $R^{8X}$ and $R^{9X}$ are preferably, for example, a hydrogen atom or the like,
$R^{1X}$ is preferably, for example, methyl, ethyl, propyl or the like, more preferably ethyl, propyl or the like,
$R^{2X}$ is preferably, for example, phenyl, thiophen-2-yl, oxazol-2-yl or the like, more preferably phenyl, oxazol-2-yl or the like,
$R^{3X}$ is preferably, for example, methyl or the like,
$R^{10X}$, $R^{11X}$ is preferably a hydrogen atom, methyl,
$A^X$ is preferably, for example, (b20)

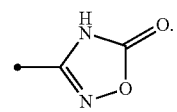

(b20)

2) In compound (IA-B),
$Z^X$ is preferably $CH_2CH_2$ or $CH_2O$,
$R^{4X}$, $R^{5X}$, $R^{6X}$, $R^{7X}$, $R^{8X}$ and $R^{9X}$ are preferably, for example, a hydrogen atom or the like,
D is CH or N, more preferably CH,
$R^{1X}$ is preferably ethyl, isopropyl, propyl, tert-butyl, methoxymethyl, cyclopropyl, benzyl, phenyl, or the like, more preferably propyl, cyclopropyl or the like,
$R^{2X}$ is preferably a hydrogen atom, methyl, more preferably a hydrogen atom,
$R^{3X}$ is preferably a hydrogen atom, methyl, 2-methoxymethyl, chlorine atom, carbamoyl, 2-hydroxyethylcarbamoyl or the like, more preferably chlorine atom, methyl or the like, $R^{10X}$ is preferably a hydrogen atom, methyl, more preferably a hydrogen atom, $R^{11X}$ is preferably a hydrogen atom, $Y^X$ is preferably, for example, methyl, ethyl, propyl, cyclopropyl, more preferably methyl, cyclopropyl, still more preferably methyl, $A^X$ is preferably, for example, the above-mentioned formula (b20).

Furthermore, a compound represented by the general formula (IA-C)

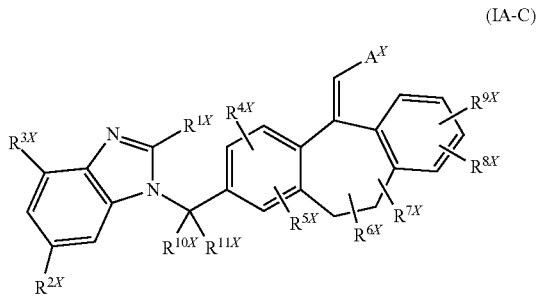

(IA-C)

wherein $R^{1X}$, $R^{2X}$, $R^{3X}$, $R^{4X}$, $R^{5X}$, $R^{6X}$, $R^{7X}$, $R^{8X}$, $R^{9X}$, $R^{10X}$, $R^{11X}$, and $A^X$ are groups recited as examples in the aforementioned formula (IA-A), or (IA-D)

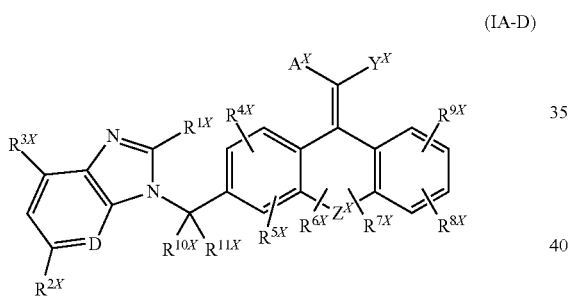

(IA-D)

wherein D, $Y^X$, $R^{1X}$, $R^{2X}$, $R^{3X}$, $R^{4X}$, $R^{5X}$, $R^{6X}$, $R^{7X}$, $R^{8X}$, $R^{9X}$, $R^{10X}$, $R^{11X}$, and $A^X$ are groups recited as examples in the aforementioned formula (IA-b), is more preferable, and the substituents represented by D, $Y^X$, $Z^X$, $R^{1X}$, $R^{2X}$, $R^{3X}$, $R^{4X}$, $R^{5X}$, $R^{6X}$, $R^{7X}$, $R^{8X}$, $R^{9X}$, $R^{10X}$, $R^{11X}$ and $A^X$ or any combination of such substituents are still more preferable.

The production methods of compound (I) are explained in the following.

In the production methods shown below, when the defined groups change under the conditions of the production methods or are inappropriate for performing the production methods, the desired compound can be produced by performing the methods for the introduction and removal of the protecting groups conventionally performed in the synthetic organic chemistry (e.g., methods described in Protective Groups in Organic Synthesis, third edition, T. W. Greene, John Wiley & Sons Inc., 1999 etc.) or the like. If necessary, the order of the reaction steps such as substituent introduction or the like can also be changed.

Production Method 1

Of compounds (I), compounds (Ia), (Ib) wherein X is cyano or carboxy can be produced according to the following steps.

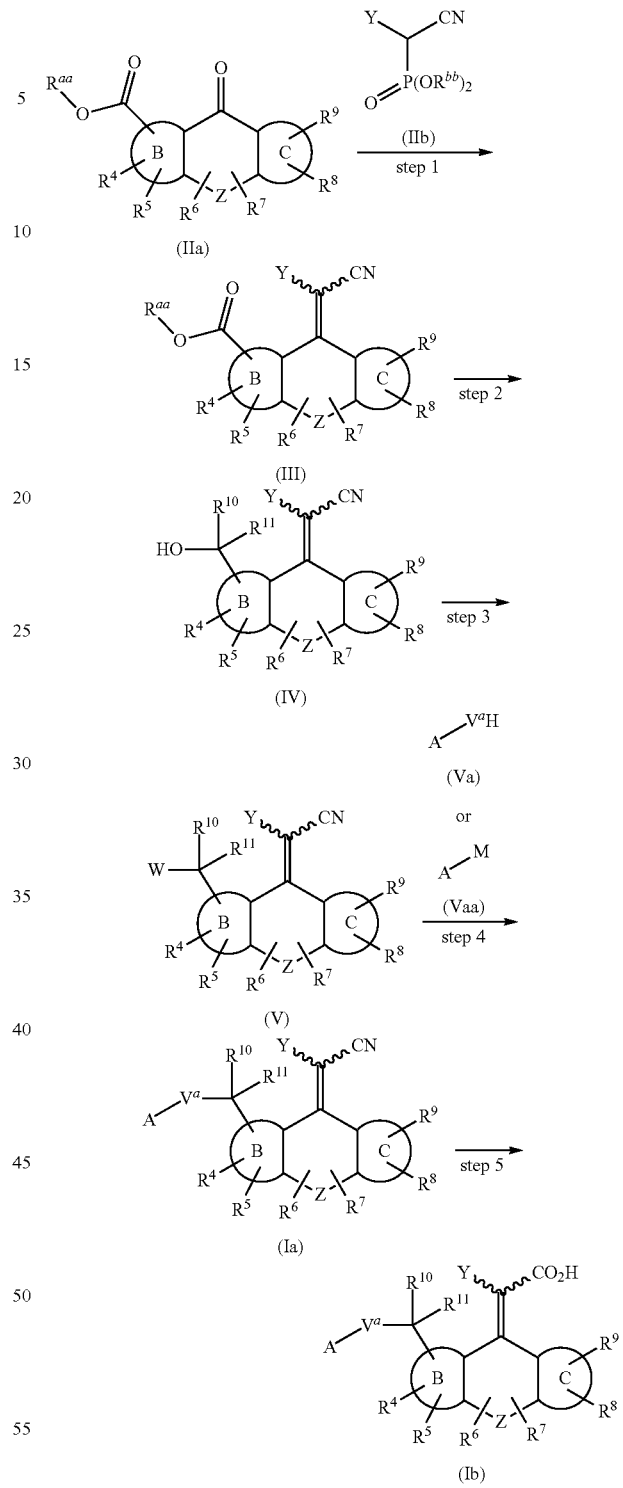

wherein A, B, C, $R^4$, $R^5$, $R^6$, $R^7$, $R^8$, $R^9$, $R^{10}$, $R^{11}$, Y and Z are each as defined above, W represents a leaving group such as a chlorine atom, a bromine atom, an iodine atom, trifluoromethanesulfonyloxy, methanesulfonyloxy, benzenesulfonyloxy, p-toluenesulfonyloxy or the like, $V^a$ represents O, $NR^4$ wherein $R^4$ is as defined above, or S, M represents lithium, sodium, $MgX^1$ ($X^1$ represents a chlorine atom, a bromine atom or the like) or the like, each of $R^{aa}$ and $R^{bb}$ represents a lower alkyl such as methyl, ethyl or the like, or aryl such as phenyl or the like.

Step 1

Compound (III) can be obtained by reacting compound (IIa) with 1 equivalent-5 equivalents of compound (IIb) in the presence of 0.1 equivalent—large excess of a base in a solvent at a temperature between −20° C. and the boiling point of the solvent to be used for 5 min-120 hr.

Examples of the base include sodium hydride, potassium hydride, butyllithium, lithium diisopropylamide (LDA), lithium bistrimethylsilylamide, sodium bistrimethylsilylamide, sodium methoxide, potassium ethoxide, potassium tert-butoxide, potassium carbonate, sodium hydroxide, diazabicycloundecene (DBU), triethylamine, diisopropylethylamine and the like. Examples of the solvent include dimethylformamide (DMF), dimethylacetamide (DMA), N-methylpyrrolidone (NMP), dimethyl sulfoxide (DMSO), tetrahydrofuran (THF), acetonitrile and the like, and these can be used alone or in a mixture.

Here, compound (IIa) can be obtained by the methods described in JP-B-2526005, WO2004/052847 (Lilly) or the like, and compound (IIb) is commercially available or can be obtained by a known method (e.g., J. Chem. Soc. Perkin Trans. 1), 1992, p. 313, Synthetic Communications, 1997, vol. 27, p. 1621, Synthesis, 1987, p. 411) or a method analogous thereto.

Step 2

Compound (IV) wherein $R^{10}$ and $R^{11}$ are the same can be obtained by reacting compound (III) with 1 equivalent—large excess of a reducing agent or alkyl metal reagent in a solvent at a temperature between −20° C. and the boiling point of the solvent to be used for 5 min-120 hr. In addition, compound (IV) wherein $R^{10}$ and $R^{11}$ are different can be synthesized by reacting compound (IV) wherein $R^{10}$ and $R^{11}$ are both hydrogen with an oxidant in a solvent to give aldehyde, treating the aldehyde with an alkyl metal reagent in the same manner as above to give a product, and reacting the product again with an oxidant to give ketone, and treating the ketone with an alkyl metal reagent in the same manner as above.

Examples of the reducing agent include sodium borohydride, lithium borohydride, lithium aluminum hydride, diisobutylaluminum hydride and the like, examples of the alkyl metal reagent include alkyllithium, alkylmagnesium chloride, alkylmagnesium bromide, alkylmagnesium iodide, alkylzinc and the like, and examples of the oxidant include 1,1,1-triacetoxy-1,1-dihydro-1,2-benziodoxol-3(1H)-one, sulfur trioxide pyridine complex, pyridinium chlorochromate and the like. Examples of the solvent include THF, ether, dioxane, dichloromethane, hexane, toluene and the like, and these can be used alone or in a mixture.

Step 3

Compound (V) can be obtained by reacting compound (IV) in the presence of 1 equivalent—large excess of a halogenating agent or sulfonylating agent in a solvent or without solvent at a temperature between −20° C. and the boiling point of the solvent to be used for 5 min-72 hr. Examples of the halogenating agent include thionyl chloride; phosphorus tribromide; boron tribromide; a combination of triphenylphosphine, 2,6-lutidine and carbon tetrachloride; a combination of triphenylphosphine, 2,6-lutidine and carbon tetrabromide; a combination of methanesulfonyl chloride and lithium chloride; a combination of methanesulfonyl chloride and lithium bromide and the like. Examples of the sulfonylating agent include trifluoromethanesulfonyl chloride, methanesulfonyl chloride, methanesulfonic acid anhydride, benzenesulfonyl chloride, p-toluenesulfonyl chloride and the like. Examples of the solvent include THF, DMF, DMA, dichloromethane, dichloroethane, acetonitrile and the like, and these can be used alone or in a mixture.

Step 4

Compound (Ia) can be obtained by reacting compound (V) with 1 equivalent-5 equivalents of compound (Va) or (Vaa) in the presence of, where necessary, 1 equivalent—large excess of a base in a solvent at a temperature between −20° C. and the boiling point of the solvent to be used for 5 min-120 hr.

Examples of the base include sodium carbonate, potassium carbonate, lithium carbonate, cesium carbonate, sodium hydrogen carbonate, potassium hydrogen carbonate, lithium hydrogencarbonate, sodium hydroxide, potassium hydroxide, lithium hydroxide, sodium methoxide, potassium ethoxide, potassium tert-butoxide, sodium hydride, potassium hydride, butyllithium, lithium diisopropylamide (LDA), lithium bistrimethylsilylamide, sodium bistrimethylsilylamide, triethylamine, diisopropylethylamine, tributylamine, dicyclohexylmethylamine and the like. Examples of the solvent include DMF, DMA, NMP, DMSO, THF, acetonitrile, isopropyl alcohol and the like, and these can be used alone or in a mixture.

Here, compound (Va) is commercially available or can be obtained by a known method (e.g., U.S. Pat. No. 5,332,744, EP-B-400835, JP-A-5-783228 and the like) or a method analogous thereto.

Step 5

Compound (Ib) can be obtained by hydrolyzing the nitrile group, for example, by reacting compound (Ia) in the presence of a base such as lithium hydroxide, sodium hydroxide, potassium hydroxide, barium hydroxide or the like in a suitable water-containing solvent such as a mixed solvent of methanol, ethanol, ethylene glycol, dioxane, glyme or water at a temperature between room temperature and the boiling point of the solvent to be used for 1 hr-120 hr, or by reacting the compound in an aqueous solution of sulfuric acid, hydrochloric acid, acetic acid or the like or a mixture of these acids at a temperature between room temperature and the boiling point of the solvent to be used for 1 hr-120 hr or the like. Alternatively, compound (Ib) can also be obtained by once obtaining amide and subjecting the amide to the above-mentioned reaction again.

Production Method 2

Of compounds (I), compounds (Ic)-(Ig) wherein X is the following formula (b15), (b19), (b20), (b22) or (b23)

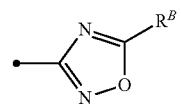
(b15)

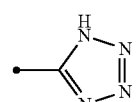
(b19)

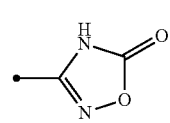
(b20)

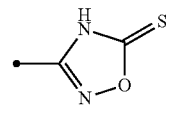
(b22)

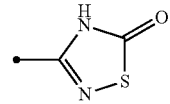
(b23)

wherein $R^B$ is as defined above, can be produced according to the following steps.

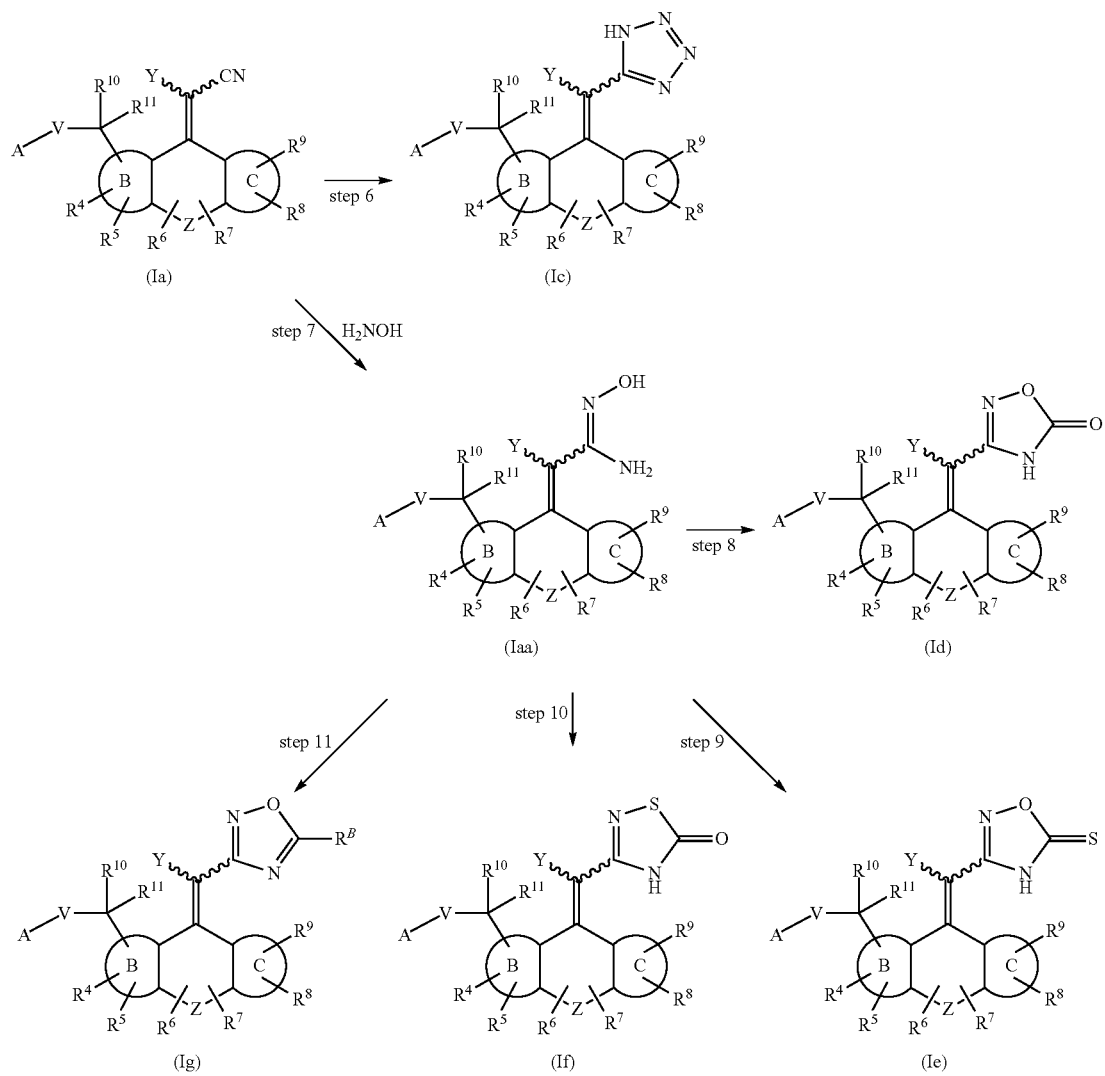

wherein A, B, C, $R^4, R^5, R^6, R^7, R^8, R^9, R^{10}, R^{11}, R^B$, V, Y and Z are each as defined above.

Step 6

Compound (Ic) can be obtained by reacting compound (Ia) obtained in step 2 with 1 equivalent to 10 equivalents of sodium azide in a solvent in the presence of 1 equivalent to large excess of a weak acid for 5 min to 120 hr at a temperature between −20° C. and the boiling point of the solvent to be used.

Examples of the weak acid include ammonium chloride, triethylamine hydrochloride and the like. Examples of the solvent include DMF, DMA, NMP, DMSO and the like, and these can be used alone or in a mixture.

In addition, in another method, compound (Ic) can also be obtained by reacting compound (Ia) with 1 equivalent to 10 equivalents of sodium azide in a solvent in the presence of 0.01 to 10 equivalents of an additive at a temperature between −10° C. and the boiling point of the solvent to be used for 1 hr to 120 hr.

Examples of the additive include tributyltin chloride, trimethyltin chloride, dibutyltin oxide and the like. Examples of the solvent include toluene, xylene and the like, and these can be used alone or in a mixture.

Step 7

Compound (Iaa) can be obtained by reacting compound (Ia) with 1 equivalent to large excess of hydroxylamine in a solvent at a temperature between −20° C. and the boiling point of the solvent to be used for 5 min to 120 hr.

As hydroxylamine, for example, an inorganic acid salt such as hydroxylamine hydrochloride or the like can be used. In this case, an equivalent of a base such as sodium methoxide or the like is preferably copresent. Examples of the solvent include methanol, ethanol, DMF, DMA, DMSO and the like, and these can be used alone or in a mixture.

Step 8

Compound (Id) can be obtained by reacting compound (Iaa) with 1 equivalent—large excess of chlorocarbonate ester in the presence of 1 equivalent—large excess of a base in a solvent such as THF, DMF, DMA, toluene, xylene or the like at a temperature between −20° C. and the boiling point of the solvent to be used for 5 min-72 hr, and then in a solvent such as THF, DMF, DMA, toluene, xylene or the like in the presence of, where necessary, catalytic amount—10 equivalents of a base at a temperature between −20° C. and the boiling point of the solvent to be used for 5 min-72 hr. The above-mentioned steps can also be performed sequentially by adding chlorocarbonate ester and a base to the reaction mixture continuously without isolating the resultant product.

Examples of chlorocarbonate ester include methyl chlorocarbonate, ethyl chlorocarbonate, propyl chlorocarbonate, phenyl chlorocarbonate and the like.

Examples of the base include triethylamine, pyridine, 4-dimethylaminopyridine, sodium hydroxide, sodium hydride, potassium tert-butoxide, sodium methoxide and the like.

Step 9

Compound (Ie) can be obtained by reacting compound (Iaa) with 1 equivalent—large excess of N,N'-thiocarbonyldiimidazole in the presence of 1 equivalent—large excess of a base in a solvent at a temperature between −20° C. and the boiling point of the solvent to be used for 5 min-72 hr.

Examples of the base include triethylamine, pyridine, 4-dimethylaminopyridine, diazabicycloundecene and the like. Examples of the solvent include THF, 1,4-dioxane, dichloromethane, chloroform, acetonitrile, acetone and the like, and these can be used alone or in a mixture.

Step 10

Compound (If) can be obtained by reacting compound (Iaa) with 1 equivalent to large excess of N,N'-thiocarbonyldiimidazole in a solvent in the presence of 1 equivalent to large excess of a Lewis acid at a temperature between −20° C. and the boiling point of the solvent to be used for 5 min to 72 hr.

Examples of Lewis acid include boron trifluoride diethyl ether complex, stannous chloride, zinc chloride, silica gel and the like. Examples of the solvent include THF, 1,4-dioxane, dichloromethane, chloroform, methanol, ethanol and the like, and these can be used alone or in a mixture.

Step 11

Compound (Ig) can be obtained by reacting compound (Iaa) with 1 equivalent—large excess of acid anhydride in the presence of, where necessary, 1 equivalent—large excess of a base in a solvent at a temperature between −20° C. and the boiling point of the solvent to be used for 5 min-72 hr. Examples of the acid anhydride include acetic anhydride, propionic anhydride, trifluoroacetic anhydride and the like. Examples of the base include triethylamine, pyridine, 4-dimethylaminopyridine, diazabicycloundecene and the like. Examples of the solvent include THF, 1,4-dioxane, dichloromethane, chloroform, acetonitrile, acetone, DMF, DMA, DMSO and the like, and these can be used alone or in a mixture. In another method, Compound (Ig) can be obtained by reacting compound (Iaa) with 1 equivalent—large excess of ortho ester in a solvent or without solvent at a temperature between −20° C. and the boiling point of the solvent to be used for 5 min-72 hr. Examples of the ortho ester include trimethyl orthoformate, triethyl orthoformate, trimethyl ortho acetate, triethyl ortho acetate and the like. Examples of the solvent include THF, 1,4-dioxane, dichloromethane, chloroform, acetonitrile, acetone, DMF, DMA, DMSO and the like, and these can be used alone or in a mixture.

Production Method 3

Of compounds (I), compounds (Ih)-(Ij) wherein X is the following formula (b26), (b16) or (b17)

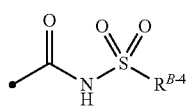

(b26)

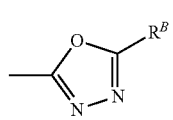

(b16)

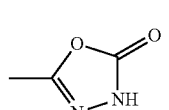

(b17)

wherein $R^B$ is as defined above, and $R^{B-4}$ is lower alkyl optionally having substituent(s), cycloalkyl optionally having substituent(s) or aryl optionally having substituent(s), can be produced according to the following steps.

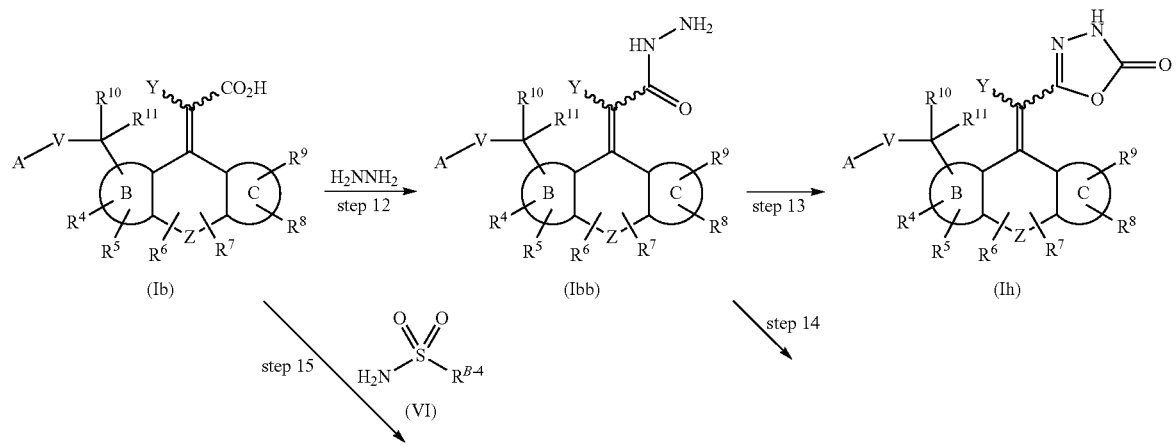

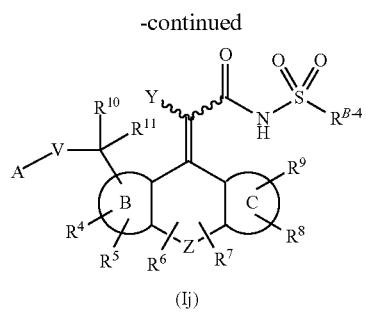
(Ij)

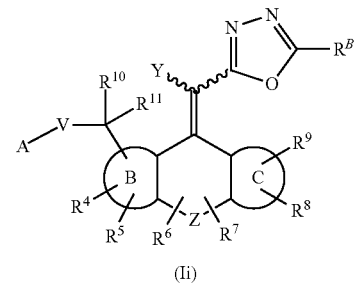
(Ii)

wherein A, B C, $R^4$, $R^5$, $R^6$, $R^7$, $R^8$, $R^9$, $R^{10}$, $R^{11}$, $R^B$, $R^{B-4}$, V, Y and Z are each as defined above.

Step 12

Compound (Ibb) can be obtained by reacting compound (Ib) in the presence of 1 equivalent-50 equivalents of a condensing agent, 1 equivalent—large excess of hydrazine and, where necessary, a base in a solvent at a temperature between −20° C. and the boiling point of the solvent to be used for 5 min-72 hr. Examples of the condensing agent include N,N'-carbonyldiimidazole, dicyclohexylcarbodiimide, 1-ethyl-3-(3-dimethylaminopropyl)carbodiimide hydrochloride and the like. Examples of the base include triethylamine, pyridine, 4-dimethylaminopyridine, diazabicycloundecene and the like. Examples of the solvent include THF, 1,4-dioxane, dichloromethane, chloroform, acetonitrile, acetone and the like, and these can be used alone or in a mixture.

Step 13

Compound (Ih) can be obtained by reacting compound (Ibb) with 1 equivalent-50 equivalents of N,N'-carbonyldiimidazole in the presence of, where necessary, a base in a solvent at a temperature between −20° C. and the boiling point of the solvent to be used for 5 min-72 hr. Examples of the base include triethylamine, pyridine, 4-dimethylaminopyridine, diazabicycloundecene and the like. Examples of the solvent include THF, 1,4-dioxane, dichloromethane, chloroform, acetonitrile, acetone and the like, and these can be used alone or in a mixture.

Step 14

Compound (Ii) can be obtained by reacting compound (Ibb) with 1 equivalent—large excess of acid anhydride in the presence of, where necessary, 1 equivalent—large excess of a base in a solvent at a temperature between −20° C. and the boiling point of the solvent to be used for 5 min-72 hr. Examples of the acid anhydride include acetic anhydride, propionic anhydride, trifluoroacetic anhydride and the like. Examples of the base include triethylamine, pyridine, 4-dimethylaminopyridine, diazabicycloundecene and the like. Examples of the solvent include THF, 1,4-dioxane, dichloromethane, chloroform, acetonitrile, acetone, DMF, DMA, DMSO and the like, and these can be used alone or in a mixture. In another method, compound (Ii) can be obtained by reacting compound (Ibb) with 1 equivalent—large excess of ortho ester in a solvent or without solvent at a temperature between −20° C. and the boiling point of the solvent to be used for 5 min-72 hr. Examples of the ortho ester include trimethyl orthoformate, triethyl orthoformate, trimethyl ortho acetate, triethyl ortho acetate and the like. Examples of the solvent include THF, 1,4-dioxane, dichloromethane, chloroform, acetonitrile, acetone, DMF, DMA, DMSO and the like, and these can be used alone or in a mixture.

Step 15

Compound (Ij) can be obtained by treating compound (Ib) with 1-50 equivalents of a carboxylic acid activator and reacting the compound with 1-50 equivalents of compound (VI) in the presence of 1-30 equivalents of a base in a solvent at a temperature between −20° C. and the boiling point of the solvent to be used for 5 min-72 hr.

Examples of the carboxylic acid activator include N,N'carbonyldiimidazole (CDI), 1-(3-dimethylaminopropyl)-3-ethylcarbodiimide (EDCI) or hydrochloride thereof, dicyclohexylcarbodiimide (DCC) and the like. Examples of the solvent include dichloromethane, acetonitrile, toluene, ethyl acetate, THF, 1,4-dioxane, DMF, NMP and the like, and these can be used alone or in a mixture. Examples of the base include diazabicycloundecene, triethylamine, 4-dimethylaminopyridine, N,N-dimethylaniline, pyridine, N-methylmorpholine and the like. Compound (VI) can be obtained as a commercially available product.

Production Method 4

Of compounds (I), a compound wherein $R^B$ is a hydrogen atom from among the compounds wherein X is the following formula (b27)-(b31) or (b6)

(b27)

(b28)

(b29)

(b30)

(b31)

-continued

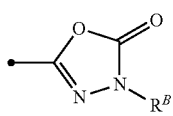
(b6)

wherein $R^B$ is as defined above, is compound (Ic), (Id), (Ie), (If) or (Ih) synthesized in production method 2 or 3, and a compound wherein $R^B$ is lower alkyl optionally having substituent(s) or cycloalkyl optionally having substituent(s) can be obtained by treating compound (Ic), (Id), (Ie), (If) or (Ih) synthesized in production method 2 or 3 with $R^{B-1}U$ wherein U is a leaving group such as chlorine atom, a bromine atom, an iodine atom, trifluoromethanesulfonyloxy, methanesulfonyloxy, benzenesulfonyloxy, p-toluenesulfonyloxy or the like, and $R^{B-1}$ is as defined above, and a base. Examples of the base include sodium hydride, sodium methoxide, potassium tert-butoxide, potassium carbonate, sodium hydroxide, diazabicycloundecene (DBU), triethylamine, diisopropylethylamine and the like.

In another method, the compound can be obtained by reacting (Ic)-(If), (Ih) with 1 equivalent-5 equivalents of $R^{B-1}OH$ wherein $R^{B-1}$ is as defined above in the presence of 1 equivalent—large excess of a condensing agent and, where necessary, 1 equivalent—large excess of a phosphine compound in a solvent at a temperature between −20° C. and the boiling point of the solvent to be used for 5 min-72 hr.

Examples of the condensing agent include diethyl azodicarboxylate, diisopropyl azodicarboxylate, di(tert-butyl) azodicarboxylate, (cyanomethylene)trimethylphosphorane, (cyanomethylene)tributylphosphorane and the like. Examples of the phosphine compound include triphenylphosphine, tributylphosphine, polymer supported triphenylphosphine and the like. Examples of the solvent include THF, DMF, dichloromethane, acetonitrile and the like, and these can be used alone or in a mixture.

The functional groups contained in $R^4, R^5, R^6, R^7, R^8, R^9, R^{10}, R^{11}$, A, B, C, V, X, Y and Z and the like in compound (I) can also be converted by a known method (e.g., the method described in Comprehensive. Organic Transformations 2nd edition, R. C. Larock, Vch Verlagsgesellschaft Mbh, 1999 and the like) or methods similar thereto.

The intermediates and the desired compounds in the above-mentioned respective production methods can be isolated and purified by applying separation purification methods usually used in the synthetic organic chemistry such as filtration, extraction, washing, drying, concentration, recrystallization, various chromatographies or the like. In addition, intermediates can also be subjected to a next reaction without particular purification.

Some of compounds (I) contain a geometric isomer, a stereoisomer such as an optical isomer or the like, a tautomer and the like. The present invention comprises all possible isomers and mixtures thereof including these.

When a salt of compound (I) is to be obtained, compound (I) obtained in the form of a salt can be directly purified. When it is obtained in a free form, compound (I) may be dissolved or suspended in a suitable solvent, and an acid or base is added thereto to form a salt, which may be isolated and purified.

While compound (I) and pharmaceutically acceptable salts thereof may exist in the form of adducts with water or various solvents, these adducts are also comprised in the present invention.

Specific examples of compound (I) obtained by the present invention are shown in Table 1 to Table 15. However, the compound of the present invention is not limited to them.

TABLE 1

| Ex. No. | A | Y | X |
|---|---|---|---|
| 1 | 2-propyl-benzimidazol-1-yl (N-methyl) | H | CN |
| 2 | 2-propyl-benzimidazol-1-yl | H | CO$_2$H |
| 3 | 2-propyl-benzimidazol-1-yl | H | CONH$_2$ |
| 4 | 2-propyl-benzimidazol-1-yl | H | tetrazolyl |
| 5 | 2-propyl-benzimidazol-1-yl | H | 1,3,4-oxadiazol-2(3H)-one |
| 6 | 2-propyl-benzimidazol-1-yl | H | 5-methyl-1,3,4-oxadiazol-2(3H)-one |
| 7 | 2-propyl-benzimidazol-1-yl | H | 1,3,4-oxadiazol-2(3H)-one (isomer) |
| 8 | 2-ethyl-5,7-dimethyl-imidazo[4,5-b]pyridin-3-yl | H | 1,3,4-oxadiazole-2-thione |
| 9 | 2-propyl-benzimidazol-1-yl | H | 1,3,4-oxadiazole |

TABLE 1-continued

| Ex. No. | A | Y | X |
|---|---|---|---|
| 10 | 2-propyl-benzimidazol-1-yl | H | 5-(trifluoromethyl)-1,2,4-oxadiazol-3-yl |
| 11 | 2-propyl-benzimidazol-1-yl | H | 1,3,4-oxadiazol-2-yl |
| 12 | 2-propyl-benzimidazol-1-yl | H | C(=O)NHS(=O)₂Me |
| 13 | 2-propyl-benzimidazol-1-yl | H | CH₂OH |
| 14 | 2-propyl-benzimidazol-1-yl | H | CH₂NHS(=O)₂Me |

TABLE 2

| Ex. No. | A | X | Y |
|---|---|---|---|
| 15 | benzimidazol-1-yl | 1H-tetrazol-5-yl | Me |
| 16 | benzimidazol-1-yl | 5-oxo-4,5-dihydro-1,2,4-oxadiazol-3-yl | Me |
| 17 | 4-methyl-2-propyl-benzimidazol-1-yl | 1H-tetrazol-5-yl | Me |
| 18 | 4-methyl-2-propyl-benzimidazol-1-yl | 5-oxo-4,5-dihydro-1,2,4-oxadiazol-3-yl | Me |
| 19 | 4-chloro-2-cyclopropyl-benzimidazol-1-yl | 5-oxo-4,5-dihydro-1,2,4-oxadiazol-3-yl | Me |
| 20 | 2-ethyl-4-phenyl-imidazol-1-yl | 1H-tetrazol-5-yl | Me |
| 21 | 2-ethyl-4-phenyl-imidazol-1-yl | 5-oxo-4,5-dihydro-1,2,4-oxadiazol-3-yl | Me |
| 22 | 3-chlorophenoxy | 5-oxo-4,5-dihydro-1,2,4-oxadiazol-3-yl | Me |
| 23 | 1H-indazol-1-yl | 5-oxo-4,5-dihydro-1,2,4-oxadiazol-3-yl | Me |
| 24 | 2H-indazol-2-yl | 5-oxo-4,5-dihydro-1,2,4-oxadiazol-3-yl | Me |

TABLE 2-continued
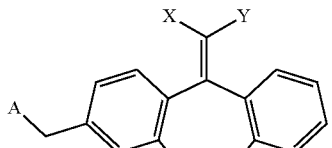
| Ex. No. | A | X | Y |
|---|---|---|---|
TABLE 3
| Ex. No. | A | X | Y |
|---|---|---|---|
| 25 | 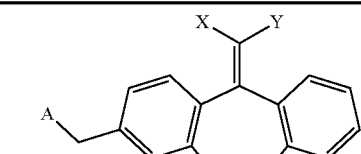 (1/2 citrate) |  | Me |
| 26 | 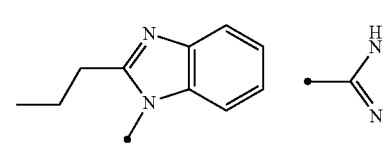 | 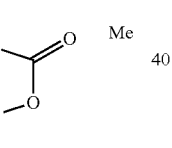 | Me |
| 27 | 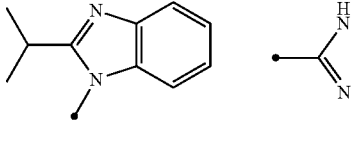 | 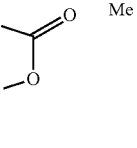 | Me |
| 28 | 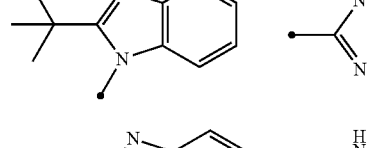 | 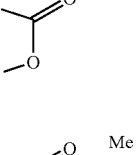 | Me |
| 29 | 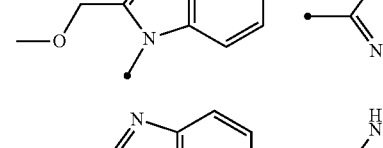 | 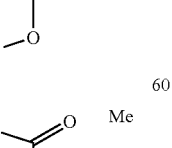 | Me |
| 30 | 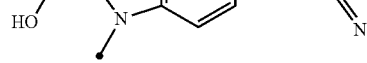 |  | Me |
| 31 | 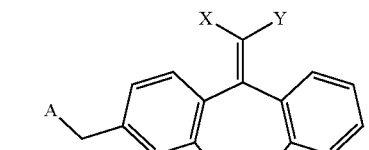 |  | Me |
TABLE 3-continued
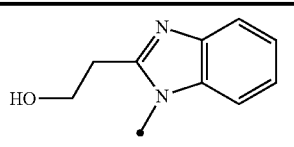
| Ex. No. | A | X | Y |
|---|---|---|---|
| 32 | 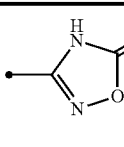 | 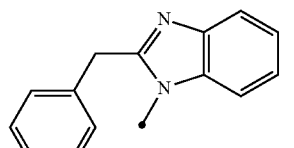 | Me |
| 33 | 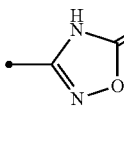 | 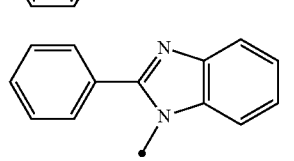 | Me |
| 34 | 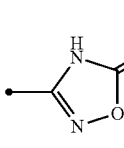 | 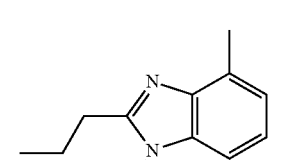 | Me |
| 35 | 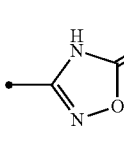 | 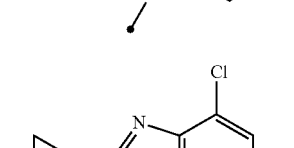 | Me |
| 36 | 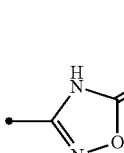 | 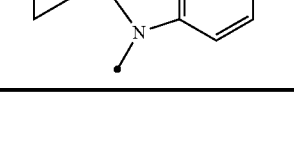 | Me |
TABLE 4
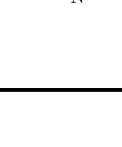
| Ex. No. | A | Y | X |
|---|---|---|---|
| 37 | 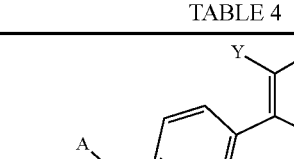 | H | 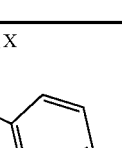 |

TABLE 4-continued
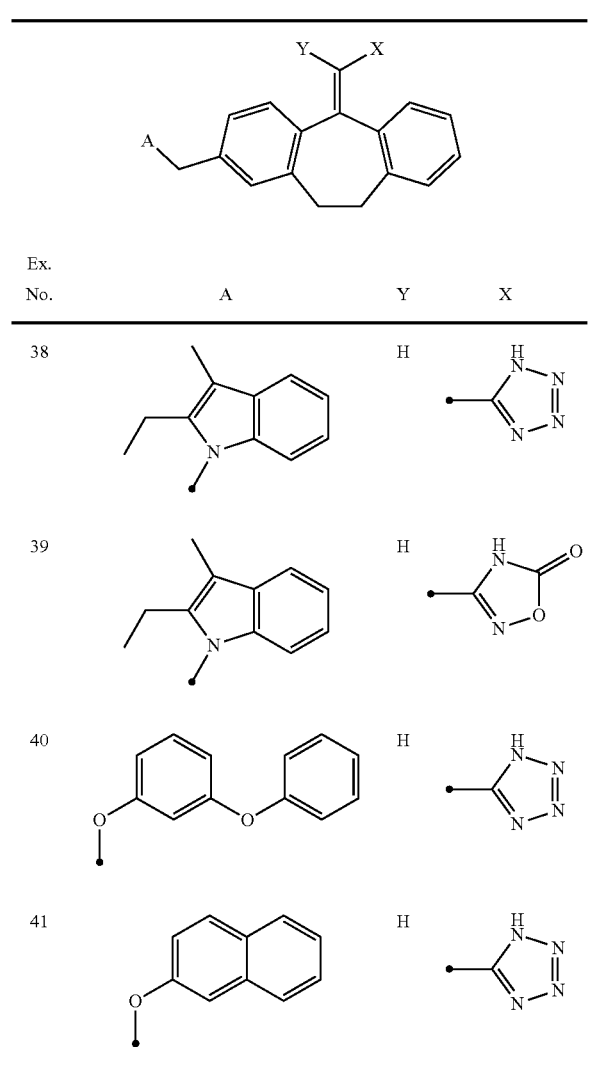
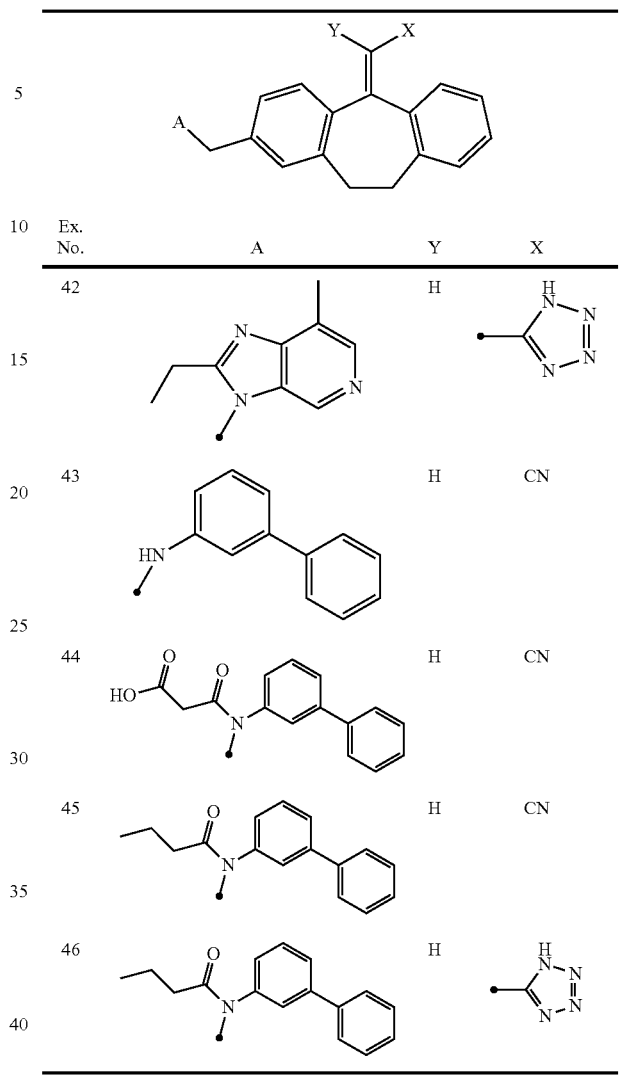
TABLE 5
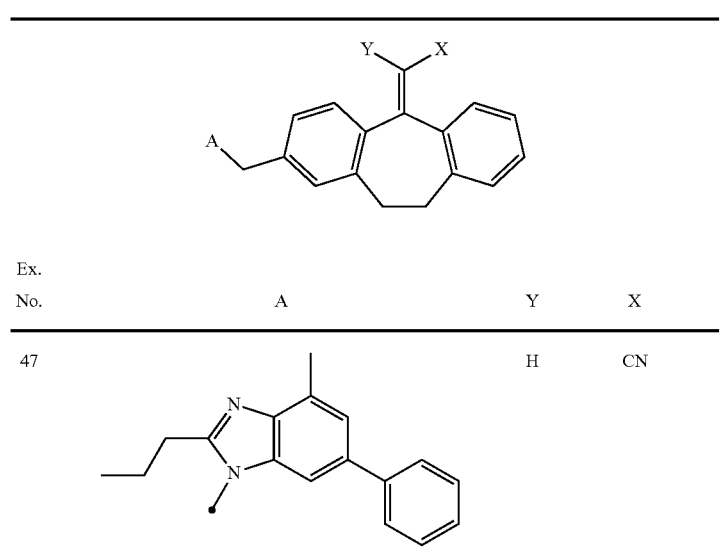

TABLE 5-continued
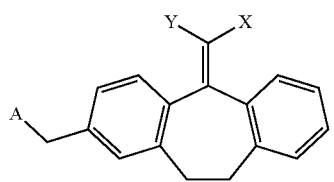
| Ex. No. | A | Y | X |
|---|---|---|---|
| 48 | (4-methyl-2-propyl-6-phenyl-benzimidazol-1-yl) | H | (1H-tetrazol-5-yl) |
| 49 | (4-methyl-2-propyl-6-phenyl-benzimidazol-1-yl) | H | (5-oxo-4H-1,2,4-oxadiazol-3-yl) |
| 50 | (4-methyl-2-ethyl-6-phenyl-benzimidazol-1-yl) | H | CN |
| 51 | (4-methyl-2-ethyl-6-phenyl-benzimidazol-1-yl) | H | (1H-tetrazol-5-yl) |
| 52 | (4-methyl-2-ethyl-6-phenyl-benzimidazol-1-yl) | H | (5-oxo-4H-1,2,4-oxadiazol-3-yl) |
| 53 | (2,4-dimethyl-6-phenyl-benzimidazol-1-yl) | H | CN |

TABLE 5-continued
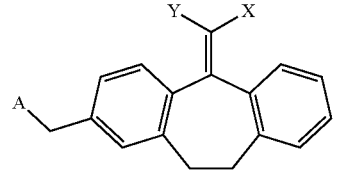
| Ex. No. | A | Y | X |
|---|---|---|---|
| 54 | 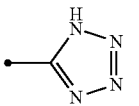 | H | 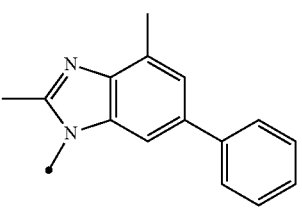 |
| 55 | 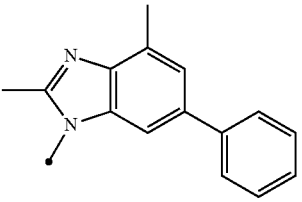 | H | CO₂H |
| 56 | 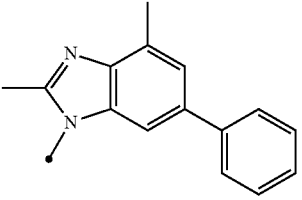 | H | CONH₂ |
| 57 | 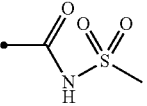 | H | 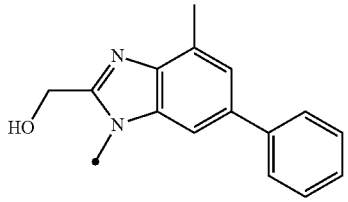 |
| 58 | 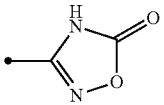 | H | 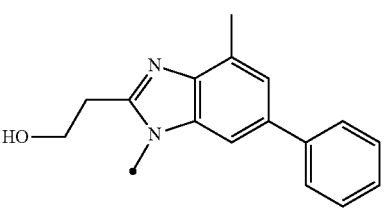 |
| 59 | 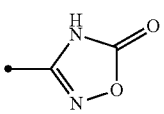 | H | 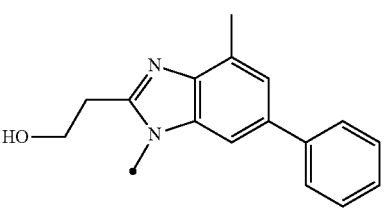 |

TABLE 5-continued

| Ex. No. | A | Y | X |
|---|---|---|---|
| 60 | 4-methyl-6-phenyl-benzimidazol-1-yl | H | tetrazole |
| 61 | 2-(2-methoxycarbonylethyl)-4-methyl-6-phenyl-benzimidazol-1-yl | H | tetrazole |
| 62 | 2-(2-(methylsulfonylaminocarbonyl)ethyl)-4-methyl-6-phenyl-benzimidazol-1-yl | H | tetrazole |
| 63 | 2-(2-(methylaminocarbonyl)ethyl)-4-methyl-6-phenyl-benzimidazol-1-yl | H | tetrazole |

TABLE 6

| Ex. No. | A | Y | X |
|---|---|---|---|
| 64 | 2-propyl-4-methyl-6-(2-chlorophenyl)-benzimidazol-1-yl | H | tetrazole |
| 65 | 2-propyl-4-methyl-6-(3-chlorophenyl)-benzimidazol-1-yl | H | tetrazole |

TABLE 6-continued

| Ex. No. | A | Y | X |
|---|---|---|---|
| 66 | 2-propyl-4-methyl-6-(4-chlorophenyl)benzimidazol-1-ylmethyl | H | tetrazol-5-yl |
| 67 | 2-propyl-4-methyl-6-(thiophen-2-yl)benzimidazol-1-ylmethyl | H | tetrazol-5-yl |
| 68 | 2-propyl-4-methyl-6-(furan-2-yl)benzimidazol-1-ylmethyl | H | tetrazol-5-yl |
| 69 | 2-propyl-4-methyl-6-(oxazol-2-yl)benzimidazol-1-ylmethyl | H | tetrazol-5-yl |
| 70 | 2-propyl-4-methyl-6-(1,3,4-oxadiazol-2-yl)benzimidazol-1-ylmethyl | H | tetrazol-5-yl |
| 71 | 2-propyl-4-methyl-6-(5-methyl-1,3,4-oxadiazol-2-yl)benzimidazol-1-ylmethyl | H | tetrazol-5-yl |
| 72 | 2-propyl-4-methyl-6-(5-oxo-4,5-dihydro-1,3,4-oxadiazol-2-yl)benzimidazol-1-ylmethyl | H | CN |

TABLE 7

| Ex. No. | A | X | Y |
|---|---|---|---|
| 73 | 2,5,7-trimethylimidazo[4,5-b]pyridin-3-ylmethyl | tetrazol-5-yl | Me |
| 74 | 2,5,7-trimethylimidazo[4,5-b]pyridin-3-ylmethyl | 5-oxo-4,5-dihydro-1,2,4-oxadiazol-3-yl | Me |
| 75 | 2-ethyl-5,7-dimethylimidazo[4,5-b]pyridin-3-ylmethyl | tetrazol-5-yl | Me |
| 76 | 2-ethyl-5,7-dimethylimidazo[4,5-b]pyridin-3-ylmethyl | 5-oxo-4,5-dihydro-1,2,4-oxadiazol-3-yl | Me |
| 77 | 2-cyclopropyl-5,7-dimethylimidazo[4,5-b]pyridin-3-ylmethyl | tetrazol-5-yl | Me |
| 78 | 2-cyclopropyl-5,7-dimethylimidazo[4,5-b]pyridin-3-ylmethyl | 5-oxo-4,5-dihydro-1,2,4-oxadiazol-3-yl | Me |

TABLE 8

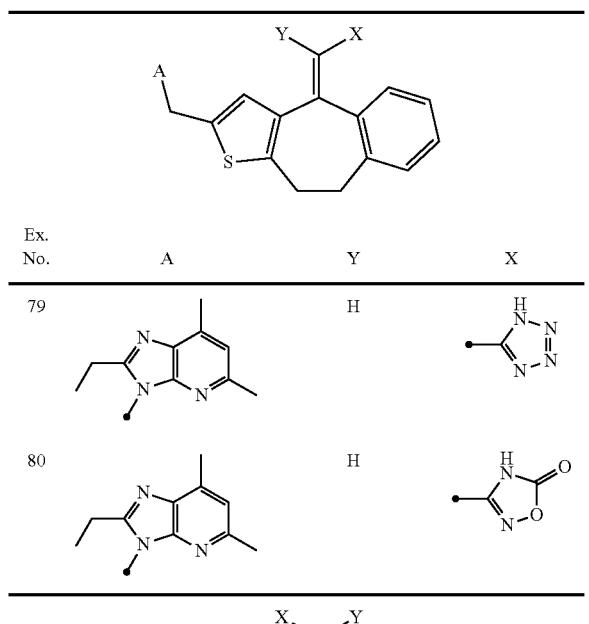

| Ex. No. | A | Y | X |
|---|---|---|---|
| 79 | imidazopyridine-ethyl | H | tetrazole |
| 80 | imidazopyridine-ethyl | H | oxadiazolone |

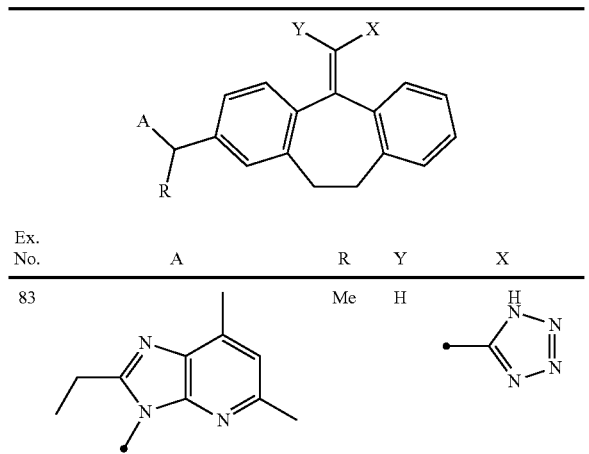

| Ex. No. | A | X | Y |
|---|---|---|---|
| 81 | imidazopyridine-ethyl | tetrazole | H |
| 82 | imidazopyridine-ethyl | oxadiazolone | H |

TABLE 9

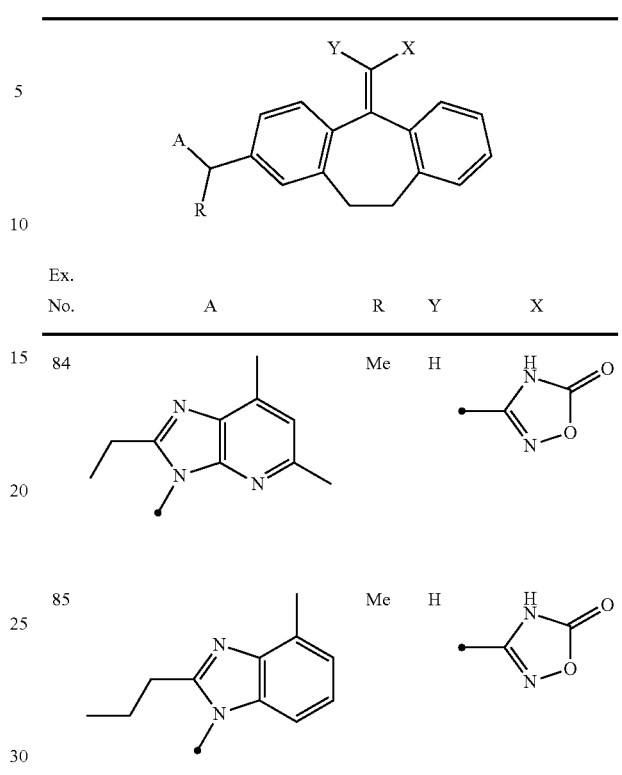

| Ex. No. | A | R | Y | X |
|---|---|---|---|---|
| 83 | imidazopyridine-ethyl | Me | H | tetrazole |
| 84 | imidazopyridine-ethyl | Me | H | oxadiazolone |
| 85 | benzimidazole-propyl | Me | H | oxadiazolone |
| 86 | benzimidazole-propyl | n-Pr | H | oxadiazolone |
| 87 | Cl-benzimidazole-ethyl | Me | H | oxadiazolone |
| 88 | Cl-benzimidazole-cyclopropyl | Me | H | oxadiazolone |
| 89 | Cl-benzimidazole-propyl | Me | H | oxadiazolone |

TABLE 10
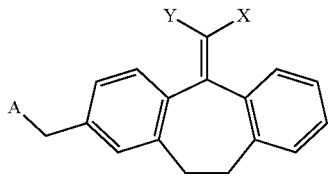
| Ex. No. | A | Y | X |
|---|---|---|---|
| 90 | 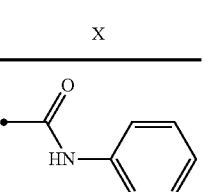 | H | 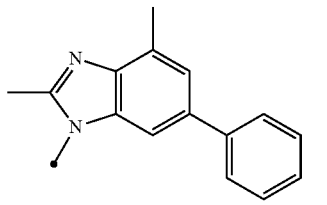 |
| 91 | 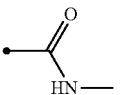 | H | 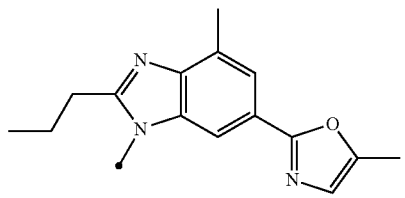 |
| 92 | 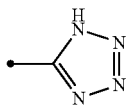 | H | 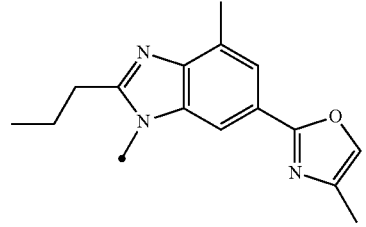 |
| 93 | 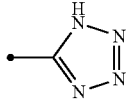 | H | 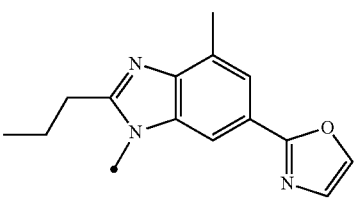 |
| 94 | 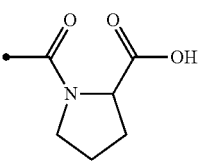 | H | 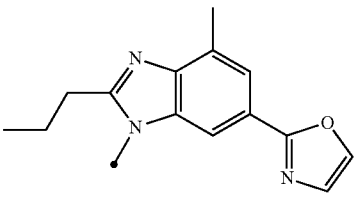 |
| 95 | 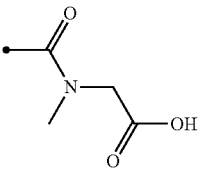 | H |  |

TABLE 11

| Ex. No. | A | X | Y |
|---|---|---|---|
| 96 | 2-(1-methyl-2-propylbenzimidazol-4-yl)propan-2-ol | 5-oxo-4H-1,2,4-oxadiazol-3-yl | Me |
| 97 | 1-methyl-2-propyl-4-phenylimidazol-5-yl | 5-oxo-4H-1,2,4-oxadiazol-3-yl | Me |
| 98 | 1-methyl-2-propyl-4-(pyridin-4-yl)imidazol-5-yl | 5-oxo-4H-1,2,4-oxadiazol-3-yl | Me |
| 99 | 1,2-dimethyl-4-phenylimidazol-5-yl | 5-oxo-4H-1,2,4-oxadiazol-3-yl | Me |
| 100 | 1-methyl-2-propyl-4-carbamoylbenzimidazol-5-yl | 5-oxo-4H-1,2,4-oxadiazol-3-yl | Me |
| 101 | 1-methyl-2-propyl-4-(4-hydroxypiperidin-1-ylcarbonyl)benzimidazol-5-yl | 5-oxo-4H-1,2,4-oxadiazol-3-yl | Me |

TABLE 11-continued

| Ex. No. | A | X | Y |
|---|---|---|---|
| 102 | 1-methyl-2-propyl-4-(N-(2-hydroxyethyl)carbamoyl)benzimidazol-5-yl | 5-oxo-4H-1,2,4-oxadiazol-3-yl | Me |
| 103 | 1-methyl-2-propyl-4-(methylsulfonylamino)benzimidazol-5-yl | 5-oxo-4H-1,2,4-oxadiazol-3-yl | Me |

TABLE 12

| Ex. No. | A | X | Y |
|---|---|---|---|
| 104 | 1-methyl-2-propyl-4-methylbenzimidazol-5-yl | 5-oxo-4H-1,2,4-oxadiazol-3-yl | H |
| 105 | 1-methyl-2-propyl-4-methylbenzimidazol-5-yl | methylsulfonylaminocarbonyl | H |
| 106 | 1-methyl-2-propyl-4-methylbenzimidazol-5-yl | 5-oxo-4H-1,3,4-oxadiazol-2-yl | H |

TABLE 12-continued

| Ex. No. | A | X | Y |
|---|---|---|---|
| 107 | 2-propyl-4-methyl-benzimidazol-1-yl | 1,3,4-oxadiazol-2-yl | H |
| 108 | 2-propyl-4-methyl-benzimidazol-1-yl | 1,3,4-oxadiazol-3-yl | H |
| 109 | 2-propyl-4-methyl-benzimidazol-1-yl | 5-(CF₃)-1,2,4-oxadiazol-3-yl | H |
| 110 | 2-propyl-benzimidazol-1-yl | 5-oxo-4H-1,2,4-oxadiazol-3-yl | cyclopropyl |
| 111 | 2-propyl-4-chloro-benzimidazol-1-yl | 5-oxo-4H-1,2,4-oxadiazol-3-yl | cyclopropyl |
| 112 | 2-cyclopropyl-4-chloro-benzimidazol-1-yl | 5-oxo-4H-1,2,4-oxadiazol-3-yl | cyclopropyl |
| 113 | 2-(methoxymethyl)-benzimidazol-1-yl | 5-oxo-4H-1,2,4-oxadiazol-3-yl | cyclopropyl |
| 114 | 2-(methoxymethyl)-4-chloro-benzimidazol-1-yl | 5-oxo-4H-1,2,4-oxadiazol-3-yl | cyclopropyl |
| 115 | 2-propyl-benzimidazol-1-yl | 5-oxo-4H-1,2,4-oxadiazol-3-yl | propyl |

TABLE 13

| Ex. No. | A | X | Y |
|---|---|---|---|
| 116 | 2-propyl-benzimidazol-1-yl | 5-oxo-4H-1,2,4-oxadiazol-3-yl | Me |

TABLE 14

| Ex. No. | A | X | Y |
|---|---|---|---|
| 117 | 2-propyl-benzimidazol-1-yl | 5-oxo-4H-1,2,4-oxadiazol-3-yl | Me |
| 118 | 2-propyl-benzimidazol-1-yl | tetrazol-5-yl | Me |
| 119 | 2-cyclopropyl-7-chloro-imidazo[4,5-b]pyridin-3-yl | 5-oxo-4H-1,2,4-oxadiazol-3-yl | Me |
| 120 | 2-cyclopropyl-4-chloro-benzimidazol-1-yl | 5-oxo-4H-1,2,4-oxadiazol-3-yl | Me |

TABLE 14-continued

| Ex. No. | A | X | Y |
|---|---|---|---|
| 121 | benzimidazole-CH2- | 1,3,4-oxadiazol-2(3H)-one-NH | Me |

TABLE 15

| Ex. No. | A | X | Y |
|---|---|---|---|
| 122 | benzimidazole-CH2- | 1,3,4-oxadiazol-2(3H)-one-NH | Me |
| 123 | benzimidazole-CH2- | tetrazole-NH | Me |
| 124 | benzimidazole-CH2- | 1,3,4-oxadiazol-2(3H)-one-NH | Me |
| 125 | benzimidazole-CH2- | tetrazole-NH | Me |

Next, the pharmacological action of the representative compound (I) is specifically explained by Test Examples.

Test Example 1

PPAR γ Activation Action Based on Transactivation Assay of PPAR γ by Transient Gene Transfer The agonist activity of compound (I) to PPAR γ was determined by a transactivation assay method using a chimeric nuclear receptor of a DNA binding region of a yeast transcription factor GAL4 and a PPAR γ ligand binding region. Specifically, the PPAR γ agonist activity of compound (I) was evaluated by the following method based on the method of Lehmann et al. (J Biol Chem., 1995, vol. 270, page 12953).

HEK293EBNA cells cultured in Dulbecco's Modified Eagle medium (Invitrogen) containing 10 v/v % fetal calf serum (Invitrogen) were used. 30 mL of the above-mentioned cells (density: $1\times10^5$ cells/mL) were inoculated in a 10 $cm^2$ culture dish (Iwaki Glass), and cultured overnight. Using SuperFect Transfection Reagent (QIAGEN), a plasmid expressing a GAL4-PPAR γ chimeric nuclear receptor fusing 174-475 amino acids, which are human PPAR γ ligand binding region, and 1-147 amino acids, which are GAL4 DNA binding region, and a reporter plasmid expressing a GAL4 responsive luciferase were transiently introduced into the cells at a proportion of 4:1. After 5 hr from transfection, the cells were detached from the culture dish, and the detached cells (density: $2\times10^4$ cells/mL) were inoculated by 100 µL in each well of a 96 well white plate (SUMITOMO BAKELITE), and cultured overnight. The medium was removed, compound (I) diluted in various concentrations with serum-free Dulbecco's Modified Eagle medium was added by 100 µL, and the mixture was reacted under a 5% carbon dioxide gas stream (5% $CO_2$) at 37° C. for 24 hr. On the other hand, as a positive control, 10 µmol/L of pioglitazone (100 µL) was added, and the mixture was reacted under a 5% carbon dioxide gas stream (5% $CO_2$) at 37° C. for 24 hr. As a substrate of luciferase, 100 µL of Steady-Glo (Promega) was added to each well and the mixture was thoroughly stirred. Immediately thereafter, the chemical luminescence due to luciferase was measured using TopCount NTX (Packard).

The agonist activity (activity rate (%)) of compound (I) to PPAR γ was calculated according to the following formula, as a relative activity when the agonist activity on addition of pioglitazone (10 µmol/L) was 100%.

$$\text{activity rate (\%)} = \frac{\begin{pmatrix}\text{luminescence intensity}\\\text{with addition of}\\\text{compound }(I)\end{pmatrix} - \begin{pmatrix}\text{luminescence intensity}\\\text{without addition of}\\\text{compound }(I)\end{pmatrix}}{\begin{pmatrix}\text{luminescence intensity}\\\text{with addition of}\\\text{pioglitazone 10 µmol/L}\end{pmatrix} - \begin{pmatrix}\text{luminescence intensity}\\\text{without addition of}\\\text{compound }(I)\end{pmatrix}} \times 100$$

The activity rate at which compound (I) shows the maximum activity is referred as efficacy and the concentration showing 50% activity rate of the efficacy was calculated as $EC_{50}$ value. The results are shown in Table 16.

TABLE 16

| compound No. | $EC_{50}$ value (nmol/L) |
|---|---|
| 5 | 399 |
| 7 | 791 |
| 8 | 175 |

TABLE 16-continued

| compound No. | EC$_{50}$ value (nmol/L) |
|---|---|
| 17 | 30 |
| 19 | 6.4 |
| 21 | 40 |
| 26 | 17 |
| 27 | 2.6 |
| 30 | 9.8 |
| 33 | 26 |
| 35 | 2.4 |
| 37 | 412 |
| 50 | 352 |
| 54 | 54 |
| 55 | 39 |
| 67 | 156 |
| 70 | 156 |
| 76 | 328 |
| 85 | 27 |
| 87 | 60 |
| 95 | 31 |
| 96 | 13 |
| 100 | 20 |
| 110 | 16 |
| 114 | 11 |
| 115 | 36 |
| 116 | 12 |
| 119 | 314 |

From the above-mentioned results, compound (I) and a pharmaceutically acceptable salt thereof of the present invention are considered to have a PPAR γ agonist activity. Accordingly, compound (I) and a pharmaceutically acceptable salt thereof of the present invention are expected to be agents for treating and/or preventing various diseases related to PPAR γ, such as type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis, growth of benign, malignant or metastatic tumor etc.), inflammatory neuropsychiatric diseases (e.g., multiple sclerosis etc.), angiogenesis and pathological angiogenesis related to tumor growth and metastasis, neurodegenerative neuropsychiatric diseases (e.g., Alzheimer's disease, Parkinson's disease etc.), cardiovascular diseases (e.g., arteriosclerosis, cardiac disease, cerebral apoplexy, renal diseases etc.), or the like.

Test Example 2

Blood Glucose- and Lipid-Lowering Action in Diabetes Mouse

Test compound was orally administered to db/db mouse (6-week-old, female), a model of spontaneous type 2 diabetes, at a dose of 30 mg/kg/day once a day for 6 days. A solvent (0.5% methylcellulose solution) was administered to the control group. After 7 days from the administration, glucose and triglycelide in plasma were measured.

A part of compound (I) of the present invention was evaluated as the above-mentioned test compound. It was confirmed that these compounds remarkably suppressed an increase of serum glucose and triglycelide, and compound (I) was confirmed to have a glucose- and lipid-lowering actions in the diabetes model in this Experiment.

Test Example 3

Ameliorating Action on Impaired Glucose Tolerance and Insulin Resistance in Type 2 Diabetic Rats A test compound is repeatedly administered orally to Zucker obese rat with type 2 diabetes, once a day for 4 weeks at a dose of 3 mg/kg. A solvent (0.5% methylcellulose solution) is administered to the control group in a similar manner. After 4 weeks of administration, an oral glucose tolerance test is performed as shown below. In addition, plasma insulin level is measured under full feeding condition.

Oral glucose tolerance test: After rat is fasted overnight, a glucose solution is orally administered at a dose of 2 g/kg. Blood samples are collected from the rat tail vein at 30 min, 60 min and 120 min after administration of the glucose solution, and the blood glucose level is measured.

While compound (I) or pharmaceutically acceptable salts thereof can be administered alone as they are, generally, they are desirably provided as various pharmaceutical preparations. In addition, such pharmaceutical preparations are used for animals and humans.

The pharmaceutical preparation relating to the present invention can contain, as an active ingredient, compound (I) or a pharmaceutically acceptable salt thereof alone or as a mixture with an active ingredient for any other treatment. Moreover, the pharmaceutical preparation can be produced by mixing the active ingredient with one or more kinds of pharmaceutically acceptable carriers (e.g., diluent, solvent, excipient or the like) according to any method well known in the technical field of pharmacy.

As the administration route, a route most effective for the treatment is desirably employed, which may be an oral or parenteral route such as intravenous route or the like.

The dosage form may be, for example, tablet, injection or the like.

A form suitable for oral administration, such as tablet or the like, can be produced by using an excipient such as lactose or the like, a disintegrant such as starch or the like, a lubricant such as magnesium stearate or the like, a binder such as hydroxypropylcellulose or the like.

A form suitable for parenteral administration, such as injection or the like, can be produced by using a diluent such as a salt solution, a glucose solution or a mixture of salt solution and a glucose solution or the like, or a solvent or the like.

While the dose and administration frequency of compound (I) or a pharmaceutically acceptable salt thereof varies depending on the mode of administration, age and body weight of patients, nature and severity of the symptom to be treated or the like, it is generally within the range of 0.01 to 1000 mg, preferably 0.05 to 100 mg, for oral administration to an adult, which is administered at once or in several portions a day. In the case of parenteral administration such as intravenous administration or the like, 0.001 to 1000 mg, preferably 0.01 to 100 mg, is administered to an adult at once or in several portions a day. However, these doses and administration frequencies vary depending on the aforementioned various conditions.

The present invention is explained in more detail in the following by Examples and Reference Examples, which are not to be construed as limitative.

The proton nuclear magnetic resonance spectrum ($^1$H NMR) used in the Examples and Reference Examples were measured at 270 MHz or 300 MHz, and exchanging protons may not be clearly observed depending on the compound and measurement conditions. The indication of the multiplicity of the signals is conventional, where br means an apparently broad signal.

Example 1

(E)-[2-(2-Propylbenzimidazol-1-yl)methyl-10,11-dihydro-5H-dibenzo[a,d]cyclohepten-5-ylidene]acetonitrile (Compound 1)

(E)-2-(2-Bromomethyl-10,11-dihydro-5H-dibenzo[a,d]cyclohepten-5-ylidene)acetonitrile (648 mg, 2.00 mmol) obtained in Reference Example B1 and 2-propylbenzimidazole (385 mg, 2.40 mmol) were dissolved in DMA (2 mL), potassium carbonate (553 mg, 4.00 mmol) was added, and the mixture was stirred at room temperature for 14 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (chloroform/methanol=97/3) to give the title compound (compound 1) (778 mg, 96%).

ESI-MS m/z: 404 (M+H)$^+$; $^1$H-NMR (CDCl$_3$, δ): 1.01 (t, J=7.4 Hz, 3H), 1.85-1.90 (m, 2H), 2.79 (t, J=7.6 Hz, 2H), 3.06 (br s, 4H), 5.29 (s, 2H), 5.67 (s, 1H), 6.79-6.88 (m, 2H), 7.11-7.35 (m, 7H), 7.43 (dd, J=7.3, 1.7 Hz, 1H), 7.76 (d, J=7.3 Hz, 1H).

Example 2

(E)-[2-(2-Propylbenzimidazol-1-yl)methyl-10,11-dihydro-5H-dibenzo[a,d]cyclohepten-5-ylidene]acetic acid (Compound 2)

(E)-[2-(2-Propylbenzimidazol-1-yl)methyl-10,11-dihydro-5H-dibenzo[a,d]cyclohepten-5-ylidene]acetonitrile (260 mg, 0.64 mmol) obtained in Example 1 was dissolved in ethanol (2.5 mL), 10 mol/L aqueous sodium hydroxide solution (1 mL) was added, and the mixture was stirred under reflux for 24 hr. The mixture was neutralized with hydrochloric acid, and extracted with ethyl acetate. The organic layer was washed with brine, dried over anhydrous magnesium sulfate, and concentrated under reduced pressure. The residue was purified by silica gel column chromatography (chloroform/methanol=90/10) to give the title compound (compound 2) (243 mg, 89%).

ESI-MS m/z: 423 (M+H)$^+$; $^1$H-NMR (CDCl$_3$, δ): 0.98 (t, J=7.3 Hz, 3H), 1.80-1.85 (m, 2H), 2.78 (t, J=7.7 Hz, 2H), 3.11 (br s, 4H), 5.26 (s, 2H), 6.20 (s, 1H), 6.73 (s, 1H), 6.82 (d, J=8.1 Hz, 1H), 7.10-7.27 (m, 8H), 7.73 (d, J=7.3 Hz, 1H).

Example 3

(E)-[2-(2-Propylbenzimidazol-1-yl)methyl-10,11-dihydro-5H-dibenzo[a,d]cyclohepten-5-ylidene]acetamide (Compound 3)

(E)-[2-(2-Propylbenzimidazol-1-yl)methyl-10,11-dihydro-5H-dibenzo[a,d]cyclohepten-5-ylidene]acetonitrile (404 mg, 1.00 mmol) obtained in Example 1 was dissolved in ethanol (8 mL), 2 mol/L aqueous sodium hydroxide solution (2 mL) was added, and the mixture was stirred at 70° C. for 2 days. Water was added to the mixture, and the mixture was extracted with chloroform. The organic layer was washed with 2 mol/L aqueous sodium hydroxide solution and brine, dried over anhydrous magnesium sulfate, and concentrated under reduced pressure. Ethyl acetate was added to the residue, and the mixture was filtered to give the title compound (compound 3) (279 mg, 66%).

ESI-MS m/z: 422 (M+H)$^+$; $^1$H-NMR (DMSO-d$_6$, δ): 0.94 (t, J=7.3 Hz, 3H), 1.73-1.78 (m, 2H), 2.79 (t, J=7.4 Hz, 2H), 3.02 (br s, 4H), 5.42 (s, 2H), 6.16 (s, 1H), 6.80 (d, J=7.9 Hz, 1H), 6.91 (s, 1H), 7.04-7.23 (m, 7H), 7.36-7.39 (m, 1H), 7.54-7.60 (m, 1H).

Example 4

(E)-2-(2-Propylbenzimidazol-1-yl)methyl-5-(1H-tetrazol-5-yl)methylene-10,11-dihydro-5H-dibenzo[a,d]cycloheptene (Compound 4)

(E)-[2-(2-Propylbenzimidazol-1-yl)methyl-10,11-dihydro-5H-dibenzo[a,d]cyclohepten-5-ylidene]acetonitrile (200 mg, 0.496 mmol) obtained in Example 1 was dissolved in toluene (5 mL), trimethylsilylazide (1.3 mL, 9.92 mmol) and dibutyltin oxide (123 mg, 0.496 mmol) were added, and the mixture was stirred at 90° C. for 24 hr. The mixture was concentrated under reduced pressure, and the residue was purified by silica gel column chromatography (chloroform/methanol=99/1) to give the title compound (compound 4) (111 mg, 50%).

ESI-MS m/z: 447 (M+H)$^+$; $^1$H-NMR (DMSO-d$_6$, δ): 0.93 (t, J=7.4 Hz, 3H), 1.75 (m, 2H), 2.79 (t, J=7.4 Hz, 2H), 2.89 (m, 2H), 3.36 (m, 2H), 5.43 (s, 2H), 6.78 (s, 1H), 6.80-7.28 (m, 8H), 7.32-7.44 (m, 2H), 7.56 (m, 1H).

Example 5

(E)-2-(2-Propylbenzimidazol-1-yl)methyl-5-(5-oxo-4,5-dihydro-1,2,4-oxadiazol-3-yl)methylene-10,11-dihydro-5H-dibenzo[a,d]cycloheptene (Compound 5)

(E)-[2-(2-Propylbenzimidazol-1-yl)methyl-10,11-dihydro-5H-dibenzo[a,d]cyclohepten-5-ylidene]acetonitrile (467 mg, 1.16 mmol) obtained in Example 1 was dissolved in ethanol (11 mL), hydroxylamine (50% aqueous solution, 2.13 mL, 34.7 mmol) was added, and the mixture was heated under reflux for 16 hr, and concentrated under reduced pressure. The obtained residue was dissolved in DMF (5.5 mL), pyridine (112 μL, 1.39 mmol) and ethyl chlorocarbonate (133 μL, 1.39 mmol) were added at 0° C., and the mixture was stirred at room temperature for 1 hr. Ethyl acetate and saturated aqueous sodium hydrogen carbonate solution were added to the mixture. The organic layer was washed with brine, dried over anhydrous magnesium sulfate, and concentrated under reduced pressure. The obtained residue was dissolved in toluene (11 mL), potassium tert-butoxide (195 mg, 1.74 mmol) was added, and the mixture was stirred at room temperature for 15 min. Ethyl acetate was added to the mixture, and the organic layer was washed with 5% aqueous citric acid solution, dried over anhydrous magnesium sulfate, and concentrated under reduced pressure. The residue was purified by silica gel column chromatography (chloroform/methanol=99/1) to give the title compound (compound 5) (295 mg, 55%).

ESI-MS m/z: 463 (M+H)$^+$; $^1$H-NMR (DMSO-d$_6$, δ): 0.93 (t, J=7.4 Hz, 3H), 1.75 (m, 2H), 2.78 (t, J=7.4 Hz, 2H), 2.82

(m, 2H), 3.25 (m, 2H), 5.43 (s, 2H), 6.32 (s, 1H), 6.83 (d, J=7.3 Hz, 1H), 6.96 (s, 1H), 7.00-7.40 (m, 8H), 7.56 (m, 1H).

Example 6

(E)-2-(2-Propylbenzimidazol-1-yl)methyl-5-(4-methyl-5-oxo-4,5-dihydro-1,2,4-oxadiazol-3-yl)methylene-10,11-dihydro-5H-dibenzo[a,d]cycloheptene (Compound 6)

(E)-2-(2-Propylbenzimidazol-1-yl)methyl-5-(5-oxo-4,5-dihydro-1,2,4-oxadiazol-3-yl)methylene-10,11-dihydro-5H-dibenzo[a,d]cycloheptene (69 mg, 0.15 mmol) obtained in Example 5 and methanol (30 μL, 0.75 mmol) were dissolved in THF (1 mL), polymer-supported triphenylphosphine (150 mg, 0.45 mmol) and di-tert-butyl azodicarboxylate (104 mg, 0.45 mmol) were added at 0° C., and the mixture was stirred at room temperature for 1 hr. The mixture was filtered, and the filtrate was concentrated under reduced pressure. The residue was purified by silica gel column chromatography (hexane/ethyl acetate=7/3 to 0/10) to give the title compound (compound 6) (65 mg, 92%).

ESI-MS m/z: 477 (M+H)$^+$; $^1$H-NMR (CDCl$_3$, δ): 1.02 (t, J=7.3 Hz, 3H), 1.86-1.92 (m, 2H), 2.79-2.82 (m, 2H), 2.84 (s, 3H), 3.10 (br s, 4H), 5.31 (s, 2H), 6.31 (s, 1H), 6.81 (s, 1H), 6.90 (d, J=7.9 Hz, 1H), 7.11-7.30 (m, 7H), 7.37 (d, J=7.9 Hz, 1H), 7.76-7.77 (m, 1H).

Example 7

(E)-2-(2-Propylbenzimidazol-1-yl)methyl-5-(5-oxo-4,5-dihydro-1,3,4-oxadiazol-2-yl)methylene-10,11-dihydro-5H-dibenzo[a,d]cycloheptene (Compound 7)

[step 1] (E)-[2-(2-Propylbenzimidazol-1-yl)methyl-10,11-dihydro-5H-dibenzo[a,d]cyclohepten-5-ylidene]acetic acid (130 mg, 0.31 mmol) obtained in Example 2 was dissolved in THF (1.5 mL), N,N'-carbonyldiimidazole (80 mg, 0.49 mmol) was added, and the mixture was stirred at room temperature for 10 min. Hydrazine monohydrate (60 μL, 1.24 mmol) was added to the reaction mixture, and the mixture was stirred at room temperature for 30 min. Water was added to the mixture, and the mixture was extracted with ethyl acetate. The organic layer was washed with brine, dried over anhydrous magnesium sulfate, and concentrated under reduced pressure. The residue was purified by silica gel column chromatography (chloroform/methanol=90/10) to give (E)-[2-(2-propylbenzimidazol-1-yl)methyl-10,11-dihydro-5H-dibenzo[a,d]cyclohepten-5-ylidene]acetohydrazide (172 mg) quantitatively.

$^1$H-NMR (CDCl$_3$, δ): 1.01 (t, J=7.5 Hz, 3H), 1.85-1.90 (m, 2H), 2.76-2.81 (m, 2H), 3.02 (br s, 4H), 3.74 (d, J=3.7 Hz, 2H), 5.28 (s, 2H), 6.18 (s, 1H), 6.35 (s, 1H), 6.72 (s, 1H), 6.85-6.87 (m, 1H), 7.12-7.31 (m, 8H), 7.75-7.76 (m, 1H).

[step 2] (E)-[2-(2-Propylbenzimidazol-1-yl)methyl-10,11-dihydro-5H-dibenzo[a,d]cyclohepten-5-ylidene]acetohydrazide (67 mg, 0.15 mmol) obtained in step 1 was dissolved in dichloromethane (1.5 mL), N,N'-carbonyldiimidazole (75 mg, 0.46 mmol) was added, and the mixture was stirred at room temperature for 2 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (ethyl acetate/methanol=95/5) to give the title compound (compound 7) (52 mg, 73%).

ESI-MS m/z: 463 (M+H)$^+$; $^1$H-NMR (DMSO-d$_6$, δ): 0.94 (t, J=7.4 Hz, 3H), 1.74-1.79 (m, 2H), 2.79 (t, J=7.4 Hz, 2H), 2.82 (br s, 2H), 3.32 (br s, 2H), 5.43 (s, 2H), 6.37 (s, 1H), 6.80 (d, J=7.6 Hz, 1H), 6.94 (s, 1H), 7.09-7.17 (m, 4H), 7.25-7.40 (m, 4H), 7.57-7.58 (m, 1H).

Example 8

(E)-2-(2-Ethyl-5,7-dimethyl-3H-imidazo[4,5-b]pyridin-3-yl)methyl-5-(5-thioxo-4,5-dihydro-1,2,4-oxadiazol-3-yl)methylene-10,11-dihydro-5H-dibenzo[a,d]cycloheptene (Compound 8)

(E)-[2-(2-Ethyl-5,7-dimethyl-3H-imidazo[4,5-b]pyridin-3-yl)methyl-10,11-dihydro-5H-dibenzo[a,d]cyclohepten-5-ylidene]acetonitrile (JP-B-2526005; 220 mg, 0.53 mmol) was dissolved in ethanol (5 mL), hydroxylamine (50% aqueous solution, 0.48 mL, 7.63 mmol) was added, and the mixture was heated under reflux for 16 hr, and concentrated under reduced pressure. The obtained residue was dissolved in acetonitrile (5 mL), N,N'-thiocarbonyldiimidazole (141 mg, 0.79 mmol) and DBU (315 μL, 2.11 mmol) were added, and the mixture was stirred at room temperature for 2 hr. Ethyl acetate was added to the mixture, and the organic layer was washed with 5% aqueous citric acid solution, dried over anhydrous magnesium sulfate, and concentrated under reduced pressure. The residue was purified by silica gel column chromatography (chloroform/methanol=95/5) to give the title compound (compound 8) (67 mg, 26%).

ESI-MS m/z: 494 (M+H)$^+$; $^1$H-NMR (CDCl$_3$, δ): 1.34 (t, J=7.5 Hz, 3H), 2.58 (s, 3H), 2.65 (s, 3H), 2.70-2.97 (m, 2H), 2.80 (q, J=7.5 Hz, 2H), 3.20-3.36 (m, 2H), 5.40-5.50 (m, 2H), 6.22 (br s, 1H), 6.82-6.85 (m, 2H), 6.90-6.94 (m, 1H), 7.09 (d, J=7.3 Hz, 1H), 7.20 (d, J=7.9 Hz, 1H), 7.30-7.45 (m, 3H).

Example 9

(E)-2-(2-Propylbenzimidazol-1-yl)methyl-5-(1,2,4-oxadiazol-3-yl)methylene-10,11-dihydro-5H-dibenzo[a,d]cycloheptene (Compound 9)

[step 1] (E)-[2-(2-Propylbenzimidazol-1-yl)methyl-10,11-dihydro-5H-dibenzo[a,d]cyclohepten-5-ylidene]acetonitrile (166 mg, 0.41 mmol) obtained in Example 1 was dissolved in ethanol (4 mL), hydroxylamine (50% aqueous solution, 1.26 mL, 20.0 mmol) was added, and the mixture was heated under reflux for 14 hr, and concentrated under reduced pressure. The residue was purified by silica gel column chromatography (chloroform/methanol=90/10) to give (E)-[2-(2-propylbenzimidazol-1-yl)methyl-10,11-dihydro-5H-dibenzo[a,d]cyclohepten-5-ylidene]-N-hydroxyacetamidine (190 mg) quantitatively.

$^1$H-NMR (CDCl$_3$, δ): 0.99 (t, J=7.3 Hz, 3H), 1.86 (dd, J=15.1, 7.6 Hz, 2H), 2.75-3.50 (m, 4H), 2.78 (dd, J=9.0, 6.4 Hz, 2H), 4.34 (s, 2H), 5.24 (s, 2H), 6.14 (s, 1H), 6.67 (s, 1H), 6.81 (d, J=8.1 Hz, 1H), 7.12-7.30 (m, 9H), 7.76 (d, J=7.7 Hz, 1H).

[step 2] To (E)-[2-(2-propylbenzimidazol-1-yl)methyl-10,11-dihydro-5H-dibenzo[a,d]cyclohepten-5-ylidene]-N-hydroxyacetamidine (65 mg, 0.149 mmol) obtained in step 1 was added triethyl orthoformate (1 mL), and the mixture was stirred at 80° C. for 2 hr. The mixture was concentrated under reduced pressure, and the residue was purified by silica gel column chromatography (hexane/ethyl acetate=80/20 to 0/100) to give the title compound (compound 9) (28 mg, 42%).

ESI-MS m/z: 447 (M+H)$^+$; $^1$H-NMR (CDCl$_3$, δ): 1.02 (t, J=7.3 Hz, 3H), 1.86-1.91 (m, 2H), 2.78-2.81 (m, 2H), 3.02-3.48 (m, 4H), 5.29 (s, 2H), 6.76-6.88 (m, 3H), 7.06-7.26 (m, 7H), 7.40 (d, J=8.1 Hz, 1H), 7.76-7.77 (m, 1H), 8.48 (s, 1H).

Example 10

(E)-2-(2-Propylbenzimidazol-1-yl)methyl-5-(5-trifluoromethyl-1,2,4-oxadiazol-3-yl)methylene-10,11-dihydro-5H-dibenzo[a,d]cycloheptene (Compound 10)

(E)-[2-(2-Propylbenzimidazol-1-yl)methyl-10,11-dihydro-5H-dibenzo[a,d]cyclohepten-5-ylidene]-N-hydroxyacetamidine (70 mg, 0.16 mmol) obtained in Example 9, step 1 was dissolved in dichloromethane (1 mL), triethylamine (67 μL, 0.48 mmol) and trifluoroacetic anhydride (68 μL, 0.48 mmol) were added, and the mixture was stirred at room temperature for 4 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=90/10 to 50/50) to give the title compound (compound 10) (41 mg, 49%).

ESI-MS m/z: 515 (M+H)$^+$; $^1$H-NMR (CDCl$_3$, δ): 1.02 (t, J=7.2 Hz, 3H), 1.80-1.96 (m, 2H), 2.72-3.48 (m, 4H), 2.80 (t, J=8.0 Hz, 2H), 5.29 (s, 2H), 6.71 (s, 1H), 6.77 (s, 1H), 6.87 (d, J=7.9 Hz, 1H), 7.06-7.30 (m, 7H), 7.38 (d, J=7.9 Hz, 1H), 7.76 (d, J=7.2 Hz, 1H).

Example 11

(E)-2-(2-Propylbenzimidazol-1-yl)methyl-5-(1,3,4-oxadiazol-2-yl)methylene-10,11-dihydro-5H-dibenzo[a,d]cycloheptene (Compound 11)

To (E)-[2-(2-propylbenzimidazol-1-yl)methyl-10,11-dihydro-5H-dibenzo[a,d]cyclohepten-5-ylidene]acetohydrazide (27 mg, 0.062 mmol) obtained in Example 7, step 1 was added triethyl orthoformate (0.5 mL), and the mixture was stirred at 120° C. for 20 hr. The mixture was concentrated under reduced pressure, and the residue was purified by silica gel column chromatography (hexane/ethyl acetate=70/30 to 0/100) to give the title compound (compound 11) (26 mg, 93%).

ESI-MS m/z: 447 (M+H)$^+$; $^1$H-NMR (CDCl$_3$, δ): 1.02 (t, J=7.4 Hz, 3H), 1.85-1.91 (m, 2H), 2.78-2.82 (m, 2H), 2.80-3.40 (m, 4H), 5.29 (s, 2H), 6.75 (s, 1H), 6.84 (s, 1H), 6.89 (d, J=7.9 Hz, 1H), 7.08-7.32 (m, 7H), 7.38 (d, J=7.9 Hz, 1H), 7.75-7.77 (m, 1H), 8.10 (d, J=0.7 Hz, 1H).

Example 12

N-{(E)-[2-(2-Propylbenzimidazol-1-yl)methyl-10,11-dihydro-5H-dibenzo[a,d]cyclohepten-5-ylidene]acetyl}methanesulfonamide (Compound 12)

(E)-[2-(2-Propylbenzimidazol-1-yl)methyl-10,11-dihydro-5H-dibenzo[a,d]cyclohepten-5-ylidene]acetic acid (60 mg, 0.14 mmol) obtained in Example 2 was dissolved in DMF (0.6 mL), N,N'-carbonyldiimidazole (92 mg, 0.57 mmol) was added, and the mixture was stirred at room temperature for 1 hr. Methanesulfonamide (68 mg, 0.71 mmol) and DBU (106 μL, 0.71 mmol) were added to the reaction mixture, and the mixture was stirred at 80° C. for 2 hr. Water and 5% aqueous citric acid solution were added to the mixture, and the mixture was extracted with ethyl acetate. The organic layer was washed with brine, dried over anhydrous magnesium sulfate, and concentrated under reduced pressure. Ethyl acetate was added to the residue, and the mixture was filtered to give the title compound (compound 12) (29 mg, 41%).

ESI-MS m/z: 500 (M+H)$^+$; $^1$H-NMR (CDCl$_3$, δ): 1.04 (t, J=7.3 Hz, 3H), 1.90-1.95 (m, 2H), 2.83-3.30 (m, 4H), 3.05 (t, J=7.9 Hz, 2H), 3.17 (s, 3H), 5.39 (s, 2H), 6.22 (s, 1H), 6.80 (s, 1H), 6.87 (d, J=8.1 Hz, 1H), 7.20-7.45 (m, 8H), 7.94 (d, J=7.7 Hz, 1H).

Example 13

(E)-[2-(2-Propylbenzimidazol-1-yl)methyl-10,11-dihydro-5H-dibenzo[a,d]cyclohepten-5-ylidene]ethanol (Compound 13)

(E)-[2-(2-Propylbenzimidazol-1-yl)methyl-10,11-dihydro-5H-dibenzo[a,d]cyclohepten-5-ylidene]acetic acid (80 mg, 0.189 mmol) obtained in Example 2 was dissolved in 1,2-dimethoxyethane (0.7 mL), N-methylmorpholine (62 μL, 0.567 mmol) and isobutyl chlorocarbonate (49 μL, 0.378 mmol) were added, and the mixture was stirred at room temperature for 1 hr. The reaction mixture was filtered, and the filtrate was added to a solution (0.6 mL) of sodium borohydride (36 mg, 0.945 mmol) in water at 0° C., and the mixture was stirred for 10 min. Water was added to the mixture, and the mixture was extracted with ethyl acetate. The organic layer was washed with brine, dried over anhydrous magnesium sulfate, and concentrated under reduced pressure. The residue was purified by silica gel column chromatography (chloroform/methanol=95/5) to give the title compound (compound 13) (43 mg, 55%).

ESI-MS m/z: 407 (M−H)$^−$; $^1$H-NMR (CDCl$_3$, δ): 1.01 (t, J=7.6 Hz, 3H), 1.87 (m, 2H), 2.79 (t, J=7.6 Hz, 2H), 2.71-3.42 (m, 4H), 4.19 (d, J=8.6 Hz, 2H), 5.27 (s, 2H), 6.03 (t, J=6.8 Hz, 1H), 6.72 (s, 1H), 6.73-6.89 (m, 2H), 6.98-7.34 (m, 7H), 7.76 (d, J=6.3 Hz, 1H).

Example 14

N-{(E)-[2-(2-Propylbenzimidazol-1-yl)methyl-10,11-dihydro-5H-dibenzo[a,d]cyclohepten-5-ylidene]ethyl}methanesulfonamide (Compound 14)

(E)-[2-(2-Propylbenzimidazol-1-yl)methyl-10,11-dihydro-5H-dibenzo[a,d]cyclohepten-5-ylidene]ethanol (50 mg, 0.122 mmol) obtained in Example 13 was dissolved in THF (1 mL), phthalimide (27 mg, 0.183 mmol), polymer-supported triphenylphosphine (102 mg, 0.305 mmol) and di-tert-butyl azodicarboxylate (70 mg, 0.305 mmol) were added, and the mixture was stirred at room temperature for 1 hr. The mixture was filtered, and the filtrate was concentrated under reduced pressure. The residue was purified by silica gel column chromatography (hexane/ethyl acetate=70/30 to 50/50) to give imide (51 mg, 52%). The obtained imide (42 mg, 0.078 mmol) was dissolved in ethanol (1.4 mL), hydrazine monohydrate (76 μL, 1.56 mmol) was added, and the mixture was stirred at room temperature for 1.5 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (chloroform/methanol=95/5 to 90/10) to give amine (13 mg, 41%). The obtained amine (13 mg, 0.032 mmol) was dissolved in dichloromethane (1 mL), pyridine (15 μL, 0.19 mmol) and methanesulfonyl chloride (7 μL, 0.10 mmol) were added at 0° C., and the mixture was stirred at room temperature for 15 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (chloroform/methanol=95/5) to give the title compound (compound 14) (5 mg, 32%).

ESI-MS m/z: 486 (M+H)$^+$; $^1$H-NMR (CDCl$_3$, δ): 1.01 (t, J=7.3 Hz, 3H), 1.83-1.88 (m, 2H), 2.70-3.35 (m, 4H), 2.79 (t, J=7.7 Hz, 2H), 2.88 (s, 3H), 3.78-3.80 (m, 2H), 4.40 (t, J=5.9 Hz, 1H), 5.27 (s, 2H), 5.89 (t, J=7.0 Hz, 1H), 6.71 (s, 1H), 6.80 (d, J=8.1 Hz, 1H), 7.01-7.25 (m, 8H), 7.75 (d, J=7.7 Hz, 1H).

Example 15

(Z)-2-(Benzimidazol-1-yl)methyl-5-[1-(1H-tetrazol-5-yl)ethylidene]-10,11-dihydro-5H-dibenzo[a,d]cycloheptene (Compound 15)

[step 1] (Z)-2-(2-Hydroxymethyl-10,11-dihydro-5H-dibenzo[a,d]cyclohepten-5-ylidene)propiononitrile (500 mg, 1.82 mmol) obtained in Reference Example B3 was dissolved in THF (19 mL), 2,6-lutidine (1.27 mL, 10.9 mmol), lithium bromide (0.947 g, 10.9 mmol) and methanesulfonic anhydride (0.791 g, 4.54 mmol) were added, and the mixture was stirred at room temperature for 16 hr. Ethyl acetate was added to the mixture, and the organic layer was washed with brine, dried over anhydrous magnesium sulfate, and concentrated under reduced pressure to give a residue.

Benzimidazole (236 mg, 2.00 mmol) was dissolved in DMF (2.8 mL), potassium carbonate (1.25 g, 9.04 mmol) was added, and the mixture was stirred for 15 min. To this mixture was added a solution of the residue obtained above in DMF (7 mL), and the mixture was stirred at room temperature for 2 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=7/3 to 4/6) to give (Z)-2-[2-(benzimidazol-1-yl)methyl-10,11-dihydro-5H-dibenzo[a,d]cyclohepten-5-ylidene]propiononitrile (536 mg, 79%).

$^1$H-NMR (CDCl$_3$, δ): 2.02 (s, 3H), 2.81 (m, 2H), 3.29 (m, 2H), 5.32 (s, 2H), 6.89 (s, 1H), 7.06 (m, 1H), 7.13-7.34 (m, 7H), 7.42 (d, J=7.9 Hz, 1H), 7.81 (m, 1H), 7.93 (s, 1H).

[step 2] Using (Z)-2-[2-(benzimidazol-1-yl)methyl-10,11-dihydro-5H-dibenzo[a,d]cyclohepten-5-ylidene]propiononitrile (253 mg, 0.674 mmol) obtained in step 1 and in the same manner as in Example 4, the title compound (compound 15) (131 mg, 46%) was obtained.

ESI-MS m/z: 419 (M+H)$^+$; $^1$H-NMR (CDCl$_3$, δ): 2.03 (s, 3H), 2.77 (m, 2H), 3.25 (m, 2H), 5.35 (s, 2H), 6.57 (d, J=7.9 Hz, 1H), 6.78 (d, J=7.9 Hz, 1H), 7.06 (s, 1H), 7.10-7.30 (m, 6H), 7.40 (m, 1H), 7.61 (m, 1H), 8.29 (s, 1H).

Example 16

(Z)-2-(Benzimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 16)

Using (Z)-2-[2-(benzimidazol-1-yl)methyl-10,11-dihydro-5H-dibenzo[a,d]cyclohepten-5-ylidene]propiononitrile (280 mg, 0.746 mmol) obtained in Example 15, step 1 and in the same manner as in Example 5, the title compound (compound 16) (55 mg, 17%) was obtained.

ESI-MS m/z: 435 (M+H)$^+$; $^1$H-NMR (DMSO-d$_6$, δ): 1.93 (s, 3H), 2.75 (m, 2H), 3.26 (m, 2H), 5.39 (s, 2H), 6.90-7.28 (m, 9H), 7.44 (m, 1H), 7.62 (m, 1H), 8.33 (s, 1H).

Example 17

(Z)-2-(4-Methyl-2-propylbenzimidazol-1-yl)methyl-5-[1-(1H-tetrazol-5-yl)ethylidene]-10,11-dihydro-5H-dibenzo[a,d]cycloheptene (Compound 17)

[step 1] Using 4-methyl-2-propylbenzimidazole (EP400835; 369 mg, 2.12 mmol) instead of benzimidazole, and in the same manner as in Example 15, step 1, (Z)-2-[2-(4-methyl-2-propylbenzimidazol-1-yl)methyl-10,11-dihydro-5H-dibenzo[a,d]cyclohepten-5-ylidene]propiononitrile (580 mg, 63%) was obtained.

$^1$H-NMR (CDCl$_3$, δ): 0.99 (t, J=7.3 Hz, 3H), 1.71-1.83 (m, 2H), 2.01 (s, 3H), 2.79 (s, 3H), 2.78 (m, 4H), 3.25 (m, 2H), 5.27 (s, 2H), 6.73 (s, 1H), 6.92-7.32 (m, 8H), 7.38 (d, J=7.9 Hz, 1H).

[step 2] Using (Z)-2-[2-(4-methyl-2-propylbenzimidazol-1-yl)methyl-10,11-dihydro-5H-dibenzo[a,d]cyclohepten-5-ylidene]propiononitrile (290 mg, 0.672 mmol) obtained in step 1 and in the same manner as in Example 4, the title compound (compound 17) (168 mg, 53%) was obtained.

ESI-MS m/z: 475 (M+H)$^+$; $^1$H-NMR (DMSO-d$_6$, δ): 0.88 (t, J=7.2 Hz, 3H), 1.65 (m, 2H), 2.03 (s, 3H), 2.55 (s, 3H), 2.77 (m, 2H), 2.70 (t, J=7.6 Hz, 2H), 3.35 (m, 2H), 5.29 (s, 2H), 6.46-6.59 (m, 2H), 6.81-7.29 (m, 8H).

Example 18

(Z)-2-(4-Methyl-2-propylbenzimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 18)

Using (Z)-2-[2-(4-methyl-2-propylbenzimidazol-1-yl)methyl-10,11-dihydro-5H-dibenzo[a,d]cyclohepten-5-ylidene]propiononitrile (290 mg, 0.672 mmol) obtained in Example 17, step 1 and in the same manner as in Example 5, the title compound (compound 18) (115 mg, 35%) was obtained.

ESI-MS m/z: 491 (M+H)$^+$; $^1$H-NMR (DMSO-d$_6$, δ): 0.88 (t, J=7.4 Hz, 3H), 1.66 (m, 2H), 1.94 (s, 3H), 2.50 (s, 3H), 2.70 (m, 2H), 2.72 (t, J=7.6 Hz, 2H), 3.25 (m, 2H), 5.35 (s, 2H), 6.71 (d, J=7.6 Hz, 1H), 6.81-7.03 (m, 4H), 7.04-7.29 (m, 5H), 12.15 (br s, 1H).

Example 19

(Z)-2-(4-Chloro-2-cyclopropylbenzimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 19)

[step 1] Using 4-chloro-2-cyclopropylbenzimidazole (769 mg, 3.99 mmol) obtained in Reference Example A1 instead of benzimidazole, and in the same manner as in Example 15 step 1, (Z)-2-[2-(4-chloro-2-cyclopropylbenzimidazol-1-yl)methyl-10,11-dihydro-5H-dibenzo[a,d]cyclohepten-5-ylidene] propiononitrile (630 mg, 635%) was obtained.

$^1$H-NMR (CDCl$_3$, δ): 1.05 (m, 2H), 1.29 (m, 2H), 1.88 (m, 1H), 2.02 (s, 3H), 2.79 (m, 2H), 3.25 (m, 2H), 5.41 (s, 2H), 6.76 (s, 1H), 6.99-7.32 (m, 8H), 7.40 (d, J=7.9 Hz, 1H).

[step 2] Using (Z)-2-[2-(4-chloro-2-cyclopropylbenzimidazol-1-yl)methyl-10,11-dihydro-5H-dibenzo[a,d]cyclohepten-5-ylidene]propiononitrile (231 mg, 0.513 mmol) obtained in step 1 and in the same manner as in Example 5, the title compound (compound 19) (154 mg, 59%) was obtained.

ESI-MS m/z: 509 (M+H)$^+$; $^1$H-NMR (DMSO-d$_6$, δ): 0.92-1.08 (m, 4H), 1.94 (s, 3H), 2.20 (m, 1H), 2.72 (m, 2H), 3.29 (m, 2H), 5.52 (s, 2H), 6.82-7.30 (m, 9H), 7.40 (d, J=7.9 Hz, 1H).

Example 20

(E)-8-(2-Ethyl-4-phenylimidazol-1-yl)methyl-11-[1-(1H-tetrazol-5-yl)ethylidene]-6,11-dihydrodibenzo[b,e]oxepine (Compound 20)

[step 1] 2-Ethyl-4-phenylimidazole (Tetrahedron Lett. 2001, p 7079; 192 mg, 1.12 mmol) was dissolved in DMF (4.8 mL), potassium carbonate (0.700 g, 5.07 mmol) was added, and the mixture was stirred for 15 min. To this mixture was added (E)-2-(8-chloromethyl-6,11-dihydrodibenzo[b,e]oxepin-11-ylidene)propiononitrile (300 mg, 1.01 mmol) obtained in Reference Example B5, and the mixture was stirred at 60° C. for 3 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=9/1 to 6/4) to give (E)-2-[8-(2-ethyl-4-phenylimidazol-1-yl)methyl-6,11-dihydrodibenzo[b,e]oxepin-11-ylidene]propiononitrile (434 mg, 99%).

$^1$H-NMR (CDCl$_3$, δ): 1.32 (t, J=7.6 Hz, 3H), 2.26 (s, 3H), 2.70 (q, J=7.6 Hz, 2H), 4.80 (d, J=12.7 Hz, 1H), 5.12 (s, 2H), 5.45 (d, J=12.7 Hz, 1H), 6.86 (d, J=8.2 Hz, 1H), 6.92 (d, J=7.4 Hz, 1H), 7.01-7.30 (m, 6H), 7.35 (t, J=7.7 Hz, 2H), 7.47 (d, J=7.9 Hz, 1H), 7.76 (d, J=7.3 Hz, 2H).

[step 2] Using (E)-2-[8-(2-ethyl-4-phenylimidazol-1-yl)methyl-6,11-dihydrodibenzo[b,e]oxepin-11-ylidene]propiononitrile (200 mg, 0.463 mmol) obtained in step 1 and in the same manner as in Example 4, the title compound (compound 20) (66 mg, 30%) was obtained.

ESI-MS m/z: 475 (M−H)$^−$; $^1$H-NMR (CDCl$_3$, δ): 1.07 (t, J=7.5 Hz, 3H), 2.39 (s, 3H), 2.50 (q, J=7.5 Hz, 2H), 4.59 (d, J=12.8 Hz, 1H), 4.94 (s, 2H), 5.54 (d, J=12.8 Hz, 1H), 6.75-6.97 (m, 5H), 7.02 (s, 1H), 7.15-7.36 (m, 5H), 7.56-7.65 (m, 2H).

Example 21

(E)-8-(2-Ethyl-4-phenylimidazol-1-yl)methyl-11-[1-(5-oxo-4,5-dihydro-1,2,4-oxadiazol-3-yl)ethylidene]-6,11-dihydrodibenzo[b,e]oxepine (Compound 21)

Using (E)-2-[8-(2-ethyl-4-phenylimidazol-1-yl)methyl-6,11-dihydrodibenzo[b,e]oxepin-11-ylidene]propiononitrile (230 mg, 0.530 mmol) obtained in Example 20, step 1 and in the same manner as in Example 5, the title compound (compound 21) (48 mg, 18%) was obtained.

ESI-MS m/z: 491 (M+H)$^+$; $^1$H-NMR (CDCl$_3$, δ): 1.29 (t, J=7.6 Hz, 3H), 2.26 (s, 3H), 2.67 (q, J=7.6 Hz, 2H), 4.78 (d, J=12.8 Hz, 1H), 5.11 (s, 2H), 5.52 (d, J=12.8 Hz, 1H), 6.84 (d, J=8.2 Hz, 1H), 6.93 (t, J=7.4 Hz, 1H), 6.95-7.35 (m, 9H), 7.70-7.80 (m, 2H).

Example 22

(E)-8-(3-Chlorophenoxy)methyl-11-[1-(5-oxo-4,5-dihydro-1,2,4-oxadiazol-3-yl)ethylidene]-6,11-dihydrodibenzo[b,e]oxepine (Compound 22)

[step 1] Using 3-chlorophenol (143 mg, 1.12 mmol) instead of 2-ethyl-4-phenylimidazole, and in the same manner as in Example 20, step 1, (E)-2-[8-(3-chlorophenoxy)methyl-6,11-dihydrodibenzo[b,e]oxepin-11-ylidene]propiononitrile (256 mg, 65%) was obtained.

$^1$H-NMR (CDCl$_3$, δ): 2.27 (s, 3H), 4.89 (d, J=12.7 Hz, 1H), 5.04 (s, 2H), 5.50 (d, J=12.7 Hz, 1H), 6.80-7.30 (m, 8H), 7.42-7.56 (m, 3H).

[step 2] Using (E)-2-[8-(3-chlorophenoxy)methyl-6,11-dihydrodibenzo[b,e]oxepin-11-ylidene]propiononitrile (108 mg, 0.278 mmol) obtained in step 1 and in the same manner as in Example 5, the title compound (compound 22) (105 mg, 85%) was obtained.

ESI-MS m/z: 445 (M−H)$^−$; $^1$H-NMR (CDCl$_3$, δ): 2.30 (s, 3H), 4.93 (d, J=12.7 Hz, 1H), 5.04 (s, 2H), 5.61 (d, J=12.7 Hz, 1H), 6.86 (d, J=8.6 Hz, 1H), 6.89-7.34 (m, 8H), 7.44 (d, J=7.9 Hz, 1H), 7.52 (s, 1H).

Example 23

(E)-8-(Indazol-1-yl)methyl-11-[1-(5-oxo-4,5-dihydro-1,2,4-oxadiazol-3-yl)ethylidene]-6,11-dihydrodibenzo[b,e]oxepine (Compound 23)

[step 1] Indazole (240 mg, 2.03 mmol) was dissolved in DMF (5.0 mL), sodium hydride (60%, 81 mg, 2.03 mmol) was added, and the mixture was stirred for 15 min. To this mixture was added (E)-2-(8-chloromethyl-6,11-dihydrodibenzo[b,e]oxepin-11-ylidene)propiononitrile (300 mg, 1.01 mmol) obtained in Reference Example B5, and the mixture was stirred at room temperature for 3 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=90/10 to 75/25) to give (E)-2-[8-(indazol-1-yl)methyl-6,11-dihydrodibenzo[b,e]oxepin-11-ylidene]propiononitrile (245 mg, 64%) and (E)-2-[8-(indazol-2-yl)methyl-6,11-dihydrodibenzo[b,e]oxepin-11-ylidene]propiononitrile (138 mg, 36%).

indazol-1-yl form: $^1$H-NMR (CDCl$_3$, δ): 2.23 (s, 3H), 4.76 (d, J=12.5 Hz, 1H), 5.40 (d, J=12.5 Hz, 1H), 5.60 (s, 2H), 6.80-7.83 (m, 10H), 8.06 (s, 1H), 8.09 (brs, 1H).

indazol-2-yl form: $^1$H-NMR (CDCl$_3$, δ): 2.25 (s, 3H), 4.80 (d, J=12.9 Hz, 1H), 5.44 (d, J=12.9 Hz, 1H), 5.62 (s, 2H), 6.80-7.40 (m, 8H), 7.48 (d, J=7.9 Hz, 1H), 7.64 (dd, J=1.0, 7.6 Hz, 1), 7.73 (dd, J=1.0, 8.6 Hz, 1H), 7.92 (s, 1H).

[step 2] Using (E)-2-[8-(indazol-1-yl)methyl-6,11-dihydrodibenzo[b,e]oxepin-11-ylidene]propiononitrile (170 mg, 0.45 mmol) obtained in step 1 and in the same manner as in Example 5, the title compound (compound 23) (138 mg, 70%) was obtained.

ESI-MS m/z: 437 (M+H)$^+$; $^1$H-NMR (CDCl$_3$, δ): 2.28 (s, 3H), 4.79 (d, J=12.8 Hz, 1H), 5.53 (s, 2H), 5.58 (d, J=12.8 Hz,

1H), 6.81 (d, J=8.2 Hz, 1H), 6.91 (t, J=7.2 Hz, 1H), 7.02-7.50 (m, 8H), 7.76 (d, J=7.9 Hz, 1H), 8.04 (s, 1H).

Example 24

(E)-8-(Indazol-2-yl)methyl-11-[1-(5-oxo-4,5-dihydro-1,2,4-oxadiazol-3-yl)ethylidene]-6,11-dihydrodibenzo[b,e]oxepine (Compound 24)

Using (E)-2-[8-(indazol-2-yl)methyl-6,11-dihydrodibenzo[b,e]oxepin-11-ylidene]propiononitrile (130 mg, 0.344 mmol) obtained in Example 23, step 1 and in the same manner as in Example 5, the title compound (compound 24) (101 mg, 67%) was obtained.
ESI-MS m/z: 437 (M+H)$^+$; $^1$H-NMR (CDCl$_3$, δ): 2.29 (s, 3H), 4.80 (d, J=12.8 Hz, 1H), 5.54 (d, J=12.8 Hz, 1H), 5.57 (s, 2H), 6.83 (d, J=8.2 Hz, 1H), 6.92 (t, J=7.3 Hz, 1H), 7.05-7.40 (m, 7H), 7.60-7.73 (m, 2H), 7.99 (s, 1H).

Example 25

(E)-8-(Benzimidazol-1-yl)methyl-11-[1-(5-oxo-4,5-dihydro-1,2,4-oxadiazol-3-yl)ethylidene]-6,11-dihydrodibenzo[b,e]oxepine.½citrate (Compound 25)

[step 1] (E)-2-(8-Hydroxymethyl-6,11-dihydrodibenzo[b,e]oxepin-11-ylidene)propiononitrile (500 mg, 1.80 mmol) obtained in Reference Example B4 was dissolved in THF (19 mL), 2,6-lutidine (1.26 mL, 10.8 mmol), lithium bromide (0.940 g, 10.8 mmol) and methanesulfonic anhydride (0.785 g, 4.51 mmol) were added, and the mixture was stirred at room temperature for 16 hr. Ethyl acetate was added to the mixture, and the organic layer was washed with brine, dried over anhydrous magnesium sulfate, and concentrated under reduced pressure to give a residue.
Benzimidazole (234 mg, 1.98 mmol) was dissolved in DMF (2.8 mL), potassium carbonate (1.25 g, 9.02 mmol) was added, and the mixture was stirred for 15 min. To this mixture was added a solution of the residue obtained above in DMF (7 mL), and the mixture was stirred at room temperature for 2 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=7/3 to 5/5) to give (E)-2-[8-(benzimidazol-1-yl)methyl-6,11-dihydrodibenzo[b,e]oxepin-11-ylidene]propiononitrile (549 mg, 81%).
$^1$H-NMR (CDCl$_3$, δ): 2.25 (s, 3H), 4.76 (d, J=12.8 Hz, 1H), 5.39 (s, 2H), 5.42 (d, J=12.8 Hz, 1H), 6.80-7.35 (m, 9H), 7.47 (d, J=7.9 Hz, 1H), 7.84 (m, 1H), 7.96 (s, 1H).
[step 2] Using (E)-2-[8-(benzimidazol-1-yl)methyl-6,11-dihydrodibenzo[b,e]oxepin-11-ylidene]propiononitrile (294 mg, 0.779 mmol) obtained in step 1 and in the same manner as in Example 5, the title compound (compound 25) (131 mg, 39%) was obtained.
ESI-MS m/z: 437 (M+H)$^+$; $^1$H-NMR (DMSO-d$_6$, δ): 2.15 (s, 3H), 2.63 (d, J=15.3 Hz, 0.5×2H), 2.74 (d, J=15.3 Hz, 0.5×2H), 4.88 (d, J=12.2 Hz, 1H), 5.46 (d, J=12.2 Hz, 1H), 5.48 (s, 2H), 6.77 (dd, J=1.3, 8.2 Hz, 1H), 6.91 (t, J=6.9 Hz, 1H), 7.05 (d, J=7.9 Hz, 1H), 7.10-7.38 (m, 5H), 7.36 (s, 1H), 7.46 (m, 1H), 7.64 (m, 1H), 8.38 (s, 1H).

Example 26

(E)-8-(2-Ethylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 26)

[step 1] 2-Ethylbenzimidazole (163 mg, 1.12 mmol) was dissolved in DMF (5.0 mL), potassium carbonate (0.700 g, 5.07 mmol) was added, and the mixture was stirred for 15 min. To this mixture was added (E)-2-(8-chloromethyl-6,11-dihydrodibenzo[b,e]oxepin-11-ylidene)propiononitrile (300 mg, 1.01 mmol) obtained in Reference Example B5, and the mixture was stirred at 60° C. for 3 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=9/1 to 5/5) to give (E)-2-[8-(2-ethylbenzimidazol-1-yl)methyl-6,11-dihydrodibenzo[b,e]oxepin-11-ylidene]propiononitrile (318 mg, 70%).
$^1$H-NMR (CDCl$_3$, δ): 1.43 (t, J=7.6 Hz, 3H), 2.25 (s, 3H), 2.84 (q, J=7.6 Hz, 2H), 4.73 (d, J=12.6 Hz, 1H), 5.35 (s, 2H), 5.41 (d, J=12.6 Hz, 1H), 6.85 (dd, J=1.0, 8.3 Hz, 1H), 6.86-7.34 (m, 8H), 7.44 (d, J=7.9 Hz, 1H), 7.78 (d, J=6.9 Hz, 1H).
[step 2] Using (E)-2-[8-(2-ethylbenzimidazol-1-yl)methyl-6,11-dihydrodibenzo[b,e]oxepin-11-ylidene]propiononitrile (157 mg, 0.387 mmol) obtained in step 1 and in the same manner as in Example 5, the title compound (compound 26) (9 mg, 5%) was obtained.
ESI-MS m/z: 465 (M+H)$^+$; $^1$H-NMR (CDCl$_3$, δ): 1.30 (t, J=7.6 Hz, 3H), 2.29 (s, 3H), 2.89 (q, J=7.6 Hz, 2H), 4.68 (d, J=12.8 Hz, 1H), 5.37 (s, 2H), 5.54 (d, J=12.8 Hz, 1H), 6.80-7.38 (m, 9H), 6.83 (dd, J=1.1, 7.3 Hz, 1H), 7.76 (m, 1H).

Example 27

(E)-8-(2-Propylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 27)

[step 1] Using 2-propylbenzimidazole (179 mg, 1.12 mmol) instead of 2-ethylbenzimidazole, and in the same manner as in Example 26, step 1, (E)-2-[8-(2-propylbenzimidazol-1-yl)methyl-6,11-dihydrodibenzo[b,e]oxepin-11-ylidene]propiononitrile (448 mg, 95%) was obtained.
$^1$H-NMR (CDCl$_3$, δ): 1.01 (t, J=7.6 Hz, 3H), 1.90 (m, 2H), 2.25 (s, 3H), 2.80 (t, J=7.6 Hz, 2H), 4.72 (d, J=12.7 Hz, 1H), 5.36 (s, 2H), 5.40 (d, J=12.7 Hz, 1H), 6.84 (d, J=8.6 Hz, 1H), 6.91 (d, J=7.6 Hz, 1H), 6.96 (s, 1H), 7.00-7.33 (m, 6H), 7.44 (d, J=7.6 Hz, 1H), 7.77 (d, J=7.9 Hz, 1H).
[step 2] Using (E)-2-[8-(2-propylbenzimidazol-1-yl)methyl-6,11-dihydrodibenzo[b,e]oxepin-11-ylidene]propiononitrile (344 mg, 0.82 mmol) obtained in step 1 and in the same manner as in Example 5, the title compound (compound 27) (46 mg, 12%) was obtained.
ESI-MS m/z: 479 (M+H)$^+$; $^1$H-NMR (CDCl$_3$, δ): 1.00 (t, J=7.6 Hz, 3H), 1.86 (q, J=7.6 Hz, 2H), 2.29 (s, 3H), 2.79 (t, J=7.6 Hz, 2H), 4.71 (d, J=12.9 Hz, 1H), 5.35 (s, 2H), 5.49 (d, J=12.9 Hz, 1H), 6.82 (dd, J=1.0, 8.3 Hz, 1H), 6.92 (t, J=7.4 Hz, 1H), 7.00 (s, 1H), 7.04-7.30 (m, 7H), 7.74 (dd, J=2.2, 6.4 Hz, 1H).

Example 28

(E)-8-(2-Isopropylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 28)

[step 1] Using 2-isopropylbenzimidazole (596 mg, 3.72 mmol) instead of 2-ethylbenzimidazole, and in the same manner as in Example 26, step 1, (E)-2-[8-(2-isopropylbenzimidazol-1-yl)methyl-6,11-dihydrodibenzo[b,e]oxepin-11-ylidene]propiononitrile (1.246 g, 80%) was obtained.

¹H-NMR (CDCl₃, δ): 1.39 (t, J=7.3 Hz, 6H), 2.24 (s, 3H), 3.12 (m, 2H), 4.72 (d, J=12.8 Hz, 1H), 5.38 (s, 2H), 5.40 (d, J=12.8 Hz, 1H), 6.85 (dd, J=1.1, 8.4 Hz, 1H), 6.88-7.32 (m, 8H), 7.43 (d, J=7.9 Hz, 1H), 7.79 (d, J=7.3 Hz, 1H).

[step 2] Using (E)-2-[8-(2-isopropylbenzimidazol-1-yl)methyl-6,11-dihydrodibenzo[b,e]oxepin-11-ylidene]propiononitrile (400 mg, 0.953 mmol) obtained in step 1 and in the same manner as in Example 5, the title compound (compound 28) (70 mg, 15%) was obtained.

ESI-MS m/z: 479 (M+H)⁺; ¹H-NMR (CDCl₃, δ): 1.37 (d, J=4.8 Hz, 3H), 1.40 (d, J=4.8 Hz, 3H), 2.29 (s, 3H), 3.12 (m, 1H), 4.74 (d, J=12.8 Hz, 1H), 5.39 (s, 2H), 5.51 (d, J=12.8 Hz, 1H), 6.83 (d, J=8.6 Hz, 1H), 6.93 (t, J=7.6 Hz, 1H), 7.00-7.30 (m, 8H), 7.77 (dd, J=1.6, 6.9 Hz, 1H).

Example 29

(E)-8-(2-tert-Butylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 29)

[step 1] Using 2-tert-butylbenzimidazole (195 mg, 1.12 mmol) instead of 2-ethylbenzimidazole, and in the same manner as in Example 26, step 1, (E)-2-[8-(2-tert-butylbenzimidazol-1-yl)methyl-6,11-dihydrodibenzo[b,e]oxepin-11-ylidene]propiononitrile (89 mg, 18%) was obtained.

¹H-NMR (CDCl₃, δ): 1.51 (s, 9H), 2.25 (s, 3H), 4.70 (d, J=12.5 Hz, 1H), 5.40 (d, J=12.5 Hz, 1H), 5.62 (s, 2H), 6.85 (dd, J=1.3, 8.1 Hz, 1H), 6.87-7.35 (m, 8H), 7.43 (d, J=7.9 Hz, 1H), 7.81 (d, J=7.9 Hz, 1H).

[step 2] Using (E)-2-[8-(2-tert-butylbenzimidazol-1-yl)methyl-6,11-dihydrodibenzo[b,e]oxepin-11-ylidene]propiononitrile (86 mg, 0.197 mmol) obtained in step 1 and in the same manner as in Example 5, the title compound (compound 29) (61 mg, 63%) was obtained.

ESI-MS m/z: 493 (M+H)⁺; ¹H-NMR(CDCl₃, δ): 1.50 (s, 9H), 2.27 (s, 3H), 4.73 (d, J=12.9 Hz, 1H), 5.55 (d, J=12.9 Hz, 1H), 5.62 (s, 2H), 6.80-7.30 (m, 10H), 7.78 (d, J=7.9 Hz, 1H).

Example 30

(E)-8-(2-Methoxymethylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 30)

[step 1] Using 2-methoxymethylbenzimidazole (100 mg, 0.617 mmol) instead of 2-ethylbenzimidazole, and in the same manner as in Example 26, step 1, (E)-2-[8-(2-methoxymethylbenzimidazol-1-yl)methyl-6,11-dihydrodibenzo[b,e]oxepin-11-ylidene]propiononitrile (176 mg, 68%) was obtained.

¹H-NMR (CDCl₃, δ): 2.24 (s, 3H), 3.36 (s, 3H), 4.70 (s, 2H), 4.73 (d, J=12.9 Hz, 1H), 5.41 (d, J=12.5 Hz, 1H), 5.50 (s, 2H), 6.84 (d, J=7.9 Hz, 1H), 6.91 (t, J=7.4 Hz, 1H), 7.00-7.10 (m, 2H), 7.15-7.35 (m, 5H), 7.43 (d, J=7.9 Hz, 1H), 7.81 (m, 1H).

[step 2] Using (E)-2-[8-(2-methoxymethylbenzimidazol-1-yl)methyl-6,11-dihydrodibenzo[b,e]oxepin-11-ylidene]propiononitrile (123 mg, 0.292 mmol) obtained in step 1 and in the same manner as in Example 5, the title compound (compound 30) (45 mg, 32%) was obtained.

ESI-MS m/z: 481 (M+H)⁺; ¹H-NMR (CDCl₃, δ): 2.29 (s, 3H), 3.35 (s, 3H), 4.68 (s, 2H), 4.73 (d, J=12.9 Hz, 1H), 5.42-5.56 (m, 3H), 6.82 (d, J=7.3 Hz, 1H), 6.92 (t, J=7.0 Hz, 1H), 7.08-7.35 (m, 8H), 7.78 (m, 1H).

Example 31

(E)-8-(2-Hydroxymethylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 31)

[step 1] Using 2-hydroxymethylbenzimidazole (276 mg, 1.86 mmol) instead of 2-ethylbenzimidazole, and in the same manner as in Example 26, step 1, (E)-2-[8-(2-hydroxymethylbenzimidazol-1-yl)methyl-6,11-dihydrodibenzo[b,e]oxepin-11-ylidene]propiononitrile (738 mg, 97%) was obtained.

¹H-NMR (CDCl₃, δ): 2.23 (s, 3H), 4.72 (d, J=12.6 Hz, 1H), 4.85 (s, 2H), 5.40 (d, J=12.6 Hz, 1H), 5.44 (s, 2H), 6.84 (d, J=8.3 Hz, 1H), 6.90 (t, J=7.4 Hz, 1H), 7.00-7.39 (m, 7H), 7.43 (d, J=7.9 Hz, 1H), 7.76 (d, J=6.3 Hz, 1H).

[step 2] Using (E)-2-[8-(2-hydroxymethylbenzimidazol-1-yl)methyl-6,11-dihydrodibenzo[b,e]oxepin-11-ylidene]propiononitrile (600 mg, 1.47 mmol) obtained in step 1 and in the same manner as in Example 5, the title compound (compound 31) (279 mg, 41%) was obtained.

ESI-MS m/z: 467 (M+H)⁺; ¹H-NMR (CDCl₃, δ): 2.15 (s, 3H), 4.70 (d, J=5.8 Hz, 2H), 4.84 (d, J=12.6 Hz, 1H), 5.46 (d, J=12.6 Hz, 1H), 5.54 (s, 2H), 6.77 (d, J=7.3 Hz, 1H), 6.91 (m, 1H), 7.04 (d, J=7.8 Hz, 1H), 7.09-7.39 (m, 7H), 7.60 (m, 1H).

Example 32

(E)-8-[2-(2-Hydroxyethyl)benzimidazol-1-yl]methyl-11-[1-(5-oxo-4,5-dihydro-1,2,4-oxadiazol-3-yl)ethylidene]-6,11-dihydrodibenzo[b,e]oxepine (Compound 32)

[step 1] Using 2-(2-hydroxyethyl)benzimidazole (603 mg, 3.72 mmol) instead of 2-ethylbenzimidazole, and in the same manner as in Example 26, step 1, (E)-2-{8-[2-(2-hydroxyethyl)benzimidazol-1-yl]methyl-6,11-dihydrodibenzo[b,e]oxepin-11-ylidene}propiononitrile (1.40 g, 89%) was obtained.

¹H-NMR (CDCl₃, δ): 2.25 (s, 3H), 2.98 (t, J=5.3 Hz, 2H), 4.12 (m, 2H), 4.27 (m, 1H), 4.73 (d, J=12.5 Hz, 1H), 5.35 (s, 2H), 5.41 (d, J=12.5 Hz, 1H), 6.84 (d, J=8.6 Hz, 1H), 6.91 (t, J=7.7 Hz, 1H), 6.99 (s, 1H), 7.04 (s, 1H), 7.05 (dd, 3¹=1.6, 7.7 Hz, 1H), 7.19-7.38 (m, 4H), 7.44 (d, J=7.9 Hz, 1H), 7.75 (dd, J=2.3, 6.9 Hz, 1H).

[step 2] Using (E)-2-{8-[2-(2-hydroxyethyl)benzimidazol-1-yl]methyl-6,11-dihydrodibenzo[b,e]oxepin-11-ylidene}propiononitrile (700 mg, 1.66 mmol) obtained in step 1 and in the same manner as in Example 5, the title compound (compound 32) (287 mg, 36%) was obtained.

ESI-MS m/z: 481 (M+H)⁺; ¹H-NMR (DMSO-d₆, δ): 2.15 (s, 3H), 3.13 (t, J=6.3 Hz, 2H), 3.85 (t, J=6.3 Hz, 2H), 4.86 (d, J=12.6 Hz, 1H), 5.47 (d, J=12.6 Hz, 1H), 5.60 (s, 2H), 6.77 (d, J=7.9 Hz, 1H), 6.91 (t, J=7.4 Hz, 1H), 7.06 (d, J=7.6 Hz, 1H), 7.10-7.35 (m, 6H), 7.49 (d, J=7.9 Hz, 1H), 7.65 (d, J=7.3 Hz, 1H).

Example 33

(E)-8-(2-Benzylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 33)

[step1] Using 2-benzylbenzimidazole (116 mg, 0.557 mmol) instead of 2-ethylbenzimidazole, and in the same manner as in Example 26, step 1, (E)-2-[8-(2-benzylbenzimidazol-1-yl)methyl-6,11-dihydrodibenzo[b,e]oxepin-11-ylidene]propiononitrile (214 mg, 82%) was obtained.

$^1$H-NMR (CDCl$_3$, δ): 2.24 (s, 3H), 4.26 (s, 2H), 4.59 (d, J=12.6 Hz, 1H), 5.21 (s, 2H), 5.32 (d, J=12.6 Hz, 1H), 6.66 (s, 1H), 6.82-7.42 (m, 14H), 7.82 (d, J=7.6 Hz, 1H).

[step 2] Using (E)-2-[8-(2-benzylbenzimidazol-1-yl)methyl-6,11-dihydrodibenzo[b,e]oxepin-11-ylidene]propiononitrile (213 mg, 0.457 mmol) obtained in step 1 and in the same manner as in Example 5, the title compound (compound 33) (99 mg, 41%) was obtained.

ESI-MS m/z: 527 (M+H)$^+$; $^1$H-NMR (CDCl$_3$, δ): 2.27 (s, 3H), 4.25 (s, 2H), 4.58 (d, J=12.7 Hz, 1H), 5.22 (s, 2H), 5.41 (d, J=12.7 Hz, 1H), 6.67 (s, 1H), 6.84 (d, J=8.2 Hz, 1H), 6.89-7.38 (m, 13H), 7.80 (d, J=7.2 Hz, 1H).

Example 34

(E)-8-(2-Phenylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 34)

[step 1] Using 2-phenylbenzimidazole (218 mg, 1.12 mmol) instead of 2-ethylbenzimidazole, and in the same manner as in Example 26, step 1, (E)-2-[8-(2-phenylbenzimidazol-1-yl)methyl-6,11-dihydrodibenzo[b,e]oxepin-11-ylidene]propiononitrile (537 mg) was obtained quantitatively.

$^1$H-NMR (CDCl$_3$, δ): 2.26 (s, 3H), 4.74 (d, J=12.9 Hz, 1H), 5.44 (d, J=12.9 Hz, 1H), 5.47 (s, 2H), 6.87 (dd, J=1.0, 7.3 Hz, 1H), 6.94 (d, J=6.9 Hz, 1H), 7.06 (s, 1H), 7.07 (d, J=7.6 Hz, 1H), 7.16-7.72 (m, 11H), 7.88 (d, J=7.6 Hz, 1H).

[step 2] Using (E)-2-[8-(2-phenylbenzimidazol-1-yl)methyl-6,11-dihydrodibenzo[b,e]oxepin-11-ylidene]propiononitrile (230 mg, 0.507 mmol) obtained in step 1 and in the same manner as in Example 5, the title compound (compound 34) (183 mg, 70%) was obtained.

ESI-MS m/z: 513 (M+H)$^+$; $^1$H-NMR (CDCl$_3$, δ): 2.23 (s, 3H), 4.68 (d, J=12.7 Hz, 1H), 5.44 (s, 2H), 5.45 (d, J=12.7 Hz, 1H), 6.83 (d, J=7.9 Hz, 1H), 6.85-7.70 (m, 14H), 7.83 (m, 1H).

Example 35

(E)-8-(2-Propyl-4-methylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 35)

[step 1] Using 4-methyl-2-propylbenzimidazole (EP400835; 1.00 g, 5.74 mmol) instead of 2-ethylbenzimidazole, and in the same manner as in Example 26, step 1, (E)-2-[8-(4-methyl-2-propylbenzimidazol-1-yl)methyl-6,11-dihydrodibenzo[b,e]oxepin-11-ylidene]propiononitrile (2.03 g, 82%) was obtained.

$^1$H-NMR (CDCl$_3$, δ): 1.00 (t, J=7.6 Hz, 3H), 1.80 (m, 2H), 2.24 (s, 3H), 2.69 (s, 3H), 2.83 (t, J=7.6 Hz, 2H), 4.72 (d, J=12.9 Hz, 1H), 5.34 (s, 2H), 5.40 (d, J=12.9 Hz, 1H), 6.80-7.32 (m, 9H), 7.43 (d, J=7.9 Hz, 1H).

[step 2] Using (E)-2-[8-(4-methyl-2-propylbenzimidazol-1-yl)methyl-6,11-dihydrodibenzo[b,e]oxepin-11-ylidene]propiononitrile (2.03 g, 4.68 mmol) obtained in step 1 and in the same manner as in Example 5, the title compound (compound 35) (1.17 g, 51%) was obtained.

ESI-MS m/z: 493 (M+H)$^+$; $^1$H-NMR (DMSO-d$_6$, δ): 0.88 (t, J=7.6 Hz, 3H), 1.66 (m, 2H), 2.14 (s, 3H), 2.49 (s, 3H), 2.75 (t, J=7.6 Hz, 2H), 4.85 (d, J=12.6 Hz, 1H), 5.43 (s, 2H), 5.45 (d, J=12.6 Hz, 1H), 6.76 (d, J=8.6 Hz, 1H), 6.88-7.08 (m, 5H), 7.12-7.28 (m, 4H).

Example 36

(E)-8-(4-Chloro-2-cyclopropylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 36)

[step 1] Using 4-chloro-2-cyclopropylbenzimidazole (764 mg, 3.97 mmol) obtained in Reference Example A1 instead of benzimidazole, and in the same manner as in Example 25, step 1, (E)-2-[8-(4-chloro-2-cyclopropylbenzimidazol-1-yl)methyl-6,11-dihydrodibenzo[b,e]oxepin-11-ylidene]propiononitrile (848 mg, 47%) was obtained.

$^1$H-NMR (CDCl$_3$, δ): 1.07 (m, 2H), 1.30 (m, 2H), 1.88 (m, 1H), 2.25 (s, 3H), 4.74 (d, J=12.7 Hz, 1H), 5.41 (d, J=12.7 Hz, 1H), 5.47 (s, 2H), 6.82-7.33 (m, 9H), 7.45 (d, J=7.9 Hz, 1H).

[step 2] Using (E)-2-[8-(4-chloro-2-cyclopropylbenzimidazol-1-yl)methyl-6,11-dihydrodibenzo[b,e]oxepin-11-ylidene]propiononitrile (345 mg, 0.763 mmol) obtained in step 1 and in the same manner as in Example 5, the title compound (compound 36) (187 mg, 48%) was obtained.

ESI-MS m/z: 511 (M+H)$^+$; $^1$H-NMR (DMSO-d$_6$, δ): 0.89-1.15 (m, 4H), 2.15 (s, 3H), 2.21 (m, 1H), 4.88 (d, J=12.6 Hz, 1H), 5.46 (d, J=12.6 Hz, 1H), 5.60 (s, 2H), 6.77 (d, J=7.3 Hz, 1H), 6.91 (m, 1H), 7.00-7.38 (m, 7H), 7.42 (d, J=7.9 Hz, 1H).

Example 37

(E)-2-(4-Phenyl-2-propylimidazol-1-yl)methyl-5-(5-oxo-4,5-dihydro-1,2,4-oxadiazol-3-yl)methylene-10,11-dihydro-5H-dibenzo[a,d]cycloheptene (Compound 37)

[step 1] Using (E)-2-(2-bromomethyl-10,11-dihydro-5H-dibenzo[a,d]cyclohepten-5-ylidene)acetonitrile (200 mg, 0.617 mmol) obtained in Reference Example B1 and in the same manner as in Example 20, step 1, (E)-2-[2-(4-phenyl-2-propylimidazol-1-yl)methyl-10,11-dihydro-5H-dibenzo[a,d]cyclohepten-5-ylidene]acetonitrile (222 mg, 87%) was obtained.

$^1$H-NMR (CDCl$_3$, δ): 1.31 (t, J=7.6 Hz, 3H), 2.69 (q, J=7.6 Hz, 2H), 3.11 (s, 4H), 5.05 (s, 2H), 5.70 (s, 1H), 6.87 (s, 1H), 6.96 (d, J=7.6 Hz, 1H), 7.06 (s, 1H), 7.18-7.47 (m, 8H), 7.73-7.76 (m, 2H).

[step 2] Using (E)-2-[2-(4-phenyl-2-propylimidazol-1-yl)methyl-10,11-dihydro-5H-dibenzo[a,d]cyclohepten-5-ylidene]acetonitrile (156 mg, 0.375 mmol) obtained in step 1 and in the same manner as in Example 5, the title compound (compound 37) (159 mg, 89%) was obtained.

ESI-MS m/z: 475 (M+H)$^+$; $^1$H-NMR (CDCl$_3$, δ): 1.31 (t, J=7.6 Hz, 3H), 2.68 (q, J=7.6 Hz, 2H), 2.76-3.07 (m, 2H), 3.08-3.44 (m, 2H), 5.06 (s, 2H), 6.83 (s, 1H), 7.02 (d, J=7.7 Hz, 1H), 7.03-7.14 (m, 2H), 7.15-7.49 (m, 8H), 7.70-7.75 (m, 2H).

Example 38

(E)-2-(2-Ethyl-3-methylindol-1-yl)methyl-5-(1H-tetrazol-5-yl)methylene-10,11-dihydro-5H-dibenzo[a,d]cycloheptene (Compound 38)

[step 1] 2-Ethyl-3-methylindole (196 mg, 1.23 mmol) was dissolved in DMF (3.2 mL), sodium hydride (60%; 49 mg, 1.23 mmol) was added, and the mixture was stirred at room temperature for 15 min. To the reaction mixture was added (E)-2-(2-bromomethyl-10,11-dihydro-5H-dibenzo[a,d]cyclohepten-5-ylidene)acetonitrile (200 mg, 0.617 mmol) obtained in Reference Example B1, and the mixture was stirred at room temperature for 2 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=9/1) to give (E)-[2-(2-ethyl-3-methylindol-1-yl)methyl-10,11-dihydro-5H-dibenzo[a,d]cyclohepten-5-ylidene]acetonitrile (117 mg, 47%).

$^1$H-NMR (CDCl$_3$, δ): 1.10 (t, J=7.6 Hz, 3H), 2.29 (s, 3H), 2.69 (q, J=7.6 Hz, 2H), 2.95-3.11 (m, 4H), 5.26 (s, 2H), 5.65 (s, 1H), 6.73 (d, J=7.9 Hz, 1H), 6.78 (s, 1H), 7.01-7.35 (m, 7H), 7.40 (m, 1H), 7.52 (d, J=5.3 Hz, 1H).

[step 2] Using (E)-[2-(2-ethyl-3-methylindol-1-yl)methyl-10,11-dihydro-5H-dibenzo[a,d]cyclohepten-5-ylidene]acetonitrile (50 mg, 0.124 mmol) obtained in step 1 and in the same manner as in Example 4, the title compound (compound 38) (37 mg, 68%) was obtained.

m/z: 446 (M+H)$^+$; $^1$H-NMR (CDCl$_3$, δ): 1.11 (t, J=7.6 Hz, 3H), 2.30 (s, 3H), 2.70 (q, J=7.6 Hz, 2H), 2.86 (m, 2H), 3.27 (m, 2H), 5.27 (s, 2H), 6.74 (s, 1H), 6.82 (d, J=8.2 Hz, 1H), 7.00-7.49 (m, 9H), 7.53 (m, 1H).

Example 39

(E)-2-(2-Ethyl-3-methylindol-1-yl)methyl-5-(5-oxo-4,5-dihydro-1,2,4-oxadiazol-3-yl)methylene-10,11-dihydro-5H-dibenzo[a,d]cycloheptene (Compound 39)

Using (E)-[2-(2-ethyl-3-methylindol-1-yl)methyl-10,11-dihydro-5H-dibenzo[a,d]cyclohepten-5-ylidene]acetonitrile (50 mg, 0.124 mmol) obtained in Example 38, step 1 and in the same manner as in Example 5, the title compound (compound 39) (37 mg, 65%) was obtained.

ESI-MS m/z: 462 (M+H)$^+$; $^1$H-NMR (CDCl$_3$, δ): 1.11 (t, J=7.6 Hz, 3H), 2.30 (s, 3H), 2.69 (q, J=7.6 Hz, 2H), 2.86 (m, 2H), 3.20 (m, 2H), 5.26 (s, 2H), 6.47 (s, 1H), 6.73 (s, 1H), 6.78 (d, J=7.9 Hz, 1H), 7.04-7.22 (m, 4H), 7.22-7.48 (m, 4H), 7.55 (m, 1H).

Example 40

(E)-2-(3-Phenoxyphenoxy)methyl-5-(1H-tetrazol-5-yl)methylene-10,11-dihydro-5H-dibenzo[a,d]cycloheptene (Compound 40)

[step 1] (E)-2-(2-Chloromethyl-10,11-dihydro-5H-dibenzo[a,d]cyclohepten-5-ylidene)acetonitrile (200 mg, 0.715 mmol) obtained in Reference Example B2 and 3-phenoxyphenol (146 mg, 0.786 mmol) were dissolved in DMF (3.2 mL), potassium carbonate (494 mg, 3.60 mmol) was added, and the mixture was stirred at 60° C. for 2 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=80/20) to give (E)-2-[2-(3-phenoxyphenoxy)methyl-10,11-dihydro-5H-dibenzo[a,d]cyclohepten-5-ylidene]acetonitrile (348 mg) quantitatively.

$^1$H-NMR (CDCl$_3$, δ): 3.03-3.23 (m, 4H), 4.97 (s, 2H), 5.72 (s, 1H), 6.53-6.75 (m, 3H), 6.95-7.40 (m, 12H), 7.45 (dd, J=1.6, 5.6 Hz, 1H).

[step 2] Using (E)-2-[2-(3-phenoxyphenoxy)methyl-10,11-dihydro-5H-dibenzo[a,d]cyclohepten-5-ylidene]acetonitrile (133 mg, 0.310 mmol) obtained in step 1 and in the same manner as in Example 4, the title compound (compound 40) (112 mg, 76%) was obtained.

ESI-MS m/z: 473 (M+H)$^+$; $^1$H-NMR (CDCl$_3$, δ): 2.78-3.13 (m, 2H), 3.25-3.45 (m, 2H), 4.98 (s, 2H), 6.60-6.75 (m, 3H), 6.95-7.58 (m, 14H).

Example 41

(E)-2-(Naphthalen-2-yloxy)methyl-5-(1H-tetrazol-5-yl)methylene-10,11-dihydro-5H-dibenzo[a,d]cycloheptene (Compound 41)

Using 2-naphthol (113 mg, 0.786 mmol) instead of 3-phenoxyphenol, and in the same manner as in Example 40, the title compound (compound 41) (42 mg, 12%) was obtained.

ESI-MS m/z: 431 (M+H)$^+$; $^1$H-NMR (CDCl$_3$, δ): 2.79-3.21 (m, 2H), 3.30-3.52 (m, 2H), 5.15 (s, 2H), 7.13 (s, 1H), 7.15-7.52 (m, 10H), 7.54 (d, J=7.9 Hz, 1H), 7.69-7.85 (m, 3H).

Example 42

(E)-2-(2-Ethyl-7-methyl-3H-imidazo[4,5-c]pyridin-3-yl)methyl-5-(1H-tetrazol-5-yl)methylene-10,11-dihydro-5H-dibenzo[a,d]cycloheptene (Compound 42)

[step 1] Using 2-ethyl-7-methyl-3H-imidazo[4,5-c]pyridine (U.S. Pat. No. 5,332,744; 462 mg, 2.87 mmol) instead of 2-propylbenzimidazole, and in the same manner as in Example 1, (E)-2-[2-(2-ethyl-7-methyl-3H-imidazo[4,5-c]pyridin-3-yl)methyl-10,11-dihydro-5H-dibenzo[a,d]cyclohepten-5-ylidene]acetonitrile (408 mg, 35%) was obtained.

$^1$H-NMR (CDCl$_3$, δ): 1.41 (t, J=7.6 Hz, 3H), 2.64 (s, 3H), 2.91 (q, J=7.6 Hz, 2H), 3.07 (s, 4H), 5.34 (s, 2H), 5.67 (s, 1H), 6.82-7.46 (m, 7H), 8.23 (s, 1H), 8.40 (s, 1H).

[step 2] Using (E)-2-[2-(2-ethyl-7-methyl-3H-imidazo[4,5-c]pyridin-3-yl)methyl-10,11-dihydro-5H-dibenzo[a,d]cyclohepten-5-ylidene]acetonitrile (70 mg, 0.173 mmol) obtained in step 1 and in the same manner as in Example 4, the title compound (compound 42) (22 mg, 28%) was obtained.

ESI-MS m/z: 448 (M+H)$^+$; $^1$H-NMR (CDCl$_3$, δ): 1.43 (3H, t, J=7.5 Hz), 2.46-3.10 (4H, m), 2.62 (3H, s), 2.94 (2H, q, J=7.5 Hz), 5.34 (2H, s), 6.68 (1H, s), 6.93-7.17 (6H, m), 7.46 (1H, d, J=8.1 Hz), 7.90 (1H, s), 8.27 (1H, s).

Example 43

(E)-[2-(Biphenyl-3-ylaminomethyl)-10,11-dihydro-5H-dibenzo[a,d]cyclohepten-5-ylidene]acetonitrile (Compound 43)

Using 3-aminobiphenyl (1.20 g, 7.09 mmol) instead of 2-propylbenzimidazole, and in the same manner as in Example 1, the title compound (compound 43) (680 mg, 46%) was obtained.

ESI-MS m/z: 413 (M+H)$^+$; $^1$H-NMR (CDCl$_3$, δ): 3.05-3.22 (m, 4H), 4.35 (s, 2H), 5.71 (s, 1H), 6.56-6.60 (m, 1H), 6.80-6.83 (m, 1H), 6.95 (d, J=7.6 Hz, 1H), 7.16-7.28 (m, 5H), 7.29-7.47 (m, 6H), 7.51-7.54 (m, 2H).

Example 44

(E)-[2-(N-(Biphenyl-3-yl)-2-carboxyacetamido)methyl-10,11-dihydro-5H-dibenzo[a,d]cyclohepten-5-ylidene]acetonitrile (Compound 44)

[step 1] Compound 43 (200 mg, 0.49 mmol) obtained in Example 43 was dissolved in DMF (1 mL), and the mixture was cooled to 0° C. Methyl 3-chloro-3-oxopropanoate (99 mg, 0.73 mmol) was added, and the mixture was stirred at room temperature for 7 hr. To this mixture was added saturated aqueous sodium hydrogen carbonate solution (20 mL), and the precipitate was collected by filtration to give (E)-[2-(N-(biphenyl-3-yl)-3-methoxy-3-oxopropanamido)methyl-10,11-dihydro-5H-dibenzo[a,d]cyclohepten-5-ylidene]acetonitrile quantitatively.

ESI-MS m/z: 513 (M+H)$^+$; $^1$H-NMR (CDCl$_3$, δ): 3.11 (br, 4H), 3.28 (s, 2H), 3.66 (s, 3H), 4.90 (s, 2H), 5.69 (s, 1H), 7.01 (d, J=7.6 Hz, 1H), 7.06 (s, 1H), 7.08-7.18 (m, 2H), 7.19-7.25 (m, 2H), 7.28-7.47 (m, 9H), 7.55 (d, J=7.6 Hz, 1H).

[step 2] (E)-[2-(N-(Biphenyl-3-yl)-3-methoxy-3-oxopropanamido)methyl-10,11-dihydro-5H-dibenzo[a,d]cyclohepten-5-ylidene]acetonitrile (52 mg, 0.10 mmol) obtained in step 1 was dissolved in ethanol (2 mL), 2 mol/L aqueous sodium hydroxide solution (0.1 mL) was added, and the mixture was stirred at room temperature for 3 hr. The mixture was adjusted to pH 2 with 2 mol/L hydrochloric acid, and the mixture was extracted with chloroform. The organic layer was washed with brine, dried over anhydrous magnesium sulfate, and concentrated under reduced pressure. The residue was purified by reversed-phase liquid chromatography (water/acetonitrile=7/3 to 1/9) to give the title compound (compound 44) (30 mg, 60%).

ESI-MS m/z: 499 (M+H)$^+$; $^1$H-NMR (CDCl$_3$, δ): 3.10 (s, 4H), 3.17 (s, 2H), 4.91 (s, 2H), 5.69 (s, 1H), 6.95 (d, J=7.6 Hz, 1H), 7.02 (s, 1H), 7.05-7.08 (m, 1H), 7.21-7.25 (m, 2H), 7.31 (d, J=7.6 Hz, 2H), 7.36 (s, 6H), 7.44-7.51 (m, 2H), 7.60-7.64 (m, 1H).

Example 45

(E)-{2-[(Biphenyl-3-ylbutyrylamino)methyl]-10,11-dihydro-5H-dibenzo[a,d]cyclohepten-5-ylidene}acetonitrile (Compound 45)

Compound 43 (27 mg, 0.066 mmol) obtained in Example 43 was dissolved in DMF (1 mL), pyridine (6.2 mg, 0.079 mmol) and butyryl chloride (8.4 mg, 0.079 mmol) were added, and the mixture was stirred at room temperature for 5 hr. Water and saturated aqueous sodium hydrogen carbonate solution were added to the mixture, and the mixture was filtered to give the title compound (compound 45) (28 mg, 88%).

ESI-MS m/z: 483 (M+H)$^+$; $^1$H-NMR (CDCl$_3$, δ) 0.84 (t, J=7.4 Hz, 3H), 1.60-1.66 (m, 2H), 2.10 (t, J=7.6 Hz, 2H), 3.08 (s, 4H), 4.87 (s, 2H), 5.69 (s, 1H), 6.94-7.11 (m, 4H), 7.19-7.24 (m, 2H), 7.31-7.41 (m, 8H), 7.43-7.48 (m, 1H), 7.53 (d, J=7.6 Hz, 1H).

Example 46

(E)-2-[(Biphenyl-3-ylbutyrylamino)methyl]-5-(1H-tetrazol-5-yl)methylene-10,11-dihydro-5H-dibenzo[a,d]cycloheptene (Compound 46)

Using the compound 45 (27 mg, 0.07 mmol) obtained in Example 45 and in the same manner as in Example 4, the title compound (compound 46) (20 mg, 95%) was obtained.

ESI-MS m/z: 526 (M+H)$^+$; $^1$H-NMR (CDCl$_3$, δ) 0.85 (t, J=7.4 Hz, 3H), 1.52-1.72 (m, 2H), 2.11 (t, J=7.4 Hz, 2H), 2.78-3.05 (m, 2H), 3.20-3.43 (m, 2H), 4.87 (d, J=3.3 Hz, 2H), 6.99 (d, J=7.9 Hz, 1H), 7.03 (s, 1H), 7.08 (s, 1H), 7.11 (d, J=9.6 Hz, 2H), 7.20 (d, J=6.9 Hz, 1H), 7.31-7.47 (m, 10H), 7.55 (d, J=7.9 Hz, 1H).

Example 47

(E)-[2-(4-Methyl-6-phenyl-2-propylbenzimidazol-1-yl)methyl-10,11-dihydro-5H-dibenzo[a,d]cyclohepten-5-ylidene]acetonitrile (Compound 47)

[step 1] Under a nitrogen atmosphere, 6-bromo-4-methyl-2-propylbenzimidazole (WO2004082621; 300 mg, 1.19 mmol) was dissolved in DMF (3 mL), and the mixture was cooled to 0° C. Potassium carbonate (829 mg, 6.00 mmol) was added, and the mixture was stirred at room temperature for 20 min. To this mixture was added (E)-2-(2-bromomethyl-10,11-dihydro-5H-dibenzo[a,d]cyclohepten-5-ylidene)acetonitrile (421 mg, 1.30 mmol) obtained in Reference Example B1, and the mixture was stirred at room temperature for 4 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=3/1 to 1/3) to give (E)-[2-(6-bromo-4-methyl-2-propylbenzimidazol-1-yl)methyl-10,11-dihydro-5H-dibenzo[a,d]cyclohepten-5-ylidene]acetonitrile (615 mg, 95%).

ESI-MS m/z: 496 (M+H)$^+$; $^1$H-NMR (CDCl$_3$, δ): 0.99 (t, J=7.3 Hz, 3H), 1.72-1.88 (m, 2H), 2.64 (s, 3H), 2.78 (t, J=7.3 Hz, 2H), 3.07 (s, 4H), 5.23 (s, 2H), 5.68 (s, 1H), 6.76 (s, 1H), 6.81 (d, J=7.9 Hz, 1H), 7.10 (s, 1H), 7.15-7.37 (m, 5H), 7.44 (d, J=6.8 Hz, 1H).

[step 2] Under a nitrogen atmosphere, (E)-[2-(6-bromo-4-methyl-2-propylbenzimidazol-1-yl)methyl-10,11-dihydro-5H-dibenzo[a,d]cyclohepten-5-ylidene]acetonitrile (910 mg, 1.83 mmol) obtained in step 1 was dissolved in DMF (25 mL), phenylboronic acid (666 mg, 5.46 mmol), cesium carbonate (1.19 g, 3.64 mmol) and tetrakis(triphenylphosphine)palladium (421 mg, 0.36 mmol) were added, and the mixture was stirred at 100° C. for 12 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=1/1 to 0/1) to give the title compound (compound 47) (703 mg, 87%).

ESI-MS m/z: 494 (M+H)$^+$; $^1$H-NMR (CDCl$_3$, δ): 1.01 (t, J=7.3 Hz, 3H), 1.72-1.90 (m, 2H), 2.74 (s, 3H), 2.83 (t, J=7.3 Hz, 2H), 3.06 (s, 4H), 5.34 (d, J=9.3 Hz, 2H), 5.66 (s, 1H), 6.82 (s, 1H), 6.86 (d, J=7.9 Hz, 1H), 7.12 (s, 1H), 7.17-7.24 (m, 2H), 7.28-7.44 (m, 7H), 7.54 (d, J=8.4 Hz, 2H).

Example 48

(E)-2-(4-Methyl-6-phenyl-2-propylbenzimidazol-1-yl)methyl-5-(1H-tetrazol-5-yl)methylene-10,11-dihydro-5H-dibenzo[a,d]cycloheptene (Compound 48)

Using compound 47 (500 mg, 1.01 mmol) obtained in Example 47 and in the same manner as in Example 4, the title compound (compound 48) (470 mg, 87%) was obtained.

ESI-MS m/z: 537 (M+H)$^+$; $^1$H-NMR (CDCl$_3$, δ): 1.00 (t, J=7.4 Hz, 3H), 1.73-1.89 (m, 2H), 2.71 (s, 3H), 2.73-2.98 (br, 2H), 2.84 (t, J=7.4 Hz, 2H), 3.15-3.39 (br, 2H), 5.33 (s, 2H), 6.76 (s, 1H), 6.95 (d, J=7.9 Hz, 1H), 7.04 (s, 1H), 7.17 (d, J=6.9 Hz, 2H), 7.28-7.46 (m, 8H), 7.55 (d, J=5.3 Hz, 2H).

Example 49

(E)-2-(4-Methyl-6-phenyl-2-propylbenzimidazol-1-yl)methyl-5-(5-oxo-4,5-dihydro-1,2,4-oxadiazol-3-yl)methylene-10,11-dihydro-5H-dibenzo[a,d]cycloheptene (Compound 49)

Using compound 47 (50 mg, 0.10 mmol) obtained in Example 47 and in the same manner as in Example 5, the title compound (compound 49) (15 mg, 28%) was obtained.
ESI-MS m/z: 553 (M+H)$^+$; $^1$H-NMR (CDCl$_3$, δ): 1.03 (t, J=7.3 Hz, 3H), 1.78-1.93 (m, 2H), 2.72-3.01 (m, 2H), 2.77 (s, 3H), 3.14-3.45 (m, 2H), 3.22 (t, J=7.9 Hz, 2H), 5.46 (s, 2H), 6.50 (s, 1H), 6.79 (s, 1H), 6.98 (d, J=8.1 Hz, 1H), 7.17 (d, J=6.6 Hz, 1H), 7.27-7.52 (m, 11H).

Example 50

(E)-[2-(2-Ethyl-4-methyl-6-phenylbenzimidazol-1-yl)methyl-10,11-dihydro-5H-dibenzo[a,d]cyclohepten-5-ylidene]acetonitrile (Compound 50)

[step 1] Using 6-bromo-2-ethyl-4-methylbenzimidazole (WO2004082621; 500 mg, 2.09 mmol) and in the same manner as in Example 47, step 1, (E)-[2-(6-bromo-2-ethyl-4-methylbenzimidazol-1-yl)methyl-10,11-dihydro-5H-dibenzo[a,d]cyclohepten-5-ylidene]acetonitrile (900 mg, 89%) was obtained.
ESI-MS m/z: 482 (M+H)$^+$; $^1$H-NMR (CDCl$_3$, δ): 1.36 (t, J=7.5 Hz, 3H), 2.65 (s, 3H), 2.83 (q, J=7.5 Hz, 2H), 3.07 (s, 4H), 5.23 (s, 2H), 5.68 (s, 1H), 6.76 (s, 1H), 6.82 (d, J=8.1 Hz, 1H), 7.11 (s, 1H), 7.17-7.35 (m, 5H), 7.43 (d, J=7.7 Hz, 1H).
[step 2] Using (E)-[2-(6-bromo-2-ethyl-4-methylbenzimidazol-1-yl)methyl-10,11-dihydro-5H-dibenzo[a,d]cyclohepten-5-ylidene]acetonitrile (200 mg, 0.41 mmol) obtained in step 1 and in the same manner as in Example 47, step 2, the title compound (compound 50) (183 mg, 93%) was obtained.
ESI-MS m/z: 480 (M+H)$^+$; $^1$H-NMR (CDCl$_3$, δ): 1.37 (t, J=7.5 Hz, 3H), 2.74 (s, 3H), 2.88 (q, J=7.5 Hz, 2H), 3.06 (s, 4H), 5.33 (s, 2H), 5.66 (s, 1H), 6.83 (s, 1H), 6.87 (d, J=7.7 Hz, 1H), 7.14 (s, 1H), 7.18-7.33 (m, 5H), 7.35-7.45 (m, 4H), 7.55 (d, J=7.6 Hz, 2H).

Example 51

(E)-2-(2-Ethyl-4-methyl-6-phenylbenzimidazol-1-yl)methyl-5-(1H-tetrazol-5-yl)methylene-10,11-dihydro-5H-dibenzo[a,d]cycloheptene (Compound 51)

Using compound 50 (100 mg, 0.21 mmol) obtained in Example 50 and in the same manner as in Example 4, the title compound (compound 51) (91 mg, 83%) was obtained.
ESI-MS m/z: 523 (M+H)$^+$; $^1$H-NMR (CDCl$_3$, δ): 1.36 (t, J=7.6 Hz, 3H), 2.70 (s, 3H), 2.72-2.98 (br, 2H), 2.88 (q, J=7.6 Hz, 2H), 3.12-3.40 (br, 2H), 5.33 (s, 2H), 6.76 (s, 1H), 6.95 (d, J=7.9 Hz, 1H), 7.04 (s, 1H), 7.16 (d, J=6.9 Hz, 2H), 7.27-7.45 (m, 8H), 7.55 (d, J=7.3 Hz, 2H).

Example 52

(E)-2-(2-Ethyl-4-methyl-6-phenylbenzimidazol-1-yl)methyl-5-(5-oxo-4,5-dihydro-1,2,4-oxadiazol-3-yl)methylene-10,11-dihydro-5H-dibenzo[a,d]cycloheptene (Compound 52)

Using compound 50 (43 mg, 0.09 mmol) obtained in step 50 and in the same manner as in Example 5, the title compound (compound 52) (16 mg, 33%) was obtained.
ESI-MS m/z: 539 (M+H)$^+$; $^1$H-NMR (CDCl$_3$, δ): $^1$H-NMR (CDCl$_3$) δ: 1.38 (t, J=7.5 Hz, 3H), 2.74 (s, 3H), 2.75-2.97 (m, 2H), 2.88 (q, J=7.5 Hz, 2H), 3.16-3.42 (m, 2H), 5.32 (s, 2H), 6.48 (s, 1H), 6.76 (s, 1H), 6.92 (d, J=6.6 Hz, 1H), 7.16 (d, J=8.8 Hz, 2H), 7.28-7.51 (m, 6H), 7.52-7.58 (m, 2H), 7.63-7.71 (m, 2H).

Example 53

(E)-[2-(2,4-Dimethyl-6-phenylbenzimidazol-1-yl)methyl-10,11-dihydro-5H-dibenzo[a,d]cyclohepten-5-ylidene]acetonitrile (Compound 53)

Using 2,4-dimethyl-6-phenylbenzimidazole (137 mg, 0.62 mmol) obtained in Reference Example A4 and in the same manner as in Example 47, step 1, the title compound (compound 53) (223 mg, 77%) was obtained.
ESI-MS m/z: 466 (M+H)$^+$; $^1$H-NMR (CDCl$_3$, δ): 2.57 (s, 3H), 2.73 (s, 3H), 3.06 (s, 4H), 5.31 (s, 2H), 5.66 (s, 1H), 6.83 (s, 1H), 6.89 (d, J=8.1 Hz, 1H), 7.17-7.24 (m, 3H), 7.28-7.34 (m, 4H), 7.37-7.44 (m, 3H), 7.56 (d, J=7.7 Hz, 2H).

Example 54

(E)-2-(2,4-Methyl-6-phenylbenzimidazol-1-yl)methyl-5-(1H-tetrazol-5-yl)methylene-10,11-dihydro-5H-dibenzo[a,d]cycloheptene (Compound 54)

Using compound 53 (100 mg, 0.21 mmol) obtained in Example 53 and in the same manner as in Example 4, the title compound (compound 54) (80 mg, 74%) was obtained.
ESI-MS m/z: 509 (M+H)$^+$; $^1$H-NMR (CDCl$_3$, δ): 2.57 (s, 3H), 2.67 (s, 3H), 2.71-2.97 (m, 2H), 3.10-3.37 (m, 2H), 5.31 (s, 2H), 6.76 (s, 1H), 6.97 (d, J=7.0 Hz, 1H), 7.03 (s, 1H), 7.14 (d, J=7.3 Hz, 1H), 7.19-7.45 (m, 9H), 7.56 (d, J=7.3 Hz, 2H).

Example 55

(E)-[2-(2,4-Dimethyl-6-phenylbenzimidazol-1-yl)methyl-10,11-dihydro-5H-dibenzo[a,d]cyclohepten-5-ylidene]acetic acid (Compound 55)

Compound 53 (80 mg, 0.17 mmol) obtained in Example 53 was suspended in ethanol (2 mL), 10 mol/L aqueous sodium hydroxide solution (3.1 mL) was added, and the mixture was stirred under reflux for 3 days. Under ice-cooling, the mixture was adjusted to pH 1 with 2 mol/L hydrochloric acid, and the mixture was extracted with ethyl acetate. The organic layer was washed with brine, dried over anhydrous magnesium sulfate, and concentrated under reduced pressure. The residue was purified by silica gel column chromatography (chloroform/methanol=98/2 to 90/10) to give the title compound (compound 55) (34 mg, 41%).
ESI-MS m/z: 485 (M+H)$^+$; $^1$H-NMR (CDCl$_3$, δ): 2.73 (s, 3H), 2.80 (s, 3H), 2.93-3.46 (m, 4H), 5.36 (s, 2H), 6.17 (s, 1H), 6.79 (s, 1H), 6.90 (d, J=7.9 Hz, 1H), 7.12-7.24 (m, 5H), 7.28-7.47 (m, 5H), 7.52 (d, J=8.3 Hz, 2H).

Example 56

(E)-[2-(2,4-Dimethyl-6-phenylbenzimidazol-1-yl)methyl-10,11-dihydro-5H-dibenzo[a,d]cyclohepten-5-ylidene]acetamide (Compound 56)

Using compound 53 (80 mg, 0.17 mmol) obtained in Example 53 and in the same manner as in Example 3, the title compound (compound 56) (12 mg, 15%) was obtained.

ESI-MS m/z: 484 (M+H)+; $^1$H-NMR (CDCl$_3$, δ) 2.85 (s, 3H), 3.03 (s, 3H), 5.37 (br s, 8H), 6.21 (s, 1H), 6.73 (s, 1H), 6.98 (s, 1H), 7.22 (d, J=7.6 Hz, 3H), 7.31-7.50 (m, 9H).

Example 57

N-{(E)-[2-(2,4-Dimethyl-6-phenylbenzimidazol-1-yl)methyl-10,11-dihydro-5H-dibenzo[a,d]cyclohepten-5-ylidene]acetyl}methanesulfonamide (Compound 57)

(E)-[2-(2,4-Dimethyl-6-phenylbenzimidazol-1-yl)methyl-10,11-dihydro-5H-dibenzo[a,d]cyclohepten-5-ylidene]acetic acid (50 mg, 0.10 mmol) obtained in Example 55 was dissolved in DMF (2 mL), and the mixture was cooled to 0° C. N,N'-carbonyldiimidazole (36 mg, 0.22 mmol) was added, and the mixture was stirred at room temperature for 2 hr. To this mixture were added methanesulfonamide (21 mg, 0.22 mmol) and DBU (21 mg, 0.22 mmol), and the mixture was stirred at 60° C. for 5 hr. 5% Aqueous citric acid solution was added to the mixture, and the precipitate was collected by filtration, and washed with water to give the title compound (compound 57) (31 mg, 55%).
ESI-MS m/z: 562 (M+H)+; $^1$H-NMR (DMSO-d$_6$, δ) 2.57 (s, 3H), 2.82-3.23 (m, 4H), 3.16 (s, 3H), 3.32 (s, 3H), 5.49 (s, 2H), 6.27 (s, 1H), 6.91 (d, J=7.6 Hz, 1H), 6.99 (s, 1H), 7.03-7.15 (m, 2H), 7.18-7.35 (m, 5H), 7.42 (t, J=7.6 Hz, 2H), 7.57 (s, 1H), 7.64 (d, J=8.3 Hz, 2H).

Example 58

(E)-2-(2-Hydroxymethyl-4-methyl-6-phenylbenzimidazol-1-yl)methyl-5-(5-oxo-4,5-dihydro-1,2,4-oxadiazol-3-yl)methylene-10,11-dihydro-5H-dibenzo[a,d]cycloheptene (Compound 58)

[step 1] Using 2-hydroxymethyl-4-methyl-6-phenylbenzimidazole (200 mg, 0.84 mmol) obtained in Reference Example A6 and in the same manner as in Example 47, step 1, (E)-[2-(2-hydroxymethyl-4-methyl-6-phenylbenzimidazol-1-yl)methyl-10,11-dihydro-5H-dibenzo[a,d]cyclohepten-5-ylidene]acetonitrile (301 mg, 75%) was obtained.
ESI-MS m/z: 482 (M+H)+; $^1$H-NMR (CDCl$_3$, δ): 2.72 (s, 3H), 3.06 (s, 4H), 4.87 (d, J=5.5 Hz, 2H), 5.44 (s, 2H), 5.65 (s, 1H), 6.86-6.95 (m, 2H), 7.17-7.23 (m, 3H), 7.27-7.35 (m, 4H), 7.37-7.44 (m, 3H), 7.52-7.57 (m, 2H).
[step 2] Using (E)-[2-(2-hydroxymethyl-4-methyl-6-phenylbenzimidazol-1-yl)methyl-10,11-dihydro-5H-dibenzo[a,d]cyclohepten-5-ylidene]acetonitrile (100 mg, 0.21 mmol) obtained in step 1 and in the same manner as in Example 5, the title compound (compound 58) (42 mg, 39%) was obtained.
ESI-MS m/z: 541 (M+H)+; $^1$H-NMR (CDCl$_3$, δ): 2.71 (s, 3H), 2.76-2.97 (m, 2H), 3.16-3.40 (m, 2H), 4.88 (s, 2H), 5.43 (s, 2H), 6.45 (s, 1H), 6.84 (s, 1H), 6.93 (d, J=8.3 Hz, 1H), 7.13 (d, J=7.3 Hz, 1H), 7.20 (s, 1H), 7.28-7.34 (m, 5H), 7.37-7.43 (m, 3H), 7.52-7.56 (m, 2H).

Example 59

(E)-2-[2-(2-Hydroxyethyl)-4-methyl-6-phenylbenzimidazol-1-yl]methyl-5-(5-oxo-4,5-dihydro-1,2,4-oxadiazol-3-yl)methylene-10,11-dihydro-5H-dibenzo[a,d]cycloheptene (Compound 59)

[step 1] Using 2-(2-hydroxyethyl)-4-methyl-6-phenylbenzimidazole (157 mg, 0.62 mmol) obtained in Reference Example A5 and in the same manner as in Example 47, step 1, (E)-{2-[2-(2-hydroxyethyl)-4-methyl-6-phenylbenzimidazol-1-yl]methyl-10,11-dihydro-5H-dibenzo[a,d]cyclohepten-5-ylidene}acetonitrile (278 mg, 91%) was obtained.
ESI-MS m/z: 496 (M+H)+; $^1$H-NMR (CDCl$_3$, δ): 2.70 (s, 3H), 2.96 (t, J=5.3 Hz, 2H), 3.06 (s, 4H), 4.12 (t, J=5.3 Hz, 2H), 5.31 (s, 2H), 5.66 (s, 1H), 6.84 (s, 1H), 6.87 (d, (7=7.7 Hz, 1H), 7.18-7.24 (m, 3H), 7.27-7.36 (m, 4H), 7.36-7.45 (m, 3H), 7.56 (d, J=8.0 Hz, 2H).
[step 2] Using (E)-{2-[2-(2-hydroxyethyl)-4-methyl-6-phenylbenzimidazol-1-yl]methyl-10,11-dihydro-5H-dibenzo[a,d]cyclohepten-5-ylidene}acetonitrile (100 mg, 0.20 mmol) obtained in step 1 and in the same manner as in Example 5, the title compound (compound 59) (24 mg, 22%) was obtained.
ESI-M/Z: 555 (M+H)+; $^1$H-NMR (CDCl$_3$, δ): 2.70 (s, 3H), 2.81-2.89 (br, 2H), 2.96 (t, J=5.5 Hz, 2H), 3.26-3.32 (br, 2H), 4.12 (t, J=5.5 Hz, 2H), 5.31 (s, 2H), 6.48 (s, 1H), 6.78 (s, 1H), 6.93 (d, J=7.9 Hz, 1H), 7.15 (d, J=7.3 Hz, 1H), 7.21 (s, 1H), 7.27-7.36 (m, 5H), 7.40 (t, J=7.3 Hz, 3H), 7.56 (d, J=7.9 Hz, 2H).

Example 60

(E)-2-(6-Phenyl-4-methylbenzimidazol-1-yl)methyl-5-(1H-tetrazol-5-yl)methylene-10,11-dihydro-5H-dibenzo[a,d]cycloheptene (Compound 60)

[step 1] (E)-{2-[2-(2-Hydroxyethyl)-4-methyl-6-phenylbenzimidazol-1-yl]methyl-10,11-dihydro-5H-dibenzo[a,d]cyclohepten-5-ylidene}acetonitrile (100 mg, 0.20 mmol) obtained in Example 59, step 1 was dissolved in acetonitrile (2 mL), 1,1,1-triacetoxy-1,1-dihydro-1,2-benziodoxol-3(1H)-one (128 mg, 0.30 mmol) was added, and the mixture was stirred at room temperature for 4 hr. Chloroform (20 mL) and saturated aqueous sodium hydrogen carbonate solution (20 mL) were added to the mixture, and the mixture was stirred at room temperature for 30 min. The organic layer was washed with brine, dried over anhydrous magnesium sulfate, and concentrated under reduced pressure. The residue was purified by silica gel column chromatography (chloroform/methanol=100/0 to 95/15) to give (E)-[2-(4-methyl-6-phenylbenzimidazol-1-yl)methyl-10,11-dihydro-5H-dibenzo[a,d]cyclohepten-5-ylidene]acetonitrile (14 mg, 15%).
ESI-MS m/z: 452 (M+H)+; $^1$H-NMR (DMSO-d$_6$, δ): 2.62 (s, 3H), 2.97-3.14 (m, 4H), 5.66 (s, 2H), 6.15 (s, 1H), 7.24-7.42 (m, 8H), 7.48 (t, J=7.4 Hz, 2H), 7.57 (s, 1H), 7.69 (d, J=7.4 Hz, 2H), 7.88 (s, 1H), 9.22 (s, 1H).
[step 2] Using (E)-[2-(4-methyl-6-phenylbenzimidazol-1-yl)methyl-10,11-dihydro-5H-dibenzo[a,d]cyclohepten-5-ylidene]acetonitrile (10 mg, 0.02 mmol) obtained in step 1 and in the same manner as in Example 4, the title compound (compound 60) (3.4 mg, 34%) was obtained.
ESI-MS m/z: 495 (M+H)+; $^1$H-NMR (CDCl$_3$, δ): 2.73 (s, 3H), 2.76-3.03 (m, 2H), 3.17-3.40 (m, 2H), 5.35 (s, 2H), 6.90 (s, 1H), 7.07 (s, 1H), 7.10 (d, J=7.9 Hz, 1H), 7.18 (d, J=6.9 Hz, 1H), 7.28-7.34 (m, 3H), 7.39-7.48 (m, 6H), 7.56 (d, J=7.9 Hz, 2H), 7.94 (s, 1H).

Example 61

(E)-2-[2-(2-Methoxycarbonylethyl)-4-methyl-6-phenylbenzimidazol-1-yl]methyl-5-(1H-tetrazol-5-yl)methylene-10,11-dihydro-5H-dibenzo[a,d]cycloheptene (Compound 61)

[step 1] Using 2-(2-methoxycarbonylethyl)-4-methyl-6-phenylbenzimidazole (400 mg, 1.36 mmol) obtained in Reference Example A7 and in the same manner as in Example 47, step 1, (E)-{2-[2-(2-methoxycarbonylethyl)-4-methyl-6-phenylbenzimidazol-1-yl]methyl-10,11-dihydro-5H-dibenzo[a,d]cyclohepten-5-ylidene}acetonitrile (590 mg, 81%) was obtained.

ESI-MS m/z: 538 (M+H)$^+$; $^1$H-NMR (CDCl$_3$, δ): 2.71 (s, 3H), 2.97 (t, J=7.3 Hz, 2H), 3.06-3.13 (m, 6H), 3.66 (s, 3H), 5.39 (s, 2H), 5.66 (s, 1H), 6.86 (s, 2H), 6.89 (d, J=7.9 Hz, 2H), 7.18-7.23 (m, 3H), 7.28-7.33 (m, 3H), 7.35-7.45 (m, 2H), 7.55 (d, J=7.9 Hz, 2H).

[step 2] Using (E)-{2-[2-(2-methoxycarbonylethyl)-4-methyl-6-phenylbenzimidazol-1-yl]methyl-10,11-dihydro-5H-dibenzo[a,d]cyclohepten-5-ylidene}acetonitrile (100 mg, 0.19 mmol) obtained in step 1 and in the same manner as in Example 4, the title compound (compound 61) (23 mg, 21%) was obtained.

ESI-MS m/z: 581 (M+H)$^+$; $^1$H-NMR (DMSO-d$_6$, δ): 2.63 (s, 3H), 2.95 (t, J=7.1 Hz, 2H), 3.31 (t, J=7.1 Hz, 2H), 3.58 (s, 3H), 3.74-4.52 (m, 4H), 5.74 (s, 2H), 6.81 (s, 1H), 6.87 (d, J=7.6 Hz, 1H), 6.98-7.10 (m, 2H), 7.13 (s, 1H), 7.17-7.30 (m, 2H), 7.32-7.51 (m, 4H), 7.56 (s, 1H), 7.68 (d, J=7.3 Hz, 2H), 7.83 (s, 1H).

Example 62

(E)-2-[2-(2-Methanesulfonylaminocarbonylethyl)-4-methyl-6-phenylbenzimidazol-1-yl]methyl-5-(1H-tetrazol-5-yl)methylene-10,11-dihydro-5H-dibenzo[a,d]cycloheptene (Compound 62)

[step 1] (E)-{2-[2-(2-Methoxycarbonylethyl)-4-methyl-6-phenylbenzimidazol-1-yl]methyl-10,11-dihydro-5H-dibenzo[a,d]cyclohepten-5-ylidene}acetonitrile (350 mg, 0.65 mmol) obtained in Example 61, step 1 was dissolved in ethanol (4 mL), 2 mol/L aqueous sodium hydroxide solution (0.8 mL) was added, and the mixture was stirred at room temperature for 2 hr. The mixture was concentrated under reduced pressure, water and 2 mol/L hydrochloric acid were added, and the precipitate was collected by filtration to give (E)-[2-{2-(2-carboxyethyl)-4-methyl-6-phenylbenzimidazol-1-yl}methyl-10,11-dihydro-5H-dibenzo[a,d]cyclohepten-5-ylidene]acetonitrile (336 mg, 99%).

ESI-MS m/z: 524 (M+H)$^+$; $^1$H-NMR (CDCl$_3$, δ): 2.73 (s, 3H), 3.03-3.14 (m, 6H), 3.16-3.24 (m, 2H), 5.43 (s, 2H), 5.67 (s, 1H), 6.86 (s, 1H), 6.89 (d, J=8.8 Hz, 1H), 7.20-7.24 (m, 2H), 7.27-7.46 (m, 8H), 7.53 (d, J=8.1 Hz, 2H).

[step 2] Using (E)-2-{2-(2-carboxyethyl)-4-methyl-6-phenylbenzimidazol-1-yl}methyl-10,11-dihydro-5H-dibenzo[a,d]cyclohepten-5-ylidene]acetonitrile (100 mg, 0.19 mmol) obtained in step 1 and in the same manner as in Example 57, (E)-{2-[2-(2-methanesulfonylaminocarbonylethyl)-4-methyl-6-phenylbenzimidazol-1-yl]methyl-10,11-dihydro-5H-dibenzo[a,d]cyclohepten-5-ylidene}acetonitrile (114 mg, 100%) was obtained.

ESI-MS m/z: 601 (M+H)$^+$; $^1$H-NMR (CDCl$_3$, δ): 2.74 (s, 3H), 2.88-2.97 (m, 2H), 3.04-3.14 (m, 6H), 3.27 (s, 3H), 5.32 (s, 2H), 5.67 (s, 1H), 6.84-6.90 (m, 2H), 7.19-7.25 (m, 2H), 7.28-7.46 (m, 8H), 7.57 (d, J=7.6 Hz, 2H).

[step 3] Using (E)-{2-[2-(2-methanesulfonylaminocarbonylethyl)-4-methyl-6-phenylbenzimidazol-1-yl]methyl-10,11-dihydro-5H-dibenzo[a,d]cyclohepten-5-ylidene}acetonitrile (60 mg, 0.10 mmol) obtained in step 2 and in the same manner as in Example 4, the title compound (compound 62) (33 mg, 52%) was obtained.

ESI-MS m/z: 644 (M+H)$^+$; $^1$H-NMR (CDCl$_3$, δ): 2.74 (s, 3H), 2.79-3.02 (m, 2H), 2.91-2.99 (m, 2H), 3.07-3.16 (m, 2H), 3.21-3.41 (m, 2H), 3.27 (s, 3H), 5.32 (s, 2H), 6.79 (s, 1H), 6.97 (d, J=7.7 Hz, 1H), 7.07 (s, 1H), 7.19 (d, J=8.1 Hz, 1H), 7.31-7.47 (m, 9H), 7.57 (d, J=7.0 Hz, 2H).

Example 63

(E)-2-[2-(2-Methylcarbamoylethyl)-4-methyl-6-phenylbenzimidazol-1-yl]methyl-5-(1H-tetrazol-5-yl)methylene-10,11-dihydro-5H-dibenzo[a,d]cycloheptene (Compound 63)

[step 1] (E)-{2-[2-(2-Carboxyethyl)-4-methyl-6-phenylbenzimidazol-1-yl]methyl-10,11-dihydro-5H-dibenzo[a,d]cyclohepten-5-ylidene}acetonitrile (100 mg, 0.19 mmol) obtained in Example 62, step 1 was dissolved in DMF (1 mL), 1-ethyl-3-(3-dimethylaminopropyl)carbodiimide (527 mg, 2.75 mmol), 1-hydroxybenzotriazole (421 mg, 2.75 mmol) and methylamine (2 mol/L THF solution; 0.38 mL, 0.72 mmol) were added, and the mixture was stirred at room temperature for 24 hr. Saturated aqueous sodium hydrogen carbonate solution and water were added to the mixture, and the precipitated solid was collected by filtration to give (E)-{2-[2-(methylcarbamoylethyl)-4-methyl-6-phenylbenzimidazol-1-yl]methyl-10,11-dihydro-5H-dibenzo[a,d]cyclohepten-5-ylidene}acetonitrile (102 mg, 100%).

ESI-MS m/z: 537 (M+H)$^+$; $^1$H-NMR (CDCl$_3$, δ): 2.71 (s, 3H), 2.76 (d, J=4.6 Hz, 3H), 2.82 (t, J=6.9 Hz, 2H), 3.06 (s, 4H), 3.11 (t, J=6.9 Hz, 3H), 5.37 (s, 2H), 5.66 (s, 1H), 6.87 (d, J=7.6 Hz, 2H), 7.17-7.24 (m, 3H), 7.27-7.34 (m, 3H), 7.36-7.44 (m, 3H), 7.56 (d, J=7.9 Hz, 2H).

[step 2] Using (E)-{2-[2-(methylcarbamoylethyl)-4-methyl-6-phenylbenzimidazol-1-yl]methyl-10,11-dihydro-5H-dibenzo[a,d]cyclohepten-5-ylidene}acetonitrile (50 mg, 0.09 mmol) obtained in step 1 and in the same manner as in Example 4, the title compound (compound 63) (48 mg, 93%) was obtained.

ESI-MS m/z: 580 (M+H)$^+$; $^1$H-NMR (CDCl$_3$, δ): 2.70 (s, 3H), 2.76 (d, J=4.6 Hz, 3H), 2.80-3.00 (m, 2H), 2.81 (t, 0'=6.9 Hz, 2H), 3.12 (t, J=6.9 Hz, 2H), 3.18-3.38 (m, 2H), 5.38 (s, 2H), 6.82 (s, 1H), 6.94 (d, J=8.3 Hz, 1H), 7.03 (s, 1H), 7.15 (d, J=7.3 Hz, 1H), 7.23 (s, 1H), 7.27-7.46 (m, 8H), 7.56 (d, J=8.3 Hz, 2H).

Example 64

(E)-2-[6-(2-Chlorophenyl)-4-methyl-2-propylbenzimidazol-1-yl]methyl-5-(1H-tetrazol-5-yl)methylene-10,11-dihydro-5H-dibenzo[a,d]cycloheptene (Compound 64)

[step 1] Using 2-chlorophenylboronic acid (94 mg, 0.60 mmol) instead of phenylboronic acid, and in the same manner as in Example 47, step 2, (E)-{2-[6-(2-chlorophenyl)-4-methyl-2-propylbenzimidazol-1-yl]methyl-10,11-dihydro-5H-dibenzo[a,d]cyclohepten-5-ylidene}acetonitrile (68 mg, 64%) was obtained.

ESI-MS m/z: 528 (M+H)$^+$; $^1$H-NMR (DMSO-d$_6$, δ): 0.95 (t, J=7.3 Hz, 3H), 1.69-1.83 (m, 2H), 2.55 (s, 3H), 2.82 (t, J=7.3 Hz, 2H), 3.01 (s, 4H), 5.46 (s, 2H), 6.12 (s, 1H), 6.90 (d, J=8.1 Hz, 1H), 7.02 (d, J=6.6 Hz, 2H), 7.26-7.41 (m, 9H), 7.48-7.52 (m, 1H).

[step 2] Using (E)-{2-[6-(2-chlorophenyl)-4-methyl-2-propylbenzimidazol-1-yl]methyl-10,11-dihydro-5H-dibenzo[a,d]cyclohepten-5-ylidene}acetonitrile (60 mg, 0.11 mmol) obtained in step 1 and in the same manner as in Example 4, the title compound (compound 64) (40 mg, 63%) was obtained.

ESI-MS m/z: 571 (M+H)$^+$; $^1$H-NMR (CDCl$_3$, δ): 0.99 (t, J=7.3 Hz, 3H), 1.72-1.88 (m, 2H), 2.71 (s, 3H), 2.70-2.93 (br,

2H), 2.85 (t, J=7.3 Hz, 2H), 3.12-3.35 (br, 2H), 5.30 (s, 2H), 6.80 (s, 1H), 6.97 (d, J=8.1 Hz, 1H), 7.03 (s, 1H), 7.10 (s, 1H), 7.14 (d, J=7.7 Hz, 1H), 7.20-7.43 (m, 9H).

Example 65

(E)-2-[6-(3-Chlorophenyl)-4-methyl-2-propylbenzimidazol-1-yl]methyl-5-(1H-tetrazol-5-yl)methylene-10,11-dihydro-5H-dibenzo[a,d]cycloheptene (Compound 65)

[step 1] Using 3-chlorophenylboronic acid (94 mg, 0.60 mmol,) instead of phenylboronic acid, and in the same manner as in Example 47, step 2, (E)-{2-[6-(3-chlorophenyl)-4-methyl-2-propylbenzimidazol-1-yl]methyl-10,11-dihydro-5H-dibenzo[a,d]cyclohepten-5-ylidene}acetonitrile (47 mg, 45%) was obtained.
ESI-MS m/z: 528 (M+H)$^+$; $^1$H-NMR (DMSO-d$_6$, δ): 0.94 (t, J=7.5 Hz, 3H), 1.67-1.82 (m, 2H), 2.58 (s, 3H), 2.78 (t, J=7.5 Hz, 2H), 2.96-3.09 (m, 4H), 5.54 (s, 2H), 6.12 (s, 1H), 6.82 (d, J=8.1 Hz, 1H), 7.02 (s, 1H), 7.23-7.48 (m, 8H), 7.59-7.65 (m, 2H), 7.68-7.72 (m, 1H).
[step 2] Using (E)-{2-[6-(3-chlorophenyl)-4-methyl-2-propylbenzimidazol-1-yl]methyl-10,11-dihydro-5H-dibenzo[a,d]cyclohepten-5-ylidene}acetonitrile (30 mg, 0.05 mmol) obtained in step 1 and in the same manner as in Example 4, the title compound (compound 65) (3.5 mg, 12%) was obtained.
ESI-MS m/z: 571 (M+H)$^+$; $^1$H-NMR (CDCl$_3$, δ): 0.99 (t, J=7.3 Hz, 3H), 1.71-1.88 (m, 2H), 2.71 (s, 3H), 2.76-3.08 (br, 2H), 2.88 (t, J=7.3 Hz, 2H), 3.16-3.38 (br, 2H), 5.28 (s, 2H), 6.70 (s, 1H), 6.91 (d, J=8.1 Hz, 1H), 7.02 (s, 1H), 7.05 (s, 1H), 7.19 (d, J=7.7 Hz, 1H), 7.20-7.47 (m, 9H).

Example 66

(E)-2-[6-(4-Chlorophenyl)-4-methyl-2-propylbenzimidazol-1-yl]methyl-5-(1H-tetrazol-5-yl)methylene-10,11-dihydro-5H-dibenzo[a,d]cycloheptene (Compound 66)

[step 1] Using 4-chlorophenylboronic acid (94 mg, 0.60 mmol) instead of phenylboronic acid, and in the same manner as in Example 47, step 2, (E)-{2-[6-(4-chlorophenyl)-4-methyl-2-propylbenzimidazol-1-yl]methyl-10,11-dihydro-5H-dibenzo[a,d]cyclohepten-5-ylidene}acetonitrile (55 mg, 52%) was obtained.
ESI-MS m/z: 528 (M+H)$^+$; $^1$H-NMR (CDCl$_3$): $^1$H-NMR (CDCl$_3$) δ: 1.00 (t, J=7.6 Hz, 3H), 1.74-1.89 (m, 2H), 2.73 (s, 3H), 2.82 (t, J=7.6 Hz, 2H), 3.06 (s, 4H), 5.32 (s, 2H), 5.66 (s, 1H), 6.82 (s, 1H), 6.85 (d, J=8.4 Hz, 1H), 7.08 (s, 1H), 7.18-7.37 (m, 7H), 7.44 (t, J=8.1 Hz, 3H).
[step 2] Using (E)-{2-[6-(4-chlorophenyl)-4-methyl-2-propylbenzimidazol-1-yl]methyl-10,11-dihydro-5H-dibenzo[a,d]cyclohepten-5-ylidene}acetonitrile (40 mg, 0.08 mmol) obtained in step 1 and in the same manner as in Example 4, the title compound (compound 66) (21 mg, 47%) was obtained.
ESI-MS m/z: 571 (M+H)$^+$; $^1$H-NMR (CDCl$_3$, δ): 1.00 (t, J=7.3 Hz, 3H), 1.73-1.89 (m, 2H), 2.71 (s, 3H), 2.74-3.01 (br, 2H), 2.84 (t, J=7.3 Hz, 2H), 3.16-3.40 (br, 2H), 5.33 (s, 2H), 6.76 (s, 1H), 6.94 (d, J=8.1 Hz, 1H), 7.05 (s, 1H), 7.11 (s, 1H), 7.17 (d, J=7.7 Hz, 1H), 7.27-7.50 (m, 9H).

Example 67

(E)-2-[4-Methyl-2-propyl-6-(2-thienyl)benzimidazol-1-yl]methyl-5-(1H-tetrazol-5-yl)methylene-10,11-dihydro-5H-dibenzo[a,d]cycloheptene (Compound 67)

[step 1] (E)-[2-{6-Bromo-4-methyl-2-propylbenzimidazol-1-yl}methyl-10,11-dihydro-5H-dibenzo[a,d]cyclohepten-5-ylidene]acetonitrile (120 mg, 0.24 mmol) obtained in Example 47, step 1,2-thienyltetrabutyltin (268 mg, 0.72 mmol) and tetrakis(triphenylphosphine)palladium (92 mg, 0.08 mmol) were dissolved in toluene (2 mL), and the mixture was stirred at 100° C. for 2.5 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=7/3 to 7/7) to give (E)-{2-[4-methyl-2-propyl-6-(2-thienyl)benzimidazol-1-yl]methyl-10,11-dihydro-5H-dibenzo[a,d]cyclohepten-5-ylidene}acetonitrile (60 mg, 52%).
ESI-MS m/z: 500 (M+H)$^+$; $^1$H-NMR (CDCl$_3$, δ): 1.00 (t, J=7.4 Hz, 3H), 1.72-1.89 (m, 2H), 2.70 (s, 3H), 2.81 (t, J=7.4 Hz, 2H), 3.06 (s, 4H), 5.30 (s, 2H), 5.67 (s, 1H), 6.82 (s, 1H), 6.87 (d, J=8.2 Hz, 1H), 7.03 (t, J=4.3 Hz, 1H), 7.12-7.24 (m, 3H), 7.27-7.48 (m, 5H), 7.59-7.68 (m, 1H).
[step 2] Using (E)-{2-[4-methyl-2-propyl-6-(2-thienyl)benzimidazol-1-yl]methyl-10,11-dihydro-5H-dibenzo[a,d]cyclohepten-5-ylidene}acetonitrile (60 mg, 0.06 mmol) obtained in step 1 and in the same manner as in Example 4, the title compound (compound 67) (10 mg, 32%) was obtained.
ESI-MS m/z: 543 (M+H)$^+$; $^1$H-NMR (DMSO-d$_6$, δ): 0.94 (t, J=7.3 Hz, 3H), 1.67-1.83 (m, 2H), 2.55 (s, 3H), 2.73-3.51 (br, 4H), 2.79 (t, J=7.6 Hz, 2H), 5.49 (s, 2H), 6.79 (s, 1H), 6.87 (t, J=6.4 Hz, 2H), 6.98-7.10 (m, 3H), 7.17-7.28 (m, 3H), 7.39-7.44 (m, 3H), 7.53 (s, 1H).

Example 68

(E)-2-[6-(2-Furanyl)-4-methyl-2-propylbenzimidazol-1-yl]methyl-5-(1H-tetrazol-5-yl)methylene-10,11-dihydro-5H-dibenzo[a,d]cycloheptene (Compound 68)

[step 1] Using 6-(2-furanyl)-4-methyl-2-propylbenzimidazole (60 mg, 0.25 mmol) obtained in Reference Example A2 and in the same manner as in Example 47, step 1, (E)-{2-[6-(2-furanyl)-4-methyl-2-propylbenzimidazol-1-yl]methyl-10,11-dihydro-5H-dibenzo[a,d]cyclohepten-5-ylidene}acetonitrile (10 mg, 30%) was obtained.
ESI-MS m/z: 484 (M+H)$^+$; $^1$H-NMR (CDCl$_3$, δ): 1.00 (t, J=7.3 Hz, 3H), 1.72-1.89 (m, 2H), 2.70 (s, 3H), 2.80 (t, J=7.3 Hz, 2H), 3.06 (s, 4H), 5.31 (s, 2H), 5.67 (s, 1H), 6.42-6.46 (m, 1H), 6.57 (d, J=3.3 Hz, 1H), 6.80 (s, 1H), 6.86 (d, J=7.9 Hz, 1H), 7.16-7.24 (m, 2H), 7.27-7.35 (m, 3H), 7.36-7.48 (m, 3H).
[step 2] Using (E)-{2-[6-(2-furanyl)-4-methyl-2-propylbenzimidazol-1-yl]methyl-10,11-dihydro-5H-dibenzo[a,d]cyclohepten-5-ylidene}acetonitrile (30 mg, 0.06 mmol) obtained in step 1 and in the same manner as in Example 4, the title compound (compound 68) (10 mg, 30%) was obtained.
ESI-MS m/z: 527 (M+H)$^+$; $^1$H-NMR (CDCl$_3$, δ): 0.98 (t, J=7.3 Hz, 3H), 1.71-1.86 (m, 2H), 2.65 (s, 3H), 2.71-2.97 (m, 2H), 2.80 (t, J=7.3 Hz, 2H), 3.10-3.43 (m, 2H), 5.32 (s, 2H), 6.42-6.46 (m, 1H), 6.57 (d, J=2.9 Hz, 1H), 6.73 (s, 1H), 6.94 (d, J=8.1 Hz, 1H), 7.03 (s, 1H), 7.16 (d, J=7.3 Hz, 1H), 7.30-7.43 (m, 7H).

Example 69

(E)-2-[4-Methyl-6-(1,3-oxazol-2-yl)-2-propylbenzimidazol-1-yl]methyl-5-(1H-tetrazol-5-yl)methylene-10,11-dihydro-5H-dibenzo[a,d]cycloheptene (Compound 69)

[step 1] Using 2-ethyl-6-(oxazol-2-yl)-4-methylbenzimidazole (207 mg, 0.85 mmol) obtained in Reference Example A3 and in the same manner as in Example 47, step 1, (E)-{2-[4-methyl-6-(oxazol-2-yl)-2-propylbenzimidazol-1-yl]methyl-10,11-dihydro-5H-dibenzo[a,d]cyclohepten-5-ylidene}acetonitrile (285 mg, 69%) was obtained.

ESI-MS m/z: 485 (M+H)$^+$; $^1$H-NMR (DMSO-d$_6$, δ): 0.94 (t, J=7.4 Hz, 3H), 1.72-1.83 (m, 2H), 2.59 (s, 3H), 2.82 (t, J=7.4 Hz, 2H), 3.02 (s, 4H), 5.55 (s, 2H), 6.13 (s, 1H), 6.81 (d, J=7.6 Hz, 1H), 6.99 (s, 1H), 7.25-7.39 (m, 6H), 7.65 (s, 1H), 7.81 (s, 1H), 8.13 (s, 1H).

[step 2] Using (E)-{2-[4-methyl-6-(oxazol-2-yl)-2-propyl-benzimidazol-1-yl]methyl-10,11-dihydro-5H-dibenzo[a,d]cyclohepten-5-ylidene}acetonitrile (100 mg, 0.21 mmol) obtained in step 1 and in the same manner as in Example 4, the title compound (compound 69) (48 mg, 43%) was obtained.

ESI-MS m/z: 528 (M+H)$^+$; $^1$H-NMR (DMSO-d$_6$, δ): 0.94 (t, J=7.4 Hz, 3H), 1.72-1.83 (m, 2H), 2.59 (s, 3H), 2.82 (t, J=7.4 Hz, 2H), 3.02 (s, 4H), 5.55 (s, 2H), 6.13 (s, 1H), 6.81 (d, J=7.6 Hz, 1H), 6.99 (s, 1H), 7.25-7.39 (m, 6H), 7.65 (s, 1H), 7.81 (s, 1H), 8.13 (s, 1H).

Example 70

(E)-2-[4-Methyl-6-(1,3,4-oxadiazol-2-yl)-2-propyl-benzimidazol-1-yl]methyl-5-(1H-tetrazol-5-yl)methylene-10,11-dihydro-5H-dibenzo[a,d]cycloheptene (Compound 70)

[step 1] (E)-[2-(6-Carboxy-4-methyl-2-propylbenzimidazol-1-yl)methyl-10,11-dihydro-5H-dibenzo[a,d]cyclohepten-5-ylidene]acetonitrile (274 mg, 0.59 mmol) obtained in Reference Example B8 was dissolved in dichloromethane (1 mL), N,N'-carbonyldiimidazole (CDI) (107 mg, 0.66 mmol) was added, and the mixture was stirred at room temperature for 20 min. To this mixture was added hydrazine monohydrate (89 mg, 1.77 mmol), and the mixture was stirred at room temperature for 3 hr. The mixture was concentrated under reduced pressure, water (20 mL) was added, and the precipitate was collected by filtration to give (E)-{2-[4-methyl-6-(hydrazinocarbonyl)-2-propylbenzimidazol-1-yl]methyl-10,11-dihydro-5H-dibenzo[a,d]cyclohepten-5-ylidene}acetonitrile (246 mg, 88%).

ESI-MS m/z: 476 (M+H)$^+$; $^1$H-NMR (CDCl$_3$, δ): 1.01 (t, J=7.3 Hz, 3H), 1.75-1.90 (m, 2H), 2.71 (s, 3H), 2.83 (t, J=7.3 Hz, 2H), 3.06 (s, 4H), 5.33 (s, 2H), 5.66 (s, 1H), 6.75-6.87 (m, 2H), 7.19-7.44 (m, 6H), 7.65 (s, 1H), 8.50-8.73 (m, 1H).

[step 2] (E)-{2-[4-Methyl-6-(hydrazinocarbonyl)-2-propyl-benzimidazol-1-yl]methyl-10,11-dihydro-5H-dibenzo[a,d]cyclohepten-5-ylidene}acetonitrile (40 mg, 0.08 mmol) obtained in step 1 was suspended in acetic acid (3 mL), triethyl orthoformate (3 mL) was added, and the mixture was stirred at 50° C. for 6 hr. Water (10 mL) was added to the mixture, and the mixture was neutralized to pH 9 with 30% aqueous ammonia solution, and extracted twice with chloroform. The organic layer was washed with brine, dried over anhydrous magnesium sulfate, and concentrated under reduced pressure. The residue was purified by silica gel column chromatography (chloroform:methanol=9:1) to give (E)-{2-[4-methyl-6-(1,3,4-oxadiazol-2-yl)-2-propylbenz-imidazol-1-yl]methyl-10,11-dihydro-5H-dibenzo[a,d]cyclohepten-5-ylidene}acetonitrile (24 mg, 58%).

ESI-MS m/z: 486 (M+H)$^+$; $^1$H-NMR (CDCl$_3$, δ): 1.02 (t, J=7.3 Hz, 3H), 1.76-1.90 (m, 2H), 2.71 (s, 3H), 2.86 (t, J=7.3 Hz, 2H), 3.08 (s, 4H), 5.43 (s, 2H), 5.76 (s, 1H), 6.86 (d, J=6.2 Hz, 2H), 7.24-7.41 (m, 5H), 7.76 (s, 2H), 8.72 (s, 1H).

[step 3] Using (E)-{2-[4-methyl-6-(1,3,4-oxadiazol-2-yl)-2-propylbenzimidazol-1-yl]methyl-10,11-dihydro-5H-dibenzo[a,d]cyclohepten-5-ylidene}acetonitrile (65 mg, 0.13 mmol) obtained in step 2 and in the same manner as in Example 4, the title compound (compound 70) (4.4 mg, 6.4%) was obtained.

ESI-MS m/z: 529 (M+H)$^+$; $^1$H-NMR (DMSO-d$_6$, δ): 0.96 (t, J=7.4 Hz, 3H), 1.68-1.86 (m, 2H), 2.64 (s, 3H), 2.76-3.42 (br, 4H), 2.96 (t, J=7.4 Hz, 2H), 5.68 (s, 2H), 6.80 (s, 1H), 6.87 (d, J=7.5 Hz, 1H), 6.94 (d, J=8.1 Hz, 1H), 7.00-7.06 (m, 2H), 7.15-7.28 (m, 2H), 7.42 (d, J=8.1 Hz, 1H), 7.80 (s, 1H), 8.05 (s, 1H), 9.30 (s, 1H).

Example 71

(E)-2-[4-Methyl-6-(5-methyl-1,3,4-oxadiazol-2-yl)-2-propylbenzimidazol-1-yl]methyl-5-(1H-tetrazol-5-yl)methylene-10,11-dihydro-5H-dibenzo[a,d]cycloheptene (Compound 71)

[step 1] Using (E)-{2-[4-methyl-6-(hydrazinocarbonyl)-2-propylbenzimidazol-1-yl]methyl-10,11-dihydro-5H-dibenzo[a,d]cyclohepten-5-ylidene}acetonitrile (150 mg, 0.32 mmol) obtained in Example 70, step 1, and triethyl orthoacetate (10.5 mL) instead of triethyl orthoformate, and in the same manner as in Example 70, step 2, (E)-{2-[4-methyl-6-(5-methyl-1,3,4-oxadiazol-2-yl)-2-propylbenz-imidazol-1-yl]methyl-10,11-dihydro-5H-dibenzo[a,d]cyclohepten-5-ylidene}acetonitrile (100 mg, 62%) was obtained.

ESI-MS m/z: 500 (M+H)$^+$; $^1$H-NMR (CDCl$_3$, δ): 1.02 (t, J=7.4 Hz, 3H), 1.74-1.92 (m, 2H), 2.58 (s, 3H), 2.73 (s, 3H), 2.83 (t, J=7.8 Hz, 2H), 3.06 (s, 4H), 5.35 (s, 2H), 5.67 (s, 1H), 6.78 (s, 1H), 6.83 (d, J=7.9 Hz, 1H), 7.18-7.37 (m, 4H), 7.43 (d, J=7.9 Hz, 1H), 7.72 (s, 2H).

[step 2] Using (E)-{2-[4-methyl-6-(5-methyl-1,3,4-oxadiazol-2-yl)-2-propylbenzimidazol-1-yl]methyl-10,11-dihydro-5H-dibenzo[a,d]cyclohepten-5-ylidene}acetonitrile (50 mg, 0.10 mmol) obtained in step 1 and in the same manner as in Example 5, the title compound (compound 71) (43 mg, 79%) was obtained.

ESI-MS m/z: 543 (M+H)$^+$; $^1$H-NMR (CDCl$_3$, δ): 1.03 (t, J=7.2 Hz, 3H), 1.76-1.94 (m, 2H), 2.62 (s, 3H), 2.76 (s, 3H), 2.77-3.04 (br, 2H), 3.15-3.44 (br, 2H), 3.19 (t, J=7.2 Hz, 2H), 5.49 (s, 2H), 6.81 (s, 1H), 6.96 (d, J=7.9 Hz, 1H), 7.02 (s, 1H), 7.12 (d, J=7.6 Hz, 1H), 7.20-7.25 (m, 1H), 7.33-7.43 (m, 2H), 7.48 (d, J=7.9 Hz, 1H), 7.91 (d, J=4.3 Hz, 2H).

Example 72

(E)-{2-[4-Methyl-6-(5-oxo-4,5-dihydro-1,3,4-oxadiazol-2-yl)-2-propylbenzimidazol-1-yl]methyl-10,11-dihydro-5H-dibenzo[a,d]cyclohepten-5-ylidene}acetonitrile (Compound 72)

(E)-{2-[4-Methyl-6-(hydrazylcarbonyl)-2-propylbenz-imidazol-1-yl]methyl-10,11-dihydro-5H-dibenzo[a,d]cyclohepten-5-ylidene}acetonitrile (150 mg, 0.32 mmol) obtained in Example 70, step 1 was dissolved in methylene chloride (2 mL), N,N'-carbonyldiimidazole (68 mg, 0.42 mmol) was added, and the mixture was stirred at room temperature for 4 hr. Acetic acid (2 mL) was added to the mixture, and the mixture was stirred at 60° C. for 6 hr. The mixture was concentrated under reduced pressure, and the residue was purified by reversed-phase liquid chromatography (water/acetonitrile=7/3 to 1/9) to give the title compound (compound 72) (12 mg, 12%).

ESI-MS m/z: 502 (M+H)$^+$; $^1$H-NMR (CDCl$_3$, δ): 1.04 (t, J=7.4 Hz, 3H), 1.80-1.96 (m, 2H), 2.53 (s, 3H), 3.04-3.22 (m,

6H), 5.43 (s, 2H), 5.69 (s, 1H), 6.95-7.02 (m, 2H), 7.18-7.23 (m, 2H), 7.29-7.35 (m, 4H), 7.44 (d, J=7.2 Hz, 1H), 11.04 (br s, 1H).

Example 73

(Z)-3-(2,5,7-Trimethyl-3H-imidazo[4,5-b]pyridin-3-yl)methyl-11-[1-(1H-tetrazol-5-yl)ethylidene]-6,11-dihydrodibenzo[b,e]oxepine (Compound 73)

[step 1] (Z)-2-(3-Hydroxymethyl-6,11-dihydrodibenzo[b,e]oxepin-11-ylidene)propiononitrile (400 mg, 1.44 mmol) obtained in Reference Example B6 and 2,5,7-trimethyl-3H-imidazo[4,5-b]pyridine (U.S. Pat. No. 5,332,744; 349 mg, 2.16 mmol) were dissolved in THF (14 mL), polymer-supported triphenylphosphine (962 mg, 2.88 mmol) and di-tert-butyl azodicarboxylate (664 mg, 2.88 mmol) were added at 0° C., and the mixture was stirred at room temperature for 2 hr. The mixture was filtered, and the filtrate was concentrated under reduced pressure. The residue was purified by silica gel column chromatography (hexane/ethyl acetate=4/6) to give (Z)-2-[3-(2,5,7-trimethyl-3H-imidazo[4,5-b]pyridin-3-yl)methyl-6,11-dihydrodibenzo[b,e]oxepin-11-ylidene]propiononitrile (310 mg, 51%).

$^1$H-NMR (DMSO-$d_6$, δ): 1.94 (s, 3H), 2.42 (s, 3H), 2.47 (s, 3H), 2.48 (s, 3H), 4.91 (d, J=12.6 Hz, 1H), 5.37 (2H, s), 5.42 (d, J=12.6 Hz, 1H), 6.47 (d, J=1.6 Hz, 1H), 6.72 (dd, J=8.1, 1.8 Hz, 1H), 6.93 (s, 1H), 7.26-7.54 (m, 5H).

[step 2] Using (Z)-2-[3-(2,5,7-trimethyl-3H-imidazo[4,5-b]pyridin-3-yl)methyl-6,11-dihydrodibenzo[b,e]oxepin-11-ylidene]propiononitrile (153 mg, 0.364 mmol) obtained in step 1 and in the same manner as in Example 4, the title compound (compound 73) (106 mg, 63%) was obtained.

ESI-MS m/z: 464 (M+H)$^+$; $^1$H-NMR (DMSO-$d_6$, δ): 2.06 (s, 3H), 2.35 (s, 3H), 2.46 (s, 6H), 4.91 (d, J=12.3 Hz, 1H), 5.26 (s, 2H), 5.71 (d, J=12.3 Hz, 1H), 6.34-6.41 (m, 3H), 6.91 (s, 1H), 7.38-7.53 (m, 4H).

Example 74

(Z)-3-(2,5,7-Trimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 74)

Using (Z)-2-[3-(2,5,7-trimethyl-3H-imidazo[4,5-b]pyridin-3-yl)methyl-6,11-dihydrodibenzo[b,e]oxepin-11-ylidene]propiononitrile (153 mg, 0.364 mmol) obtained in Example 73, step 1 and in the same manner as in Example 5, the title compound (compound 74) (36 mg, 21%) was obtained.

ESI-MS m/z: 480 (M+H)$^+$, $^1$H-NMR (DMSO-$d_6$, δ): 1.98 (s, 3H), 2.38 (s, 3H), 2.47 (s, 6H), 4.86 (d, J=12.3 Hz, 1H), 5.32 (s, 2H), 5.59 (d, J=12.3 Hz, 1H), 6.38 (d, J=1.6 Hz, 1H), 6.61 (dd, J=8.1, 1.8 Hz, 1H), 6.91-6.92 (m, 2H), 7.30-7.51 (m, 4H).

Example 75

(Z)-3-(2-Ethyl-5,7-dimethyl-3H-imidazo[4,5-b]pyridin-3-yl)methyl-11-[1-(1H-tetrazol-5-yl)ethylidene]-6,11-dihydrodibenzo[b,e]oxepine (Compound 75)

[step 1] Using 2-ethyl-5,7-dimethyl-3H-imidazo[4,5-b]pyridine (U.S. Pat. No. 5,332,744; 284 mg, 1.62 mmol) instead of 2,5,7-trimethyl-3H-imidazo[4,5-b]pyridine, and in the same manner as in Example 73, step 1, (Z)-2-[3-(2-ethyl-5,7-dimethyl-3H-imidazo[4,5-b]pyridin-3-yl)methyl-6,11-dihydrodibenzo[b,e]oxepin-11-ylidene]propiononitrile (271 mg, 38%) was obtained.

$^1$H-NMR (CDCl$_3$, δ): 1.31 (t, J=7.6 Hz, 3H), 2.01 (s, 3H), 2.55 (s, 3H), 2.61 (d, J=0.5 Hz, 3H), 2.75 (q, J=7.6 Hz, 2H), 4.77 (d, J=12.6 Hz, 1H), 5.33-5.39 (m, 2H), 5.43 (d, J=12.6 Hz, 1H), 6.47 (d, J=1.7 Hz, 1H), 6.73 (dd, J=8.1, 1.8 Hz, 1H), 6.86 (s, 1H), 7.12-7.16 (m, 1H), 7.36-7.37 (m, 3H), 7.44 (d, J=7.9 Hz, 1H).

[step 2] Using (Z)-2-[3-(2-ethyl-5,7-dimethyl-3H-imidazo[4,5-b]pyridin-3-yl)methyl-6,11-dihydrodibenzo[b,e]oxepin-11-ylidene]propiononitrile (270 mg, 0.621 mmol) obtained in step 1 and in the same manner as in Example 4, the title compound (compound 75) (159 mg, 54%) was obtained.

ESI-MS m/z: 478 (M+H)$^+$; $^1$H-NMR (DMSO-$d_6$, δ): 1.18 (t, J=7.5 Hz, 3H), 2.06 (s, 3H), 2.46 (s, 3H), 2.49 (s, 3H), 2.66 (q, J=7.5 Hz, 2H), 4.91 (d, J=12.3 Hz, 1H), 5.27 (s, 2H), 5.71 (d, J=12.3 Hz, 1H), 6.33-6.38 (m, 3H), 6.92 (s, 1H), 7.38-7.53 (m, 4H).

Example 76

(Z)-3-(2-Ethyl-5,7-dimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 76)

Using (Z)-2-[3-(2-ethyl-5,7-dimethyl-3H-imidazo[4,5-b]pyridin-3-yl)methyl-6,11-dihydrodibenzo[b,e]oxepin-11-ylidene]propiononitrile (150 mg, 0.345 mmol) obtained in Example 75, step 1 and in the same manner as in Example 5, the title compound (compound 76) (107 mg, 63%) was obtained.

ESI-MS m/z: 494 (M+H)$^+$; $^1$H-NMR (DMSO-$d_6$, δ): 1.19 (t, J=7.5 Hz, 3H), 1.98 (s, 3H), 2.47 (s, 3H), 2.49 (s, 3H), 2.69 (q, J=7.5 Hz, 2H), 4.86 (d, J=12.5 Hz, 1H), 5.33 (s, 2H), 5.59 (d, J=12.5 Hz, 1H), 6.39 (d, J=1.6 Hz, 1H), 6.58 (dd, J=8.1, 1.8 Hz, 1H), 6.89-6.92 (m, 2H), 7.30-7.51 (m, 4H).

Example 77

(Z)-3-(2-Cyclopropyl-7-methyl-3H-imidazo[4,5-b]pyridin-3-yl)methyl-11-[1-(1H-tetrazol-5-yl)ethylidene]-6,11-dihydrodibenzo[b,e]oxepine (Compound 77)

[step 1] Using 2-cyclopropyl-7-methyl-3H-imidazo[4,5-b]pyridine (U.S. Pat. No. 5,332,744; 656 mg, 3.79 mmol) instead of 2,5,7-trimethyl-3H-imidazo[4,5-b]pyridine, and in the same manner as in Example 73, step 1, (Z)-2-[3-(2-cyclopropyl-7-methyl-3H-imidazo[4,5-b]pyridin-3-yl)methyl-6,11-dihydrodibenzo[b,e]oxepin-11-ylidene]propiononitrile (274 mg, 17%) was obtained.

$^1$H-NMR (DMSO-$d_6$, δ): 1.01-1.08 (m, 4H), 1.93 (s, 3H), 2.19-2.22 (m, 1H), 2.49 (s, 3H), 4.92 (d, J=12.7 Hz, 1H), 5.42 (d, J=12.7 Hz, 1H), 5.53 (s, 2H), 6.60 (d, J=1.5 Hz, 1H), 6.81 (dd, J=8.1, 1.8 Hz, 1H), 7.03 (dd, J=4.9, 0.8 Hz, 1H), 7.26-7.29 (m, 1H), 7.41-7.54 (m, 4H), 8.08 (d, J=4.9 Hz, 1H).

[step 2] Using (Z)-2-[3-(2-cyclopropyl-7-methyl-3H-imidazo[4,5-b]pyridin-3-yl)methyl-6,11-dihydrodibenzo[b,e]oxepin-11-ylidene]propiononitrile (135 mg, 0.312 mmol) obtained in step 1 and in the same manner as in Example 4, the title compound (compound 77) (71 mg, 48%) was obtained.

ESI-MS m/z: 476 (M+H)$^+$; $^1$H-NMR (DMSO-$d_6$, δ): 0.96-1.00 (m, 4H), 2.06 (s, 3H), 2.08-2.15 (m, 1H), 2.47 (s, 3H), 4.92 (d, J=12.3 Hz, 1H), 5.41 (s, 2H), 5.71 (d, J=12.3 Hz, 1H), 6.37-6.49 (m, 3H), 7.01 (d, J=4.9 Hz, 1H), 7.38-7.53 (m, 4H), 8.06 (d, J=304.9 Hz, 1H).

Example 78

(Z)-3-(2-Cyclopropyl-7-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 78)

Using (Z)-2-[3-(2-cyclopropyl-7-methyl-3H-imidazo[4,5-b]pyridin-3-yl)methyl-6,11-dihydrodibenzo[b,e]oxepin-11-ylidene]propiononitrile (135 mg, 0.312 mmol) obtained in Example 77, step 1 and in the same manner as in Example 5, the title compound (compound 78) (83 mg, 54%) was obtained.

ESI-MS m/z: 492 (M+H)$^+$; $^1$H-NMR (DMSO-d$_6$, δ): 0.99-1.00 (m, 4H), 1.98 (s, 3H), 2.14-2.16 (m, 1H), 2.48 (s, 3H), 4.86 (d, J=12.3 Hz, 1H), 5.47 (s, 2H), 5.59 (d, J=12.3 Hz, 1H), 6.52 (d, J=1.6 Hz, 1H), 6.69 (dd, J=8.1, 1.6 Hz, 1H), 6.92 (d, J=8.1 Hz, 1H), 7.02 (d, J=5.4 Hz, 1H), 7.30-7.51 (m, 4H), 8.07 (d, J=4.9 Hz, 1H).

Example 79

(E)-2-(2-Ethyl-5,7-dimethyl-3H-imidazo[4,5-b]pyridin-3-yl)methyl-4-(1H-tetrazol-5-yl)methylene-4H-9,10-dihydrobenzo[4,5]cyclohepta[1,2-b]thiophene (Compound 79)

[step 1] Using (E)-(2-hydroxymethyl-4H-9,10-dihydrobenzo[4,5]cyclohepta[1,2-b]thiophen-4-ylidene)acetonitrile (200 mg, 0.748 mmol) obtained in Reference Example B7 instead of (Z)-2-(3-hydroxymethyl-6,11-dihydrodibenzo[b,e]oxepin-11-ylidene)acetonitrile, and in the same manner as in Example 73, step 1, (E)-[2-(2-ethyl-5,7-dimethyl-3H-imidazo[4,5-b]pyridin-3-yl)methyl-4H-9,10-dihydrobenzo[4,5]cyclohepta[1,2-b]thiophen-4-ylidene]acetonitrile (120 mg, 38%) was obtained.

$^1$H-NMR (CDCl$_3$, δ): 1.41 (t, J=7.5 Hz, 3H), 2.61 (s, 6H), 2.90 (q, J=7.5 Hz, 2H), 3.02 (s, 4H), 5.46 (s, 2H), 5.65 (s, 1H), 6.81 (s, 1H), 6.89 (s,) 1H, 7.21-7.37 (m, 3H), 7.46-7.49 (m, 1H).

[step 2] Using (E)-[2-(2-ethyl-5,7-dimethyl-3H-imidazo[4,5-b]pyridin-3-yl)methyl-4H-9,10-dihydrobenzo[4,5]cyclohepta[1,2-b]thiophen-4-ylidene]acetonitrile (65 mg, 0.153 mmol) obtained in step 1 and in the same manner as in Example 4, the title compound (compound 79) (42 mg, 59%) was obtained.

ESI-MS m/z: 468 (M+H)$^+$; $^1$H-NMR (CDCl$_3$, δ): 1.39 (t, J=7.6 Hz, 3H), 2.57 (s, 3H), 2.61 (s, 3H), 2.84-2.95 (m, 4H), 3.12-3.23 (m, 2H), 5.49 (d, J=3.3 Hz, 2H), 6.90 (s, 1H), 6.98 (d, J=7.4 Hz, 2H), 7.14 (d, J=7.4 Hz, 1H), 7.24-7.43 (m, 3H).

Example 80

(E)-2-(2-Ethyl-5,7-dimethyl-3H-imidazo[4,5-b]pyridin-3-yl)methyl-4-(5-oxo-4,5-dihydro-1,2,4-oxadiazol-3-yl)methylene-4H-9,10-dihydrobenzo[4,5]cyclohepta[1,2-b]thiophene (Compound 80)

Using (E)-[2-(2-ethyl-5,7-dimethyl-3H-imidazo[4,5-b]pyridin-3-yl)methyl-4H-9,10-dihydrobenzo[4,5]cyclohepta[1,2-b]thiophen-4-ylidene]acetonitrile (62 mg, 0.147 mmol) obtained in Example 79, step 1 and in the same manner as in Example 5, the title compound (compound 80) (61 mg, 85%) was obtained.

ESI-MS m/z: 484 (M+H)$^+$; $^1$H-NMR (CDCl$_3$, δ): 1.41 (t, J=7.6 Hz, 3H), 2.61 (s, 6H), 2.84-2.95 (m, 4H), 3.16-3.30 (m, 2H), 5.48 (s, 2H), 6.45 (s, 1H), 6.87-6.89 (m, 2H), 7.17 (dd, J=7.4, 1.0 Hz, 1H), 7.26-7.44 (m, 3H).

Example 81

(Z)-2-(2-Ethyl-5,7-dimethyl-3H-imidazo[4,5-b]pyridin-3-yl)methyl-4-(1H-tetrazol-5-yl)methylene-4H-9,10-dihydrobenzo[4,5]cyclohepta[1,2-b]thiophene (Compound 81)

[step 1] Using (Z)-(2-hydroxymethyl-4H-9,10-dihydrobenzo[4,5]cyclohepta[1,2-b]thiophen-4-ylidene)acetonitrile (200 mg, 0.748 mmol) obtained in Reference Example B7 and in the same manner as in Example 79, step 1, (Z)-[2-(2-ethyl-5,7-dimethyl-3H-imidazo[4,5-b]pyridin-3-yl)methyl-4H-9,10-dihydrobenzo[4,5]cyclohepta[1,2-b]thiophen-4-ylidene]acetonitrile (126 mg, 40%) was obtained.

$^1$H-NMR (CDCl$_3$, δ): 1.41 (t, J=7.5 Hz, 3H), 2.60 (s, 6H), 2.95 (q, J=7.5 Hz, 2H), 3.01-3.08 (m, 4H), 5.43 (s, 1H), 5.52 (s, 2H), 6.87 (s, 1H), 7.16-7.33 (m, 4H), 7.45 (s, 1H).

[step 2] Using (Z)-[2-(2-ethyl-5,7-dimethyl-3H-imidazo[4,5-b]pyridin-3-yl)methyl-4H-9,10-dihydrobenzo[4,5]cyclohepta[1,2-b]thiophen-4-ylidene]acetonitrile (65 mg, 0.153 mmol) obtained in step 1 and in the same manner as in Example 4, the title compound (compound 81) (57 mg, 80%) was obtained.

ESIMS m/z: 468 (M+H)$^+$; $^1$H-NMR (CDCl$_3$, δ): 1.33 (t, J=7.6 Hz, 3H), 2.53 (s, 3H), 2.59 (s, 3H), 2.80 (q, J=7.6 Hz, 2H), 2.99 (s, 4H), 5.37 (s, 2H), 6.41 (s, 1H), 6.73 (s, 1H), 6.89 (s, 1H), 7.17-7.33 (m, 4H).

Example 82

(Z)-2-(2-Ethyl-5,7-dimethyl-3H-imidazo[4,5-b]pyridin-3-yl)methyl-4-(5-oxo-4,5-dihydro-1,2,4-oxadiazol-3-yl)methylene-4H-9,10-dihydrobenzo[4,5]cyclohepta[1,2-b]thiophene (Compound 82)

Using (Z)-[2-(2-ethyl-5,7-dimethyl-3H-imidazo[4,5-b]pyridin-3-yl)methyl-4H-9,10-dihydrobenzo[4,5]cyclohepta[1,2-b]thiophen-4-ylidene]acetonitrile (63 mg, 0.148 mmol) obtained in Example 81, step 1 and in the same manner as in Example 5, the title compound (compound 82) (54 mg, 75%) was obtained.

ESI-MS m/z: 484 (M+H)$^+$; $^1$H-NMR (CDCl$_3$, δ): 1.39 (t, J=7.6 Hz, 3H), 2.57 (s, 3H), 2.59 (s, 3H), 2.86 (q, (7=7.6 Hz, 2H), 3.02-3.09 (m, 4H), 5.45 (s, 2H), 6.24 (s, 1H), 6.67 (s, 1H), 6.88 (s, 1H), 7.19-7.30 (m, 4H).

Example 83

(E)-2-[1-(2-Ethyl-5,7-dimethyl-3H-imidazo[4,5-b]pyridin-3-yl)ethyl]-5-(1H-tetrazol-5-yl)methylene-10,11-dihydro-5H-dibenzo[a,d]cycloheptene (Compound 83)

[step 1] (E)-(2-Hydroxymethyl-10,11-dihydro-5H-dibenzo[a,d]cyclohepten-5-ylidene)acetonitrile (JP-B-2526005; 523 mg, 2.00 mmol) was dissolved in dichloromethane (5 mL), 1,1,1-triacetoxy-1,1-dihydro-1,2-benziodoxol-3(1H)-one (1.10 g, 2.60 mmol) was added at 0° C., and the mixture was stirred at room temperature for 45 min. Isopropyl alcohol (0.5 mL) and water were added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=70/30 to 0/100) to give (E)-(2-formyl-10,11-dihydro-5H-dibenzo[a,d]cyclohepten-5-ylidene)acetonitrile (518 mg, 100%).

$^1$H-NMR (CDCl$_3$, δ): 3.16-3.24 (m, 4H), 5.76 (s, 1H), 7.23-7.39 (m, 3H), 7.45 (d, (7=8.1 Hz, 1H), 7.49 (dd, J=7.3, 1.5 Hz, 1H), 7.68 (s, 1H), 7.73 (dd, J=7.7, 1.5 Hz, 1H), 9.99 (s, 1H).

[step 2] (E)-(2-Formyl-10,11-dihydro-5H-dibenzo[a,d]cyclohepten-5-ylidene)acetonitrile (218 mg, 0.84 mmol) obtained in step 1 was dissolved in THF (4 mL), methylmagnesium chloride (3 mol/L THF solution; 0.42 mL, 1.26 mmol) was added at −78° C., and the mixture was warmed to −10° C. over 40 min. Saturated aqueous ammonium chloride solution was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=100/0 to 50/50) to give (E)-[2-(1-hydroxyethyl)-10,11-dihydro-5H-dibenzo[a,d]cyclohepten-5-ylidene]acetonitrile (212 mg, 92%).

$^1$H-NMR (CDCl$_3$, δ): 1.42 (d, J=6.3 Hz, 3H), 3.02-3.15 (m, 4H), 4.81 (q, J=6.3 Hz, 1H), 5.68 (s, 1H), 7.13-7.44 (m, 7H).

[step 3] (E)-[2-(1-Hydroxyethyl)-10,11-dihydro-5H-dibenzo[a,d]cyclohepten-5-ylidene]acetonitrile (100 mg, 0.36 mmol) obtained in step 2 and 2-ethyl-5,7-dimethyl-3H-imidazo[4,5-b]pyridine (193 mg, 1.10 mmol) were dissolved in THF (1.5 mL), polymer-supported triphenylphosphine (734 mg, 15 mmol) and di-tert-butyl azodicarboxylate (70 mg, 0.305 mmol) were added, and the mixture was stirred at room temperature for 1 hr. The mixture was filtered, and the filtrate was concentrated under reduced pressure. The residue was purified by silica gel column chromatography (hexane/ethyl acetate=40/60 to 30/70) to give (E)-{2-[1-(2-ethyl-5,7-dimethyl-3H-imidazo[4,5-b]pyridin-3-yl)ethyl]-10,11-dihydro-5H-dibenzo[a,d]cyclohepten-5-ylidene}acetonitrile (71 mg, 45%).

$^1$H-NMR (CDCl$_3$, δ): 1.27 (t, J=7.4 Hz,) 3H, 2.01 (d, J=7.2 Hz, 3H), 2.56 (s, 3H), 2.57-2.79 (m, 2H), 2.61 (s, 3H), 3.04-3.08 (m, 4H), 5.68 (s, 1H), 6.07 (q, J=7.2 Hz, 1H), 6.87 (s, 1H), 7.02 (s, 1H), 7.07-7.35 (m, 5H), 7.44 (dd, J=7.1, 1.5 Hz, 1H).

[step 4] Using (E)-{2-[1-(2-ethyl-5,7-dimethyl-3H-imidazo[4,5-b]pyridin-3-yl)ethyl]-10,11-dihydro-5H-dibenzo[a,d]cyclohepten-5-ylidene}acetonitrile (25 mg, 0.081 mmol) obtained in step 3 and in the same manner as in Example 4, the title compound (compound 83) (20 mg, 52%) was obtained.

ESI-MS m/z: 476 (M+H)$^+$; $^1$H-NMR (CDCl$_3$, δ): 1.24 (t, J=7.6 Hz, 3H), 2.02 (d, J=7.3 Hz, 3H), 2.56 (s, 3H), 2.57 (s, 3H), 2.58-3.00 (m, 4H), 3.23 (m, 2H), 6.09 (q, J=7.3 Hz, 1H), 6.87 (s, 1H), 6.91-7.50 (m, 8H).

Example 84

(E)-2-[1-(2-Ethyl-5,7-dimethyl-3H-imidazo[4,5-b]pyridin-3-yl)ethyl]-5-(5-oxo-4,5-dihydro-1,2,4-oxadiazol-3-yl)methylene-10,11-dihydro-5H-dibenzo[a,d]cycloheptene (Compound 84)

Using (E)-{2-[1-(2-ethyl-5,7-dimethyl-3H-imidazo[4,5-b]pyridin-3-yl)ethyl]-10,11-dihydro-5H-dibenzo[a,d]cyclohepten-5-ylidene}acetonitrile (30 mg, 0.083 mmol) obtained in Example 83, step 3 and in the same manner as in Example 5, the title compound (compound 84) (23 mg, 57%) was obtained.

ESI-MS m/z: 492 (M+H)$^+$; $^1$H-NMR (CDCl$_3$, δ): 1.27 (t, J=7.6 Hz, 3H), 2.02 (d, J=7.6 Hz, 3H), 2.56 (s, 3H), 2.61 (s, 3H), 2.60-3.01 (m, 4H), 3.15-3.42 (m, 2H), 6.06 (q, J=7.2 Hz, 1H), 6.50 (s, 1H), 6.87 (s, 1H), 7.00 (m, 1H), 7.07-7.46 (m, 6H).

Example 85

(E)-2-[1-(2-Propyl-4-methylbenzimidazol-1-yl)ethyl]-5-(5-oxo-4,5-dihydro-1,2,4-oxadiazol-3-yl)methylene-10,11-dihydro-5H-dibenzo[a,d]cycloheptene (Compound 85)

[step 1] (E)-[2-(1-Hydroxyethyl)-10,11-dihydro-5H-dibenzo[a,d]cyclohepten-5-ylidene]acetonitrile (67 mg, 0.24 mmol) obtained in Example 83, step 2 was dissolved in dichloromethane (1 mL), boron tribromide (1.0 mol/L dichloromethane solution; 0.73 mL, 0.73 mmol) was added at 0° C., and the mixture was stirred for 20 min. Water was added to the mixture, and the mixture was extracted with ethyl acetate. The organic layer was washed with brine, dried over anhydrous magnesium sulfate, and concentrated under reduced pressure. The obtained residue was dissolved in DMA (0.5 mL), 2-propyl-4-methylbenzimidazole (63 mg, 0.36 mmol) and potassium carbonate (100 mg, 0.72 mmol) were added, and the mixture was stirred at 70° C. for 4 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=50/50) to give (E)-{2-[1-(2-propyl-4-methylbenzimidazol-1-yl)ethyl]-10,11-dihydro-5H-dibenzo[a,d]cyclohepten-5-ylidene}acetonitrile (46 mg, 45%).

$^1$H-NMR (CDCl$_3$, δ): 1.03 (t, J=7.4 Hz, 3H), 1.77-1.86 (m, 2H), 1.94 (d, J=7.3 Hz, 3H), 2.66 (s, 3H), 2.91 (t, J=8.0 Hz, 2H), 3.07 (br s, 4H), 5.68 (q, J=7.3 Hz, 1H), 5.69 (s, 1H), 6.75-6.76 (m, 1H), 6.89-7.02 (m, 4H), 7.24-7.31 (m, 4H), 7.42-7.45 (m, 1H).

[step 2] Using (E)-{2-[1-(2-propyl-4-methylbenzimidazol-1-yl)ethyl]-10,11-dihydro-5H-dibenzo[a,d]cyclohepten-5-ylidene}acetonitrile (45 mg, 0.104 mmol) obtained in step 1 and in the same manner as in Example 5, the title compound (compound 85) (23 mg, 45%) was obtained.

ESI-MS m/z: 491 (M+H)$^+$; $^1$H-NMR(CDCl$_3$, δ): 1.02 (t, J=7.3 Hz, 3H), 1.75-1.86 (m, 2H), 1.94 (d, J=7.0 Hz, 3H), 2.65 (s, 3H), 2.80-2.97 (m, 4H), 3.16-3.38 (m, 2H), 5.67 (q, J=7.0 Hz, 1H), 6.50 (d, J=4.8 Hz, 1H), 6.77 (d, J=7.3 Hz, 1H), 6.88-6.99 (m, 3H), 7.04 (d, J=8.1 Hz, 1H), 7.17 (d, J=6.6 Hz, 1H), 7.30-7.42 (m, 4H).

Example 86

(E)-2-[1-(2-Propyl-4-methylbenzimidazol-1-yl)butyl]-5-(5-oxo-4,5-dihydro-1,2,4-oxadiazol-3-yl)methylene-10,11-dihydro-5H-dibenzo[a,d]cycloheptene (Compound 86)

[step 1] Using (E)-(2-formyl-10,11-dihydro-5H-dibenzo[a,d]cyclohepten-5-ylidene)acetonitrile (245 mg, 0.95 mmol) obtained in Example 83, step 1, and propylmagnesium bromide (2.0 mol/L THF solution; 0.71 mL, 1.42 mmol) instead of methylmagnesium chloride, and in the same manner as in Example 83, step 2, (E)-[2-(1-hydroxybutyl)-10,11-dihydro-5H-dibenzo[a,d]cyclohepten-5-ylidene]acetonitrile (184 mg, 64%) was obtained.

$^1$H-NMR (CDCl$_3$, δ): 0.92 (t, J=7.3 Hz, 3H), 1.28-1.48 (m, 2H), 1.58-1.77 (m, 2H), 3.06-3.18 (m, 4H), 4.62-4.68 (m, 1H), 5.71 (s, 1H), 7.13-7.36 (m, 6H), 7.45 (dd, J=7.5, 1.6 Hz, 1H).

[step 2] Using (E)-[2-(1-hydroxybutyl)-10,11-dihydro-5H-dibenzo[a,d]cyclohepten-5-ylidene]acetonitrile (184 mg, 0.61 mmol) obtained in step 1 and in the same manner as in Example 85, step 1, (E)-{2-[1-(2-propyl-4-methylbenzimidazol-1-yl)butyl]-10,11-dihydro-5H-dibenzo[a,d]cyclohepten-5-ylidene}acetonitrile (56 mg, 20%) was obtained.

$^1$H-NMR (CDCl$_3$, δ): 0.91 (t, J=7.1 Hz, 3H), 1.01 (t, J=7.3 Hz, 3H), 1.28-1.34 (m, 1H), 1.74-1.89 (m, 3H), 2.29-2.50 (m, 2H), 2.67 (s, 3H), 2.85-2.91 (m, 2H), 3.07 (br s, 4H), 5.48 (dd, J=10.3, 5.1 Hz, 1H), 5.68 (s, 1H), 6.89-7.02 (m, 5H), 7.18-7.35 (m, 4H), 7.44 (dd, J=7.1, 1.6 Hz, 1H).

[step 3] Using (E)-{2-[1-(2-propyl-4-methylbenzimidazol-1-yl)butyl]-10,11-dihydro-5H-dibenzo[a,d]cyclohepten-5-ylidene}acetonitrile (56 mg, 0.122 mmol) obtained in step 2 and in the same manner as in Example 5, the title compound (compound 86) (30 mg, 47%) was obtained.

ESI-MS m/z: 519 (M+H)$^+$; $^1$H-NMR (CDCl$_3$, δ): 0.93 (t, J=7.2 Hz, 3H), 1.00 (t, J=7.2 Hz, 3H), 1.20-1.73 (m, 2H), 1.80 (m, 2H), 2.39 (m, 2H), 2.66 (s, 3H), 2.72-3.00 (m, 4H), 3.28 (m, 2H), 5.47 (dd, J=5.3, 9.9 Hz, 1H), 6.49 (m, 1H), 6.80-7.54 (m, 10H).

Example 87

(E)-2-[1-(4-Chloro-2-ethylbenzimidazol-1-yl)ethyl]-5-(5-oxo-4,5-dihydro-1,2,4-oxadiazol-3-yl)methylene-10,11-dihydro-5H-dibenzo[a,d]cycloheptene (Compound 87)

[step 1] (E)-[2-(1-Hydroxyethyl)-10,11-dihydro-5H-dibenzo[a,d]cyclohepten-5-ylidene]acetonitrile (0.228 g, 0.829 mmol) obtained in Example 83, step 2 was dissolved in dichloromethane (4 mL), boron tribromide (1 mol/L dichloromethane solution, 2.5 mL, 2.48 mmol) was added, and the mixture was stirred at room temperature for 1 hr. Water was added to the reaction mixture, and the mixture was extracted three times with ethyl acetate. The combined organic layers were dried over anhydrous magnesium sulfate, and concentrated under reduced pressure to give a residue.

4-Chloro-2-ethylbenzimidazole (0.164 g, 0.912 mmol) was dissolved in DMA (3 mL), potassium carbonate (0.340 g, 2.49 mmol) was added, and the mixture was stirred for 15 min. To this mixture was added the residue obtained above, and the mixture was stirred at 60° C. for 2 hr. Water was added to the mixture, and the mixture was extracted three times with ethyl acetate. The combined organic layers were dried over anhydrous magnesium sulfate, and concentrated under reduced pressure. The obtained residue was purified by silica gel column chromatography (hexane/ethyl acetate=1/2) to give (E)-{2-[1-(4-chloro-2-ethylbenzimidazol-1-yl)ethyl]-10,11-dihydro-5H-dibenzo[a,d]cyclohepten-5-ylidene}acetonitrile (0.118 g, 32%).

[step 2] Using (E)-{2-[1-(4-chloro-2-ethylbenzimidazol-1-yl)ethyl]-10,11-dihydro-5H-dibenzo[a,d]cyclohepten-5-ylidene}acetonitrile (0.118 g, 0.269 mmol) obtained in step 1 and in the same manner as in Example 5, the title compound (compound 87) (0.035 g, 28%) was obtained.

ESI-MS m/z: 497 (M+H)$^+$; $^1$H-NMR (CDCl$_3$, δ): 1.43 (t, J=7.6 Hz, 3H), 1.96 (d, J=7.0 Hz, 3H), 2.75-3.07 (m, 4H), 3.10-3.49 (m, 2H), 5.70 (q, J=7.0 Hz, 1H), 6.48-6.58 (m, 1H), 6.67-6.79 (m, 1H), 6.79-6.90 (m, 2H), 6.90-7.02 (m, 1H), 7.02-7.11 (m, 1H), 7.14-7.25 (m, 2H), 7.24-7.50 (m, 3H).

Example 88

(E)-2-[1-(4-Chloro-2-cyclopropylbenzimidazol-1-yl)ethyl]-5-(5-oxo-4,5-dihydro-1,2,4-oxadiazol-3-yl)methylene-10,11-dihydro-5H-dibenzo[a,d]cycloheptene (Compound 88)

[step 1] Using 4-chloro-2-cyclopropylbenzimidazole (0.164 g, 0.912 mmol) instead of 4-chloro-2-ethylbenzimidazole, and in the same manner as in Example 87, step 1, (E)-{2-[1-(4-chloro-2-cyclopropylbenzimidazol-1-yl)ethyl]-10,11-dihydro-5H-dibenzo[a,d]cyclohepten-5-ylidene}acetonitrile (0.270 g, 72%) was obtained.

[step 2] Using (E)-{2-[1-(4-chloro-2-cyclopropylbenzimidazol-1-yl)ethyl]-10,11-dihydro-5H-dibenzo[a,d]cyclohepten-5-ylidene}acetonitrile (0.270 g, 0.600 mmol) obtained in step 1 and in the same manner as in Example 5, the title compound (compound 88) (0.004 g, 1.3%) was obtained.

ESI-MS m/z: 509 (M+H)$^+$; $^1$H-NMR (CDCl$_3$, δ): 0.84-1.04 (m, 2H), 1.09-1.26 (m, 2H), 1.71-1.91 (m, 4H), 2.62-2.95 (m, 2H), 3.01-3.32 (m, 2H), 5.86 (q, J=7.0 Hz, 1H), 6.33-6.45 (m, 1H), 6.57-6.68 (m, 1H), 6.70-6.91 (m, 2H), 6.93-7.37 (m, 7H).

Example 89

(E)-2-[1-(4-Chloro-2-propylbenzimidazol-1-yl)ethyl]-5-(5-oxo-4,5-dihydro-1,2,4-oxadiazol-3-yl)methylene-10,11-dihydro-5H-dibenzo[a,d]cycloheptene (Compound 89)

[step 1] Using 4-chloro-2-propylbenzimidazole (0.124 g, 0.639 mmol) instead of 4-chloro-2-ethylbenzimidazole, and in the same manner as in Example 87, step 1, (E)-{2-[1-(4-chloro-2-propylbenzimidazol-1-yl)ethyl]-10,11-dihydro-5H-dibenzo[a,d]cyclohepten-5-ylidene}acetonitrile (0.050 g, 19%) was obtained.

[step 2] Using (E)-{2-[1-(4-chloro-2-propylbenzimidazol-1-yl)ethyl-10,11-dihydro-5H-dibenzo[a,d]cyclohepten-5-ylidene}acetonitrile (0.050 g, 0.110 mmol) obtained in the above-mentioned step 1 and in the same manner as in Example 5, the title compound (compound 89) (0.003 g, 5%) was obtained.

ESI-MS m/z: 511 (M+H)$^+$; $^1$H-NMR (CDCl$_3$, δ): 1.06 (t, J=7.4 Hz, 3H), 1.78-1.96 (m, 2H), 2.02 (d, J=6.9 Hz, 3H), 2.76-3.07 (m, 2H), 3.08-3.54 (m, 4H), 5.72-5.89 (m, 1H), 6.45-6.58 (m, 1H), 6.78-6.96 (m, 2H), 7.01-7.51 (m, 8H).

Example 90

(E)-N-Phenyl-[2-(2,4-dimethyl-6-phenylbenzimidazol-1-yl)methyl-10,11-dihydro-5H-dibenzo[a,d]cyclohepten-5-ylidene]acetamide (Compound 90)

(E)-[2-(2,4-Dimethyl-6-phenylbenzimidazol-1-yl)methyl-10,11-dihydro-5H-dibenzo[a,d]cyclohepten-5-ylidene]acetic acid (0.050 g, 0.103 mmol) obtained in Example 55 was dissolved in DMF (1 mL), aniline (0.018 mL, 0.200 mmol), 1-ethyl-3-(3-dimethylaminopropyl)carbodiimide (0.047 g, 0.240 mmol) and 1-hydroxybenzotriazole (0.032 g, 0.240 mmol) were added, and the mixture was stirred at room temperature for 15 hr. Saturated aqueous sodium hydrogen carbonate solution was added to the mixture, and the precipitated solid was collected by suction filtration to give the title compound (compound 90) (0.048 g, 83%).

ESI-MS m/z: 560 (M+H)$^+$; $^1$H-NMR (CDCl$_3$, δ): 2.58 (s, 3H), 2.73 (s, 3H), 2.88-3.30 (m, 4H), 5.30 (s, 2H), 6.31 (s, 1H), 6.73-6.81 (m, 2H), 6.91-7.08 (m, 5H), 7.15-7.44 (m, 11H), 7.53-7.59 (m, 2H).

Example 91

(E)-[2-(2,4-Dimethyl-6-phenylbenzimidazol-1-yl) methyl-10,11-dihydro-5H-dibenzo[a,d]cyclohepten-5-ylidene]-N-methylacetamide (Compound 91)

Using methylamine hydrochloride (0.028 g, 0.412 mmol) instead of aniline, and in the same manner as in Example 90, the title compound (compound 91) (0.056 g, 54%) was obtained.

ESI-MS m/z: 498 (M+H)$^+$; $^1$H-NMR (CDCl$_3$, δ): 2.52-2.64 (m, 6H), 2.72 (s, 3H), 2.77-3.26 (m, 4H), 4.98-5.13 (m, 1H), 5.28 (s, 2H), 6.21 (s, 1H), 6.72 (s, 1H), 6.90-6.93 (m, 1H), 7.15-7.45 (m, 10H), 7.51-7.62 (m, 2H).

Example 92

(E)-2-[4-Methyl-6-(5-methyl-1,3-oxazol-2-yl)-2-propylbenzimidazol-1-yl]methyl-5-(1H-tetrazol-5-yl)methylene-10,11-dihydro-5H-dibenzo[a,d]cycloheptene (Compound 92)

[step 1] 4-Methyl-6-(5-methyl-1,3-oxazol-2-yl)-2-propylbenzimidazole (120 mg, 0.47 mmol) obtained in Reference Example A10 was dissolved in DMF (2.8 mL), (E)-2-(2-bromomethyl-10,11-dihydro-5H-dibenzo[a,d]cyclohepten-5-ylidene)acetonitrile (160 mg, 0.49 mmol) obtained in Reference Example B1 and potassium carbonate (325 mg, 2.35 mmol) were added, and the mixture was stirred at 60° C. for 4 hr. Water was added to the mixture, and the mixture was extracted with ethyl acetate. The organic layer was washed with water, dried over anhydrous magnesium sulfate, and concentrated under reduced pressure. The residue was purified by silica gel column chromatography (hexane/ethyl acetate=80/20 to 30/70) to give (E)-{2-[4-methyl-6-(5-methyl-1,3-oxazol-2-yl)-2-propylbenzimidazol-1-yl]methyl-10,11-dihydro-5H-dibenzo[a,d]cyclohepten-5-ylidene}acetonitrile (157 mg, 67%).

[step 2] Using (E)-{2-[4-methyl-6-(5-methyl-1,3-oxazol-2-yl)-2-propylbenzimidazol-1-yl]methyl-10,11-dihydro-5H-dibenzo[a,d]cyclohepten-5-ylidene}acetonitrile (50 mg, 0.10 mmol) obtained in step 1 and in the same manner as in Example 4, the title compound (compound 92) (28 mg, 52%) was obtained.

ESI-MS m/z: 542 (M+H)$^+$; $^1$H-NMR (CDCl$_3$, δ): 1.00 (t, J=7.3 Hz, 3H), 1.74-1.89 (m, 2H), 2.37 (d, J=1.0 Hz, 3H), 2.71 (s, 3H), 2.74-2.97 (m, 4H), 3.12-3.38 (m, 2H), 5.34 (s, 2H), 6.71 (s, 1H), 6.74-6.77 (m, 1H), 6.88-6.95 (m, 1H), 7.04 (s, 1H), 7.14 (d, J=7.3 Hz, 1H), 7.27-7.31 (m, 1H), 7.33-7.45 (m, 3H), 7.67 (s, 1H), 7.73 (s, 1H).

Example 93

(E)-2-[4-Methyl-6-(4-methyl-1,3-oxazol-2-yl)-2-propylbenzimidazol-1-yl]methyl-5-(1H-tetrazol-5-yl)methylene-10,11-dihydro-5H-dibenzo[a,d]cycloheptene (Compound 93)

[step 1] Using (E)-2-(2-bromomethyl-10,11-dihydro-5H-dibenzo[a,d]cyclohepten-5-ylidene)acetonitrile (56 mg, 0.17 mmol) obtained in Reference Example B1 and 4-methyl-6-(4-methyl-1,3-oxazol-2-yl)-2-propylbenzimidazole (40 mg, 0.16 mmol) obtained in Reference Example A11, step 3, and in the same manner as in Example 92, step 1, (E)-{2-[4-methyl-6-(4-methyl-1,3-oxazol-2-yl)-2-propylbenzimidazol-1-yl]methyl-10,11-dihydro-5H-dibenzo[a,d]cyclohepten-5-ylidene}acetonitrile (76 mg, 97%) was obtained.

[step 2] Using (E)-{2-[4-methyl-6-(4-methyl-1,3-oxazol-2-yl)-2-propylbenzimidazol-1-yl]methyl-10,11-dihydro-5H-dibenzo[a,d]cyclohepten-5-ylidene}acetonitrile (75 mg, 0.15 mmol) obtained in step 1 and in the same manner as in Example 4, the title compound (compound 93) (21 mg, 26%) was obtained.

ESI-MS m/z: 542 (M+H)$^+$; $^1$H-NMR (CDCl$_3$, δ): 1.00 (t, J=7.3 Hz, 3H), 1.74-1.89 (m, 2H), 2.21 (d, J=1.1 Hz, 3H), 2.71 (s, 3H), 2.77-2.85 (m, 2H), 2.85-3.00 (m, 2H), 3.12-3.40 (m, 2H), 5.34 (s, 2H), 6.70 (s, 1H), 6.89-6.95 (m, 1H), 7.05 (s, 1H), 7.14-7.18 (m, 1H), 7.28-7.33 (m, 1H), 7.35-7.46 (m, 4H), 7.69 (s, 1H), 7.76 (s, 1H).

Example 94

(E)-1-(−{2-[4-Methyl-6-(1,3-oxazol-2-yl)-2-propylbenzimidazol-1-yl]methyl-10,11-dihydro-5H-dibenzo[a,d]cyclohepten-5-ylidene}acetyl)pyrrolidine-2-carboxylic acid (Compound 94)

[step 1] Using (E)-{2-[4-methyl-6-(1,3-oxazol-2-yl)-2-propylbenzimidazol-1-yl]methyl-10,11-dihydro-5H-dibenzo[a,d]cyclohepten-5-ylidene}acetonitrile (71 mg, 0.15 mmol) obtained in Example 69, step 1 and in the same manner as in Example 55, (E)-{2-[4-methyl-6-(1,3-oxazol-2-yl)-2-propylbenzimidazol-1-yl]methyl-10,11-dihydro-5H-dibenzo[a,d]cyclohepten-5-ylidene}acetic acid (42 mg, 57%) was obtained.

[step 2] (E)-{2-[4-Methyl-6-(oxazol-2-yl)-2-propylbenzimidazol-1-yl]methyl-10,11-dihydro-5H-dibenzo[a,d]cyclohepten-5-ylidene}acetic acid (125 mg, 0.25 mmol) obtained in step 1 was dissolved in DMF (2.5 mL), (DL)-methylpyrrolidine-2-carboxylate hydrochloride (82 mg, 0.50 mmol), 1-ethyl-3-(3-dimethylaminopropyl)carbodiimide (57 mg, 0.30 mmol), triethylamine (69 μL, 0.50 mmol) and 1-hydroxybenzotriazole (46 mg, 0.30 mmol) were added, and the mixture was stirred at room temperature for 4 hr. Saturated aqueous sodium hydrogen carbonate solution (10 mL) was added to the mixture, and the mixture was extracted with chloroform (70 mL). The organic layer was washed with brine, dried over anhydrous magnesium sulfate, and concentrated under reduced pressure. The residue was purified by silica gel column chromatography (chloroform/methanol=99/1 to 93/7) to give (DL,E)-methyl 1-{{2-[4-methyl-6-(1,3-oxazol-2-yl)-2-propylbenzimidazol-1-yl]methyl-10,11-dihydro-5H-dibenzo[a,d]cyclohepten-5-ylidene}acetyl}pyrrolidine-2-carboxylate (57 mg, 80%).

[step 3] (DL,E)-Methyl 1-{{2-[4-methyl-6-(1,3-oxazol-2-yl)-2-propylbenzimidazol-1-yl]methyl-10,11-dihydro-5H-dibenzo[a,d]cyclohepten-5-ylidene}acetyl}pyrrolidine-2-carboxylate (49 mg, 0.08 mmol) obtained in the above-mentioned step 2 was dissolved in ethanol (1.2 mL) and water (0.4 mL), lithium hydroxide monohydrate (17 mg, 0.40 mmol) was added, and the mixture was stirred at room temperature for 3 hr. 4 mol/L Hydrochloric acid (5 mL) was added to the mixture, and the mixture was extracted with chloroform (60 mL). The organic layer was dried over anhydrous magnesium sulfate, and concentrated under reduced pressure. The residue was purified by C18 reversed-phase column chromatography (0.05% TFA aqueous solution/acetonitrile=70/30 to 40/60) to give the title compound (compound 94) (18 mg, 38%).

ESI-MS m/z: 601 (M+H)$^+$; $^1$H-NMR (DMSO-d$_6$, δ): 0.96 (t, J=7.3 Hz, 3H), 1.58-2.10 (m, 6H), 2.60 (s, 3H), 2.85 (t, J=7.4 Hz, 2H), 3.15-4.00 (m, 6H), 4.06-4.41 (m, 1H), 5.47 (s, 2H), 6.25 (br s, 1H), 6.83-6.91 (m, 1H), 6.95 (br s, 1H), 6.98-7.06 (m, 1H), 7.08-7.17 (m, 3H), 7.20-7.32 (m, 2H), 7.66 (s, 1H), 7.80 (s, 1H), 7.97 (s, 1H).

Example 95

(E)-2-[N-Methyl 2-({2-[4-methyl-6-(1,3-oxazol-2-yl)-2-propylbenzimidazol-1-yl]methyl-10,11-dihydro-5H-dibenzo[a,d]cyclohepten-5-ylidene}acetamido)]acetic acid (Compound 95)

[step 1] (E)-{2-[4-Methyl-6-(oxazol-2-yl)-2-propylbenzimidazol-1-yl]methyl-10,11-dihydro-5H-dibenzo[a,d]cyclohepten-5-ylidene}acetic acid (190 mg, 0.38 mmol) obtained in Example 94, step 1 was dissolved in DMF (3.8 mL), methyl 2-(methylamino)acetate hydrochloride (125 mg, 0.75 mmol), 1-ethyl-3-(3-dimethylaminopropyl)carbodiimide (87 mg, 0.45 mmol), triethylamine (105 μL, 0.75 mmol) and 1-hydroxybenzotriazole (69 mg, 0.45 mmol) were added, and the mixture was stirred at room temperature for 2 hr. Saturated aqueous sodium hydrogen carbonate solution (10 mL) was added to the mixture, and the mixture was extracted with ethyl acetate (75 mL). The organic layer was washed with brine, dried over anhydrous magnesium sulfate, and concentrated under reduced pressure. The residue was purified by silica gel column chromatography (chloroform/methanol=98/2 to 95/5) to give (E)-methyl 2-{N-methyl-2-{{2-[4-methyl-6-(1,3-oxazol-2-yl)-2-propylbenzimidazol-1-yl]methyl-10,11-dihydro-5H-dibenzo[a,d]cyclohepten-5-ylidene}acetamido}}acetate (77 mg, 65%).
[step 2] Using (E)-methyl 2-[N-methyl-2-({2-[4-methyl-6-(1,3-oxazol-2-yl)-2-propylbenzimidazol-1-yl]methyl-10,11-dihydro-5H-dibenzo[a,d]cyclohepten-5-ylidene}acetamido)]acetate (65 mg, 0.11 mmol) obtained in step 1 and in the same manner as in Example 94, step 2, the title compound (compound 95) (22 mg, 35%) was obtained.

ESI-MS m/z: 575 (M+H)$^+$; $^1$H-NMR (DMSO-d$_6$, δ): 0.96 (t, J=7.5 Hz, 3H), 1.74-1.85 (m, 2H), 2.59 (s, 3H), 2.72-3.18 (m, 6H), 3.03 (s, 3H), 3.79-4.08 (m, 2H), 5.46 (s, 2H), 6.29 (br s, 1H), 6.83-6.90 (m, 1H), 6.94 (br s, 1H), 6.97-7.06 (m, 1H), 7.07-7.16 (m, 3H), 7.20-7.23 (m, 1H), 7.24-7.32 (m, 1H), 7.60-7.65 (m, 1H), 7.78 (s, 1H), 7.95-7.98 (m, 1H).

Example 96

(E)-8-[(4-Hydroxypropan-2-yl)-2-propylbenzimidazol-1-yl]methyl-11-[1-(5-oxo-4,5-dihydro-1,2,4-oxadiazol-3-yl)ethylidene]-6,11-dihydrodibenzo[b,e]oxepine (Compound 96)

[step 1] Using (2-propylbenzimidazol-4-yl)propan-2-ol (190 mg, 0.642 mmol) obtained in Reference Example A15 instead of 2-ethylbenzimidazole, and in the same manner as in Example 26, step 1, (E)-2-{8-[(4-hydroxypropan-2-yl)-2-propylbenzimidazol-1-yl]methyl-6,11-dihydrodibenzo[b,e]oxepin-11-ylidene}propiononitrile (295 mg, quantitatively) was obtained.
[step 2] Using (E)-2-{8-[(4-hydroxypropan-2-yl)-2-propylbenzimidazol-1-yl]methyl-6,11-dihydrodibenzo[b,e]oxepin-11-ylidene}propiononitrile (147 mg, 0.308 mmol) obtained in step 1 and in the same manner as in Example 5, the title compound (compound 96) (100 mg, 61%) was obtained.

ESI-MS m/z: 537 (M+H)$^+$; $^1$H-NMR (CDCl$_3$, δ): 1.00 (t, J=7.3 Hz, 3H), 1.72 (s, 6H), 1.84 (m, 2H), 2.28 (s, 3H), 2.76 (t, J=7.3 Hz, 2H), 4.76 (d, J=12.9 Hz, 1H), 5.34 (s, 2H), 5.52 (d, J=12.9 Hz, 1H), 6.80-6.99 (m, 2H), 7.00-7.30 (m, 8H).

Example 97

(E)-11-[1-(5-Oxo-4,5-dihydro-1,2,4-oxadiazol-3-yl)ethylidene]-8-(4-phenyl-2-propylimidazol-1-yl)methyl-6,11-dihydrodibenzo[b,e]oxepine (Compound 97)

[step 1] Using 4-phenyl-2-propylimidazole (0.091 g, 0.489 mmol) obtained in Reference Example A8 instead of benzimidazole, and in the same manner as in Example 25, step 1, (E)-2-{8-(4-phenyl-2-propylimidazol-1-yl)methyl-6,11-dihydrodibenzo[b,e]oxepin-11-ylidene}propiononitrile (0.182 g, 91%) was obtained.
[step 2] Using (E)-2-[8-(4-phenyl-2-propylimidazol-1-yl)methyl-6,11-dihydrodibenzo[b,e]oxepin-11-ylidene]propiononitrile (0.182 g, 0.410 mmol) obtained in step 1 and in the same manner as in Example 5, the title compound (compound 97) (0.075 g, 36%) was obtained.

ESI-MS m/z: 505 (M+H)$^+$; $^1$H-NMR (CDCl$_3$, δ): 0.97 (t, J=7.6 Hz, 3H), 1.67-1.87 (m, 2H), 2.26 (s, 3H), 2.63 (t, J=7.6 Hz, 2H), 4.78 (d, J=12.6 Hz, 1H), 5.11 (s, 2H), 5.52 (d, J=12.6 Hz, 1H), 6.81-6.87 (m, 1H), 6.87-6.95 (m, 1H), 6.98-7.11 (m, 4H), 7.11-7.27 (m, 3H), 7.27-7.39 (m, 2H), 7.68-7.79 (m, 2H).

Example 98

(E)-11-[1-(5-Oxo-4,5-dihydro-1,2,4-oxadiazol-3-yl)ethylidene]-8-[2-propyl-4-(4-pyridyl)imidazol-1-yl]methyl-6,11-dihydrodibenzo[b,e]oxepine (Compound 98)

[step 1] Using 2-propyl-4-(4-pyridyl)imidazole (0.044 g, 0.235 mmol) obtained in Reference Example A9 instead of benzimidazole, and in the same manner as in Example 25, step 1, (E)-2-{8-[2-propyl-4-(4-pyridyl)imidazol-1-yl]methyl-6,11-dihydrodibenzo[b,e]oxepin-11-ylidene}propiononitrile (0.043 g, 40%) was obtained.
[step 2] Using (E)-2-{8-[2-propyl-4-(4-pyridyl)imidazol-1-yl]methyl-6,11-dihydrodibenzo[b,e]oxepin-11-ylidene}propiononitrile (0.043 g, 0.096 mmol) obtained in Example 98, step 1 and in the same manner as in Example 5, the title compound (compound 98) (0.004 g, 8%) was obtained.

ESI-MS m/z: 506 (M+H)$^+$; $^1$H-NMR (CDCl$_3$, δ): 0.93-1.04 (m, 3H), 1.67-1.85 (m, 2H), 2.28-2.37 (m, 3H), 2.55-2.71 (m, 2H), 4.59-4.75 (m, 1H), 5.07-5.16 (m, 2H), 5.38-5.51 (m, 1H), 6.79-6.89 (m, 2H), 6.89-7.02 (m, 1H), 7.07-7.32 (m, 5H), 7.55-7.68 (m, 2H), 8.32-8.45 (m, 2H).

Example 99

(E)-8-(2-Methyl-4-phenylimidazol-1-yl)methyl-11-[1-(5-oxo-4,5-dihydro-1,2,4-oxadiazol-3-yl)ethylidene]-6,11-dihydrodibenzo[b,e]oxepine (Compound 99)

[step 1] Using 4-iodo-2-methylimidazole (Synthesis-Stuttgart, 1994, 7, 681-682, 0.310 g, 0.149 mmol) instead of benzimidazole, and in the same manner as in Example 25, step 1, (E)-2-[8-(4-iodo-2-methylimidazol-1-yl)methyl-6,11-dihydrodibenzo[b,e]oxepin-11-ylidene]propiononitrile (0.300 g, 64%) was obtained.

[step 2] (E)-2-[8-(4-Iodo-2-methylimidazol-1-yl)methyl-6,11-dihydrodibenzo[b,e]oxepin-11-ylidene]propiononitrile (0.150 g, 3.21 mmol) obtained in step 1 was dissolved in DMF (2 mL), phenylboronic acid (0.051 g, 0.417 mmol), tetrakistriphenylphosphine palladium (0.056 g, 0.048 mmol) and sodium carbonate (0.085 g, 0.803 mmol) were added, and the mixture was heated under reflux for 3 hr. Water was added to the reaction mixture, and the mixture was extracted three times with ethyl acetate. The combined organic layers were dried over anhydrous magnesium sulfate, and concentrated under reduced pressure. The obtained residue was purified by silica gel column chromatography (hexane//ethyl acetate=1/2) to give (E)-2-[8-(2-iodo-4-phenylimidazol-1-yl)methyl-6,11-dihydrodibenzo[b,e]oxepin-11-ylidene]propiononitrile (0.079 g, 58%).

[step 3] Using (E)-2-[8-(2-iodo-4-phenylimidazol-1-yl)methyl-6,11-dihydrodibenzo[b,e]oxepin-11-ylidene]propiononitrile (0.079 g, 0.189 mmol) obtained in step 2 and in the same manner as in Example 5, the title compound (compound 99) (0.007 g, 18%) was obtained.

ESI-MS m/z: 477 (M+H)$^+$; $^1$H-NMR (CDCl$_3$, δ): 2.17 (s, 3H), 2.29 (s, 3H), 4.59 (d, J=12.6 Hz, 1H), 5.02 (s, 2H), 5.42 (d, J=12.6 Hz, 1H), 6.78-6.86 (m, 2H), 6.86-6.98 (m, 1H), 7.04-7.15 (m, 2H), 7.16-7.25 (m, 3H), 7.28-7.37 (m, 3H), 7.60-7.69 (m, 2H).

Example 100

(E)-1-{11-[1-(5-Oxo-4,5-dihydro-1,2,4-oxadiazol-3-yl)ethylidene]-6,11-dihydrodibenzo[b,e]oxepin-8-yl}methyl-2-propylbenzimidazole-4-carboxamide (Compound 100)

[step 1] Methyl 2-propyl-1H-benzimidazole-4-carboxylate (600 mg, 2.75 mmol) obtained in Reference Example A12 was dissolved in DMF (3.6 mL), (E)-2-(8-chloromethyl-6,11-dihydrobenzo[b,e]oxepin-11-ylidene)propiononitrile (853 mg, 2.89 mmol) obtained in Reference Example B5 and potassium carbonate (1.9 g, 13.8 mmol) were added, and the mixture was stirred at 60° C. for 4 hr. Water was added to the mixture, and the mixture was extracted with ethyl acetate. The organic layer was washed with water, dried over anhydrous magnesium sulfate, and concentrated under reduced pressure. The residue was purified by silica gel column chromatography (hexane/ethyl acetate=80/20 to 30/70) to give (E)-methyl 1-[11-(1-cyanoethylidene)-6,11-dihydrodibenzo[b,e]oxepin-8-yl]methyl-2-propylbenzimidazole-4-carboxylate (970 mg, 74%).

[step 2] (E)-Methyl 1-[11-(1-cyanoethylidene)-6,11-dihydrodibenzo[b,e]oxepin-8-yl]methyl-2-propylbenzimidazole-4-carboxylate (870 mg, 1.82 mmol) obtained in step 1 was dissolved in ethanol (13 mL) and THF (2.6 mL), 4 mmol/L aqueous sodium hydroxide solution (8.7 mL) was added, and the mixture was stirred at 70° C. for 30 min. The mixture was concentrated under reduced pressure, adjusted to pH 3 by adding 4 mol/L hydrochloric acid under ice-cooling, and the mixture was stirred for 30 min. The precipitated solid was collected by filtration to give (E)-1-[11-(1-cyanoethylidene)-6,11-dihydrodibenzo[b,e]oxepin-8-yl]methyl-2-propylbenzimidazole-4-carboxylic acid (785 mg, 93%).

[step 3] (E)-1-[11-(1-Cyanoethylidene)-6,11-dihydrodibenzo[b,e]oxepin-8-yl]methyl-2-propylbenzimidazole-4-carboxylic acid (250 mg, 0.54 mmol) obtained in step 2 was dissolved in THF (2.7 mL), N,N'-carbonyldiimidazole (114 mg, 0.70 mmol) was added, and the mixture was stirred at room temperature for 5 hr. Ammonia (25% aqueous solution, 110 μL, 1.62 mmol) was added to the mixture, and the mixture was stirred at room temperature for 15 hr. The mixture was adjusted to pH 6 with 1 mol/L hydrochloric acid, and the mixture was extracted with ethyl acetate (65 mL). The organic layer was washed with saturated aqueous sodium hydrogen carbonate solution, dried over anhydrous magnesium sulfate, and concentrated under reduced pressure. The residue was purified by silica gel column chromatography (hexane/ethyl acetate=70/30 to 40/60) to give (E)-1-[11-(1-cyanoethylidene)-6,11-dihydrodibenzo[b,e]oxepin-8-yl]methyl-2-propylbenzimidazole-4-carboxamide (249 mg, quantitative).

[step 4] Using (E)-1-[11-(1-cyanoethylidene)-6,11-dihydrodibenzo[b,e]oxepin-8-yl]methyl-2-propylbenzimidazole-4-carboxamide (249 mg, 0.54 mmol) obtained in step 3 and in the same manner as in Example 5, the title compound (compound 100) (81 mg, 29%) was obtained.

ESI-MS m/z: 522 (M+H)$^+$; $^1$H-NMR (DMSO-d$_6$, δ): 0.93 (t, J=7.3 Hz, 3H), 1.66-1.82 (m, 2H), 2.17 (s, 3H), 2.86 (t, J=7.5 Hz, 2H), 4.90 (d, J=12.5 Hz, 1H), 5.46 (d, J=12.5 Hz, 1H), 5.57 (s, 2H), 6.78 (d, J=8.1 Hz, 1H), 6.93 (t, J=7.3 Hz, 1H), 7.04-7.12 (m, 2H), 7.15-7.33 (m, 4H), 7.64-7.76 (m, 2H), 7.83 (d, J=7.3 Hz, 1H), 9.28 (t, J=3.3 Hz, 1H), 12.15 (br s, 1H).

Example 101

(E)-8-[4-(4-Hydroxypiperidine-1-carbonyl)-2-propylbenzimidazol-1-yl]methyl-11-[1-(5-oxo-4,5-dihydro-1,2,4-oxadiazol-3-yl)ethylidene]-6,11-dihydrodibenzo[b,e]oxepine (Compound 101)

[step 1] (E)-1-[11-(1-Cyanoethylidene)-6,11-dihydrodibenzo[b,e]oxepin-8-yl]methyl-2-propylbenzimidazole-4-carboxylic acid (220 mg, 0.48 mmol) obtained in Example 100, step 2 was dissolved in DMF (4.0 mL), 4-hydroxypiperidine (96 mg, 0.95 mmol), 1-ethyl-3-(3-dimethylaminopropyl)carbodiimide (109 mg, 0.57 mmol) and 1-hydroxybenzotriazole (87 mg, 0.57 mmol) were added, and the mixture was stirred at room temperature for 15 hr. Saturated aqueous sodium hydrogen carbonate solution (15 mL) was added to the mixture, and the precipitated solid was collected by filtration. The residue was purified by silica gel column chromatography (chloroform/methanol=99/1 to 93/7) to give (E)-2-{8-[4-(4-hydroxy-1-piperidinecarbonyl)-2-propylbenzimidazol-1-yl]methyl-6,11-dihydrodibenzo[b,e]oxepin-11-ylidene}propiononitrile (260 mg, 100%).

[step 2] Using (E)-2-{8-[4-(4-hydroxy-1-piperidinecarbonyl)-2-propylbenzimidazol-1-yl]methyl-6,11-dihydrodibenzo[b,e]oxepin-11-ylidene}propiononitrile (260 mg, 0.48 mmol) obtained in step 1 and in the same manner as in Example 5, the title compound (compound 101) (85 mg, 30%) was obtained.

ESI-MS m/z: 606 (M+H)$^+$; $^1$H-NMR (DMSO-d$_6$, δ): 0.89 (t, J=7.3 Hz, 3H), 1.28-1.51 (m, 2H), 1.58-1.75 (m, 3H), 1.76-1.89 (m, 1H), 2.17 (s, 3H), 2.79 (t, J=7.5 Hz, 2H), 2.91-3.05 (m, 1H), 3.19-3.27 (m, 1H), 3.65-3.80 (m, 1H), 4.07-4.21 (m, 1H), 4.75 (d, J=3.7 Hz, 1H), 4.89 (d, J=12.8 Hz, 1H), 5.47 (d, J=12.8 Hz, 1H), 5.51 (s, 2H), 6.79 (d, J=8.4 Hz, 1H), 6.93 (t, J=7.1 Hz, 1H), 7.04-7.12 (m, 3H), 7.14-7.27 (m, 4H), 7.49 (d, J=7.7 Hz, 1H), 12.14 (br s, 1H).

Example 102

(E)-N-(2-Hydroxyethyl) 1-{11-[1-(5-oxo-4,5-dihydro-1,2,4-oxadiazol-3-yl)ethylidene]-6,11-dihydrodibenzo[b,e]oxepin-8-yl}methyl-2-propylbenzimidazole-4-carboxamide (Compound 102)

[step 1] (E)-1-[11-(1-Cyanoethylidene)-6,11-dihydrodibenzo[b,e]oxepin-8-yl]methyl-2-propylbenzimidazole-4-carboxylic acid (220 mg, 0.48 mmol) obtained in Example 100, step 2 was dissolved in DMF (4.0 mL), 2-aminoethanol (57 µL, 0.95 mmol), 1-ethyl-3-(3-dimethylaminopropyl)carbodiimide (109 mg, 0.57 mmol) and 1-hydroxybenzotriazole (87 mg, 0.57 mmol) were added, and the mixture was stirred at room temperature for 15 hr. Saturated aqueous sodium hydrogen carbonate solution (15 mL) was added to the mixture, and the precipitated solid was collected by filtration. The residue was purified by silica gel column chromatography (chloroform/methanol=99/1 to 95/5) to give (E)-N-(2-hydroxyethyl) 1-[11-(1-cyanoethylidene)-6,11-dihydrodibenzo[b,e]oxepin-8-yl]methyl-2-propylbenzimidazole-4-carboxamide (241 mg, 99%).

[step 2] Using (E)-N-(2-hydroxyethyl) 1-[11-(1-cyanoethylidene)-6,11-dihydrodibenzo[b,e]oxepin-8-yl]methyl-2-propylbenzimidazole-4-carboxamide (240 mg, 0.47 mmol) obtained in step 1 and in the same manner as in Example 5, the title compound (compound 102) (70 mg, 26%) was obtained.

ESI-MS m/z: 566 (M+H)$^+$; $^1$H-NMR (DMSO-d$_6$, δ): 0.94 (t, J=7.3 Hz, 3H), 1.69-1.87 (m, 2H), 2.17 (s, 3H), 2.85 (t, J=7.4 Hz, 2H), 3.44-3.64 (m, 4H), 4.82 (t, J=5.0 Hz, 1H), 4.89 (d, J=12.9 Hz, 1H), 5.46 (d, J=12.9 Hz, 1H), 5.57 (s, 2H), 6.78 (d, J=8.3 Hz, 1H), 6.93 (t, J=6.9 Hz, 1H), 7.06 (s, 2H), 7.17-7.33 (m, 4H), 7.67 (d, J=7.3 Hz, 1H), 7.84 (d, J=6.9 Hz, 1H), 10.04 (t, J=5.3 Hz, 1H), 12.15 (br s, 1H).

Example 103

(E)-N-{1-{11-[1-(5-Oxo-4,5-dihydro-1,2,4-oxadiazol-3-yl)ethylidene]-6,11-dihydrodibenzo[b,e]oxepin-8-yl}methyl-2-propylbenzimidazol-4-yl}methanesulfonamide (Compound 103)

[step 1] (E)-1-[11-(1-Cyanoethylidene)-6,11-dihydrodibenzo[b,e]oxepin-8-yl]methyl-2-propylbenzimidazole-4-carboxylic acid (220 mg, 0.48 mmol) obtained in Example 100, step 2 was dissolved in chloroform (9.0 mL), triethylamine (1.3 mL, 9.3 mmol) and diphenylphosphoryl azide (2.1 mL, 9.3 mmol) were added, and the mixture was stirred at room temperature for 5 hr. tert-Butanol (9 mL) was added to the mixture, and the mixture was stirred at 100° C. for 42 hr. Saturated aqueous sodium hydrogen carbonate solution (20 mL) was added to the mixture, and the mixture was extracted with chloroform (80 mL). The organic layer was dried over anhydrous magnesium sulfate, and dried under reduced pressure. The residue was purified by silica gel column chromatography (hexane/ethyl acetate=100/0 to 40/60) to give (E)-tert-butyl 1-[11-(1-cyanoethylidene)-6,11-dihydrodibenzo[b,e]oxepin-8-yl]methyl-2-propylbenzimidazol-4-ylcarbamate (90 mg, 9%).

[step 2] (E)-tert-Butyl 1-[11-(1-cyanoethylidene)-6,11-dihydrodibenzo[b,e]oxepin-8-yl]methyl-2-propylbenzimidazol-4-ylcarbamate (100 mg, 0.19 mmol) obtained in step 1 was dissolved in dichloromethane (1 mL), trifluoroacetic acid (0.31 mL) was added dropwise, and the mixture was stirred at room temperature for 2 hr. Under ice-cooling, saturated aqueous sodium hydrogen carbonate solution (15 mL) was added to the mixture, and the mixture was extracted with chloroform (75 mL). The organic layer was dried over anhydrous magnesium sulfate, and dried under reduced pressure. The residue was purified by silica gel column chromatography (hexane/ethyl acetate=70/30 to 20/80) to give (E)-2-[8-(4-amino-2-propylbenzimidazol-1-yl)methyl-6,11-dihydrodibenzo[b,e]oxepin-11-ylidene]propiononitrile (40 mg, 49%).

[step 3] (E)-2-[8-(4-Amino-2-propylbenzimidazol-1-yl)methyl-6,11-dihydrodibenzo[b,e]oxepin-11-ylidene]propiononitrile (40 mg, 0.09 mmol) obtained in step 2 was dissolved in dichloromethane (1.5 mL), pyridine (0.14 mL), dimethylaminopyridine (2 mg, 0.02 mmol) and methanesulfonyl chloride (7.8 µL, 0.10 mmol) were added, and the mixture was stirred at room temperature for 4 hr. 2 mmol/L Hydrochloric acid (10 mL) was added to the mixture, and the mixture was extracted with chloroform (60 mL). The organic layer was washed with saturated aqueous sodium hydrogen carbonate solution, dried over anhydrous magnesium sulfate, and concentrated under reduced pressure. The residue was purified by silica gel column chromatography (hexane/ethyl acetate=80/20 to 20/80) to give (E)-N-{1-[11-(1-cyanoethylidene)-6,11-dihydrodibenzo[b,e]oxepin-8-yl]methyl-2-propylbenzimidazol-4-yl}methanesulfonamide (47 mg, 100%).

[step 4] Using (E)-N-{1-[11-(1-cyanoethylidene)-6,11-dihydrodibenzo[b,e]oxepin-8-yl]methyl-2-propylbenzimidazol-4-yl}methanesulfonamide (45 mg, 0.090 mmol) obtained in step 3 and in the same manner as in Example 5, the title compound (compound 103) (14 mg, 28%) was obtained.

ESI-MS m/z: 572 (M+H)$^+$; $^1$H-NMR (CDCl$_3$, δ): 0.97 (t, J=7.4 Hz, 3H), 1.73-1.90 (m, 2H), 2.30 (s, 3H), 2.85 (t, J=7.6 Hz, 2H), 3.11 (s, 3H), 4.76 (d, J=12.9 Hz, 1H), 5.38 (s, 2H), 5.53 (d, J=12.9 Hz, 1H), 6.80-6.86 (m, 1H), 6.90-7.00 (m, 2H), 7.02-7.08 (m, 2H), 7.10-7.24 (m, 4H), 7.43 (d, J=7.3 Hz, 1H).

Example 104

(E)-8-(4-Methyl-2-propylbenzimidazol-1-yl)methyl-11-(5-oxo-4,5-dihydro-1,2,4-oxadiazol-3-yl)methylene-6,11-dihydrodibenzo[b,e]oxepine (Compound 104)

[step 1] Using (E)-2-(8-bromomethyl-6,11-dihydrodibenzo[b,e]oxepin-11-ylidene)acetonitrile (1.5 g, 4.6 mmol) obtained in Reference Example B13 and 4-methyl-2-propylbenzimidazole (EP400835; 842 mg, 4.83 mmol) and in the same manner as in Example 92, step 1, (E)-2-{8-(4-methyl-2-propylbenzimidazol-1-yl)methyl-6,11-dihydrodibenzo[b,e]oxepin-11-ylidene}acetonitrile (1.47 g, 76%) was obtained.

[step 2] (E)-2-{8-(4-Methyl-2-propylbenzimidazol-1-yl)methyl-6,11-dihydrodibenzo[b,e]oxepin-11-ylidene}acetonitrile (150 mg, 0.34 mmol) obtained in step 1 was dissolved in ethanol (1.8 mL), hydroxylamine (50% aqueous solution, 1.1 mL, 17.9 mmol) was added, and the mixture was stirred under reflux for 18 hr. Water was added to the mixture, and the mixture was extracted with chloroform. The organic layer was dried over anhydrous magnesium sulfate, and concentrated under reduced pressure. The obtained residue was dissolved in dichloromethane (1.8 mL), triethylamine (75 µL, 0.54 mmol) and ethyl chlorocarbonate (51 µL, 0.54 mmol) were added at 0° C., and the mixture was stirred at room temperature for 30 min. Water was added to the mixture, and the mixture was extracted with chloroform. The organic layer was dried over anhydrous magnesium sulfate, and concentrated under reduced pressure. The obtained residue was dissolved in toluene (0.9 mL) and THF (0.9 mL), potassium tert-butoxide (80 mg, 0.72 mmol) was added, and the mixture was stirred at room temperature for 20 min. 5% Aqueous citric acid solution was added to the mixture, and the mixture was extracted with chloroform. The organic layer was dried over anhydrous magnesium sulfate, and concentrated under reduced pressure. The residue was purified by silica gel column chromatography (hexane/ethyl acetate=70/30 to 10/90) to give the title compound (compound 104) (119 mg, 70%).

ESI-MS m/z: 479 (M+H)$^+$; $^1$H-NMR (DMSO-d$_6$, δ): 0.93 (t, J=7.3 Hz, 3H), 1.64-1.81 (m, 2H), 2.52 (s, 3H), 2.81 (t, J=7.7 Hz, 2H), 4.91-5.39 (m, 2H), 5.50 (s, 2H), 6.57 (s, 1H), 6.79 (d, J=8.4 Hz, 1H), 6.91-7.11 (m, 4H), 7.18-7.32 (m, 4H), 7.39-7.45 (m, 1H).

Example 105

(E)-N-{2-[8-(4-Methyl-2-propylbenzimidazol-1-yl)methyl-6,11-dihydrodibenzo[b,e]oxepin-11-ylidene]acetyl}methanesulfonamide (Compound 105)

[step 1] Using (E)-2-[8-(4-methyl-2-propylbenzimidazol-1-yl)methyl-6,11-dihydrodibenzo[b,e]oxepin-11-ylidene]acetonitrile (800 mg, 1.91 mmol) obtained in Example 104, step 1 and in the same manner as in Example 55, (E)-2-[8-(4-methyl-2-propylbenzimidazol-1-yl)methyl-6,11-dihydrodibenzo[b,e]oxepin-11-ylidene]acetic acid (838 mg, 100%) was obtained.
[step 2] Using (E)-2-[8-(4-methyl-2-propylbenzimidazol-1-yl)methyl-6,11-dihydrodibenzo[b,e]oxepin-11-ylidene]acetic acid (250 mg, 0.57 mmol) obtained in step 1 and in the same manner as in Example 12, the title compound (compound 105) (125 mg, 43%) was obtained.

ESI-MS m/z: 516 (M+H)$^+$; $^1$H-NMR (CDCl$_3$, δ): 1.01 (t, J=7.3 Hz, 3H), 1.73-1.90 (m, 2H), 2.70 (s, 3H), 2.85 (t, J=7.9 Hz, 2H), 3.20 (s, 3H), 4.80-5.30 (m, 2H), 5.37 (s, 2H), 6.30 (s, 1H), 6.81 (d, J=8.3 Hz, 1H), 6.91 (t, J=7.4 Hz, 1H), 6.97-7.15 (m, 5H), 7.21-7.35 (m, 3H).

Example 106

(E)-8-(4-Methyl-2-propylbenzimidazol-1-yl)methyl-11-(2-oxo-2,3-dihydro-1,3,4-oxadiazol-5-yl)methylene-6,11-dihydrodibenzo[b,e]oxepine (Compound 106)

[step 1] (E)-2-[8-(4-Methyl-2-propylbenzimidazol-1-yl)methyl-6,11-dihydrodibenzo[b,e]oxepin-11-ylidene]acetic acid (300 mg, 0.68 mmol) obtained in Example 105, step 1 was dissolved in THF (6.8 mL) and dichloromethane (6 mL), N,N'-carbonyldiimidazole (444 mg, 2.74 mmol) was added, and the mixture was stirred at room temperature for 4 hr. To the mixture was added hydrazine monohydrate (0.33 mL, 6.84 mmol), and the mixture was stirred at room temperature for 5 hr. Water was added to the mixture, and the mixture was extracted with chloroform (70 mL). The organic layer was dried over anhydrous magnesium sulfate, and concentrated under reduced pressure. The residue was purified by silica gel column chromatography (chloroform/methanol=100/0 to 85/15) to give (E)-2-[8-(4-methyl-2-propylbenzimidazol-1-yl)methyl-6,11-dihydrodibenzo[b,e]oxepin-11-ylidene]acetohydrazide (309 mg, 100%).
[step 2] (E)-2-[8-(4-Methyl-2-propylbenzimidazol-1-yl)methyl-6,11-dihydrodibenzo[b,e]oxepin-11-ylidene]acetohydrazide (118 mg, 0.25 mmol) obtained in step 1 was dissolved in dichloromethane (2.5 mL), N,N'-carbonyldiimidazole (120 mg, 0.74 mmol) was added, and the mixture was stirred at room temperature for 3 hr. Water was added to the mixture, and the mixture was extracted with ethyl acetate (80 mL). The organic layer was dried over anhydrous magnesium sulfate, and concentrated under reduced pressure. The residue was purified by silica gel column chromatography (chloroform/methanol=100/0 to 93/7) to give the title compound (compound 106) (30 mg, 25%).

ESI-MS m/z: 479 (M+H)$^+$; $^1$H-NMR (DMSO-d$_6$, δ): 0.93 (t, J=7.3 Hz, 3H), 1.67-1.81 (m, 2H), 2.52 (s, 3H), 2.81 (t, J=7.7 Hz, 2H), 4.72-5.10 (m, 1H), 5.21-5.64 (m, 1H), 5.52 (s, 2H), 6.57 (s, 1H), 6.76 (dd, J=1.1, 8.1 Hz, 1H), 6.91-7.07 (m, 4H), 7.20-7.28 (m, 3H), 7.33 (d, J=7.7 Hz, 1H), 7.42 (dd, J=1.6, 7.9 Hz, 1H), 12.42 (br s, 1H).

Example 107

(E)-8-(4-Methyl-2-propylbenzimidazol-1-yl)methyl-11-(1,3,4-oxadiazol-2-yl)methylene-6,11-dihydrodibenzo[b,e]oxepine (Compound 107)

To (E)-2-[8-(4-methyl-2-propylbenzimidazol-1-yl)methyl-6,11-dihydrodibenzo[b,e]oxepin-11-ylidene]acetohydrazide (118 mg, 0.25 mmol) obtained in Example 106, step 1 was added triethoxymethane (2.1 mL), and the mixture was stirred at 120° C. for 5 hr. The mixture was concentrated under reduced pressure, and the residue was purified by silica gel column chromatography (hexane/ethyl acetate=70/30 to 10/90) to give the title compound (compound 107) (18 mg, 16%).

ESI-MS m/z: 463 (M+H)$^+$; $^1$H-NMR (CDCl$_3$, δ): 1.01 (t, J=7.3 Hz, 3H), 1.74-1.90 (m, 2H), 2.70 (s, 3H), 2.81-2.91 (m, 2H), 4.51-5.58 (m, 2H), 5.37 (s, 2H), 6.83 (dd, J=1.0, 8.3 Hz, 1H), 6.93-7.14 (m, 7H), 7.20-7.26 (m, 2H), 7.43 (dd, J=1.7, 7.9 Hz, 1H), 8.12 (d, J=0.7 Hz, 1H).

Example 108

(E)-8-(4-Methyl-2-propylbenzimidazol-1-yl)methyl-11-(1,2,4-oxadiazol-3-yl)methylene-6,11-dihydrodibenzo[b,e]oxepine (Compound 108)

[step 1] (E)-2-{8-(4-Methyl-2-propylbenzimidazol-1-yl)methyl-6,11-dihydrodibenzo[b,e]oxepin-11-ylidene}acetonitrile (310 mg, 0.74 mmol) obtained in Example 104, step 1 was dissolved in ethanol (3.7 mL), hydroxylamine (50% aqueous solution, 2.3 mL, 36.95 mmol) was added, and the mixture was stirred under reflux for 16 hr. Water was added to the mixture, and the precipitated solid was collected by filtration to give (E)-2-[8-(4-methyl-2-propylbenzimidazol-1-yl)methyl-6,11-dihydrodibenzo[b,e]oxepin-11-ylidene]acetaldoxime (304 mg, 91%).
[step 2] Using (E)-2-[8-(4-methyl-2-propylbenzimidazol-1-yl)methyl-6,11-dihydrodibenzo[b,e]oxepin-11-ylidene]acetaldoxime (150 mg, 0.33 mmol) obtained in step 1 and in the same manner as in Example 107, the title compound (compound 108) (7.1 mg, 5%) was obtained.

ESI-MS m/z: 463 (M+H)$^+$; $^1$H-NMR (CDCl$_3$, δ): 1.00 (t, J=7.4 Hz, 3H), 1.71-1.89 (m, 2H), 2.69 (s, 3H), 2.85 (t, J=7.9 Hz, 2H), 4.50-5.57 (m, 2H), 5.36 (s, 2H), 6.82 (dd, J=1.2, 8.4 Hz, 1H), 6.89-7.00 (m, 3H), 7.01-7.25 (m, 6H), 7.46 (dd, J=1.7, 7.9 Hz, 1H), 8.48 (s, 1H).

Example 109

(E)-8-(4-Methyl-2-propylbenzimidazol-1-yl)methyl-11-(5-trifluoromethyl-1,2,4-oxadiazol-3-yl)methylene-6,11-dihydrodibenzo[b,e]oxepine (Compound 109)

(E)-2-[8-(4-Methyl-2-propylbenzimidazol-1-yl)methyl-6,11-dihydrodibenzo[b,e]oxepin-11-ylidene]acetaldoxime (150 mg, 0.33 mmol) obtained in Example 108, step 1 was dissolved in dichloromethane (3.3 mL), bistrifluoroacetic acid anhydride (0.14 mL, 0.99 mmol) and triethylamine (0.14 mL, 0.99 mmol) were added, and the mixture was stirred at room temperature for 17 hr. To the mixture was added saturated aqueous sodium hydrogen carbonate solution (15 mL), and the mixture was extracted with ethyl acetate (75 mL). The organic layer was dried over anhydrous magnesium sulfate, and concentrated under reduced pressure. The residue was purified by silica gel column chromatography (hexane/ethyl acetate=70/30 to 40/60) to give the title compound (compound 109) (75 mg, 43%).

ESI-MS m/z: 531 (M+H)$^+$; $^1$H-NMR (CDCl$_3$, δ): 1.00 (t, J=7.4 Hz, 3H), 1.70-1.89 (m, 2H), 2.70 (s, 3H), 2.85 (t, J=7.9 Hz, 2H), 4.55-5.69 (m, 2H), 5.37 (s, 2H), 6.79-6.86 (m, 1H), 6.89 (s, 1H), 6.91-7.11 (m, 6H), 7.16 (d, J=7.9 Hz, 1H), 7.21-7.30 (m, 1H), 7.44 (dd, J=1.3, 7.9 Hz, 1H).

Example 110

(E)-11-Cyclopropyl(5-oxo-4,5-dihydro-1,2,4-oxadiazol-3-yl)methylene-8-(2-propylbenzimidazol-1-yl)methyl-6,11-dihydrodibenzo[b,e]oxepine (Compound 110)

[step 1] (E)-2-(8-Hydroxymethyl-6,11-dihydrodibenzo[b,e]oxepin-11-ylidene)cyclopropylacetonitrile (0.200 g, 0.661 mmol) obtained in Reference Example B9 was dissolved in THF (2 mL), 2,6-lutidine (0.460 mL, 3.96 mmol), lithium bromide (0.344 g, 3.96 mmol) and methanesulfonic anhydride (0.288 g, 1.65 mmol) were added, and the mixture was stirred at room temperature for 16 hr. Water was added to the mixture and the mixture was extracted 3 times with ethyl acetate. The combined organic layer was dried over anhydrous magnesium sulfate, and concentrated under reduced pressure to give a residue.

2-Propylbenzimidazole (0.091 g, 0.571 mmol) was dissolved in DMF (2 mL), potassium carbonate (0.375 g, 2.72 mmol) was added and the mixture was stirred for 15 min. To this mixture was added the residue obtained above, and the mixture was stirred at 60° C. for 2 hr. Water was added to the mixture and the mixture was extracted 3 times with ethyl acetate. The combined organic layer was dried over anhydrous magnesium sulfate, and concentrated under reduced pressure. The obtained residue was purified by silica gel column chromatography (hexane/ethyl acetate=1/2) to give (E)-2-[8-(2-propylbenzimidazol-1-yl)methyl-6,11-dihydrodibenzo[b,e]oxepin-11-ylidene]cyclopropylacetonitrile (0.201 g, 64%).

[step 2] Using (E)-2-[8-(2-propylbenzimidazol-1-yl)methyl-6,11-dihydrodibenzo[b,e]oxepin-11-ylidene]cyclopropylacetonitrile (0.200 g, 0.449 mmol) obtained in step 1 and in the same manner as in Example 5, the title compound (compound 110) (0.036 g, 15%) was obtained.

ESI-MS m/z: 505 (M+H)$^+$; $^1$H-NMR (DMSO-d$_6$, δ): 0.64-0.84 (m, 2H), 0.81-1.06 (m, 5H), 1.55-1.79 (m, 2H), 1.91-2.10 (m, 1H), 2.72-2.88 (m, 2H), 4.87 (d, J=12.6 Hz, 1H), 5.45-5.63 (m, 3H), 6.79 (d, J=8.2 Hz, 1H), 6.88-7.20 (m, 1H), 6.99-7.13 (m, 2H), 7.13-7.29 (m, 4H), 7.34-7.54 (m, 2H), 7.54-7.68 (m, 1H), 12.18 (br s, 1H).

Example 111

(E)-8-(4-Chloro-2-propylbenzimidazol-1-yl)methyl-11-cyclopropyl(5-oxo-4,5-dihydro-1,2,4-oxadiazol-3-yl)methylene-6,11-dihydrodibenzo[b,e]oxepine (Compound 111)

[step 1] Using 4-chloro-2-propylbenzimidazole (0.034 g, 0.175 mmol) instead of 2-propylbenzimidazole, and in the same manner as in Example 110, step 1, (E)-2-[8-(4-chloro-2-propylbenzimidazol-1-yl)methyl-6,11-dihydrodibenzo[b,e]oxepin-11-ylidene]cyclopropylacetonitrile (0.072 g, 72%) was obtained.

[step 2] Using (E)-2-[8-(4-chloro-2-propylbenzimidazol-1-yl)methyl-6,11-dihydrodibenzo[b,e]oxepin-11-ylidene]cyclopropylacetonitrile (0.070 g, 0.146 mmol) obtained in step 1 and in the same manner as in Example 5, the title compound (compound 111) (0.020 g, 25%) was obtained.

ESI-MS m/z: 539 (M+H)$^+$; $^1$H-NMR (CDCl$_3$, δ): 0.46-0.64 (m, 1H), 0.72-0.87 (m, 1H), 0.87-1.08 (m, 5H), 1.54-1.96 (m, 2H), 2.02-2.21 (m, 1H), 2.35-2.77 (m, 2H), 4.19 (d, J=13.2 Hz, 1H), 5.20-5.46 (m, 3H), 6.48-6.56 (m, 1H), 6.72-6.83 (m, 1H), 6.89-7.02 (m, 2H), 7.03-7.39 (m, 5H), 7.48-7.59 (m, 1H).

Example 112

(E)-8-(4-Chloro-2-cyclopropylbenzimidazol-1-yl)methyl-11-cyclopropyl(5-oxo-4,5-dihydro-1,2,4-oxadiazol-3-yl)methylene-6,11-dihydrodibenzo[b,e]oxepine (Compound 112)

[step 1] Using 4-chloro-2-cyclopropylbenzimidazole (WO2008096829, 0.034 g, 0.175 mmol) instead of 2-propylbenzimidazole, and in the same manner as in Example 110, step 1, (E)-2-{8-(4-chloro-2-cyclopropylbenzimidazol-1-yl)methyl-6,11-dihydrodibenzo[b,e]oxepin-11-ylidene}cyclopropylacetonitrile (0.080 g, 80%) was obtained.

[step 2] Using (E)-2-[8-(4-chloro-2-cyclopropylbenzimidazol-1-yl)methyl-6,11-dihydrodibenzo[b,e]oxepin-11-ylidene]cyclopropylacetonitrile (0.078 g, 0.163 mmol) obtained in step 1 and in the same manner as in Example 5, the title compound (compound 112) (0.010 g, 15%) was obtained.

ESI-MS m/z: 537 (M+H)$^+$; $^1$H-NMR(CDCl$_3$, δ): 0.82-1.06 (m, 4H), 1.09-1.31 (m, 4H), 1.78-1.93 (m, 1H), 1.98-2.14 (m, 1H), 4.63 (d, J=12.9 Hz, 1H), 5.39-5.48 (m, 2H), 5.57 (d, J=12.9 Hz, 1H), 6.77-6.86 (m, 1H), 6.86-7.07 (m, 3H), 7.11-7.34 (m, 5H), 7.45-7.52 (m, 1H).

Example 113

(E)-8-[2-(Methoxymethyl)benzimidazol-1-yl]methyl-11-cyclopropyl(5-oxo-4,5-dihydro-1,2,4-oxadiazol-3-yl)methylene-6,11-dihydrodibenzo[b,e]oxepine (Compound 113)

[step 1] Using (E)-2-(8-hydroxymethyl-6,11-dihydrobenzo[b,e]oxepin-11-ylidene)cyclopropylacetonitrile (170 mg, 0.56 mmol) obtained in Reference Example B9, step 3 and in the same manner as in Reference Example B1, (E)-2-(8-bromomethyl-6,11-dihydrobenzo[b,e]oxepin-11-ylidene)cyclopropylacetonitrile (169 mg, 83%) was obtained.

[step 2] Using (E)-2-(8-bromomethyl-6,11-dihydrobenzo[b,e]oxepin-11-ylidene)cyclopropylacetonitrile (75 mg, 0.21 mmol) obtained in step 1 and 2-methoxymethylbenzimidazole (32 mg, 0.20 mmol) obtained in Reference Example A13, and in the same manner as in Example 92, step 1, (E)-2-{8-[2-(methoxymethyl)benzimidazol-1-yl]methyl-6,11-dihydrobenzo[b,e]oxepin-11-ylidene}cyclopropylacetonitrile (66 mg, 75%) was obtained.

[step 3] Using (E)-2-[8-(2-methoxymethylbenzimidazol-1-yl)methyl-6,11-dihydrodibenzo[b,e]oxepin-11-ylidene]cyclopropylacetonitrile (65 mg, 0.15 mmol) obtained in step 2 and in the same manner as in Example 5, the title compound (compound 113) (8 mg, 11%) was obtained.

ESI-MS m/z: 507 (M+H)$^+$; $^1$H-NMR (DMSO-d$_6$, δ): 0.30-0.43 (m, 1H), 0.66-0.81 (m, 2H), 0.87-1.00 (m, 1H), 1.95-2.06 (m, 1H), 3.24 (d, J=1.0 Hz, 3H), 4.65 (s, 2H), 4.86 (d, J=12.6 Hz, 1H), 5.46-5.55 (m, 3H), 6.79 (d, J=8.3 Hz, 1H), 6.90-6.99 (m, 1H), 7.01-7.06 (m, 1H), 7.09-7.28 (m, 5H), 7.34-7.45 (m, 2H), 7.60-7.68 (m, 1H), 12.18 (s, 1H).

Example 114

(E)-8-(4-Chloro-2-methoxymethylbenzimidazol-1-yl)methyl-11-cyclopropyl(5-oxo-4,5-dihydro-1,2,4-oxadiazol-3-yl)methylene-6,11-dihydrodibenzo[b,e]oxepine (Compound 114)

[step 1] Using (E)-2-(8-bromomethyl-6,11-dihydrobenzo[b,e]oxepin-11-ylidene)cyclopropylacetonitrile (75 mg, 0.20 mmol) obtained in Example 113, step 1 and 4-chloro-2-methoxymethylbenzimidazole (38 mg, 0.19 mmol) obtained in Reference Example A14, and in the same manner as in Example 92, step 1, (E)-2-[8-(4-chloro-2-methoxymethylbenzimidazol-1-yl)methyl-6,11-dihydrodibenzo[b,e]oxepin-11-ylidene]cyclopropylacetonitrile (76 mg, 82%) was obtained.

[step 2] Using (E)-2-[8-(4-chloro-2-methoxymethylbenzimidazol-1-yl)methyl-6,11-dihydrodibenzo[b,e]oxepin-11-ylidene]cyclopropylacetonitrile (75 mg, 0.16 mmol) obtained in step 1 and in the same manner as in Example 5, the title compound (compound 114) (40 mg, 48%) was obtained.

ESI-MS m/z: 541 (M+H)$^+$; $^1$H-NMR (DMSO-d$_6$, δ): 0.30-0.42 (m, 1H), 0.65-0.80 (m, 2H), 0.88-0.99 (m, 1H), 1.93-2.06 (m, 1H), 3.24 (s, 3H), 4.69 (s, 2H), 4.87 (d, J=12.9 Hz, 1H), 5.50 (d, J=12.9 Hz, 1H), 5.54 (s, 2H), 6.76-6.82 (m, 1H), 6.90-6.98 (m, 1H), 7.01-7.06 (m, 1H), 7.10-7.31 (m, 5H), 7.34-7.39 (m, 1H), 7.42 (dd, J=1.5, 7.8 Hz, 1H), 12.17 (s, 1H).

Example 115

(E)-11-[1-(5-Oxo-4,5-dihydro-1,2,4-oxadiazol-3-yl)butylidene]-8-(2-propylbenzimidazol-1-yl)methyl-6,11-dihydrodibenzo[b,e]oxepine (Compound 115)

[step 1] (E)-2-(2-Hydroxymethyl-5,11-dihydrobenzooxepino[3,4-b]pyridine)pentanenitrile (0.370 g, 1.21 mmol) obtained in Reference Example B11 was dissolved in THF (6 mL), 2,6-lutidine (0.840 mL, 7.28 mmol), lithium bromide (0.630 g, 7.28 mmol) and, methanesulfonic anhydride (0.527 g, 3.03 mmol) were added, and the mixture was stirred at room temperature for 16 hr. Water was added to the mixture and the mixture was extracted 3 times with ethyl acetate. The combined organic layer was dried over anhydrous magnesium sulfate, and concentrated under reduced pressure to give a residue.

2-Propylbenzimidazole (0.084 g, 0.526 mmol) was dissolved in DMF (2 mL), potassium carbonate (0.330 g, 2.39 mmol) was added and the mixture was stirred for 15 min. To this mixture was added the residue obtained above, and the mixture was stirred at 60° C. for 2 hr. Water was added to the mixture and the mixture was extracted 3 times with ethyl acetate. The combined organic layer was dried over anhydrous magnesium sulfate, and concentrated under reduced pressure. The obtained residue was purified by silica gel column chromatography (hexane/ethyl acetate=1/2) to give (E)-2-{8-(2-propylbenzimidazol-1-yl)methyl-6,11-dihydrodibenzo[b,e]oxepin-11-ylidene}pentanenitrile (0.110 g, 35%).

[step 2] Using (E)-2-[8-(2-propylbenzimidazol-1-yl)methyl-6,11-dihydrodibenzo[b,e]oxepin-11-ylidene]pentanenitrile (0.110 g, 0.246 mmol) obtained in step 1 and in the same manner as in Example 5, the title compound (compound 115) (0.026 g, 20%) was obtained.

ESI-MS m/z: 507 (M+H)$^+$; $^1$H-NMR (CDCl$_3$, δ): 0.81-0.99 (m, 6H), 1.42-1.61 (m, 2H), 1.66-1.88 (m, 2H), 2.51-2.97 (m, 4H), 4.68 (d, J=13.0 Hz, 1H), 5.36 (s, 2H), 5.56 (d, J=13.0 Hz, 1H), 6.78-6.87 (m, 1H), 6.87-7.02 (m, 3H), 7.04-7.38 (m, 6H), 7.72-7.84 (m, 1H), 12.18 (s, 1H).

Example 116

(E)-2-Fluoro-8-(2-propylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 116)

[step 1] (E)-2-(2-Fluoro-8-hydroxymethyl-6,11-dihydrodibenzo[b,e]oxepin-11-ylidene)propiononitrile (0.115 g, 0.299 mmol) obtained in Reference Example B12 was dissolved in THF (1.5 mL), 2,6-lutidine (0.21 mL, 1.79 mmol), lithium bromide (0.156 g, 1.79 mmol) and methanesulfonic anhydride (0.130 g, 0.747 mmol) were added, and the mixture was stirred at room temperature for 16 hr. Water was added to the mixture and the mixture was extracted 3 times with ethyl acetate. The combined organic layer was dried over anhydrous magnesium sulfate, and concentrated under reduced pressure to give a residue.

2-Propylbenzimidazole (0.032 g, 0.199 mmol) was dissolved in DMF (1.5 mL), potassium carbonate (0.125 g, 907 mmol) was added and the mixture was stirred for 15 min. To this mixture was added the residue obtained above, and the mixture was stirred at 60° C. for 2 hr. Water was added to the mixture and the mixture was extracted 3 times with ethyl acetate. The combined organic layer was dried over anhydrous magnesium sulfate, and concentrated under reduced pressure. The obtained residue was purified by silica gel column chromatography (hexane/ethyl acetate=1/1) to give (E)-2-[2-fluoro-8-(2-propylbenzimidazol-1-yl)methyl-6,11-dihydrodibenzo[b,e]oxepin-11-ylidene]propiononitrile (0.063 g, 48%).

[step 2] Using (E)-2-[2-fluoro-8-(2-propylbenzimidazol-1-yl)methyl-6,11-dihydrodibenzo[b,e]oxepin-11-ylidene]propiononitrile (0.063 g, 0.127 mmol) obtained in step 1 and in the same manner as in Example 5, the title compound (compound 116) (0.016 g, 25%) was obtained.

ESI-MS m/z: 497 (M+H)$^+$; $^1$H-NMR (CDCl$_3$, δ): 0.96 (t, J=7.4 Hz, 3H), 1.73-1.91 (m, 2H), 2.31 (s, 3H), 2.72-2.82 (m, 2H), 4.52-4.66 (d, J=12.8 Hz, 1H), 5.28-5.42 (m, 3H), 6.71-6.97 (m, 4H), 6.97-7.06 (m, 1H), 7.08-7.25 (m, 5H), 7.58-7.73 (m, 1H).

Example 117

(E)-5-[1-(5-Oxo-4,5-dihydro-1,2,4-oxadiazol-3-yl)ethylidene]-2-(2-propylbenzimidazol-1-yl)methyl-5,11-dihydrobenzooxepino[3,4-b]pyridine (Compound 117)

[step 1] (E)-2-(2-Hydroxymethyl-5,11-dihydrobenzooxepino[3,4-b]pyridine)propiononitrile (0.190 g, 0.683 mmol) obtained in Reference Example B10 was dissolved in THF (3 mL), 2,6-lutidine (0.480 mL, 4.16 mmol), lithium bromide (0.360 g, 4.16 mmol) and methanesulfonic anhydride (0.297 g, 1.71 mmol) were added, and the mixture was stirred at room temperature for 16 hr. Water was added to the mixture and the mixture was extracted 3 times with ethyl acetate. The combined organic layer was dried over anhydrous magnesium sulfate, and concentrated under reduced pressure to give a residue.

2-Propylbenzimidazole (0.093 g, 0.581 mmol) was dissolved in DMF (2 mL), potassium carbonate (0.364 g, 2.64 mmol) was added and the mixture was stirred for 15 min. To this mixture was added the residue obtained above, and the mixture was stirred at 60° C. for 2 hr. Water was added to the mixture and the mixture was extracted 3 times with ethyl acetate. The combined organic layer was dried over anhydrous magnesium sulfate, and concentrated under reduced pressure. The obtained residue was purified by silica gel column chromatography (hexane/ethyl acetate=4/1) to give (E)-2-[2-(2-propylbenzimidazol-1-yl)methyl-5,11-dihydrobenzooxepino[3,4-b]pyridin-5-ylidene]propiononitrile (0.180 g, 63%).

[step 2] Using (E)-2-[2-(2-propylbenzimidazol-1-yl)methyl-5,11-dihydrobenzooxepino[3,4-b]pyridin-5-ylidene]propiononitrile (0.120 g, 0.286 mmol) obtained in step 1 and in the same manner as in Example 5, the title compound (compound 117) (0.085 g, 62%) was obtained.

ESI-MS m/z: 480 (M+H)$^+$; $^1$H-NMR (CDCl$_3$, δ): 0.88 (t, J=7.6 Hz, 3H), 1.64-1.86 (m, 2H), 2.21 (s, 3H), 2.74 (t, J=7.6 Hz, 2H), 4.76 (d, J=14.4 Hz, 1H), 5.12-5.38 (m, 3H), 6.76 (d, J=8.0 Hz, 1H), 6.88-7.05 (m, 2H), 7.09-7.32 (m, 5H), 7.43-7.57 (m, 2H), 11.19 (br s, 1H).

Example 118

(E)-2-(2-Propylbenzimidazol-1-yl)methyl-5-[1-(1H-tetrazol-5-yl)ethylidene]-5,11-dihydrobenzooxepino[3,4-b]pyridine (Compound 118)

Using (E)-2-[2-(2-propylbenzimidazol-1-yl)methyl-5,11-dihydrobenzooxepino[3,4-b]pyridin-5-ylidene]propiononitrile (0.050 g, 0.119 mmol) obtained in Example 117, step 1 and in the same manner as in Example 4, the title compound (compound 118) (0.005 g, 9%) was obtained.

ESI-MS m/z: 464 (M+H)$^+$; $^1$H-NMR (DMSO-d$_6$, δ): 0.94 (t, J=7.6 Hz, 3H), 1.62-1.84 (m, 2H), 2.23 (s, 3H), 2.85 (t, J=7.6 Hz, 2H), 4.86 (d, J=13.5 Hz, 1H), 5.51 (s, 2H), 5.66 (d, J=13.5 Hz, 1H), 6.88 (d, J=8.3 Hz, 1H), 6.93-6.98 (m, 1H), 6.99-7.09 (m, 1H), 7.09-7.20 (m, 3H), 7.24-7.36 (m, 2H), 7.38-7.50 (m, 1H), 7.50-7.60 (m, 1H).

Example 119

(E)-2-(7-Chloro-2-cyclopropyl-3H-imidazo[4,5-b]pyridin-3-yl)methyl-5-[1-(5-oxo-4,5-dihydro-1,2,4-oxadiazol-3-yl)ethylidene]-5,11-dihydrobenzooxepino[3,4-b]pyridine (Compound 119)

[step 1] Using 7-chloro-2-cyclopropyl-3H-imidazo[4,5-b]pyridine (0.095 g, 0.484 mmol) instead of 2-propylbenzimidazole, and in the same manner as in Example 117, step 1, (E)-2-[2-(4-chloro-2-cyclopropylbenzimidazol-1-yl)methyl-5,11-dihydrobenzooxepino[3,4-b]pyridin-5-ylidene]propiononitrile (0.117 g, 40%) was obtained.

[step 2] Using (E)-2-[2-(7-chloro-2-cyclopropyl-3H-imidazo[4,5-b]pyridin-3-yl)methyl-5,11-dihydrobenzooxepino[3,4-b]pyridin-5-ylidene]propiononitrile (0.117 g, 0.259 mmol) obtained in Example 119, step 1 and in the same manner as in Example 5, the title compound (compound 119) (0.076 g, 57%) was obtained.

ESI-MS m/z: 513 (M+H)$^+$; $^1$H-NMR (CDCl$_3$, δ): 0.95-1.17 (m, 2H), 1.18-1.34 (m, 2H), 1.94-2.13 (m, 1H), 2.21 (s, 3H), 4.89 (d, (7=15.0 Hz, 1H), 5.40 (d, J=15.0 Hz, 1H), 5.58 (s, 2H), 6.90 (d, J=8.0 Hz, 1H), 7.00-7.12 (m, 2H), 7.12-7.23 (m, 2H), 7.23-7.38 (m, 1H), 7.47 (d, J=8.0 Hz, 1H), 8.04 (d, J=5.5 Hz, 1H), 9.71 (br s, 1H).

Example 120

(E)-2-(4-Chloro-2-cyclopropylbenzimidazol-1-yl)methyl-5-[1-(5-oxo-4,5-dihydro-1,2,4-oxadiazol-3-yl)ethylidene]-5,11-dihydrobenzooxepino[3,4-b]pyridine (Compound 120)

[step 1] Using 4-chloro-2-cyclopropylbenzimidazole (0.095 g, 0.484 mmol) instead of 2-propylbenzimidazole and in the same manner as in Example 117, step 1, (E)-2-{2-(4-chloro-2-cyclopropylbenzimidazol-1-yl)methyl-5,11-dihydrobenzooxepino[3,4-b]pyridin-5-ylidene}propiononitrile (0.147 g, 50%) was obtained.

[step 2] Using (E)-2-[2-(4-chloro-2-cyclopropylbenzimidazol-1-yl)methyl-5,11-dihydrobenzooxepino[3,4-b]pyridin-5-ylidene]propiononitrile (0.147 g, 0.325 mmol) obtained in step 1 and in the same manner as in Example 5, the title compound (compound 120) (0.014 g, 8%) was obtained.

ESI-MS m/z: 512 (M+H)$^+$; $^1$H-NMR (CDCl$_3$, δ): 0.89-1.08 (m, 2H), 1.17-1.34 (m, 2H), 1.86-2.01 (m, 1H), 2.22 (s, 3H), 4.93 (d, J=14.8 Hz, 1H), 5.39-5.55 (m, 3H), 6.75 (d, J=8.0 Hz, 1H), 6.99-7.38 (m, 7H), 7.45 (d, J=8.0 Hz, 1H).

Example 121

(Z)-5-[1-(5-Oxo-4,5-dihydro-1,2,4-oxadiazol-3-yl)ethylidene]-2-(2-propylbenzimidazol-1-yl)methyl-5,11-dihydrobenzooxepino[3,4-b]pyridine (Compound 121)

[step 1] Propyl(Z)-5-(1-cyanoethylidene)-5,11-dihydrobenzooxepino[3,4-b]pyridine-2-carboxylate (0.189 g, 0.565 mmol) obtained in Reference Example B10, step 3 was dissolved in THF (2 mL), lithium borohydride (0.062 g, 2.82 mmol) was added and the mixture was stirred at 60° C. for 3 hr. To the reaction mixture was added dropwise 1 mol/L hydrochloric acid under ice-cooling, and the mixture was extracted 3 times with ethyl acetate. The combined organic layer was dried over anhydrous magnesium sulfate, and concentrated under reduced pressure. The obtained residue was purified by silica gel column chromatography (hexane/ethyl acetate=1/3) to give (Z)-2-(2-hydroxymethyl-5,11-dihydrobenzooxepino[3,4-b]pyridine)propiononitrile (0.111 g, 71%).

[step 2] (Z)-2-(2-Hydroxymethyl-5,11-dihydrobenzooxepino[3,4-b]pyridine)propiononitrile (0.111 g, 0.396 mmol) obtained in step 1 was dissolved in THF (2 mL), 2,6-lutidine (0.276 mL, 2.37 mmol), lithium bromide (0.206 g, 2.37 mmol) and methanesulfonic anhydride (0.172 g, 0.989 mmol) were added and the mixture was stirred at room temperature for 16 hr. Water was added to the mixture and the mixture was extracted 3 times with ethyl acetate. The combined organic layer was dried over anhydrous magnesium sulfate, and concentrated under reduced pressure to give a residue.

2-Propylbenzimidazole (0.053 g, 0.333 mmol) was dissolved in DMF (2 mL), potassium carbonate (0.218 g, 1.58 mmol) was added and the mixture was stirred for 15 min. To this mixture was added the residue obtained above, and the mixture was stirred at 60° C. for 2 hr. Water was added to the mixture and the mixture was extracted 3 times with ethyl acetate. The combined organic layer was dried over anhydrous magnesium sulfate, and concentrated under reduced pressure. The obtained residue was purified by silica gel column chromatography (hexane/ethyl acetate=1/3) to give (Z)-2-[2-(2-propylbenzimidazol-1-yl)methyl-5,11-dihydrobenzooxepino[3,4-b]pyridine]propiononitrile (0.094 g, 56%).
[step 3] Using (Z)-2-[2-(2-propylbenzimidazol-1-yl)methyl-5,11-dihydrobenzooxepino[3,4-b]pyridine]propiononitrile (0.090 g, 0.214 mmol) obtained in step 2 and in the same manner as in Example 5, the title compound (compound 121) (0.026 g, 25%) was obtained.
ESI-MS m/z: 480 (M+H)$^+$; $^1$H-NMR (CDCl$_3$, δ): 0.95 (t, (7=7.6 Hz, 3H), 1.67-1.86 (m, 2H), 1.96 (s, 3H), 2.90 (t, J=7.6 Hz, 2H), 4.85 (d, J=12.6 Hz, 1H), 5.60 (s, 2H), 5.76 (d, J=12.6 Hz, 1H), 6.78-6.90 (m, 2H), 6.92-7.03 (m, 1H), 7.07-7.31 (m, 4H), 7.42-7.53 (m, 1H), 7.53-7.65 (m, 1H), 7.82 (d, J=7.8 Hz, 1H).

Example 122

(Z)-5-[1-(5-Oxo-4,5-dihydro-1,2,4-oxadiazol-3-yl) ethylidene]-8-(2-propylbenzimidazol-1-yl)methyl-5, 11-dihydrobenzooxepino[3,4-b]pyridine (Compound 122)

[step 1] Using (Z)-2-(8-chloromethyl-5,11-dihydrobenzooxepino[3,4-b]pyridin-5-ylidene)propiononitrile (0.054 g, 0.182 mmol) obtained in Reference Example B14 and in the same manner as in Example 1, (Z)-2-[8-(2-propylbenzimidazol-1-yl)methyl-5,11-dihydrobenzooxepino[3,4-b]pyridin-5-ylidene]propiononitrile (0.054 g, 70%) was obtained.
[step 2] Using (Z)-2-[8-(2-propylbenzimidazol-1-yl)methyl-5,11-dihydrobenzooxepino[3,4-b]pyridin-5-ylidene]propiononitrile (0.036 g, 0.075 mmol) obtained in step 1 and in the same manner as in Example 5, the title compound (compound 122) (0.016 g, 45%) was obtained.
ESI-MS m/z: 480 (M+H)$^+$; $^1$H-NMR (CDCl$_3$, δ): 0.94 (t, J=7.3 Hz, 3H), 1.79 (m, 2H), 2.17 (s, 3H), 2.75 (m, 2H), 4.71 (d, J=13.1 Hz, 1H), 5.25 (s, 2H), 5.39 (d, J=13.1 Hz, 1H), 6.45 (s, 1H), 6.68 (d, J=7.9 Hz, 1H), 7.10 (t, J=7.9 Hz, 1H), 7.15-7.39 (m, 4H), 7.58-7.73 (m, 2H), 8.54 (m, 1H).

Example 123

(Z)-8-(2-Propylbenzimidazol-1-yl)methyl-5-(1H-tetrazol-5-yl)methylene-5,11-dihydrobenzooxepino [3,4-b]pyridine (Compound 123)

Using (Z)-2-[8-(2-propylbenzimidazol-1-yl)methyl-5,11-dihydrobenzooxepino[3,4-b]pyridin-5-ylidene]propiononitrile (0.016 g, 0.038 mmol) obtained in Example 122, step 1 and in the same manner as in Example 4, the title compound (compound 123) (0.0073 g, 41%) was obtained.
ESI-MS m/z: 464 (M+H)$^+$; $^1$H-NMR (CDCl$_3$, δ): 0.88 (t, J=7.4 Hz, 3H), 1.75 (m, 2H), 2.18 (s, 3H), 2.20 (m, 2H), 4.36 (d, J=13.7 Hz, 1H), 4.94 (d, J=16.8 Hz, 1H), 5.08 (d, J=16.8 Hz, 1H), 5.12 (d, J=13.7 Hz, 1H), 6.18 (s, 1H), 6.68 (d, J=7.3 Hz, 1H), 6.77 (d, J=7.9 Hz, 1H), 6.99-7.55 (m, 5H), 7.77 (d, J=6.9 Hz, 1H), 8.51 (d, J=4.6 Hz, 1H).

Example 124

(E)-5-[1-(5-Oxo-4,5-dihydro-1,2,4-oxadiazol-3-yl) ethylidene]-8-(2-propylbenzimidazol-1-yl)methyl-5, 11-dihydrobenzooxepino[3,4-b]pyridine (Compound 124)

[step 1] Using (E)-2-(8-chloromethyl-5,11-dihydrobenzooxepino[3,4-b]pyridin-5-ylidene)propiononitrile (0.184 g, 0.622 mmol) obtained in Reference Example B15 and in the same manner as in Example 1, (E)-2-[8-(2-propylbenzimidazol-1-yl)methyl-5,11-dihydrobenzooxepino[3,4-b]pyridin-5-ylidene]propiononitrile (0.220 g, 84%) was obtained.
[step 2] Using (E)-2-[8-(2-propylbenzimidazol-1-yl)methyl-5,11-dihydrobenzooxepino[3,4-b]pyridin-5-ylidene]propiononitrile (0.108 g, 0.26 mmol) obtained in Example 124, step 1 and in the same manner as in Example 5, the title compound (compound 124) (0.043 g, 34%) was obtained.
ESI-MS m/z: 480 (M+H)$^+$; $^1$H-NMR (CDCl$_3$, δ): 0.97 (t, J=7.6 Hz, 3H), 1.81 (m, 2H), 2.21 (s, 3H), 2.87 (t, J=7.6 Hz, 2H), 4.65 (d, J=14.4 Hz, 1H), 4.95 (d, J=14.4 Hz, 1H), 5.32 (s, 2H), 6.70 (s, 1H), 6.79 (d, J=7.9 Hz, 1H), 7.10-7.32 (m, 5H), 7.49-7.65 (m, 2H), 8.43 (d, J=1.3 Hz, 1H).

Example 125

(E)-8-(2-Propylbenzimidazol-1-yl)methyl-5-(1H-tetrazol-5-yl)methylene-5,11-dihydrobenzooxepino [3,4-b]pyridine (compound 125)

Using (E)-2-[8-(2-propylbenzimidazol-1-yl)methyl-5,11-dihydrobenzooxepino[3,4-b]pyridin-5-ylidene]propiononitrile (0.108 g, 0.26 mmol) obtained in Example 124, step 1 and in the same manner as in Example 4, the title compound (compound 125) (0.055 g, 45%) was obtained.
ESI-MS m/z: 464 (M+H)$^+$; $^1$H-NMR (CDCl$_3$, δ): 0.93 (t, J=7.4 Hz, 3H), 1.75 (m, 2H), 2.24 (s, 3H), 2.79 (t, J=7.4 Hz, 2H), 4.91 (d, J=12.9 Hz, 1H), 5.45 (s, 2H), 5.69 (d, J=12.9 Hz, 1H), 6.63 (s, 1H), 6.68 (d, J=7.3 Hz, 1H), 7.11-7.21 (m, 4H), 7.37 (d, J=7.9 Hz, 1H), 7.44 (m, 1H), 7.69 (m, 1H), 8.41 (m, 1H).

Reference Example A1

4-Chloro-2-cyclopropylbenzimidazole

2-Chloro-6-nitroaniline (3.00 g, 17.4 mmol) and pyridine (7.0 mL, 86.9 mmol) were dissolved in DMA (17 mL), cyclopropanecarbonyl chloride (4.0 mL, 43.5) was added and the mixture was stirred at 50° C. for 3 hr. To the mixture were added methanol (10 mL) and aqueous ammonia (9 mL), and the mixture was stirred at room temperature for 30 min. Water (10 mL) was added, and the precipitated solid was collected by filtration. The solid was suspended in ethanol (38 mL) and water (38 mL), ferrous sulfate 7 hydrate (13.86 g, 49.9 mmol) and aqueous ammonia (19 mL) were added, and the mixture was stirred at 50° C. for 4 hr. The mixture was filtered, and the filtrate was extracted with ethyl acetate, washed with brine, dried over anhydrous magnesium sulfate and concentrated under reduced pressure. Acetic acid (8 mL) was added to the residue, and the mixture was stirred at 90° C. for 1 hr. The mixture was concentrated under reduced pressure, neutralized with aqueous sodium hydroxide solution, and extracted with ethyl acetate. The organic layer was washed with brine, dried over anhydrous magnesium sulfate and concentrated under reduced pressure. Ethyl acetate (5 mL) and diisopropyl ether (5 mL) were added to the residue, and the precipitated solid was collected by filtration to give the title compound (1.20 g, 36%).
ESI-MS m/z: 193 (M+H)$^+$; $^1$H-NMR (CDCl$_3$, δ): 1.11-1.25 (m, 4H), 2.01-2.14 (m, 1H), 7.05-7.55 (m, 3H).

Reference Example A2

6-(2-Furanyl)-4-methyl-2-propylbenzimidazole

Under a nitrogen atmosphere, 6-bromo-4-methyl-2-propylbenzimidazole (WO2004082621; 200 mg, 0.83 mmol) was dissolved in toluene (4 mL), tributyl(2-furanyl)tin (0.78 mL, 2.49 mmol) and tetrakis(triphenylphosphine)palladium (288 mg, 0.25 mmol) were added, and the mixture was stirred at 100° C. for 3 days. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=8/2 to 1/9) to give the title compound (60 mg, 30%).

$^1$H-NMR (CDCl$_3$, δ): 1.03 (t, J=7.3 Hz, 3H), 1.79-1.97 (m, 2H), 2.64 (s, 3H), 2.89 (t, J=7.3 Hz, 2H), 6.45-6.48 (m, 1H), 6.51-6.54 (m, 1H), 6.59 (d, J=4.0 Hz, 1H), 7.37 (s, 1H), 7.75 (s, 1H).

Reference Example A3

4-Methyl-6-(2-oxazolyl)-2-propylbenzimidazole

[step 1] 6-Methoxycarbonyl-4-methyl-2-propylbenzimidazole (EP502314; 500 mg, 2.29 mmol) was suspended in ethanol (15 mL), 4 mol/L aqueous sodium hydroxide solution (3.1 mL) was added, and the mixture was stirred under reflux for 7 hr. The mixture was concentrated under reduced pressure, and water (20 mL) was added. Under ice-cooling, the mixture was adjusted to pH 1 with 2 mol/L hydrochloric acid, and extracted with chloroform. The organic layer was washed with brine, dried over anhydrous magnesium sulfate, and concentrated under reduced pressure. The residue was dissolved in dichloromethane, aminoacetaldehyde dimethylacetal (0.50 mL, 4.58 mmol), 1-ethyl-3-(3-dimethylaminopropyl)carbodiimide (527 mg, 2.75 mmol) and 1-hydroxybenzotriazole (421 mg, 2.75 mmol) were added, and the mixture was stirred at room temperature for 6 hr. To the mixture were added saturated aqueous sodium hydrogen carbonate solution (100 mL) and chloroform (100 mL), and the organic layer was washed with brine, dried over anhydrous magnesium sulfate, and concentrated under reduced pressure to give 6-(2,2-dimethoxyethylcarbamoyl)-4-methyl-2-propylbenzimidazole.

ESI-MS m/z; 306 (M+H)$^+$; $^1$H-NMR (CDCl$_3$, δ): 1.02 (t, J=7.3 Hz, 3H), 1.82-1.97 (m, 2H), 2.65 (s, 3H), 2.92 (t, J=7.3 Hz, 2H), 3.45 (s, 6H), 3.64 (t, J=5.3 Hz, 2H), 4.52 (t, J=5.3 Hz, 1H), 6.42 (s, 1H), 7.89 (s, 1H).

[step 2] To 7.7% phosphorus pentaoxide-methanesulfonic acid (Eaton's reagent; 10 mL) was added 6-(2,2-dimethoxyethylcarbamoyl)-4-methyl-2-propylbenzimidazole (400 mg, 1.31 mmol) obtained in step 1, and the mixture was stirred at 130° C. for 7 hr. The reaction solution was added to ice-cooled aqueous solution (100 mL) and the mixture was stirred for 30 min. After stirring, saturated aqueous sodium hydrogen carbonate solution (80 mL) and ethyl acetate (200 mL) were added to the mixture. The organic layer was washed with brine, dried over anhydrous magnesium sulfate, and concentrated under reduced pressure. The residue was purified by silica gel column chromatography (hexane/ethyl acetate=20/80 to 0/100) to give the title compound (207 mg, 66%).

ESI-MS m/z; 242 (M+H)$^+$; $^1$H-NMR (CDCl$_3$, δ): 1.07 (t, J=7.3, 1.8 Hz, 3H), 1.80-1.95 (m, 2H), 2.68 (s, 3H), 2.92 (t, J=7.3 Hz, 2H), 7.25 (d, J=9.9 Hz, 1H), 7.71 (s, 1H), 7.77 (s, 1H), 7.87 (d, J=9.9 Hz, 1H).

Reference Example A4

2,4-Dimethyl-6-phenylbenzimidazole

[step 1] To a mixture of 4-bromo-2-methylaniline (9.00 g, 48.3 mmol) and acetic anhydride (54 mL) was added dropwise under ice-cooling fuming nitric acid (8.10 mL, 194 mmol) over 20 min. Under ice-cooling, the mixture was stirred for 1 hr and water and ethyl acetate were added to the mixture, and the mixture was extracted. The organic layer was washed with saturated aqueous sodium hydrogen carbonate solution and brine, dried over anhydrous magnesium sulfate, and concentrated under reduced pressure. Ethyl acetate-hexane (1/1, 24 mL) was added to the residue, and the precipitated solid was collected by filtration. The obtained solid was suspended in ethanol (40 mL), concentrated hydrochloric acid (25 mL) was added, and the mixture was stirred under reflux for 4 hr. To the mixture were added ethanol (10 mL) and water (7 mL), and the mixture was stirred at 90° C. for 30 min. The reaction solution was allowed to cool to room temperature, and the precipitated solid was collected by filtration to give 4-bromo-6-methyl-2-nitroaniline (3.87 g, 35%).

ESI-MS m/z; 232 (M+H)$^+$; $^1$H-NMR (CDCl$_3$, δ): 2.24 (s, 3H), 6.17 (s, 2H), 7.38 (s, 1H), 8.19 (s, 1H).

[step 2] Under a nitrogen atmosphere, 4-bromo-6-methyl-2-nitroaniline (2.80 g, 12.1 mmol) obtained in step 1 was dissolved in DMF (60 mL), phenylboronic acid (4.40 g, 36.3 mmol), cesium carbonate (7.90 g, 24.2 mmol) and tetrakis(triphenylphosphine)palladium (1.40 g, 2.42 mmol) were added, and the mixture was stirred at 100° C. for 4 hr. Water was added to the mixture, and the mixture was extracted with ethyl acetate. The organic layer was washed with brine, dried over anhydrous magnesium sulfate, and concentrated under reduced pressure. The residue was purified by silica gel column chromatography (hexane/ethyl acetate=1/1 to 0/1) to give 4-amino-3-methyl-5-nitrobiphenyl (2.25 g, 81%).

$^1$H-NMR (CDCl$_3$, δ) 2.32 (s, 3H), 6.21 (s, 2H), 7.29-7.37 (m, 1H), 7.39-7.49 (m, 2H), 7.51-7.63 (m, 3H), 8.27-8.33 (m, 1H).

[step 3] 4-Amino-3-methyl-5-nitrobiphenyl (100 mg, 0.44 mmol) obtained in step 2 was dissolved in ethanol-ethyl acetate (1/1, 4 mL), and the mixture was stirred in the presence of 10% palladium carbon (10 mg) under a hydrogen atmosphere at room temperature for 20 hr. The mixture was filtered, and the filtrate was concentrated under reduced pressure to give 3,4-diamino-5-methylbiphenyl (87 mg, 100%).

$^1$H-NMR (CDCl$_3$, δ): 2.26 (s, 3H), 3.34-3.53 (m, 4H), 6.86-6.93 (m, 2H), 7.21-7.28 (m, 1H), 7.35-7.40 (m, 2H), 7.50-7.53 (m, 2H).

[step 4] 3,4-Diamino-5-methylbiphenyl (150 mg, 0.64 mmol) obtained in step 3 was suspended in acetic acid (4 mL), trimethyl ortho acetate (0.14 mL, 0.76 mmol) was added, and the mixture was stirred at 110° C. for 18 hr. Under ice-cooling, 28% aqueous ammonia solution (5 mL) was added to the mixture, and the mixture was extracted with ethyl acetate (20 mL). The organic layer was washed with brine, dried over anhydrous magnesium sulfate, and concentrated under reduced pressure to give the title compound (137 mg, 96%).

ESI-MS m/z; 223 (M+H)$^+$; $^1$H-NMR (CDCl$_3$, δ): 2.65 (s, 3H), 2.66 (s, 3H), 7.29 (s, 1H), 7.34 (d, J=7.3 Hz, 1H), 7.44 (t, J=7.6 Hz, 2H), 7.53 (s, 1H), 7.62 (d, J=7.6 Hz, 2H).

Reference Example A5

2-(2-Hydroxyethyl)-4-methyl-6-phenylbenzimidazole 3,4-Diamino-5-methylbiphenyl (516 mg, 2.20 mmol) obtained in Reference Example A4, step 3 and 2-hydroxypropionitrile (470 mg, 6.61 mmol) were suspended in water (2 mL), concentrated hydrochloric acid (1 mL) was added, and the mixture was stirred under reflux for 2 days. Under ice-cooling, 28% aqueous ammonia solution was added to the mixture, and the mixture was extracted with ethyl acetate.

The organic layer was washed with brine, dried over anhydrous magnesium sulfate, and concentrated under reduced pressure. The residue was purified by silica gel column chromatography (chloroform/methanol=97/3 to 90/10) to give the title compound (260 mg, 47%).

ESI-MS m/z; 253 (M+H)$^+$; $^1$H-NMR (CDCl$_3$, δ): 2.64 (s, 3H), 3.18 (t, J=5.5 Hz, 2H), 4.13 (t, J=5.5 Hz, 2H), 7.28-7.37 (m, 2H), 7.39-7.48 (m, 2H), 7.51-7.66 (m, 3H).

Reference Example A6

2-(2-Hydroxymethyl)-4-methyl-6-phenylbenzimidazole

Using 3,4-diamino-5-methylbiphenyl (260 mg, 1.11 mmol) obtained in Reference Example A4, step 3, and 50% hydroxyacetonitrile (0.38 mL, 3.33 mmol,) instead of 2-hydroxypropionitrile, and in the same manner as in Reference Example A5, the title compound (214 mg, 70%) was obtained.

ESI-MS m/z; 239 (M+H)$^+$; $^1$H-NMR (CDCl$_3$, δ): 2.65 (s, 3H), 4.90 (s, 2H), 7.25 (s, 1H), 7.32 (d, J=7.6 Hz, 1H), 7.43 (t, J=7.6 Hz, 2H), 7.58 (s, 1H), 7.63 (d, J=7.6 Hz, 2H).

Reference Example A7

2-(2-Methoxycarbonylethyl)-4-methyl-6-phenylbenzimidazole

4-Amino-3-methyl-5-nitrobiphenyl (400 mg, 1.75 mmol) obtained in Reference Example A4, step 2 was dissolved in dichloromethane (5 mL), methyl 4-chloro-4-oxobutyrate (527 mg, 3.50 mmol) was added, and the mixture was stirred for 6 hr. To the mixture was added saturated aqueous sodium hydrogen carbonate solution (5 mL), and the mixture was extracted with ethyl acetate (20 mL). The organic layer was washed with saturated aqueous sodium hydrogen carbonate solution and brine, dried over anhydrous magnesium sulfate, and concentrated under reduced pressure. Ethyl acetate-hexane (1/5, 20 mL) was added to the residue, and the precipitated solid was collected by filtration. The obtained solid was dissolved in methanol-ethyl acetate (1/1, 20 mL), and the mixture was stirred in the presence of 10% palladium carbon (90 mg) under a hydrogen atmosphere at room temperature for 1 day. The mixture was filtered, and the filtrate was concentrated under reduced pressure. The residue was dissolved in acetic acid (20 mL), and the mixture was stirred at 100° C. for 1 hr. The mixture was concentrated under reduced pressure, saturated aqueous sodium hydrogen carbonate solution (20 mL) was added, and the mixture was extracted twice with ethyl acetate (50 mL). The organic layer was washed with saturated aqueous sodium hydrogen carbonate solution and brine, dried over anhydrous magnesium sulfate and concentrated under reduced pressure. The residue was purified by silica gel column chromatography (hexane/ethyl acetate=1/1 to 0/1) to give the title compound (404 mg, 78%).

ESI-MS m/z; 295 (M+H)$^+$; $^1$H-NMR (CDCl$_3$, δ): 2.64 (s, 3H), 2.89 (t, J=6.3 Hz, 2H), 3.25 (t, J=6.3 Hz, 2H), 3.75 (s, 3H), 7.27-7.36 (m, 3H), 7.39-7.48 (m, 2H), 7.58-7.65 (m, 2H).

Reference Example B1

(E)-2-(2-Bromomethyl-10,11-dihydro-5H-dibenzo[a,d]cyclohepten-5-ylidene)acetonitrile (E)-(2-Hydroxymethyl-10,11-dihydro-5H-dibenzo[a,d]cyclohepten-5-ylidene)acetonitrile (JP-B-2526005; 10.00 g, 38.3 mmol) was dissolved in THF (380 mL), 2,6-lutidine (26.7 mL, 230 mmol), lithium bromide (19.94 g, 230 mmol) and methanesulfonic anhydride (16.67 g, 95.7 mmol) were added, and the mixture was stirred at room temperature for 16 hr. Ethyl acetate was added to the mixture, and the organic layer was washed with brine, dried over anhydrous magnesium sulfate, and concentrated under reduced pressure to give a residue. Ethyl acetate (10 mL) and hexane (5 mL) were added to the residue, and the mixture was filtered to give the title compound (9.18 g, 74%).

$^1$H-NMR (CDCl$_3$, δ): 3.11-3.16 (m, 4H), 4.43 (s, 2H), 5.72 (s, 1H), 7.18 (s, 1H), 7.23-7.37 (m, 5H), 7.45 (dd, J=7.3, 1.7 Hz, 1H).

Reference Example B2

(E)-2-(2-Chloromethyl-10,11-dihydro-5H-dibenzo[a,d]cyclohepten-5-ylidene)acetonitrile (E)-(2-Hydroxymethyl-10,11-dihydro-5H-dibenzo[a,d]cyclohepten-5-ylidene)acetonitrile (JP-B-2526005; 2.61 g, 10.0 mmol) was dissolved in THF (26 mL), triethylamine (2.09 mL, 15.0 mmol), methanesulfonyl chloride (1.16 mL, 15.0 mmol) and lithium chloride (0.636 g, 15.0 mmol) were added, and the mixture was stirred at 50° C. for 2 hr. Ethyl acetate was added to the mixture, and the organic layer was washed with brine. The organic layer was dried over anhydrous magnesium sulfate, and concentrated under reduced pressure. Isopropyl ether (30 mL) was added to the obtained residue, and the mixture was filtered to give the title compound (2.59 g, 93%).

$^1$H-NMR (CDCl$_3$, δ): 3.11-3.17 (m, 4H), 4.53 (s, 2H), 5.71 (s, 1H), 7.18-7.37 (m, 6H), 7.43-7.47 (m, 1H).

Reference Example B3

(E)-2-(2-Hydroxymethyl-10,11-dihydro-5H-dibenzo[a,d]cyclohepten-5-ylidene)propiononitrile and (Z)-2-(2-hydroxymethyl-10,11-dihydro-5H-dibenzo[a,d]cyclohepten-5-ylidene)propiononitrile

[step 1] 5-Oxo-10,11-dihydro-5H-dibenzo[a,d]cycloheptene-2-carboxylic acid (JP-B-2526005, 19.9 g, 79 mmol) and triethyl orthoformate (17.0 mL, 102 mmol) were dissolved in ethanol (130 mL), concentrated sulfuric acid (1.68 mL, 32 mmol) was added, and the mixture was stirred under reflux for 12 hr. The mixture was diluted with ethyl acetate, and the organic layer was washed with saturated aqueous sodium hydrogen carbonate solution, dried over anhydrous magnesium sulfate and concentrated under reduced pressure. The residue was purified by silica gel column chromatography (hexane/ethyl acetate=90/10) to give ethyl 5-oxo-10,11-dihydro-5H-dibenzo[a,d]cycloheptene-2-carboxylate (20.8 g, 94%).

ESI-MS m/z: 281 (M+H)$^+$; $^1$H-NMR (CDCl$_3$, δ): 1.42 (t, J=7.2 Hz, 3H), 3.21-3.30 (m, 4H), 4.40 (q, J=7.2 Hz, 2H), 7.24 (d, J=7.5 Hz, 1H), 7.34 (td, J=7.5, 1.3 Hz, 1H), 7.46 (td, J=7.5, 1.5 Hz, 1H), 7.92-8.04 (m, 4H).

[step 2] To a solution of sodium hydride (60%, 0.856 g, 21.4 mmol) and diethyl 1-cyanoethylphosphonate (4.09 g, 21.4 mmol) in DMF (35 mL) was added a solution of ethyl 10,11-dihydro-5-oxo-5H-dibenzo[a,d]cycloheptene-2-carboxylate (3.0 g, 10.7 mmol) obtained in step 1 in DMF (10 mL) under ice-cooling, and the mixture was stirred at 80° C. for 3 hr. Water was added to the mixture, and the mixture was extracted with ethyl acetate. The organic layer was dried over anhydrous magnesium sulfate, and concentrated under reduced pressure to give a residue. The obtained residue was dissolved in THF (50 mL), lithium borohydride (1.11 g, 50.9 mmol) was added, and the mixture was stirred at 50° C. for 5 hr. The mixture was neutralized with 2 mol/L hydrochloric acid, and extracted with ethyl acetate. The organic layer was dried over anhydrous magnesium sulfate, and concentrated under reduced pressure. The residue was purified by silica gel column chromatography (chloroform/ethyl acetate=98/2) to give (E)-2-(2-hydroxymethyl-10,11-dihydro-5H-dibenzo[a,d]cyclohepten-5-ylidene)propiononitrile (0.730 g, 27%) and (Z)-2-(2-hydroxymethyl-10,11-dihydro-5H-dibenzo[a,d]cyclohepten-5-ylidene)propiononitrile (0.728 g, 27%).

E-form; $^1$H-NMR (CDCl$_3$, δ): 2.04 (s, 3H), 2.82-2.95 (m, 2H), 3.27-3.40 (m, 2H), 4.67 (d, (7=5.8 Hz, 2H), 7.08 (d, (7=7.8 Hz, 1H), 7.13-7.29 (m, 5H), 7.41 (dd, (7=7.1, 1.8 Hz, 1H).

Z-form; $^1$H-NMR (CDCl$_3$, δ): 2.03 (s, 3H), 2.81-2.97 (m, 2H), 3.26-3.40 (m, 2H), 4.64 (d, J=5.6 Hz, 2H), 7.07 (d, J=7.1 Hz, 1H), 7.16-7.28 (m, 5H), 7.43 (d, J=7.8 Hz, 1H).

Reference Example B4

(E)-2-(8-Hydroxymethyl-6,11-dihydrodibenzo[b,e]oxepin-11-ylidene)propiononitrile and (Z)-2-(8-hydroxymethyl-6,11-dihydrodibenzo[b,e]oxepin-11-ylidene)propiononitrile Using methyl 11-oxo-6,11-dihydrodibenzo[b,e]oxepin-8-carboxylate (JP-B-2526005, 1.00 g, 3.73 mmol) and in the same manner as in Reference Example B3, step 2, the title E-form (0.260 g, 25%) and Z isomer thereof (0.178 g, 17%) were obtained.

E-form; $^1$H-NMR (CDCl$_3$, δ): 2.23 (s, 3H), 4.61 (s, 2H), 4.82 (d, J=12.6 Hz, 1H), 5.45 (d, J=12.6 Hz, 1H), 6.83-6.92 (m, 2H), 7.05 (dd, J=7.8, 1.7 Hz, 1H), 7.18-7.24 (m, 1H), 7.30-7.34 (m, 2H), 7.42 (d, J=8.3 Hz, 1H).

Z-form; $^1$H-NMR (CDCl$_3$, δ): 2.03 (s, 3H), 4.72 (br s, 2H), 4.85 (d, J=12.6 Hz, 1H), 5.48 (d, J=12.6 Hz, 1H), 6.82 (dd, J=8.2, 1.1 Hz, 1H), 6.93-6.98 (m, 1H), 7.16 (d, J=7.9 Hz, 1H), 7.22-7.27 (m, 1H), 7.37 (dd, J=7.8, 1.7 Hz, 1H), 7.42 (br s, 1H), 7.51 (dd, J=7.9, 1.6 Hz, 1H).

Reference Example B5

(E)-2-(8-Chloromethyl-6,11-dihydrodibenzo[b,e]oxepin-11-ylidene)propiononitrile (E)-2-(8-Hydroxymethyl-6,11-dihydrodibenzo[b,e]oxepin-11-ylidene)propiononitrile (2.77 g, 10.0 mmol) obtained in Reference Example B4 was dissolved in THF (28 mL), triethylamine (2.09 mL, 15.0 mmol), methanesulfonyl chloride (1.16 mL, 15.0 mmol) and lithium chloride (0.636 g, 15.0 mmol) were added, and the mixture was stirred at 50° C. for 2 hr. Ethyl acetate was added to the mixture, and the organic layer was washed with brine, dried over anhydrous magnesium sulfate, and concentrated under reduced pressure. Isopropyl ether (10 mL) was added to the obtained residue, and the mixture was filtered to give the title compound (2.87 g, 97%).

$^1$H-NMR (CDCl$_3$, δ): 2.27 (s, 3H), 4.59 (s, 2H), 4.87 (d, J=12.8 Hz, 1H), 5.48 (d, J=12.8 Hz, 1H), 6.86-6.95 (m, 2H), 7.07 (dd, J=7.8, 1.8 Hz, 1H), 7.21-7.28 (m, 1H), 7.41-7.50 (m, 3H).

Reference Example B6

(Z)-2-(3-Hydroxymethyl-6,11-dihydrodibenzo[b,e]oxepin-11-ylidene)propiononitrile

[step 1] Lithium diisopropylamide (2.0 mol/L heptane/THF/ethylbenzene solution, 100 mL, 200 mmol) was diluted with THF (40 mL), a solution of propiononitrile (7.13 mL, 100 mmol) in THF (40 mL) was added dropwise while stirring at 0° C. over 15 min. After stirring at 0° C. for 30 min, a solution of diethyl chlorophosphate (14.4 mL, 100 mmol) in THF (40 mL) was added dropwise over 45 min. After stirring at room temperature for 2 hr, methyl 11-oxo-6,11-dihydrodibenzo[b,e]oxepine-3-carboxylate (JP-B-2526005, 10.7 g, 40 mmol) was added, and the mixture was stirred at room temperature for 1.5 hr. To the mixture were added ethyl acetate and water, and the mixture was extracted with 3 times with ethyl acetate. The organic layer was washed with brine, dried over anhydrous magnesium sulfate, and concentrated under reduced pressure. The residue was purified by silica gel column chromatography (ethyl acetate:hexane=15:85) to give (Z)-11-(1-cyanoethylidene)-6,11-dihydrodibenzo[b,e]oxepine-3-carboxylic acid methyl ester (4.47 g, 14.6 mmol, 37%) and (E)-11-(1-cyanoethylidene)-6,11-dihydrodibenzo[b,e]oxepine-3-carboxylic acid methyl ester (6.40 g, 21.0 mmol, 53%).

Z-form; $^1$H-NMR (DMSO-d$_6$, δ): 1.98 (s, 3H), 3.83 (s, 3H), 5.03 (d, J=12.7 Hz, 1H), 5.55 (d, J=12.7 Hz, 1H), 7.33-7.65 (m, 7H).

E-form; $^1$H-NMR (DMSO-d$_6$, δ): 2.20 (s, 3H), 3.83 (s, 3H), 5.04 (d, J=12.7 Hz, 1H), 5.57 (d, J=12.7 Hz, 1H), 7.34-7.62 (m, 7H).

[step 2] (Z)-11-(1-Cyanoethylidene)-6,11-dihydrodibenzo[b,e]oxepine-3-carboxylic acid methyl ester (0.557 g, 1.82 mmol) was suspended in THF (9 mL), lithium borohydride (0.199 g, 9.12 mmol) was added and the mixture was stirred at 50° C. for 8 hr. To the mixture was added ice, and the mixture was neutralized to pH 2 with 1 mol/L hydrochloric acid, and extracted twice with ethyl acetate. The organic layer was washed with brine, dried over anhydrous magnesium sulfate, and concentrated under reduced pressure. Isopropyl alcohol (13 mL) was added to the residue, and the mixture was filtered to give the title compound (0.364 g, 72%).

$^1$H-NMR (CDCl$_3$, δ): 2.03 (s, 3H), 4.60 (s, 2H), 4.85 (d, J=12.6 Hz, 1H), 5.48 (d, J=12.6 Hz, 1H), 6.84 (s, 1H), 6.95 (dd, J=8.1, 1.2 Hz, 1H), 7.15-7.19 (m, 1H), 7.36-7.42 (m, 3H), 7.51 (d, J=8.1 Hz, 1H).

Reference Example B7

(E)-(2-Hydroxymethyl-4H-9,10-dihydrobenzo[4,5]cyclohepta[1,2-b]thiophen-4-ylidene)acetonitrile and (Z)-(2-hydroxymethyl-4H-9,10-dihydrobenzo[4,5]cyclohepta[1,2-b]thiophen-4-ylidene)acetonitrile To a solution of sodium hydride (60%, 0.453 g, 11.3 mmol) and diethyl cyanomethylphosphonate (2.01 g, 11.3 mmol) in DMF (10 mL) was added a solution of 2-bromo-4H-9,10-dihydrobenzo[4,5]cyclohepta[1,2-b]thiophen-4-one (Helvetica Chimica Acta, 1966, vol. 26, p 214; 1.66 g, 5.66 mmol) in DMF (20 mL) under ice-cooling, and the mixture was stirred at 80° C. for 1 hr. Water was added to the mixture, and the mixture was extracted with ethyl acetate. The organic layer was dried over anhydrous magnesium sulfate, and concentrated under reduced pressure to give a residue. The residue was purified by silica gel column chromatography (hexane/ethyl acetate=85/15) to give nitrile (1.41 g, 79%). The obtained nitrile (1.41 g, 4.46 mmol), palladium acetate (0.200 g, 0.892 mmol), 1,3-bis(diphenylphosphino)propane (0.368 g, 0.892 mmol) and cesium carbonate (2.91 g, 8.92 mmol) were dissolved in propanol (28 mL) and DMF (28 mL) and, under a carbon monoxide atmosphere, the mixture was stirred at 50° C. for 1 hr. Water was added to the mixture, and the mixture was extracted with ethyl acetate. The organic layer was dried over anhydrous magnesium sulfate, and concentrated under reduced pressure to give a residue. The residue was purified by silica gel column chromatography (hexane/ethyl acetate=80/20) to give propyl ester (0.907 g, 63%). The obtained propyl ester (0.785 g, 2.43 mmol) was dissolved in THF (24 mL), lithium borohydride (0.264 g, 12.2 mmol) was added and the mixture was stirred at 50° C. for 10 hr. The mixture was neutralized with 2 mol/L hydrochloric acid, and extracted with ethyl acetate. The organic layer was dried over anhydrous magnesium sulfate, and concentrated under reduced pressure. The residue was purified by silica gel column chromatography (hexane/ethyl acetate=100/0 to 60/40) to give (E)-(2-hydroxymethyl-4H-9,10-dihydrobenzo[4,5]cyclohepta[1,2-b]thiophen-4-ylidene)acetonitrile (0.384 mg, 51%) and (Z)-(2-hydroxymethyl-4H-9,10-dihydrobenzo[4,5]cyclohepta[1,2-b]thiophen-4-ylidene)acetonitrile (0.328 mg, 44%).

E-form; $^1$H-NMR (CDCl$_3$, δ): 3.07-3.12 (m, 4H), 4.74 (d, J=5.8 Hz, 2H), 5.75 (s, 1H), 6.90 (s, 1H), 7.26-7.39 (m, 3H), 7.49-7.52 (m, 1H).

Z-form; $^1$H-NMR (CDCl$_3$, δ): 3.07-3.20 (m, 4H), 4.77 (d, J=6.3 Hz, 2H), 5.45 (s, 1H), 7.18-7.36 (m, 4H), 7.40 (s, 1H).

Reference Example B8

(E)-[2-(6-Carboxy-4-methyl-2-propylbenzimidazol-1-yl)methyl-10,11-dihydro-5H-dibenzo[a,d]cyclohepten-5-ylidene]acetonitrile

[step 1] 6-Methoxycarbonyl-4-methyl-2-propylbenzimidazole (EP502314; 1.19 g, 5.13 mmol) was dissolved in DMF (15 mL), potassium tert-butoxide (0.60 g, 5.3 mmol) was added at 0° C., and the mixture was stirred for 10 min. To this mixture was added a solution of (E)-(2-bromomethyl-10,11-dihydro-5H-dibenzo[a,d]cyclohepten-5-ylidene)acetonitrile obtained in Reference Example B1 in DMF (8 mL), and the mixture was stirred at room temperature for 2 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=3/1 to t/3) to give (E)-[2-(6-methoxycarbonyl-4-methyl-2-propylbenzimidazol-1-yl)methyl-10,11-dihydro-5H-dibenzo[a,d]cyclohepten-5-ylidene]acetonitrile (1.78 g, 73%).

ESI-MS m/z; 476 (M+H)$^+$; $^1$H-NMR (CDCl$_3$, δ): 1.00 (t, J=7.3 Hz, 3H), 1.75-1.89 (m, 2H), 2.70 (s, 3H), 2.82 (t, J=7.8 Hz, 2H), 3.06 (br s, 4H), 3.88 (s, 3H), 5.33 (s, 2H), 5.67 (s, 1H), 6.68 (s, 1H), 6.81 (dd, J=8.1, 1.4 Hz, 1H), 7.20-7.34 (m, 4H), 7.43 (dd, J=7.4, 1.8 Hz, 1H), 7.74 (d, J=1.0 Hz, 1H), 7.77 (d, J=1.0 Hz, 1H).

[step 2] (E)-[2-(6-Methoxycarbonyl-4-methyl-2-propylbenzimidazol-1-yl)methyl-10,11-dihydro-5H-dibenzo[a,d]cyclohepten-5-ylidene]acetonitrile (500 mg, 1.05 mmol) obtained in step 1 was dissolved in ethanol (7.5 mL), 2 mol/L aqueous sodium hydroxide solution (2.5 mL) was added, and the mixture was stirred under reflux for 30 min. The mixture was adjusted to pH 2 with 2 mol/L hydrochloric acid, and the precipitated solid was collected by filtration to give the title compound (554 mg) quantitatively.

ESI-MS m/z; 462 (M+H)$^+$; $^1$H-NMR (CDCl$_3$, δ): 1.01 (t, J=7.4 Hz, 3H), 1.76-1.87 (m, 2H), 2.72 (s, 3H), 2.87 (t, J=7.6 Hz, 2H), 3.08 (br, 4H), 5.35 (s, 2H), 5.67 (s, 1H), 6.78 (s, 1H), 6.83 (d, J=7.9 Hz, 1H), 7.18-7.37 (m, 4H), 7.43 (d, J=7.9 Hz, 1H), 7.81 (d, J=9.6 Hz, 2H).

Reference Example A16

4-Iodo-2-propylimidazole

[step 1] 2-Propylimidazole (3.0 g, 27.3 mmol) was dissolved in dioxane/water (55 mL/55 mL), sodium hydrogen carbonate (8.67 g, 81.8 mmol) and iodine (15.0 g, 59.9 mmol) were added, and the mixture was stirred at room temperature overnight. Water was added to the reaction mixture and the mixture was extracted 3 times with ethyl acetate. The combined organic layer was dried over anhydrous magnesium sulfate, and concentrated under reduced pressure to give 4,5-diiodo-2-propylimidazole (7.09 g, 72%).

[step 2] 4,5-Diiodo-2-propylimidazole (3.0 g, 8.31 mmol) obtained in Reference Example A16, step 1 was dissolved in ethanol/water (60 mL/60 mL), sodium sulfite (8.40 g, 66.5 mmol) was added, and the mixture was heated under reflux overnight. After completion of the reaction, the mixture was extracted 3 times with chloroform. The combined organic layer was dried over anhydrous magnesium sulfate, and concentrated under reduced pressure to give 4-iodo-2-propylimidazole (1.73 g, 88%).

ESI-MS m/Z; 237 (M+H)$^+$; $^1$H-NMR (CDCl$_3$, δ): 0.95 (t, J=7.5 Hz, 3H), 1.60-1.83 (m, 2H), 2.74 (t, J=7.6 Hz, 2H), 7.06 (s, 1H).

Reference Example A8

4-Phenyl-2-propylimidazole

[step 1] 4-Iodo-2-propylimidazole obtained in Reference Example A16 was dissolved in dioxane/water (2 mL/1 mL), phenylboronic acid (0.108 g, 0.889 mmol), 1,1-bisdiphenylphosphinoferrocene dichloropalladium (0.052 g, 0.064 mmol) and sodium carbonate (0.202 g, 1.91 mmol) were added, and the mixture was heated under reflux for 3 hr. The reaction mixture was concentrated under reduced pressure, and the obtained residue was purified by silica gel column chromatography (hexane/ethyl acetate=1/2) to give 4-phenyl-2-propylimidazole (0.091 g, 77%).

ESI-MS m/z; 187 (M+H)$^+$; $^1$H-NMR (CDCl$_3$, δ): 0.86 (t, J=7.5 Hz, 3H), 1.52-1.86 (m, 2H), 2.65 (t, J=7.5 Hz, 2H), 7.12-7.38 (m, 4H), 7.60-7.78 (m, 2H), 11.58 (br s, 1H).

Reference Example A9

2-Propyl-4-(4-pyridyl)imidazole

[step 1] 4-Iodo-2-propylimidazole obtained in Reference Example A16 was dissolved in dioxane/water (2 mL/1 mL), 4-pyridineboronic acid (0.108 g, 0.889 mmol), 1,1-bisdiphenylphosphinoferrocene dichloropalladium (0.052 g, 0.064 mmol) and sodium carbonate (0.202 g, 1.91 mmol) were added, and the mixture was heated under reflux for 3 hr. The reaction mixture was concentrated under reduced pressure, and the obtained residue was purified by silica gel column chromatography (hexane/ethyl acetate=1/2) to give 2-propyl-4-(4-pyridyl)imidazole (0.044 g, 37%).

ESI-MS m/z; 188 (M+H)$^+$; $^1$H-NMR (CDCl$_3$, δ): 0.65-1.13 (m, 3H), 1.54-1.98 (m, 2H), 2.43-2.98 (m, 2H), 6.82-7.11 (m, 1H), 7.18-7.83 (m, 3H), 8.32-8.61 (m, 1H), 9.97 (br s, 1H).

Reference Example A10

4-Methyl-6-(5-methyl-1,3-oxazol-2-yl)-2-propylbenzimidazole

[step 1] 6-Methoxycarbonyl-4-methyl-2-propylbenzimidazole (EP502314; 2.1 g, 9.04 mmol) was suspended in ethanol (65 mL), 4 mol/L aqueous sodium hydroxide solution (21 mL) was added, and the mixture was stirred under reflux for 3 hr. The mixture was concentrated under reduced pressure, and water (80 mL) was added. Under ice-cooling, the mixture was adjusted to pH 1 with 2 mol/L hydrochloric acid, and the precipitated solid was collected by filtration. The obtained solid (300 mg, 1.38 mmol) was dissolved in DMF (12 mL), 1-amino-2-propanol (0.21 mL, 2.75 mmol), 1-ethyl-3-(3-dimethylaminopropyl)carbodiimide (316 mg, 1.65 mmol) and 1-hydroxybenzotriazole (253 mg, 1.65 mmol) were added, and the mixture was stirred at room temperature for 13 hr. To the mixture were added saturated aqueous sodium hydrogen carbonate solution (40 mL) and chloroform (150 mL), and the organic layer was washed with brine, dried over anhydrous magnesium sulfate, and concentrated under reduced pressure. Chloroform (5 mL) was added to the residue, and the mixture was stirred at room temperature for 1 hr, and filtered to give 6-(2-hydroxypropylcarbamoyl)-4-methyl-2-propylbenzimidazole (255 mg, 68%).

[step 2] Under a nitrogen atmosphere, 6-(2-hydroxypropylcarbamoyl)-4-methyl-2-propylbenzimidazole (240 mg, 0.87 mmol) obtained in step 1 was dissolved in dichloromethane (11 mL), 1,1,1-triacetoxy-1,1-dihydro-1,2-benzoiodoxol-3(1H)-one (555 mg, 1.31 mmol) was added at 0° C., and the mixture was stirred at room temperature for 4 hr. To the mixture was added saturated aqueous sodium hydrogen carbonate solution (20 mL), and the mixture was extracted with chloroform. The organic layer was dried over anhydrous magnesium sulfate, and concentrated under reduced pressure. The residue was purified by silica gel chromatography (chloroform/methanol=97/3 to 90/10) to give 6-(2-oxopropylcarbamoyl)-4-methyl-2-propylbenzimidazole (208 mg, 87%).

[step 3] To 6-(2-oxopropylcarbamoyl)-4-methyl-2-propylbenzimidazole (145 mg, 0.53 mmol) obtained in step 2 was added concentrated sulfuric acid (1.6 mL), and the mixture was stirred at 130° C. for 1.5 hr. To the ice-cooled mixture were added 4 mol/L aqueous sodium hydroxide solution (8 mL) and ethyl acetate (15 mL), and the mixture was stirred for 1 hr and extracted with ethyl acetate. The organic layer was washed with brine, dried over anhydrous magnesium sulfate, and concentrated under reduced pressure. The residue was purified by silica gel column chromatography (chloroform/methanol=98/2 to 93/7) to give the title compound (93 mg, 69%).

ESI-MS m/z; 256 (M+H)$^+$; $^1$H-NMR (CDCl$_3$, δ): 0.90 (t, J=7.3 Hz, 3H), 1.73-1.89 (m, 2H), 2.38 (d, J=0.7 Hz, 3H), 2.55 (s, 3H), 2.86 (t, J=7.7 Hz, 2H), 6.80 (d, J=1.5 Hz, 1H), 7.68 (s, 1H), 8.00 (s, 1H).

Reference Example A11

4-Methyl-6-(4-methyl-1,3-oxazol-2-yl)-2-propylbenzimidazole

[step 1] 6-Methoxycarbonyl-4-methyl-2-propylbenzimidazole (EP502314; 2.1 g, 9.04 mmol) was suspended in ethanol (65 mL), 4 mol/L aqueous sodium hydroxide solution (21 mL) was added, and the mixture was stirred under reflux for 3 hr. The mixture was concentrated under reduced pressure, and water (80 mL) was added. Under ice-cooling, the mixture was adjusted to pH 1 with 2 mol/L hydrochloric acid, and the precipitated solid was collected by filtration. The obtained solid (289 mg, 1.32 mmol) was dissolved in DMF (11 mL), 2-amino-1-propanol (0.21 mL, 2.65 mmol), 1-ethyl-3-(3-dimethylaminopropyl)carbodiimide (305 mg, 1.59 mmol) and 1-hydroxybenzotriazole (243 mg, 1.59 mmol) were added, and the mixture was stirred at room temperature for 15 hr. To the mixture were added saturated aqueous sodium hydrogen carbonate solution (40 mL) and water, and the mixture was extracted with ethyl acetate (150 mL). The organic layer was dried over anhydrous magnesium sulfate, and concentrated under reduced pressure. The residue was purified by silica gel column chromatography (chloroform/methanol=95/5 to 89/11) to give N-(1-hydroxypropan-2-yl)-4-methyl-2-propyl-1H-benzimidazole-6-carboxamide (267 mg, 73%).

[step 2] Under a nitrogen atmosphere, N-(1-hydroxypropan-2-yl)-4-methyl-2-propyl-1H-benzimidazole-6-carboxamide (85 mg, 0.31 mmol) obtained in step 1 was dissolved in dichloromethane (4 mL), 1,1,1-triacetoxy-1,1-dihydro-1,2-benzoiodoxol-3(1H)-one (196 mg, 0.46 mmol) was added at 0° C., and the mixture was stirred at room temperature for 4 hr. To the mixture was added saturated aqueous sodium hydrogen carbonate solution (20 mL), and the mixture was extracted with chloroform. The organic layer was dried over anhydrous magnesium sulfate, and concentrated under reduced pressure. The residue was purified by silica gel chromatography (chloroform/methanol=94/6 to 90/10) to give 4-methyl-N-(1-oxopropan-2-yl)-2-propyl-1H-benzimidazole-6-carboxamide (42 mg, 50%).

[step 3] To 4-methyl-N-(1-oxopropan-2-yl)-2-propyl-1H-benzimidazole-6-carboxamide (40 mg, 0.15 mmol) obtained in step 2 was added phosphorus pentaoxide-methanesulfonic acid (Eaton's reagent, 1 mL), and the mixture was stirred at 130° C. for 1.5 hr. To the ice-cooled mixture was added 4 mol/L aqueous sodium hydroxide solution (5 mL), and the mixture was stirred for 1 hr, and extracted with ethyl acetate. The organic layer was washed with brine, dried over anhydrous magnesium sulfate, and concentrated under reduced pressure. The residue was purified by silica gel column chromatography (chloroform/methanol=97/3 to 93/7) to give the title compound (20 mg, 54%).

ESI-MS m/z; 256 (M+H)$^+$; $^1$H-NMR (CDCl$_3$, δ): 0.92 (t, J=7.3 Hz, 3H), 1.74-1.89 (m, 2H), 2.22 (d, J=1.1 Hz, 3H), 2.56 (s, 3H), 2.86 (t, J=7.7 Hz, 2H), 7.38-7.41 (m, 1H), 7.71-7.74 (m, 1H), 7.95-8.00 (m, 1H).

Reference Example A12

Methyl 2-propyl-1H-benzimidazole-4-carboxylate

[step 1] To methyl 2-aminobenzoate (1.5 g, 9.92 mmol) was added butyric anhydride (4.9 mL, 29.76 mmol), and the mixture was stirred at room temperature for 2 hr. Under ice-cooling, fuming nitric acid (1.6 mL) was added dropwise to the mixture, and the mixture was stirred at 0° C. for 20 min. The mixture was adjusted to pH 7 with water and 4 mol/L aqueous sodium hydroxide solution, and extracted with ethyl acetate (150 mL). The organic layer was dried over anhydrous magnesium sulfate, and concentrated under reduced pressure. The residue was purified by silica gel column chromatography (hexane/ethyl acetate=100/0 to 60/40) to give methyl 2-butyramido-3-nitrobenzoate (1.26 g, 48%).

[step 2] Methyl 2-butyramido-3-nitrobenzoate (1.65 g, 6.2 mmol) obtained in step 1 was dissolved in methanol (34 mL), and the mixture was stirred in the presence of 10% palladium carbon (413 mg) under a hydrogen atmosphere at room temperature for 6 hr. The mixture was filtered, and the filtrate was concentrated under reduced pressure to give methyl 3-amino-2-butyramidobenzoate (1.46 g, 100%).

[step 3] To methyl 3-amino-2-butyramidobenzoate (1.46 g, 6.2 mmol) obtained in step 2 was added acetic acid (9.0 mL), and the mixture was stirred at 80° C. for 1.5 hr. The mixture was concentrated under reduced pressure, saturated aqueous sodium hydrogen carbonate solution (300 mL) was added, and the mixture was extracted with ethyl acetate. The organic layer was dried over anhydrous magnesium sulfate, and concentrated under reduced pressure. The residue was purified by silica gel column chromatography (hexane/ethyl acetate=80/20 to 50/50) to give the title compound (1.18 g, 87%).

ESI-MS m/z: 219 (M+H)$^+$; $^1$H-NMR (CDCl$_3$, δ): 1.06 (t, J=7.3 Hz, 3H), 1.85-2.02 (m, 2H), 2.94 (t, J=7.7 Hz, 2H), 4.00 (s, 3H), 7.27 (t, J=7.7 Hz, 1H), 7.85 (dd, J=7.7, 0.7 Hz, 1H), 7.92 (dd, J=8.1, 0.7 Hz, 1H), 10.15 (br s, 1H).

Reference Example A13

2-Methoxymethylbenzimidazole

2-Chloromethylbenzimidazole (1.67 g, 10 mmol) was suspended in methanol (34 mL), 28% sodium methoxide methanol solution (9.6 mL, 50 mmol) and water (50 mL) were added, and the mixture was stirred at room temperature for 20 min. The precipitated solid was collected by filtration, and purified by silica gel column chromatography (chloroform/methanol=100/0 to 93/7) to give the title compound (303 mg, 19%).

ESI-MS m/z: 163 (M+H)$^+$; $^1$H-NMR (CDCl$_3$, δ): 3.49 (s, 3H), 4.79 (s, 2H), 7.27-7.31 (m, 2H), 7.59-7.64 (m, 2H).

Reference Example A14

4-Chloro-2-methoxymethylbenzimidazole

[step 1] 3-Chloro-2-nitroaniline (2.0 g, 11.6 mmol) was dissolved in dichloromethane (58 mL), triethylamine (2.6 mL, 18.5 mmol) and methoxyacetyl chloride (1.4 mL, 15.1 mmol) were added at 0° C., and the mixture was stirred under reflux for 18 hr. To the mixture was added 4 mol/L hydrochloric acid (90 mL), and the mixture was extracted with chloroform. The organic layer was washed with saturated aqueous sodium hydrogen carbonate solution and brine, dried over anhydrous magnesium sulfate, and concentrated under reduced pressure. The residue was purified by silica gel column chromatography (hexane/ethyl acetate=90/10 to 50/50) to give N-(3-chloro-2-nitrophenyl)-2-methoxyacetamide (1.7 g, 62%).

[step 2] N-(3-Chloro-2-nitrophenyl)-2-methoxyacetamide (900 mg, 3.68 mmol) obtained in step 1 was dissolved in ethanol (7.4 mL), tin chloride dihydrate (4.0 g, 17.7 mmol) was added and the mixture was stirred at 100° C. for 4 hr. The mixture was adjusted to pH 10 with 4 mol/L aqueous sodium hydroxide solution and filtered. The filtrate was extracted with ethyl acetate, and the organic layer was dried over anhydrous magnesium sulfate, and concentrated under reduced pressure to give the title compound (710 mg, 98%).

ESI-MS m/z: 197 (M+H)$^+$; $^1$H-NMR (CDCl$_3$, δ): 3.53 (s, 3H), 4.81 (s, 2H), 7.16-7.23 (m, 1H), 7.26-7.29 (m, 1H), 7.50 (dd, J=7.9, 0.9 Hz, 1H).

Reference Example A15

(2-Propylbenzimidazol-4-yl)propan-2-ol

[step 1] To a mixture of methyl 2-amino-5-bromobenzoate (2.3 g, 10.0 mmol) and propionic anhydride (14 mL) was added dropwise fuming nitric acid (2.1 mL, 50.0 mmol) under ice-cooling. After stirring at 70° C. for 15 min, water and ethyl acetate were added to the mixture, and the mixture was extracted. The organic layer was washed with saturated aqueous sodium hydrogen carbonate solution and brine, dried over anhydrous magnesium sulfate, and concentrated under reduced pressure. The residue was purified by silica gel column chromatography (hexane/ethyl acetate=70/30) to give methyl 3-amino-5-bromo-2-butylamidobenzoate (1.23 g, 36%).

[step 2] Methyl 3-amino-5-bromo-2-butylamidobenzoate (1.22 g, 3.53 mmol) obtained in step 1 was dissolved in methanol (20 mL) and the mixture was stirred in the presence of 10% palladium carbon (240 mg) under a hydrogen atmosphere at room temperature for 7 hr. The mixture was filtered, and the filtrate was concentrated under reduced pressure. The residue was dissolved in acetic acid (1 mL), and the mixture was stirred at 100° C. for 1 hr. The mixture was concentrated under reduced pressure, and the residue was purified by silica gel column chromatography (chloroform/methanol=90/10) to give methyl 2-propylbenzimidazole-4-carboxylate (0.299 g, 39%).

[step 3] Methyl 2-propylbenzimidazole-4-carboxylate (0.295 g, 1.35 mmol) obtained in step 2 was dissolved in THF (10 mL), 3 mol/L methylmagnesium chloride THF solution (4.5 mL, 13 mmol) was added under ice-cooling, and the mixture was stirred at room temperature for 1 hr. To the mixture were added water and ethyl acetate, and the mixture was extracted. The organic layer was washed with saturated aqueous sodium hydrogen carbonate solution and brine, dried over anhydrous magnesium sulfate, and concentrated under reduced pressure. The residue was purified by silica gel column chromatography (chloroform/methanol=90/10) to give the title compound (0.201 g, 68%).

ESI-MS m/z: 219 (M+H)$^+$; $^1$H-NMR (CDCl$_3$, δ): 1.03 (t, J=7.3 Hz, 3H), 1.71 (s, 6H), 1.95-1.82 (m, 2H), 2.87 (t, J=7.5 Hz, 2H), 7.58-6.70 (m, 3H), 9.92-9.88 (m, 1H).

Reference Example B9

(E)-2-(8-Hydroxymethyl-6,11-dihydrodibenzo[b,e]oxepin-11-ylidene)cyclopropylacetonitrile

[step 1] N-Lithium diisopropylamide (2.0 mol/L heptane/THF/ethylbenzene solution, 26 mL, 51.9 mmol) was diluted with THF (40 mL), cyclopropylacetonitrile (2.4 mL, 25.9 mmol) was added dropwise over 15 min with stirring at 0° C. After stirring at room temperature for 1 hr, diethyl chlorophosphate (3.7 mL, 25.9 mmol) was added dropwise at 0° C. After stirring at room temperature for 2 hr, a solution (20 mL) of 8-bromo-6,11-dihydrodibenzo[b,e]oxepin-11-one (WO1990015599, 2.50 g, 8.65 mmol) in DMF was added, and the mixture was stirred at room temperature for 1.5 hr. To the mixture were added ethyl acetate and water, and the mixture was extracted 3 times with ethyl acetate. The organic layer was washed with brine, dried over anhydrous magnesium sulfate, and concentrated under reduced pressure. The residue was purified by silica gel column chromatography (hexane/ethyl acetate=9/1) to give (E)-2-(8-bromo-6,11-dihydrodibenzo[b,e]oxepin-11-ylidene)cyclopropylacetonitrile and (Z)-2-(8-bromo-6,11-dihydrodibenzo[b,e]oxepin-11-ylidene)cyclopropylacetonitrile (1.14 g, 37%).

[step 2] (E)-2-(8-Bromo-6,11-dihydrodibenzo[b,e]oxepin-11-ylidene)cyclopropylacetonitrile and (Z)-2-(8-bromo-6,11-dihydrodibenzo[b,e]oxepin-11-ylidene)cyclopropylacetonitrile (1.14 g, 3.24 mmol) obtained in step 1 were dissolved in DMF/n-PrOH (12 mL/6 mL), palladium acetate (0.217 g, 0.972 mmol), 1,3-bisdiphenylphosphinopropane (0.400 g, 0.972 mmol) and cesium carbonate (1.26 g, 3.89 mmol) were added, and the mixture was stirred at 70° C. for 3 hr under a carbon monooxide atmosphere. Ethyl acetate and water were added to the reaction mixture, and the mixture was extracted 3 times with ethyl acetate. The combined organic layer was washed with brine, dried over anhydrous magnesium sulfate, and concentrated under reduced pressure. The residue was purified by silica gel column chromatography (hexane/ethyl acetate=50/50) to give propyl(E)-11-cyanocyclopropylmethylene-6,11-dihydrodibenzo[b,e]oxepine-8-carboxylate and propyl(Z)-11-cyanocyclopropylmethylene-6,11-dihydrodibenzo[b,e]oxepine-8-carboxylate (0.880 g, 75%).

[step 3] Propyl(E)-11-cyanocyclopropylmethylene-6,11-dihydrodibenzo[b,e]oxepine-8-carboxylate and propyl(Z)-11-cyanocyclopropylmethylene-6,11-dihydrodibenzo[b,e]oxepine-8-carboxylate (0.880 g, 2.45 mmol) obtained in step 2 were dissolved in THF, lithium borohydride (0.267 g, 12.3 mmol) was added, and the mixture was stirred with heating at 60° C. for 3 hr. Under ice-cooling, 2 mol/L hydrochloric acid was added, and the mixture was neutralized with sodium hydrogen carbonate, and extracted 3 times with ethyl acetate. The combined organic layer was dried over anhydrous magnesium sulfate, and the solvent was evaporated under reduced pressure. The residue was purified by silica gel column chromatography (chloroform) to give (E)-2-(8-hydroxymethyl-6,11-dihydrodibenzo[b,e]oxepin-11-ylidene)cyclopropylacetonitrile (0.210 g, 28%).

ESI-MS m/z; 304 (M+H)$^+$; $^1$H-NMR (CDCl$_3$, δ): 0.79-1.17 (m, 4H), 1.67 (t, J=6.0 Hz, 1H), 1.96-2.14 (m, 1H), 4.72 (d, J=6.0 Hz, 2H), 4.88 (d, J=12.6 Hz, 1H), 5.55 (d, J=12.6 Hz, 1H), 6.79-7.02 (m, 2H), 7.19-7.30 (m, 1H), 7.32-7.52 (m, 4H).

Reference Example B10

(E)-2-(2-Hydroxymethyl-5,11-dihydrobenzooxepino [3,4-b]pyridine)propiononitrile

[step 1] To a solution (100 mL) of 5,11-dihydrobenzooxepino[3,4-b]pyridine (Synthesis, 1997, 1, 113-116, 5.00 g, 23.7 mmol) in chloroform was added m-chloroperbenzoic acid (4.89 g, 28.4 mmol), and the mixture was stirred at room temperature overnight. To the reaction mixture was added sodium hydrogen carbonate, and the mixture was extracted 3 times with chloroform. The combined organic layer was dried over anhydrous magnesium sulfate, and concentrated under reduced pressure. The obtained residue was dissolved in chloroform (10 mL), phosphorus oxychloride (35 mL) was added and the mixture was stirred with heating at 90° C. for 3 hr. The reaction mixture was concentrated under reduced pressure, the obtained black oil was dissolved in ethyl acetate, and the solution was added dropwise to aqueous sodium hydrogen carbonate solution under ice-cooling. The mixture was extracted 3 times with ethyl acetate, and the combined organic layer was dried over anhydrous magnesium sulfate, and concentrated under reduced pressure. The obtained residue was purified by silica gel column chromatography (hexane/ethyl acetate=4/1) to give 2-chloro-5,11-dihydrobenzooxepino[3,4-b]pyridin-5-one (3.50 g, 59%).

[step 2] N-Lithium diisopropylamide (2.0 mol/L heptane/THF/ethylbenzene solution, 20 mL, 39.8 mmol) was diluted with THF (25 mL), propionitrile (1.4 mL, 19.9 mmol) was added dropwise over 15 min with stirring at 0° C. After stirring at room temperature for 1 hr, diethyl chlorophosphate (2.9 mL, 19.9 mmol) was added dropwise at 0° C. After stirring at room temperature for 2 hr, a solution (20 mL) of 2-chloro-5,11-dihydrobenzooxepino[3,4-b]pyridin-5-one (1.95 g, 7.96 mmol) in DMF was added, and the mixture was stirred at room temperature for 1.5 hr. To the mixture were added ethyl acetate and water, and the mixture was extracted 3 times with ethyl acetate. The organic layer was washed with brine, dried over anhydrous magnesium sulfate, and concentrated under reduced pressure. The residue was purified by silica gel column chromatography (hexane/ethyl acetate=9/1) to give (E)-2-(2-chloro-5,11-dihydrobenzooxepino[3,4-b]pyridin-5-ylidene)propiononitrile and (Z)-2-(2-chloro-5,11-dihydrobenzooxepino[3,4-b]pyridin-5-ylidene)propiononitrile (1.79 g, 80%).

[step 3] Using (E)-2-(2-chloro-5,11-dihydrobenzooxepino[3,4-b]pyridin-5-ylidene)propiononitrile and (Z)-2-(2-chloro-5,11-dihydrobenzooxepino[3,4-b]pyridin-5-ylidene)propiononitrile (0.890 g, 3.16 mmol) obtained in Reference Example B10, step 2, instead of (E)-2-(3-bromo-6,11-dihydrodibenzo[b,e]oxepin-11-ylidene)cyclopropylacetonitrile and (Z)-2-(3-bromo-6,11-dihydrodibenzo[b,e]oxepin-11-ylidene)cyclopropylacetonitrile, and in the same manner as in Reference Example B9, step 2, propyl(E)-5-(1-cyanoethylidene)-5,11-dihydrobenzooxepino[3,4-b]pyridine-2-carboxylate (0.374 g, 35%) and propyl(Z)-5-(1-cyanoethylidene)-5,11-dihydrobenzooxepino[3,4-b]pyridine-2-carboxylate (0.203 g, 20%) were obtained.

[step 4] Using propyl(E)-5-(1-cyanoethylidene)-5,11-dihydrobenzooxepino[3,4-b]pyridine-2-carboxylate (0.370 g, 1.11 mmol) obtained in Reference Example B10, step 3 instead of propyl(E)-11-cyanocyclopropylmethylene-6,11-dihydrodibenzo[b,e]oxepine-8-carboxylate and propyl(Z)-11-cyanocyclopropylmethylene-6,11-dihydrodibenzo[b,e]oxepine-8-carboxylate, and in the same manner as in Reference Example B9, step 3, (E)-2-(2-hydroxymethyl-5,11-dihydrobenzooxepino[3,4-b]pyridin-5-ylidene)propiononitrile (0.191 g, 62%) was obtained.

ESI-MS m/z; 279 (M+H)$^+$; $^1$H-NMR (CDCl$_3$, δ): 2.10 (s, 3H), 4.73-4.86 (m, 2H), 4.95-5.19 (m, 1H), 5.46-5.66 (m, 1H), 6.90-7.13 (m, 2H), 7.21-7.38 (m, 2H), 7.46-7.60 (m, 2H).

Reference Example B11

(E)-2-(8-Hydroxymethyl-6,11-dihydrodibenzo[b,e] oxepin-11-ylidene)pentanenitrile

[step 1] Using pentanenitrile (2.7 mL, 25.9 mol) instead of cyclopropylacetonitrile, and in the same manner as in Reference Example B9, step 1, (E)-2-(8-bromo-6,11-dihydrodibenzo[b,e]oxepin-11-ylidene)pentanenitrile and (Z)-2-(8-bromo-6,11-dihydrodibenzo[b,e]oxepin-11-ylidene)pentanenitrile (1.90 g, 51%) were obtained.

[step 2] Using (E)-2-(8-bromo-6,11-dihydrodibenzo[b,e]oxepin-11-ylidene)pentanenitrile and (Z)-2-(8-bromo-6,11-dihydrodibenzo[b,e]oxepin-11-ylidene)pentanenitrile (1.9 g, 5.37 mmol) obtained in Reference Example B11, step 1, instead of (E)-2-(8-bromo-6,11-dihydrodibenzo[b,e]oxepin-11-ylidene)cyclopropylacetonitrile and (Z)-2-(8-bromo-6,11-dihydrodibenzo[b,e]oxepin-11-ylidene)cyclopropylacetonitrile, and in the same manner as in Reference Example B9, step 2, propyl(E)-11-(1-cyanobutylidene)-6,11-dihydrodibenzo[b,e]oxepine-8-carboxylate and propyl(Z)-11-(1-cyanobutylidene)-6,11-dihydrodibenzo[b,e]oxepine-8-carboxylate (1.05 g, 54%) were obtained.

[step 3] Using propyl(E)-11-(1-cyanobutylidene)-6,11-dihydrodibenzo[b,e]oxepine-8-carboxylate and propyl(Z)-11-(1-cyanobutylidene)-6,11-dihydrodibenzo[b,e]oxepine-8-carboxylate (1.05 g, 2.91 mmol) instead of propyl(E)-11-(1-cyanocyclopropylmethylene)-6,11-dihydrodibenzo[b,e]oxepine-8-carboxylate and propyl(Z)-11-(1-cyanocyclopropylmethylene)-6,11-dihydrodibenzo[b,e]oxepine-8-carboxylate, and in the same manner as in Example B9, step 3, (E)-2-(8-hydroxymethyl-6,11-dihydrodibenzo[b,e]oxepin-11-ylidene)pentanenitrile (0.370 g, 41%) was obtained.

ESI-MS m/z; 306 (M+H)$^+$; $^1$H-NMR (CDCl$_3$, δ): 0.99 (t, J=7.2 Hz, 3H), 1.65-1.86 (m, 2H), 2.49-2.65 (m, 2H), 4.72 (d, J=6.0 Hz, 2H), 4.88 (d, J=12.6 Hz, 1H), 5.50 (d, J=12.6 Hz, 1H), 6.83-6.99 (m, 2H), 6.99-7.09 (m, 1H), 7.20-7.30 (m, 1H), 7.33-7.43 (m, 2H), 7.43-7.52 (m, 1H).

Reference Example B12

(E)-11-(2-Fluoro-8-hydroxymethyl-6,11-dihydrodibenzo[b,e]oxepin-5-ylidene)propiononitrile

[step 1] 5-Bromophthalide (6.00 g, 28.2 mmol) was dissolved in DMF (10 mL), 4-fluorophenol (3.15 g, 28.2 Jinni) was added, and the mixture was heated to 120° C. 28% Sodium methoxide methanol solution (5.5 mL, 28.2 mmol) was added and the mixture was stirred with heating for 4 hr. 2 mol/L Hydrochloric acid was added dropwise to the reaction mixture to neutralize the reaction mixture, and the mixture was extracted 3 times with chloroform. The combined organic layer was dried over anhydrous magnesium sulfate, and concentrated under reduced pressure. The obtained residue was purified by silica gel column chromatography (chloroform/methanol=9/1) to give 4-bromo-2-(4-fluorophenoxy)methylbenzoic acid (3.37 g, 36%).

[step 2] 4-Bromo-2-(4-fluorophenoxy)methylbenzoic acid (3.37 g, 10.4 mmol) obtained in step 1 was dissolved in dichloromethane (35 mL), trifluoroacetic anhydride (2.2 mL) and boron trifluoride diethyl ether complex (0.091 mL, 0.726 mmol) were added, and the mixture was stirred at room temperature for 6 hr. 2 mol/L Aqueous sodium hydroxide solution was added to the reaction mixture, and the mixture was extracted 3 times with dichloromethane. The combined organic layer was dried over anhydrous magnesium sulfate, and concentrated under reduced pressure. The obtained residue was crystallized from ethanol and collected by filtration to give 8-bromo-2-fluoro-6,11-dihydrodibenzo[b,e]oxepin-11-one (1.10 g, 34%).

[step 3] Using 8-bromo-2-fluoro-6,11-dihydrodibenzo[b,e]oxepin-11-one (1.10 g, 3.58 mmol) obtained in step 2 instead of 2-chloro-5,11-dihydrobenzooxepino[3,4-b]pyridin-5-one, and in the same manner as in Reference Example B10, step 2, (E)-2-[8-bromo-2-fluoro-6,11-dihydrodibenzo[b,e]oxepin-11-ylidene]propiononitrile and (Z)-2-[8-bromo-2-fluoro-6,11-dihydrodibenzo[b,e]oxepin-11-ylidene]propiononitrile (0.980 g, 79%) was obtained.

[step 4] Using (E)-2-[8-bromo-2-fluoro-6,11-dihydrodibenzo[b,e]oxepin-11-ylidene]propiononitrile and (Z)-2-[8-bromo-2-fluoro-6,11-dihydrodibenzo[b,e]oxepin-11-ylidene]propiononitrile (0.980 g, 2.85 mmol) obtained in step 3 instead of (E)-2-(8-bromo-6,11-dihydrodibenzo[b,e]oxepin-11-ylidene)cyclopropylacetonitrile and (Z)-2-(8-bromo-6,11-dihydrodibenzo[b,e]oxepin-11-ylidene)cyclopropylacetonitrile, and in the same manner as in Reference Example B9, step 2, propyl(E)-11-(1-cyanoethylidene)-2-fluoro-6,11-dihydrodibenzo[b,e]oxepine-8-carboxylate (0.210 g, 21%) was obtained.

[step 5] Using propyl(E)-11-(1-cyanoethylidene)-2-fluoro-6,11-dihydrodibenzo[b,e]oxepine-8-carboxylate (0.210 g, 0.598 mmol) obtained in step 4 instead of propyl(E)-11-(1-cyanocyclopropylmethylene-6,11-dihydrodibenzo[b,e]oxepine-8-carboxylate and propyl(Z)-11-cyanocyclopropylmethylene-6,11-dihydrodibenzo[b,e]oxepine-8-carboxylate, and in the same manner as in Reference Example B9, step 3, (E)-2-(2-fluoro-8-hydroxymethyl-6,11-dihydrodibenzo[b,e]oxepin-11-ylidene)propiononitrile (0.230 g, 100%) was obtained.

ESI-MS m/z; 296 (M+H)$^+$; $^1$H-NMR (CDCl$_3$, δ): 2.20-2.36 (m, 3H), 4.85 (s, 3H), 5.33-5.54 (m, 1H), 6.74-6.90 (m, 2H), 6.90-7.03 (m, 3H), 7.20-7.54 (m, 3H).

Reference Example B13

(E)-2-(8-Bromomethyl-6,11-dihydrodibenzo[b,e]oxepin-11-ylidene)acetonitrile

[step 1] Under ice-cooling, sodium hydride (1.9 g, 47.13 mmol) was suspended in DMF (20 mL), a solution of diethyl cyanomethylsulfonate (9.2 mL, 56.55 mmol) in DMF (20 mL) was gradually added dropwise, and the mixture was stirred at room temperature for 1 hr. To the mixture was added a solution of 8-bromo-6,11-dihydrodibenzo[b,e]oxepin-11-one (WO9015599; 11 g, 37.70 mmol) in DMF (80 mL), and the mixture was stirred at room temperature for 2 hr. To the mixture was added water (80 mL), and the mixture was stirred at room temperature for 30 min. The precipitated solid was collected by filtration to give (E)-2-(8-bromo-6,11-dihydrodibenzo[b,e]oxepin-11-ylidene)acetonitrile and (Z)-2-(8-bromo-6,11-dihydrodibenzo[b,e]oxepin-11-ylidene)acetonitrile as a mixture (11.48 g, 97%, E/Z=3/1).

[step 2] A mixture (11.48 g, 36.78 mmol) of (E)-2-(8-bromo-6,11-dihydrodibenzo[b,e]oxepin-11-ylidene)acetonitrile and (Z)-2-(8-bromo-6,11-dihydrodibenzo[b,e]oxepin-11-ylidene)acetonitrile obtained in step 1, palladium acetate (0.31 g, 1.84 mmol), 1,3-bisdiphenylphosphinopropane (0.76 g, 1.84 mmol) and cesium carbonate (17.98 g, 55.17 mmol) were suspended in ethanol (57 mL) and DMF (57 mL), and the mixture was stirred under a carbon monoxide atmosphere at 70° C. for 1.5 hr. To the mixture was added 2 mol/L aqueous sodium hydroxide solution (25 mL), and the mixture was stirred at 70° C. for 3 hr. Under ice-cooling, the mixture was adjusted to pH=3 with 2 mol/L hydrochloric acid, and extracted with ethyl acetate. The organic layer was washed with water and brine, dried over anhydrous magnesium sulfate, and concentrated under reduced pressure. The residue (8.2 g, 29.39 mmol) was dissolved in THF (50 mL), borane-THF 1 mol/L solution (44 mL, 44.09 mmol) was added under ice-cooling, and the mixture was stirred at room temperature for 4 hr. To the mixture were added ethyl acetate (100 mL) and water (50 mL), and the mixture was stirred at 50° C. for 1.5 hr, and extracted with ethyl acetate. The organic layer was washed with 1 mol/L hydrochloric acid, saturated aqueous sodium hydrogen carbonate solution and brine, dried over anhydrous magnesium sulfate, and concentrated under reduced pressure. The residue was purified by silica gel column chromatography (hexane/ethyl acetate=90/10 to 60/40) to give (E)-2-(8-hydroxymethyl-6,11-dihydrodibenzo[b,e]oxepin-11-ylidene)acetonitrile (2.65 g, 34%) and (Z)-2-(8- hydroxymethyl-6,11-dihydrodibenzo[b,e]oxepin-11-ylidene)acetonitrile (962 mg, 12%).

[step 3] (E)-2-(8-Hydroxymethyl-6,11-dihydrodibenzo[b,e]oxepin-11-ylidene)acetonitrile (3.5 g, 13.3 mmol) obtained in step 2 was dissolved in THF (133 mL), 2,6-lutidine (9.3 mL, 79.8 mmol), lithium bromide (6.9 g, 79.8 mmol) and methanesulfonic anhydride (5.8 g, 33.3 mmol) were added, and the mixture was stirred at room temperature for 5 hr. To the mixture was added water (50 mL), and the mixture was extracted with ethyl acetate (200 mL). The organic layer was washed with 1 mol/L hydrochloric acid (300 mL), saturated aqueous sodium hydrogen carbonate solution (200 mL) and brine, dried over anhydrous magnesium sulfate, and concentrated under reduced pressure. To the residue was added silica gel and the mixture was suction filtered, and the filtrate was concentrated under reduced pressure to give the title compound (3.63 g, 84%).

ESI-MS m/z; 326 (M+H)$^+$; $^1$H-NMR (DMSO-$d_6$, δ): 4.77 (s, 2H), 5.19 (s, 2H), 6.40 (s, 1H), 6.84-6.91 (m, 1H), 6.98-7.06 (m, 1H), 7.31-7.42 (m, 1H), 7.44-7.51 (m, 1H), 7.54-7.70 (m, 3H).

Reference Example B14

(Z)-2-(8-Chloromethyl-5,11-dihydrobenzooxepino[3,4-b]pyridin-5-ylidene)propiononitrile

[step 1] 4-Azaphthalide (15.0 g, 111.0 mmol) and 3-bromophenol (21.0 g, 121.4 mmol) were suspended in xylene (450 mL), and 28% sodium methoxide methanol solution (31.5 mL, 166.5 mmol) was added dropwise at 140° C. After stirring at 140° C. for 1 hr, DMF (10 mL) was added and the mixture was further stirred for 3 hr. Water and toluene were added to the reaction mixture, and the mixture was partitioned. The aqueous layer was neutralized with hydrochloric acid and the precipitated solid was collected by filtration to give 2-(3-bromophenoxymethyl)nicotinic acid (16.75 g, 49%).

[step 2] 2-(3-Bromophenoxymethyl)nicotinic acid (10.0 g, 32.5 mmol) obtained in step 1 and polyphosphoric acid (70 g) were stirred at 170° C. for 3 hr. The reaction mixture was added to ice, and the mixture was neutralized with aqueous sodium hydroxide solution and extracted with ethyl acetate. The organic layer was washed with brine, dried over anhydrous magnesium sulfate and concentrated under reduced pressure. The residue was purified by silica gel column chromatography (chloroform) to give 8-bromo-5-oxo-5,11-dihydrobenzooxepino[3,4-b]pyridine (2.52 g, 27%).

[step 3] Using 8-bromo-5-oxo-5,11-dihydrobenzooxepino[3,4-b]pyridine (3.70 g, 12.8 mmol) obtained in step 2 and in the same manner as in Reference Example B10, step 2, (Z)-2-(8-hydroxymethyl-5,11-dihydrobenzooxepino[3,4-b]pyridin-5-ylidene)propiononitrile (0.086 g, 2%) and (E)-2-(8-hydroxymethyl-5,11-dihydrobenzooxepino[3,4-b]pyridin-5-ylidene)propiononitrile (0.224 g, 6%) were obtained.

[step 4] Using (Z)-2-(8-hydroxymethyl-5,11-dihydrobenzooxepino[3,4-b]pyridin-5-ylidene)propiononitrile (0.084 g, 0.30 mmol) obtained in step 3 and in the same manner as in Reference Example B2, the title compound (0.056 g, 63%) was obtained.

ESI-MS m/z: 297 (M+H)$^+$; $^1$H-NMR (CDCl$_3$, δ): 2.07 (s, 3H), 4.50 (s, 2H), 5.10 (brs, 1H), 5.54 (brs, 1H), 7.01 (d, J=1.7 Hz, 1H), 7.07 (dd, J=7.9, 1.7 Hz, 1H), 7.32 (dd, J=7.9, 5.0 Hz, 1H), 7.55-7.50 (m, 2H), 8.59 (dd, J=4.6, 1.7 Hz, 1H).

Reference Example B15

(E)-2-(8-Chloromethyl-5,11-dihydrobenzooxepino[3,4-b]pyridin-5-ylidene)propiononitrile Using (E)-2-(8-hydroxymethyl-5,11-dihydrobenzooxepino[3,4-b]pyridin-5-ylidene)propiononitrile (0.222 g, 0.80 mmol) obtained in Reference Example B14, step 3 and in the same manner as in Reference Example B2, the title compound (0.186 g, 78%) was obtained.

ESI-MS m/z: 297 (M+H)$^+$; $^1$H-NMR (CDCl$_3$, δ): 2.24 (s, 3H), 4.51 (s, 2H), 5.09 (d, J=11.9 Hz, 1H), 5.55 (d, J=11.9 Hz, 1H), 7.11-7.04 (m, 3H), 7.34 (dd, J=7.7, 5.0 Hz, 1H), 7.86 (dd, J=7.7, 1.4 Hz, 1H), 8.58 (dd, J=5.0, 1.4 Hz, 1H).

INDUSTRIAL APPLICABILITY

According to the present invention, a tricyclic compound having a PPAR γ agonist activity, which is useful as an agent for treating and/or preventing type 2 diabetes, impaired glucose tolerance, insulin resistance syndrome, hypertension, hyperlipidemia, metabolic syndrome, visceral obesity, obesity, hypertriglyceridemia, inflammatory skin diseases, inflammatory diseases, proliferative diseases, inflammatory neuropsychiatric diseases, angiogenesis and pathological angiogenesis relating to tumor growth and metastasis, neurodegenerative neuropsychiatric diseases, cardiovascular diseases such as arteriosclerosis, cardiac disease, cerebral apoplexy, renal diseases etc., or the like, or a pharmaceutically acceptable salt thereof can be provided.

The invention claimed is:

1. A tricyclic compound represented by formula

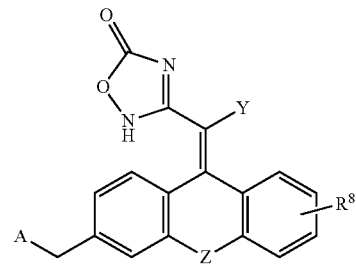

wherein
Y is a hydrogen atom, lower alkyl optionally having substituent(s), or cycloalkyl optionally having substituent(s),
Z is —CH$_2$O— or —OCH$_2$—,
R$^8$ is a hydrogen atom or halogen, and
A is an aromatic heterocyclic group optionally having substituent(s),
or a pharmaceutically acceptable salt thereof.

2. The tricyclic compound or the pharmaceutically acceptable salt thereof according to claim 1, wherein A is group (a38) or (a39)

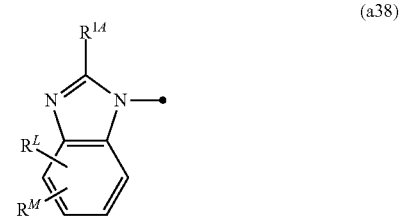

-continued (a39)

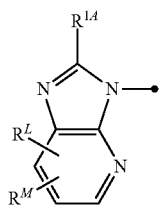

wherein

R$^{14}$ is lower alkyl optionally having substituent(s), aryl optionally having substituent(s), or cycloalkyl optionally having substituent(s), and R$^L$ and R$^M$ are the same or different and each is a hydrogen atom, halogen, carbamoyl, lower alkylcarbamoyl optionally having substituent(s), lower alkyl optionally having substituent(s), or lower alkylsulfonylamino optionally having substituent(s).

3. The tricyclic compound or the pharmaceutically acceptable salt thereof according to claim 2, wherein A is group (a38).

4. The tricyclic compound or the pharmaceutically acceptable salt thereof according to claim 1, wherein Y is lower alkyl.

5. The tricyclic compound or the pharmaceutically acceptable salt thereof according to claim 1, wherein Y is methyl.

6. The tricyclic compound or the pharmaceutically acceptable salt thereof according to claim 1, wherein Z is —CH$_2$O—.

7. The tricyclic compound or the pharmaceutically acceptable salt thereof according to claim 1, wherein R$^8$ is a hydrogen atom.

8. A pharmaceutical composition comprising the tricyclic compound or the pharmaceutically acceptable salt thereof according to claim 1, as an active ingredient.

9. A pharmaceutical composition comprising the tricyclic compound or the pharmaceutically acceptable salt thereof according to claim 2, as an active ingredient.

10. A pharmaceutical composition comprising the tricyclic compound or the pharmaceutically acceptable salt thereof according to claim 3, as an active ingredient.

11. A pharmaceutical composition comprising the tricyclic compound or the pharmaceutically acceptable salt thereof according to claim 4, as an active ingredient.

12. A pharmaceutical composition comprising the tricyclic compound or the pharmaceutically acceptable salt thereof according to claim 5, as an active ingredient.

13. A pharmaceutical composition comprising the tricyclic compound or the pharmaceutically acceptable salt thereof according to claim 6, as an active ingredient.

14. A pharmaceutical composition comprising the tricyclic compound or the pharmaceutically acceptable salt thereof according to claim 7, as an active ingredient.

* * * * *

UNITED STATES PATENT AND TRADEMARK OFFICE
CERTIFICATE OF CORRECTION

PATENT NO.        : 8,486,980 B2
APPLICATION NO.   : 13/057599
DATED             : July 16, 2013
INVENTOR(S)       : Yanagisawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 93 days.

Signed and Sealed this
Eighth Day of September, 2015

Michelle K. Lee
*Director of the United States Patent and Trademark Office*